(12) United States Patent
Li et al.

(10) Patent No.: US 9,783,513 B2
(45) Date of Patent: Oct. 10, 2017

(54) STAT3 INHIBITORS AND THEIR ANTICANCER USE

(71) Applicants: Ohio State Innovation Foundation, Columbus, OH (US); Research Institute at Nationwide Children's Hospital, Columbus, OH (US)

(72) Inventors: Chenglong Li, Dublin, OH (US); Wenying Yu, Columbus, OH (US); Jiayuh Lin, Dublin, OH (US)

(73) Assignees: Ohio State Innovation Foundation, Columbus, OH (US); Research Institute at Nationwide Children's Hospital, Columbus, OH (US)

( * ) Notice: Subject to any disclaimer, the term of this patent is extended or adjusted under 35 U.S.C. 154(b) by 0 days.

(21) Appl. No.: 14/421,776

(22) PCT Filed: Aug. 16, 2013

(86) PCT No.: PCT/US2013/055474
§ 371 (c)(1),
(2) Date: Feb. 13, 2015

(87) PCT Pub. No.: WO2014/028909
PCT Pub. Date: Feb. 20, 2014

(65) Prior Publication Data
US 2015/0232434 A1 Aug. 20, 2015

Related U.S. Application Data

(60) Provisional application No. 61/683,776, filed on Aug. 16, 2012, provisional application No. 61/798,780, filed on Mar. 15, 2013.

(51) Int. Cl.
| | |
|---|---|
| *C07C 50/12* | (2006.01) |
| *C07D 275/06* | (2006.01) |
| *C07D 213/74* | (2006.01) |
| *C07C 307/02* | (2006.01) |
| *C07D 233/54* | (2006.01) |
| *C07D 211/26* | (2006.01) |
| *C07D 295/135* | (2006.01) |
| *C07D 401/04* | (2006.01) |
| *C07D 405/04* | (2006.01) |
| *C07D 409/04* | (2006.01) |

(52) U.S. Cl.
CPC .......... *C07D 275/06* (2013.01); *C07C 307/02* (2013.01); *C07D 211/26* (2013.01); *C07D 213/74* (2013.01); *C07D 233/54* (2013.01); *C07D 295/135* (2013.01); *C07D 401/04* (2013.01); *C07D 405/04* (2013.01); *C07D 409/04* (2013.01)

(58) Field of Classification Search
CPC .. C07C 307/02; C07D 275/06; C07D 213/74; C07D 233/54; C07D 295/135; C07D 401/04; C07D 405/04; C07D 409/04; C07D 211/26
USPC ....................................................... 552/297
See application file for complete search history.

(56) References Cited

U.S. PATENT DOCUMENTS

| | | |
|---|---|---|
| 8,178,559 B2 | 5/2012 | Breitenstein et al. |
| 2002/0065255 A1 | 5/2002 | Bay et al. |
| 2007/0015841 A1 | 1/2007 | Tawa et al. |
| 2011/0104186 A1 | 5/2011 | Valiante et al. |
| 2011/0212911 A1 | 9/2011 | Li et al. |
| 2012/0196852 A1 | 8/2012 | Liu et al. |

FOREIGN PATENT DOCUMENTS

| | | |
|---|---|---|
| WO | WO 97/21432 A1 | 6/1997 |
| WO | WO-2012/097351 | 7/2012 |

OTHER PUBLICATIONS

Lin, L. et. al. (2010) "A Novel Small Molecule, LLL12, Inhibits STAT3 Phosphorylation and Activities and Exhibits Potent Growth-Suppressive Activity in Human Cancer Cells," Neoplasia 12(1):39-50.
International Search Report (ISA/US) for International Application No. PCT/US2013/055474, mailed Jan. 17, 2014, 3 pages.
Extended Search Report for EP Patent Application No. 13830001.7, issued on Dec. 3, 2015 in 5 pages.
Guranda, D.T., et al., "Drug Synthesis Methods and Manufacturing Technology", Pharmaceutical Chemistry Journal, vol. 44, No. 5, 2010, pp. 254-260.

*Primary Examiner* — Barbara P Badio
(74) *Attorney, Agent, or Firm* — Foley & Lardner LLP; Antoinette F. Konski; Lydia B. Choi

(57) ABSTRACT

In one aspect, the invention relates to substituted 6-amino-5,8-dioxo-5,8-dihydronaphthalene-1-sulfonamide analogs and derivatives thereof, substituted 4-amino-5H-naphtho[1,8-cd]isothiazol-5-one 1,1-dioxide analogs and derivatives thereof, and related compounds, which are useful as inhibitors of STAT protein activity; synthetic methods for making the compounds; pharmaceutical compositions comprising the compounds; and methods of treating disorders of uncontrolled cellular proliferation associated with a STAT protein activity dysfunction using the compounds and compositions. This abstract is intended as a scanning tool for purposes of searching in the particular art and is not intended to be limiting of the present invention.

24 Claims, 47 Drawing Sheets

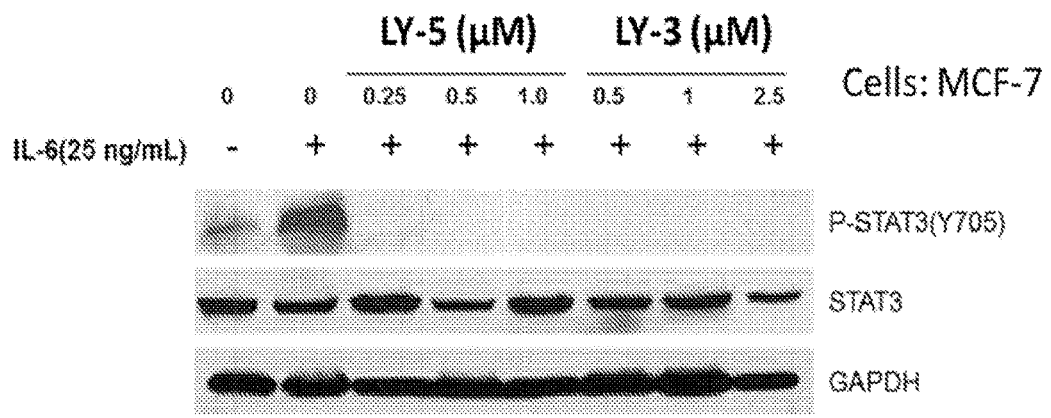
Figure 3
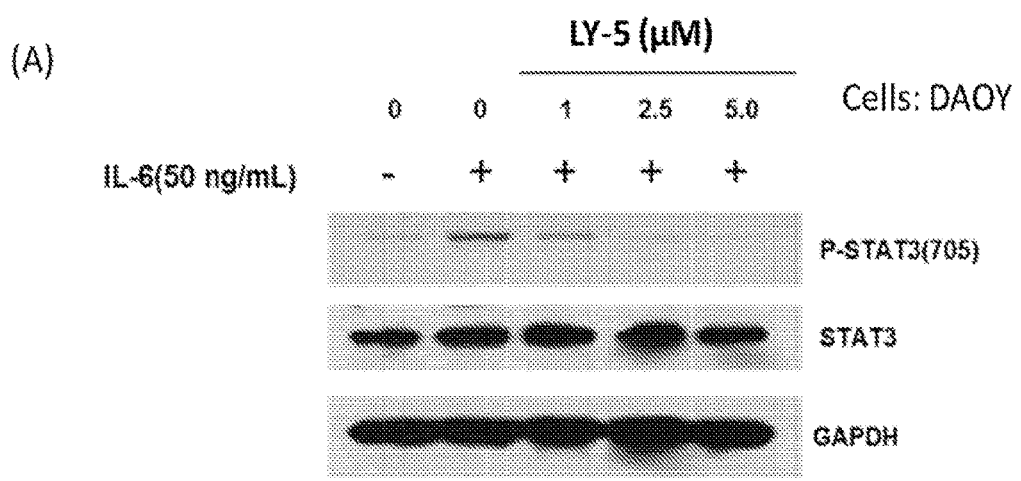
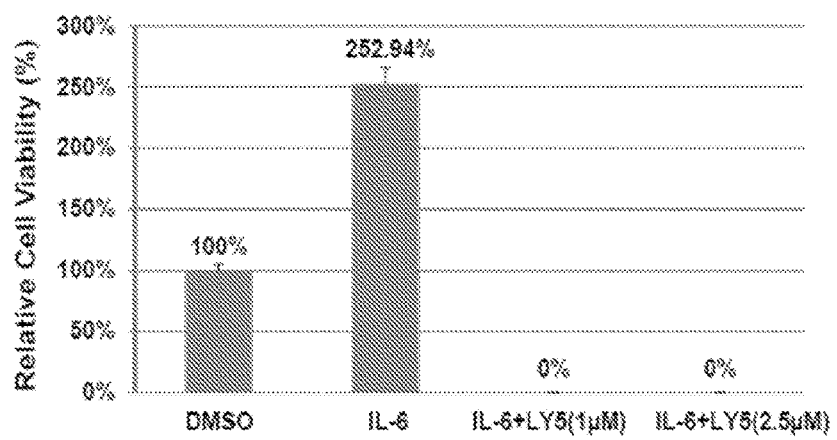
Figure 4

Site pY705    Side pocket

Figure 38
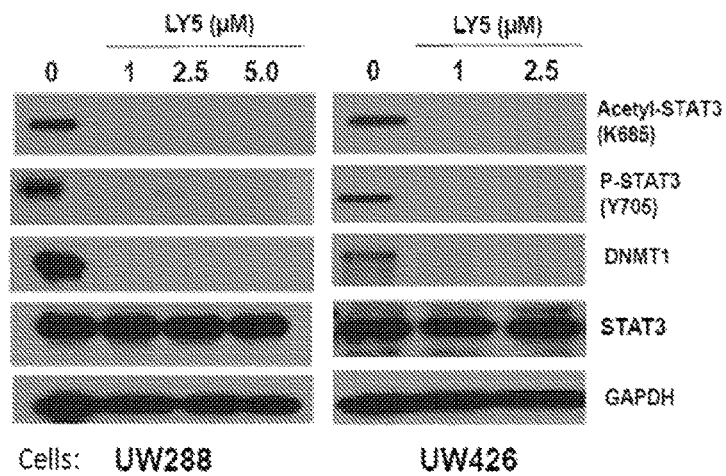
Figure 39
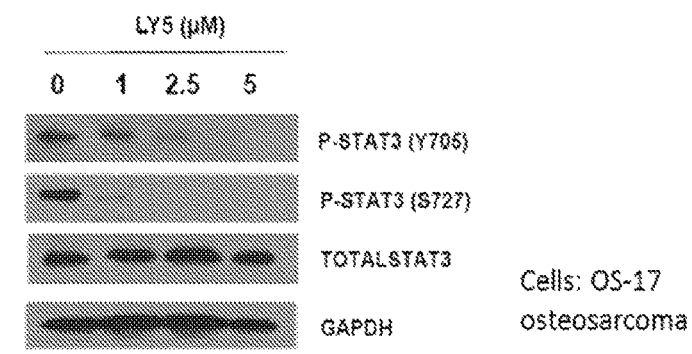
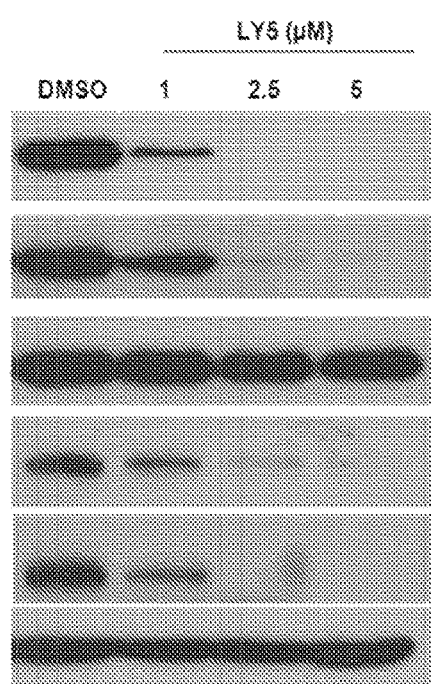
Figure 40

Assay: HUVEC cell migration

| KINOMEscan Gene Symbol | %Ctrl @ 100nM | %Ctrl @ 500nM |
|---|---|---|
| KIT(V559D,T670I) | 100 | 88 |
| LKB1 | 100 | 71 |
| MAP3K4 | 100 | 100 |
| MAPKAPK2 | 100 | 100 |
| MARK3 | 89 | 95 |
| MEK1 | 100 | 100 |
| MEK2 | 100 | 100 |
| MET | 87 | 78 |
| MKNK1 | 100 | 100 |
| MKNK2 | 100 | 100 |
| MLK1 | 81 | 67 |
| p38-alpha | 100 | 91 |
| p38-beta | 90 | 72 |
| PAK1 | 92 | 86 |
| PAK2 | 100 | 95 |
| PAK4 | 100 | 85 |
| PCTK1 | 100 | 100 |
| PDGFRA | 100 | 100 |
| PDGFRB | 98 | 85 |
| PDPK1 | 100 | 100 |
| PIK3C2B | 100 | 100 |
| PIK3CA | 100 | 100 |
| PIK3CG | 100 | 100 |
| PIM1 | 94 | 87 |
| PIM2 | 100 | 100 |
| PIM3 | 99 | 86 |
| PKAC-alpha | 100 | 100 |
| PLK1 | 100 | 79 |
| PLK3 | 100 | 26 |
| PLK4 | 100 | 100 |
| PRKCE | 100 | 92 |
| RAF1 | 100 | 83 |
| RET | 93 | 100 |
| RIOK2 | 100 | 82 |
| ROCK2 | 100 | 100 |

Figure 60

| Kinase | %Ctrl @ 1000nM | %Ctrl @ 1000nM |
|---|---|---|
| RSK2(Kin.Dom.1-N-terminal) | 100 | 90 |
| SNARK | 100 | 100 |
| SRC | 100 | 100 |
| SRPK3 | 60 | 100 |
| TGFBR1 | 100 | 100 |
| TIE2 | 100 | 100 |
| TRKA | 100 | 100 |
| TSSK1B | 78 | 75 |
| TYK2(JH1domain-catalytic) | 100 | 88 |
| ULK2 | 100 | 100 |
| VEGFR2 | 100 | 100 |
| YANK3 | 64 | 68 |
| ZAP70 | 100 | 100 |

%Ctrl Legend

0<x<1 | 1≤x<10 | 10≤x<35 | x≥35

STAT3 INHIBITORS AND THEIR ANTICANCER USE

CROSS-REFERENCE TO RELATED APPLICATIONS

This application is a National Stage Entry of International Patent Application No. PCT/US2013/055474, filed Aug. 16, 2013, which claims the benefit of U.S. Provisional Application No. 61/683,776, filed on Aug. 16, 2013, and 61/798,780, filed on Mar. 15, 2013, each of which are incorporated herein by reference in their entirety.

STATEMENT REGARDING FEDERALLY SPONSORED RESEARCH

This invention was made with government support under grant number 1R21CA133652-01A1 awarded by the National Institutes of Health. The United States government has certain rights in the invention.

BACKGROUND

Constitutive activation of STAT3 has been found in a wide variety of cancers, including breast cancer, sarcomas, and other cancers, promoting it as a very attractive therapeutic target. Cytokines, hormones, and growth factors binding to the cell surface receptors can activate the JAK-STAT signaling pathway. The receptors are activated and phosphorylated by JAK kinase(s). Subsequently, the STAT3 monomer is phosphorylated at Tyrosine705 (pTyr705) by the same kinases through its SH2 domain binding to pY loop of the activated receptors, leading to STAT3 homodimer through its SH2 dimerization. The dimerized STAT3 then translocates into the nucleus and binds to DNA, turning on a host of oncogenes. Altogether, these events such as cell proliferation and apoptosis resistance.

Several series of STAT3 dimerization inhibitors have previously been discovered via both computational and experimental methods. For example, phosphopeptide mimics were initially developed as STAT3 inhibitors to compete with the native phosphopeptide of the STAT3 protein. One specific example is PM-73G, a phosphopeptide mimic STAT3 inhibitor that can completely inhibit STAT3 Tyr705 phosphorylation at 0.5-1 µM level in various cancer cell lines (Mandal, P. K., et al. *J. Med. Chem.* 2011, 54, 3549-3563). Another phosphopeptide mimic, pCinn-Leu-cis-3,4-methanoPro-Gln-NHBn, has the lowest reported $IC_{50}$ value at 69 µM, as determined by fluorescence polarization method (Mandal, P. K., et al. *J. Med. Chem.* 2009, 52, 6126-6141). Peptidomimetics have also been designed to target the STAT3 SH2 domain. Peptidomimetics are derived from phosphopeptides that mimic peptides but do not necessarily contain phosphate groups. For example, XZH-5 was designed using a structure-based approach to inhibit the formation of STAT3 dimers (Liu, A., et al., *Cancer Sci.* 102, 1381-1387; Liu, Y., et al. *Apoptosis* 16, 502-510). Various small molecules have also been reported to inhibit STAT3 dimerization, making them as more druggable candidates. STA-21 discovered by structure-based virtual screening was the first reported small inhibitor. It inhibits STAT3 dimerization, DNA binding, and STAT3-dependent luciferase reporter activity in breast cancer cells (Song, H., et al., *Proc. Natl. Acad. Sci. U.S.A.* 2005, 102, 4700-4705). Another small molecule, Stattic, was discovered by high-throughput screening and has been shown to selectively inhibit activation, dimerization, and nuclear translocation of STAT3, increasing apoptosis in STAT3-dependent cancer cell lines (Schust, J., et al., *Chem. Biol.* 2006, 13, 1235-1242). Among all the reported nonpeptidomimetic small inhibitors, 5-hydroxy-9,10-dioxo-9,10-dihydroanthracene-1-sulfonamide (LLL12) has the lowest $IC_{50}$ (0.16-3.09 µM; Lin, L., et al., *Int. J. cancer.* 2012, 130, 1459-69), inhibiting STAT3 phosphorylation and the growth of human cancer cells. However, so far, there are no FDA-approved STAT3-targeting drugs. Thus, the search for more druggable STAT3 inhibitors with higher potency and better bioavailability remains extremely important.

Accordingly, there is still a scarcity of compounds that are both potent, efficacious, and selective inhibitors of STAT3 and also effective in the treatment of diseases associated with STAT3 activity and diseases in which the STAT3 is involved. These needs and other needs are satisfied by the disclosed compounds, compositions, and methods herein.

SUMMARY

In accordance with the purpose(s) of the invention, as embodied and broadly described herein, the invention, in one aspect, relates to compounds useful for STAT inhibition, methods of making same, pharmaceutical compositions comprising same, and methods of treating STAT related diseases using same.

Disclosed are compounds having a structure represented by a formula:

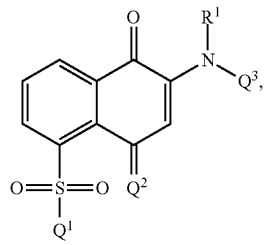

wherein $R^1$ is selected from hydrogen and C1-C3 alkyl; wherein $Q^1$ is $-NR^{2a}R^{2b}$ and wherein $Q^2$ is O; or wherein $Q^1$ and $Q^2$ are together N; wherein each of $R^{2a}$ and $R^{2b}$, when present, is independently selected from hydrogen and C1-C3 alkyl; wherein $Q^3$ is selected from $-(C1-C6)-Ar^1$, $Ar^1$, $-(C1-C6)-Cy^1$, and $Cy^1$; wherein $Ar^1$, when present, is selected from phenyl, naphthyl, monocyclic heteroaryl, and bicyclic heteroaryl; and wherein $Ar^1$ is substituted with 0, 1, 2, or 3 groups independently selected from halogen, —CN, —OH, $-NH_2$, $-NO_2$, C1-C6 alkyl, C1-C6 monohaloalkyl, C1-C6 polyhaloalkyl, C1-C6 hydroxyalkyl, C1-C6 monoalkylamino, C1-C6 dialkylamino, $-(C1-C6)NR^{4a}R^{4b}$, $-(C1-C6)-(C=O)R^3$, $-(C1-C6)-(C=O)OR^3$, $-(C1-C6)(C=O)NR^{4a}R^{4b}$, $-(C1-C6)-Ar^2$, $Ar^2$, $-(C1-C6)-Cy^2$, $Cy^2$, and $-S(O)_nNR^{5a}R^{5b}$; wherein n is 0, 1, or 2; wherein each $R^3$, when present, is independently selected from hydrogen, C1-C6 alkyl, C1-C6 monohaloalkyl, C1-C6 polyhaloalkyl, C1-C6 hydroxyalkyl, and C1-C6 aminoalkyl; wherein each of $R^{4a}$ and $R^{4b}$, when present, is independently selected from hydrogen, C1-C6 alkyl, C1-C6 monohaloalkyl, C1-C6 polyhaloalkyl, C1-C6 hydroxyalkyl, and C1-C6 aminoalkyl; wherein each of $R^{5a}$ and $R^{5b}$ when present, is independently selected from hydrogen, C1-C6 alkyl, C1-C6 monohaloalkyl, C1-C6 polyhaloalkyl, C1-C6 hydroxyalkyl, C1-C6 aminoalkyl, and $-(C=O)NR^{6a}R^{6b}$; wherein each of $R^{6a}$ and $R^{6b}$, when present, is independently selected from hydrogen and C1-C6 alkyl; wherein each $Ar^2$, when present, is independently selected from is phenyl and monocyclic heteroaryl; and wherein $Ar^2$ is substituted with 0, 1, 2, or 3 groups independently selected from halogen, —CN, —OH, —NH$_2$, —NO$_2$, C1-C6 alkyl, C1-C6 monohaloalkyl, C1-C6 polyhaloalkyl, C1-C6 hydroxyalkyl, C1-C6 aminoalkyl, C1-C6 monoalkylamino, and C1-C6 dialkylamino; wherein each $Cy^2$, when present, is independently selected from C3-C8 cycloalkyl and C2-C7 heterocycloalkyl; and wherein $Cy^2$ is substituted with 0, 1, 2, or 3 groups independently selected from halogen, —CN, —OH, —NH$_2$, —NO$_2$, C1-C6 alkyl, C1-C6 monohaloalkyl, C1-C6 polyhaloalkyl, C1-C6 hydroxyalkyl, C1-C6 aminoalkyl, C1-C6 monoalkylamino, C1-C6 dialkylamino, —(C=O)$R^7$, —(C=O)O$R^7$, —(C=O)N$R^{8a}R^{8b}$, —(C=O)—(C1-C6 alkyl)$Ar^3$, —(C=O)—O—(C1-C6 alkyl)$Ar^3$, and —(C=O)—N$R^{8a}$—(C1-C6 alkyl)$Ar^3$; wherein each $R^7$, when present, is independently selected from hydrogen, C1-C6 alkyl, C1-C6 monohaloalkyl, and C1-C6 polyhaloalkyl; wherein each of $R^{8a}$ and $R^{8b}$, when present, is independently selected from hydrogen, C1-C6 alkyl, C1-C6 monohaloalkyl, and C1-C6 polyhaloalkyl; wherein each $Ar^3$, when present, is independently selected from phenyl and monocyclic heteroaryl substituted with 0, 1, 2, or 3 groups independently selected from halogen, —CN, —OH, —NH$_2$, —NO$_2$, C1-C6 alkyl, C1-C6 monohaloalkyl, and C1-C6 polyhaloalkyl; wherein $Cy^1$, when present, is selected from C3-C8 cycloalkyl and C2-C7 heterocycloalkyl; and wherein $Cy^2$ is substituted with 0, 1, 2, or 3 groups independently selected from halogen, —CN, —OH, —NH$_2$, —NO$_2$, C1-C6 alkyl, C1-C6 monohaloalkyl, C1-C6 polyhaloalkyl, C1-C6 hydroxyalkyl, C1-C6 monoalkylamino, C1-C6 dialkylamino, —(C1-C6)N$R^{4a}R^{4b}$, —(C1-C6)-(C=O)$R^3$, —(C1-C6)-(C=O)O$R^3$, —(C1-C6)-(C=O)N$R^{4a}R^{4b}$, —(C1-C6)-$Ar^2$, $Ar^2$, —(C1-C6)-$Cy^2$, $Cy^2$, and —S(O)$_n$N$R^{5a}R^{5b}$; or a pharmaceutically acceptable salt, solvate, or polymorph thereof.

Also disclosed are pharmaceutical compositions comprising a therapeutically effective amount of a disclosed compound and a pharmaceutically acceptable carrier.

Disclosed are methods for the treatment of a disorder associated with STAT3 activity in a mammal comprising the step of administering to the mammal a therapeutically effective amount of at least one of the disclosed compounds, or a pharmaceutically acceptable salt, solvate, or polymorph thereof.

Also disclosed are methods for inhibition of STAT activity in a mammal comprising the step of administering to the mammal a therapeutically effective amount of at least one of the disclosed compounds, or a pharmaceutically acceptable salt, solvate, or polymorph thereof.

Also disclosed are methods for inhibiting STAT3 activity in at least one cell, comprising the step of contacting the at least one cell with an effective amount of at least one of the disclosed compounds, or a pharmaceutically acceptable salt, solvate, or polymorph thereof.

Also disclosed are kits comprising at least one of the disclosed compounds, or a pharmaceutically acceptable salt, hydrate, solvate, or polymorph thereof; and one or more of: (a) at least one agent known to decrease STAT3 activity; (b) at least one agent known to increase STAT3 activity; (c) at least one agent know to treat a disease of uncontrolled cellular proliferation; (d) at least one agent known to treat psoriasis; (e) at least one agent known to treat pulmonary arterial hypertension; or (f) instructions for treating a disorder associated with a STAT3 dysfunction.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the invention.

FIG. 3 shows that LY-3 and LY-5 inhibit IL-6 induced STAT3 phosphorylation in MCF-7 breast cancer cells. The MCF-7 cells were serum-starved overnight, then left untreated or treated with LY-3 (0.5-2.5 µM) or LY-5 (0.25-1 µM) for 5 h, followed by stimulation by IL-6 (25 ng/mL). The cells were harvested at 30 minutes and analyzed by Western blot assays.

FIG. 4 shows that LY-5 inhibits IL-6 induced STAT3 phosphorylation in DAOY cancer cells. The DAOY cells were serum-starved overnight, then left untreated or treated with LY-5 (1-5 µM) for 2 h, followed by stimulation by IL-6 (50 ng/mL). The cells were harvested at 30 minutes and analyzed by Western blot assays.

The treatment lasted for 21 days. The results showed that LY-5 significantly suppresses (p<0.001) the tumor growth.

Figure 8:
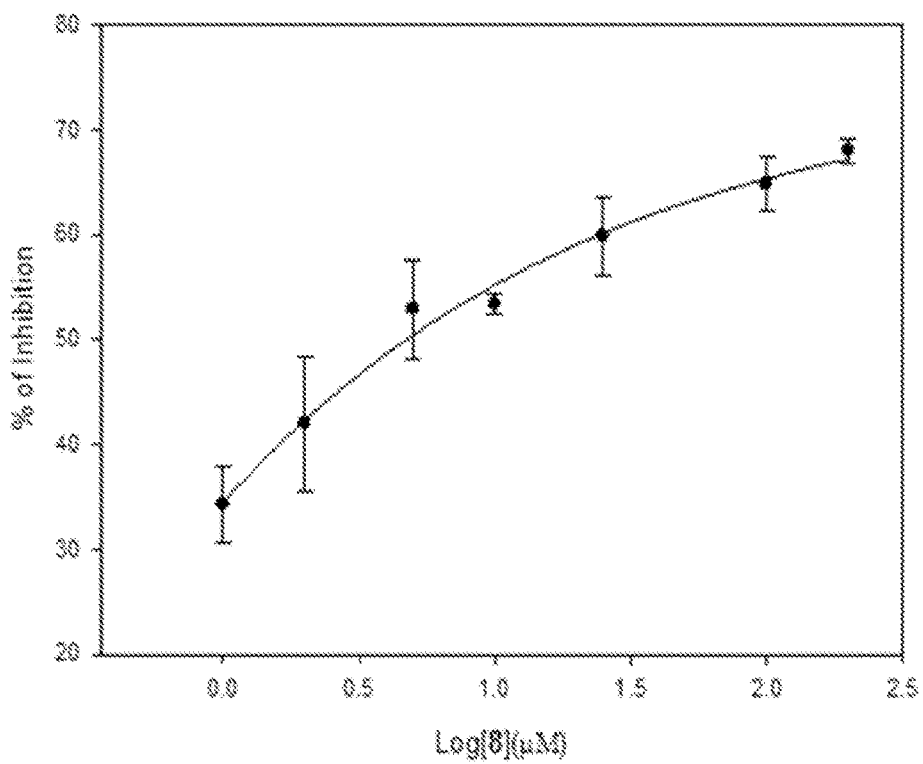

FIG. 8 shows that compound LY-5 binds to STAT3 SH2 protein. Inhibition of binding of fluorescein-labeled phosphopeptides to the SH2 domains of STAT3 by LY-5 at 37° C. was assayed by fluorescence polarization. Error bars represent standard deviation.

Figure 9:
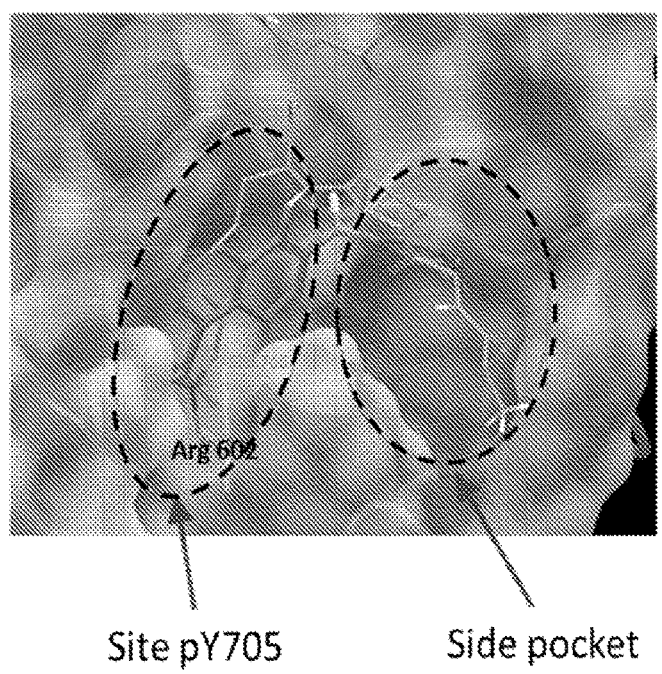

FIG. 9 shows the docking model of STAT3 inhibitor LY-5 binding to the STAT3 SH2 domain (PDB: 1BG1), generated by AutoDock4 and viewed by Maestro. The two key binding pockets are called "site pY705" (left circle) and "side pocket" (right circle). Carbon atoms of LY-5 are colored yellow, and those of the pTyr peptide are colored gray.

Figure 10:
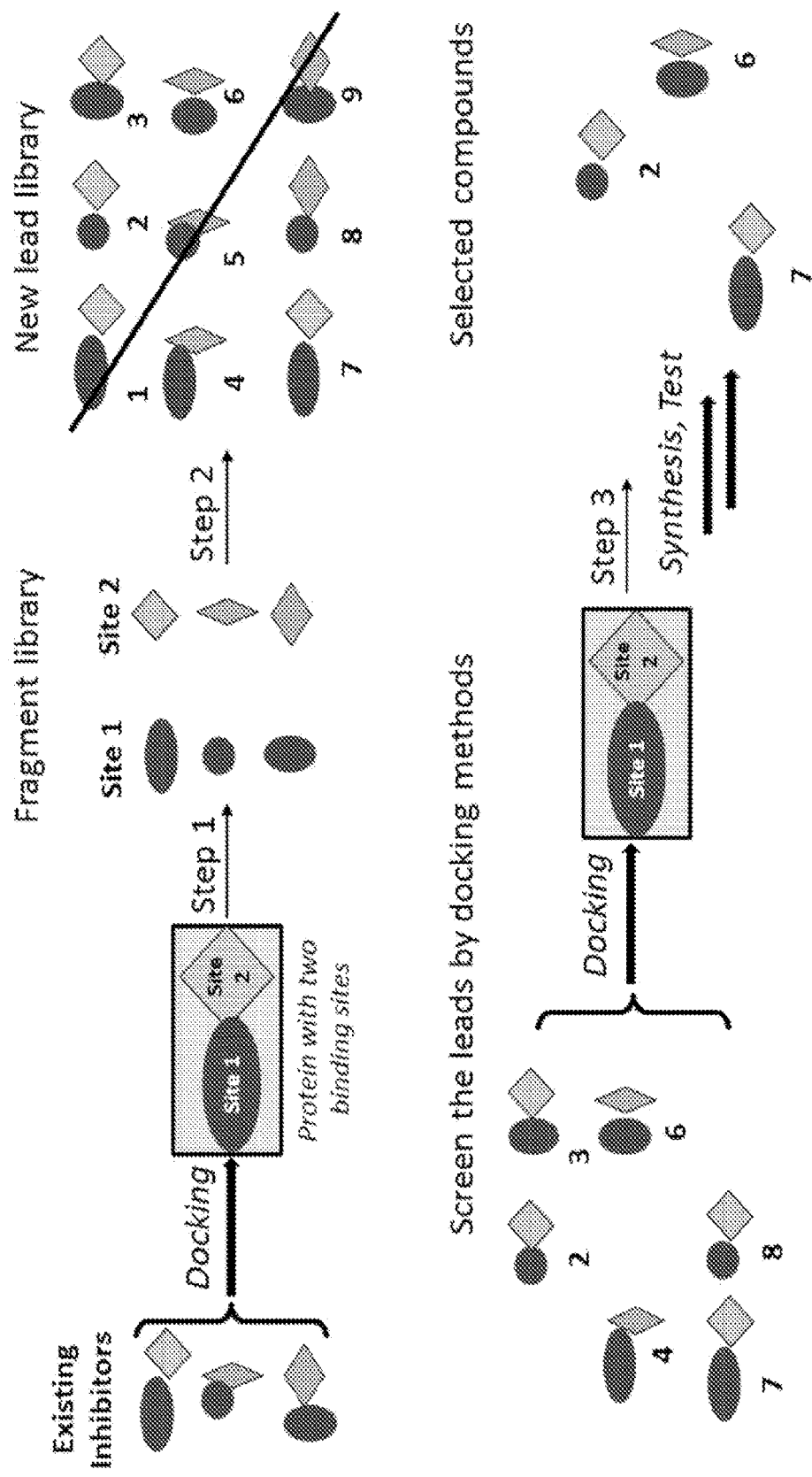

FIG. 10 shows the site-directed fragment-based drug discovery (FBDD) strategy. Step 1: Fragment libraries are categorized from existing inhibitors according to their binding modes. Step 2: New lead library is merged from randomly selected fragments from site-specific fragment sub-libraries. (Any existing inhibitors are removed from the new lead library.) Leads are selected after evaluating docking modes to the target. Step 3: Final hits are identified after synthesis and testing.

Figure 11:
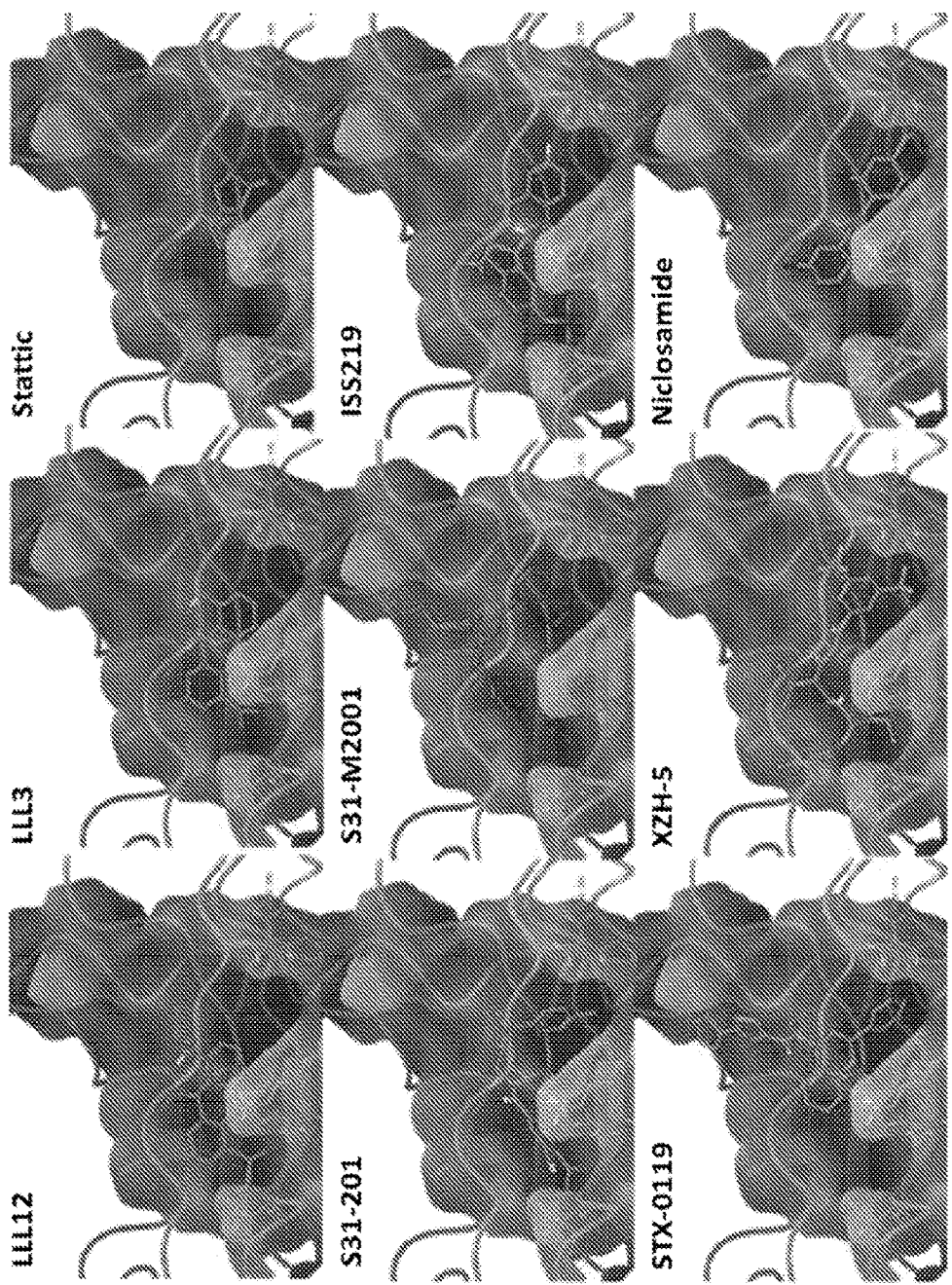

FIG. 11 shows the docking modes of the selected known STAT3 (shown in FIG. 12) inhibitors with the STAT3 SH2 domain (PDB: 1BG1), generated by AutoDock4. Surface representation was created with Maestro.

Figure 12:
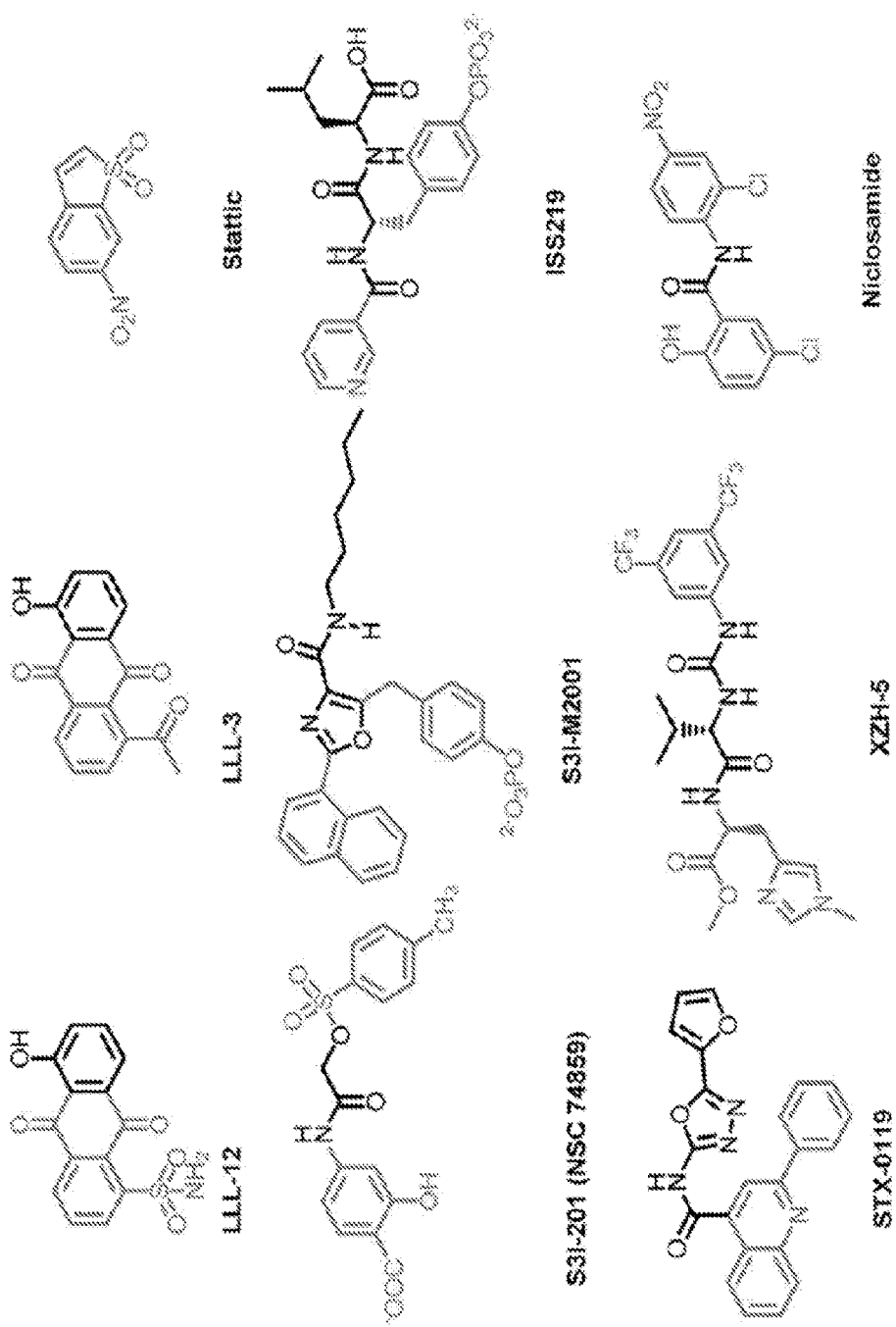

FIG. 12 shows the chemical structures of the selected STAT3 dimerization inhibitors. According to the docking modes in FIG. 11, the fragments binding to the pY705 site shown in FIG. 13.

Figure 13:
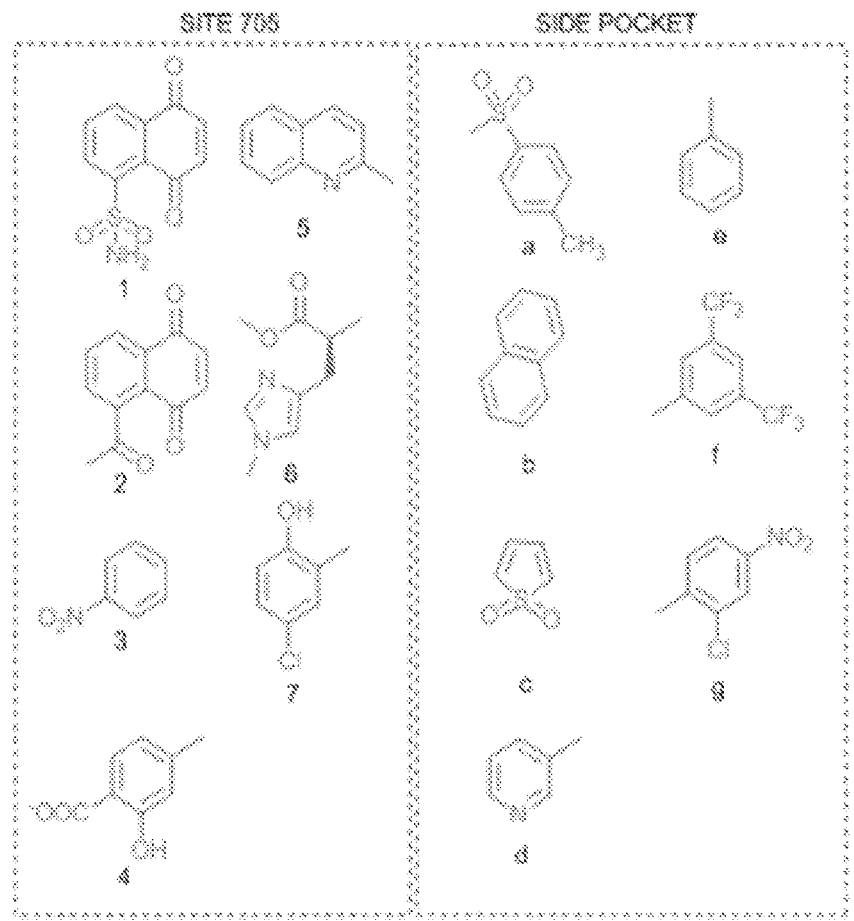

FIG. 13 shows the categorized fragment sub-libraries, site pY705 (1-7) and side pocket (a-g). (The fragment phosphotyrosine group was not included in the fragment libraries due to its peptidomimetic property.)

Figure 14:
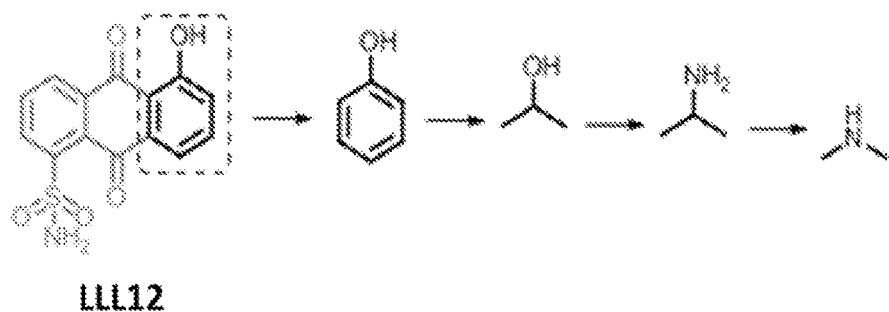

FIG. 14 shows the evolution of the linker design.

Figure 15:
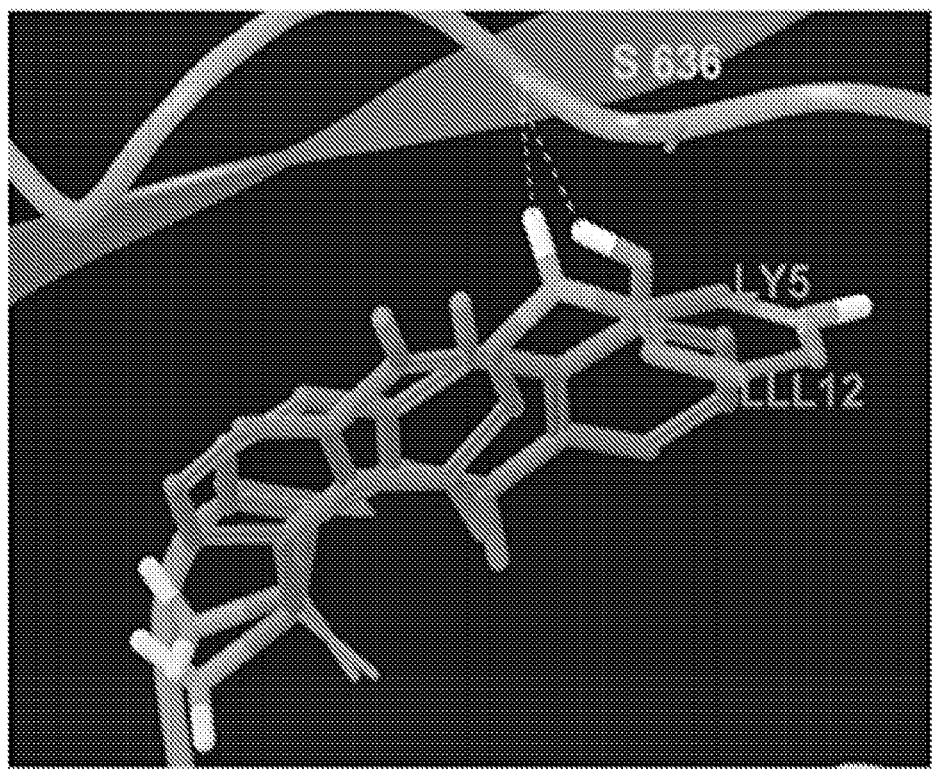

FIG. 15 shows the docking modes of LLL12 and LY-5. Both linkers, the hydroxyl group in LLL12 and secondary amine group in LY-5, form hydrogen bonds with the Ser636.

Figure 16:
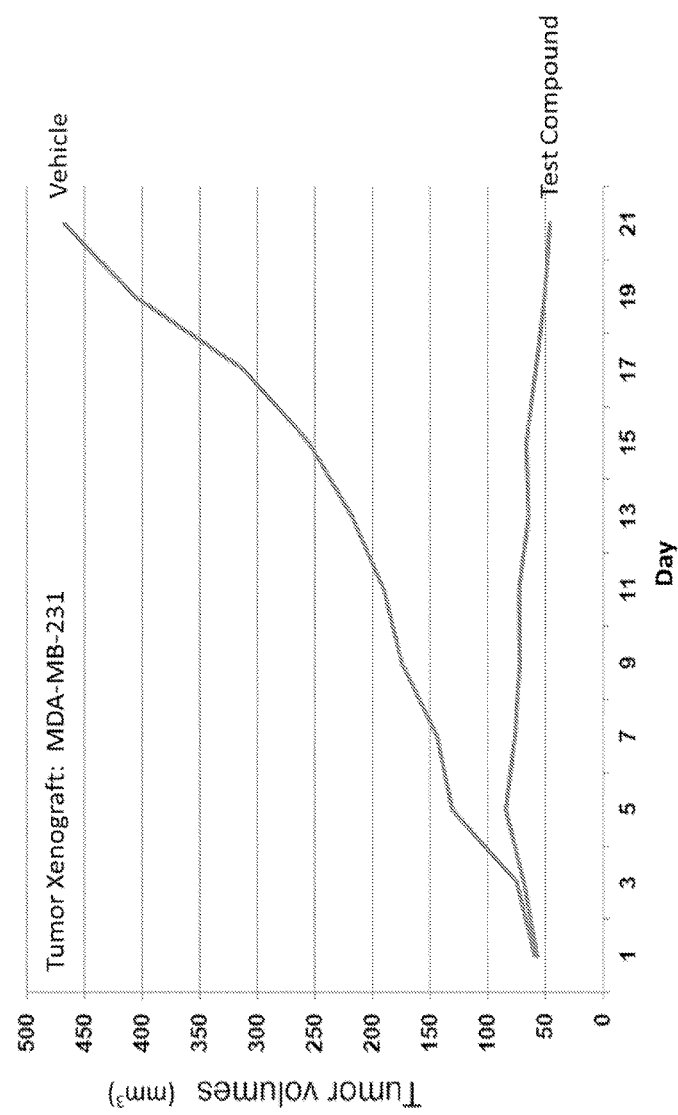

FIG. 16 shows that compound LY-5 suppresses tumor growth of MDA-MB-231 breast cancer-initiating cells in a mouse tumor model in vivo. LY-5 was administered daily by intraperitoneal injection (at 5 mg/kg in a volume of about ~100 μL) for 21 days. Tumor growth was determined by measuring length and width of the tumor every other day with a caliper. The tumor volume was calculated according to the formula: tumor volume=$0.5236 \times L \times W^2$, revealing a decrease in tumor growth.

Figure 17:
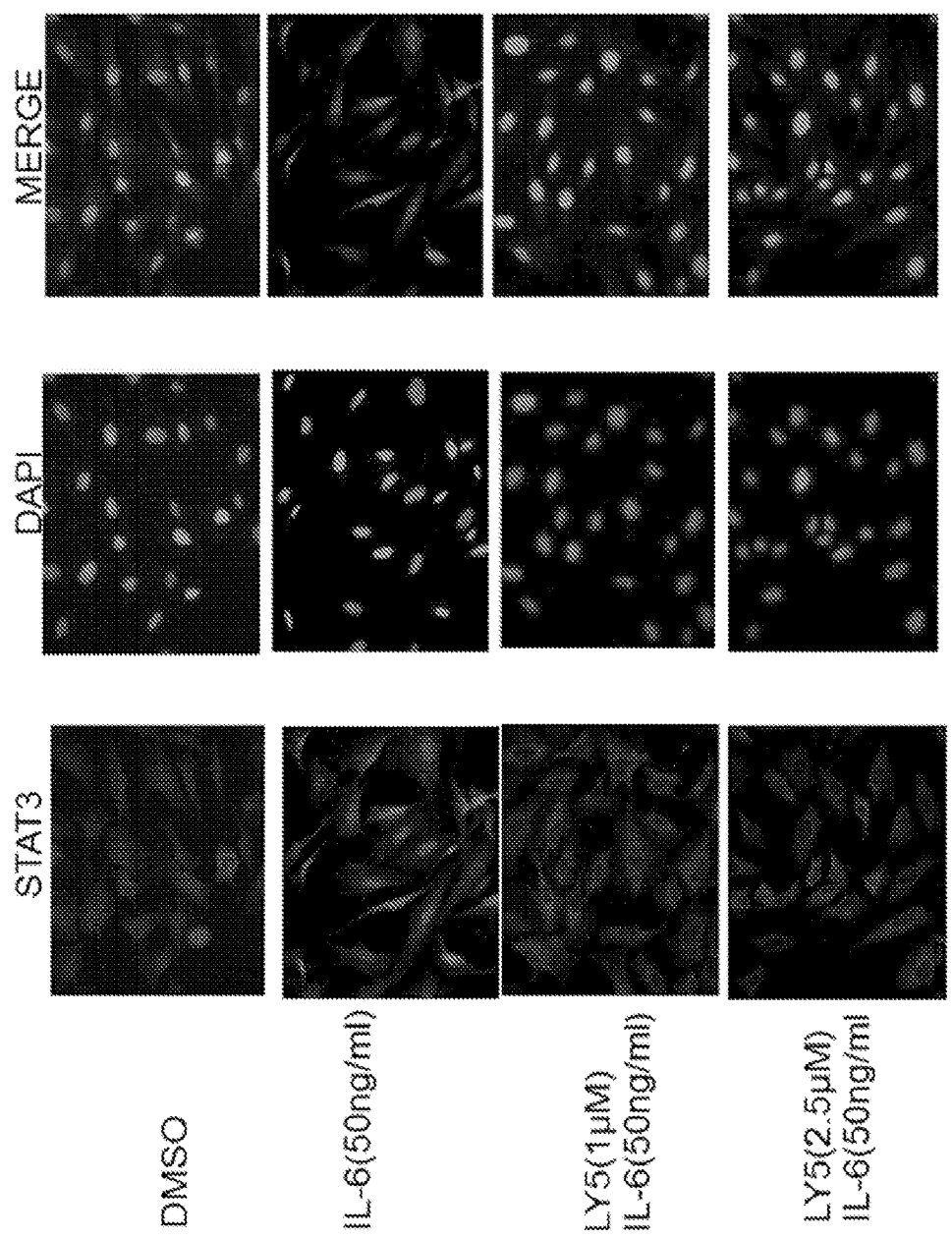

FIG. 17 shows that compound LY-5 inhibits IL-6 induced STAT3 nuclear translocation. SJSA human osteosarcoma cell lines were serum-starved for 24 h, then left treated or un-treated with LY-5 (1 or 2.5 μM) for 4 h, followed by stimulation with IL-6 (50 ng/mL). The cells were harvested at 30 minutes and analyzed by immunofluorescence.

Figure 18:
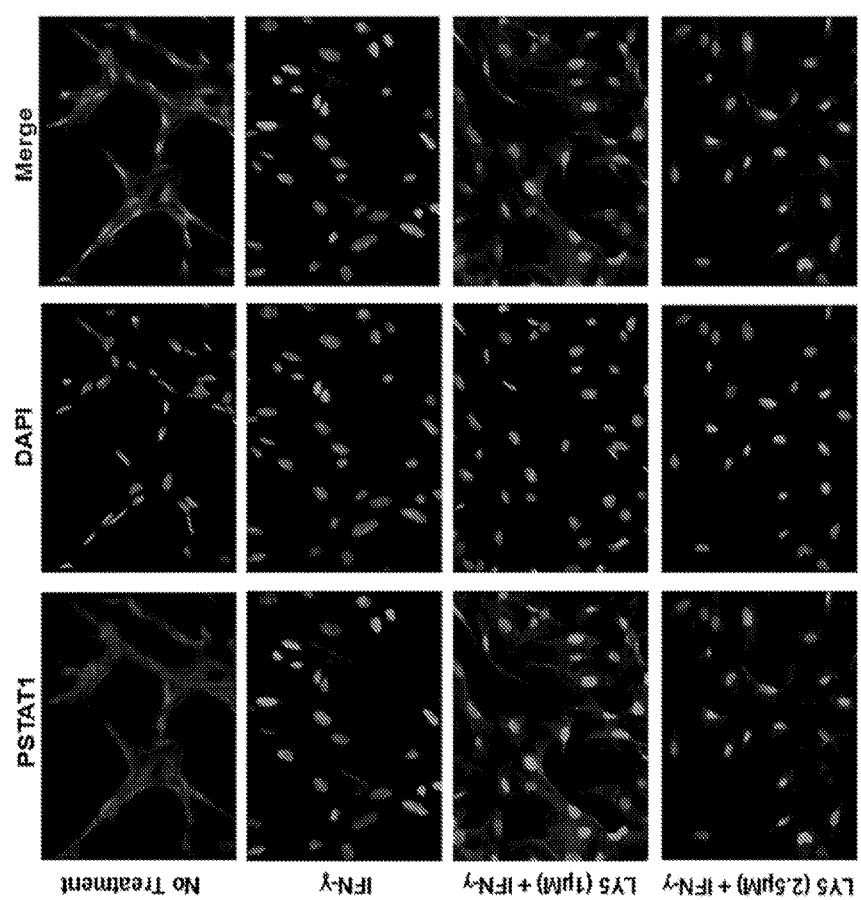

FIG. 18 shows that compound LY-5 does not inhibit IFN-γ induced STAT3 nuclear translocation. SJSA human osteosarcoma cell lines were serum-starved for 24 h, then left treated or un-treated with LY-5 (1 or 2.5 μM) for 4 h, followed by stimulation by IFN-γ (50 ng/mL). The cells were harvested at 30 minutes and analyzed by immunofluorescence.

Figure 19:
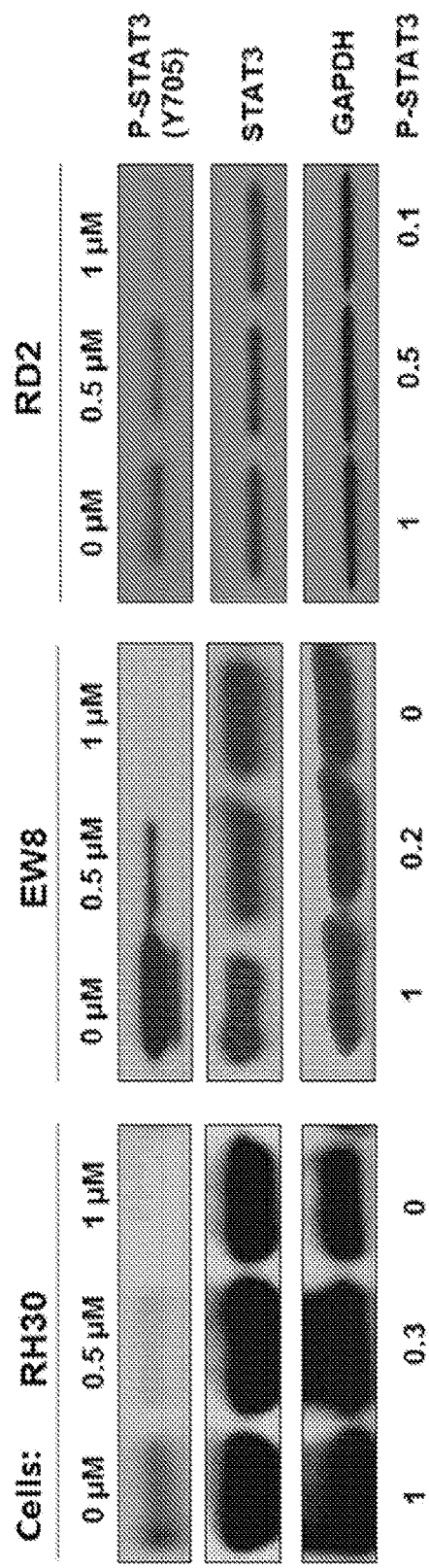

FIG. 19 shows that compound LY-5 inhibits constitutive STAT3 phosphorylation at Y705. Human Rhabdomyosarcoma cell lines RH30 and RD2 and Ewing's sarcoma cell line EW8 were treated with LY-5 (0-1 μM) for 2 h, then whole-cell extracts were prepared and phospho-STAT3 was detected by Western blot assay, revealing a decrease in STAT3 phosphorylation.

Figure 20:
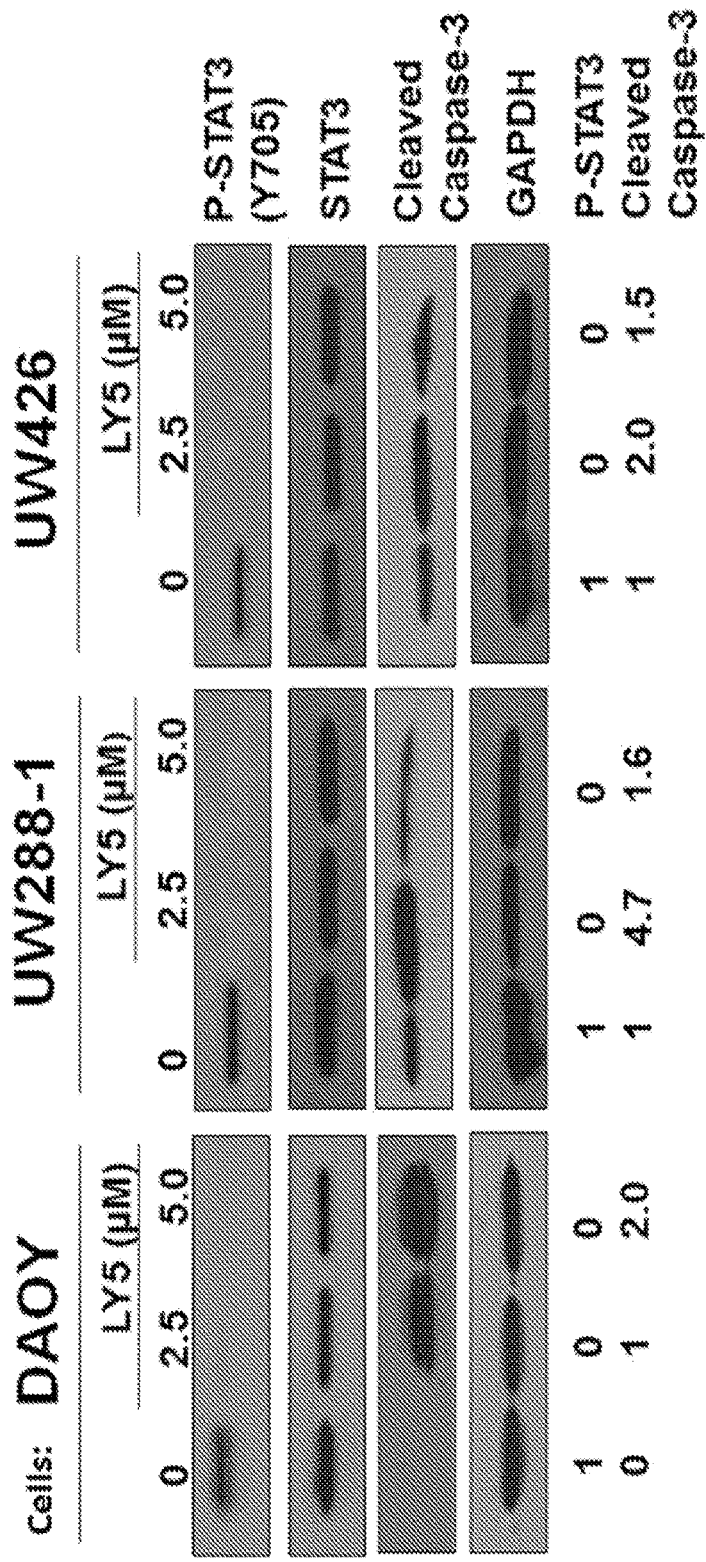

FIG. 20 shows that compound LY-5 inhibits constitutive STAT3 phosphorylation at Y705. DAOY cancer cell line and medulloblastoma cell lines UW288-1 and UW426 were treated with LY-5 (0-5 μM) for 2 h, then whole-cell extracts were prepared and phospho-STAT3 was detected by Western blot assay, revealing a decrease in STAT3 phosphorylation.

Figure 21:
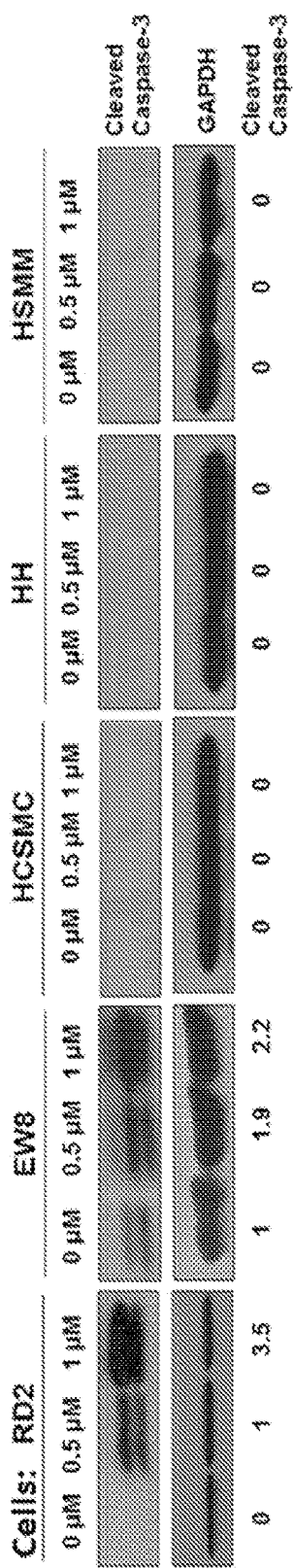

FIG. 21 shows that compound LY-5 induces apoptosis in Human Rhabdomyosarcoma cells (RD2) and Ewing's sarcoma cells (EW8), but not in normal human colonic smooth muscle cells (HCSMC), human hepatocytes (HH) and normal human skeletal muscle myoblasts (HSMM). The cell lines were treated with LY-5 (0-1 μM) for 2 h, then whole-cell extracts were prepared and cleaved caspase-3 was detected by Western blot assay, revealing apoptosis in RD2 and EW8 calls, but not in HCSMC, HH and HSMM cells.

Figure 22:
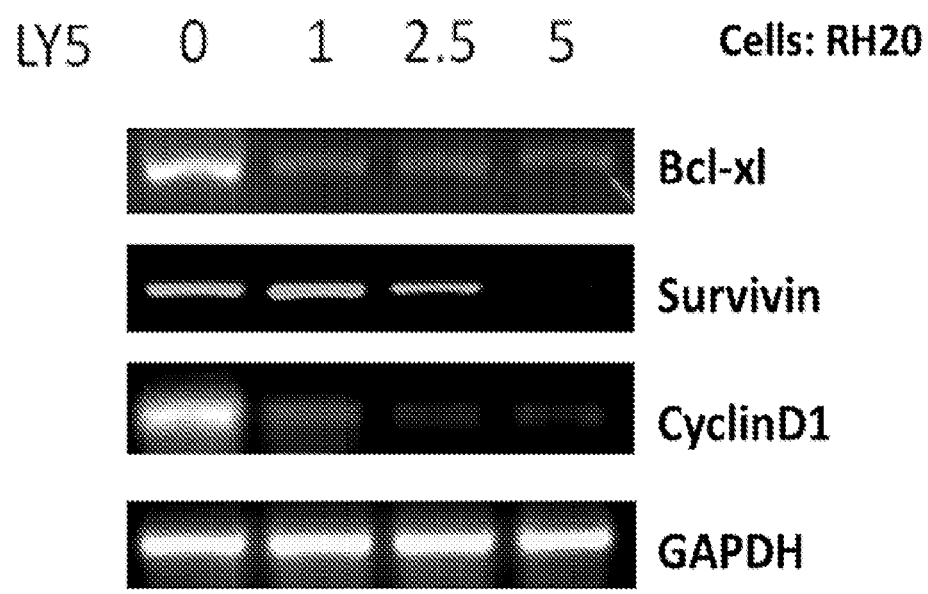

FIG. 22 shows that compound LY-5 inhibits downstream gene expression of Bcl-xL, survivin and cyclinD1. Human Rhabdomyosarcoma cell line RH30 was treated with LY-5 (0-5 μM) for 2 h, then whole-cell extracts were prepared and gene expression was detected by Western blot assay, revealing a decrease in gene expression of Bcl-xL, survivin and cyclinD1.

Figure 23:
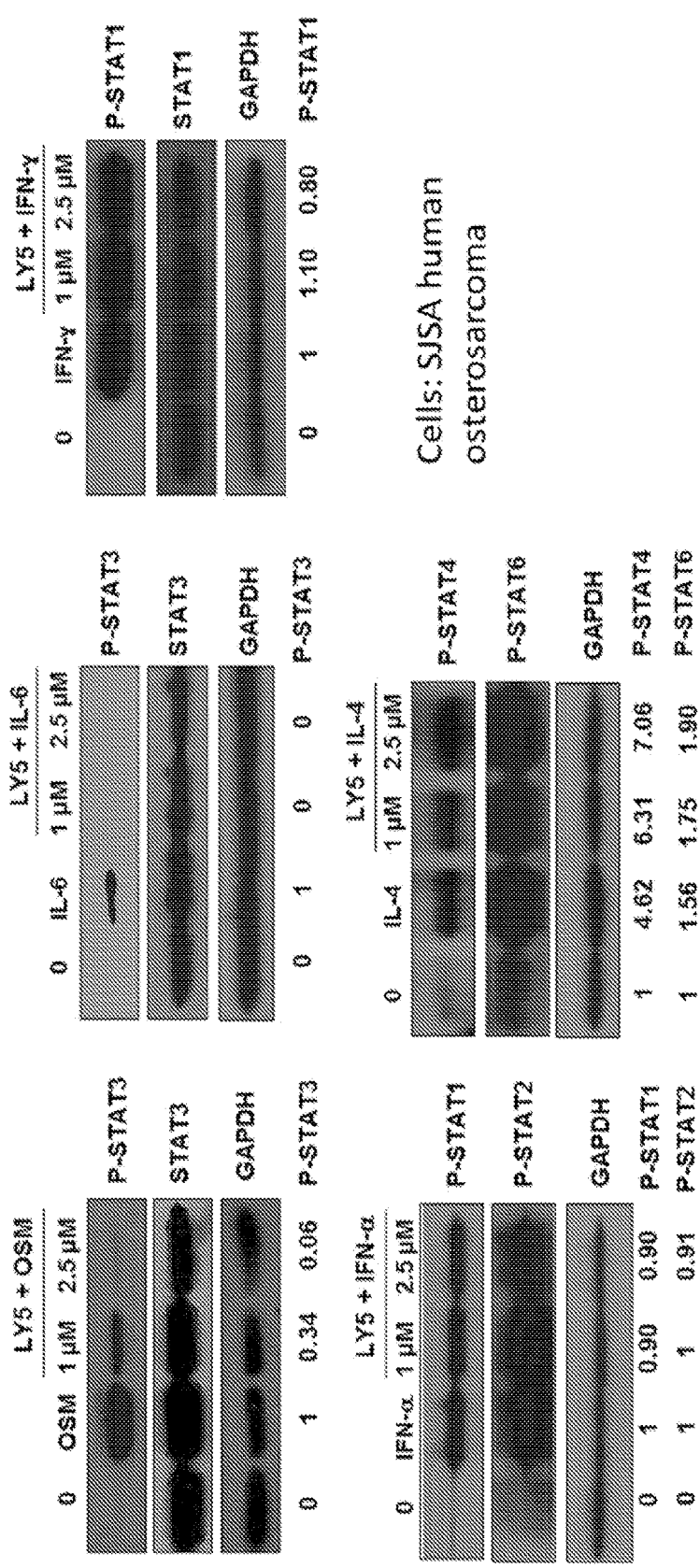

FIG. 23 shows that compound LY-5 inhibits OSM and IL-6 induced STAT3 phosphorylation at Y705, but not IFN-γ, IFN-α and IL-4 induced STAT1, STAT2, STAT4 and STAT6 phosphorylation in SJSA human osteosarcoma cell lines. The cells were serum-starved for 24 h, then left treated or un-treated with LY-5 (0-2.5 μM) for 3 h, followed by stimulation by OSM (50 ng/ml), IL-6 (25-50 ng/ml), IFN-γ (50 ng/ml), IFN-α (50 ng/ml), or IL-4 (50 ng/ml). The cells were harvested at 30 minutes and analyzed by Western blot assays.

Figure 24:
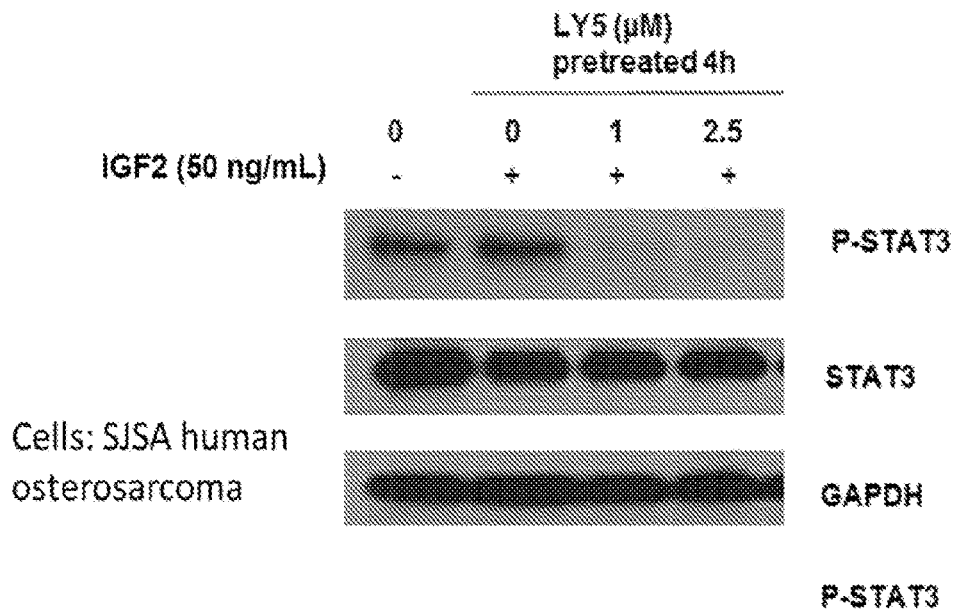

FIG. 24 shows that compound LY-5 inhibits IGF2 induced STAT3 phosphorylation. SJSA human osteosarcoma cell lines were serum-starved 24 h, then left treated or un-treated with LY-5 (0-2.5 μM) for 4 h, followed by stimulation by IGF2 (50 ng/mL). The cells were harvested at 30 minutes and analyzed by Western blot assays.

Figure 25:
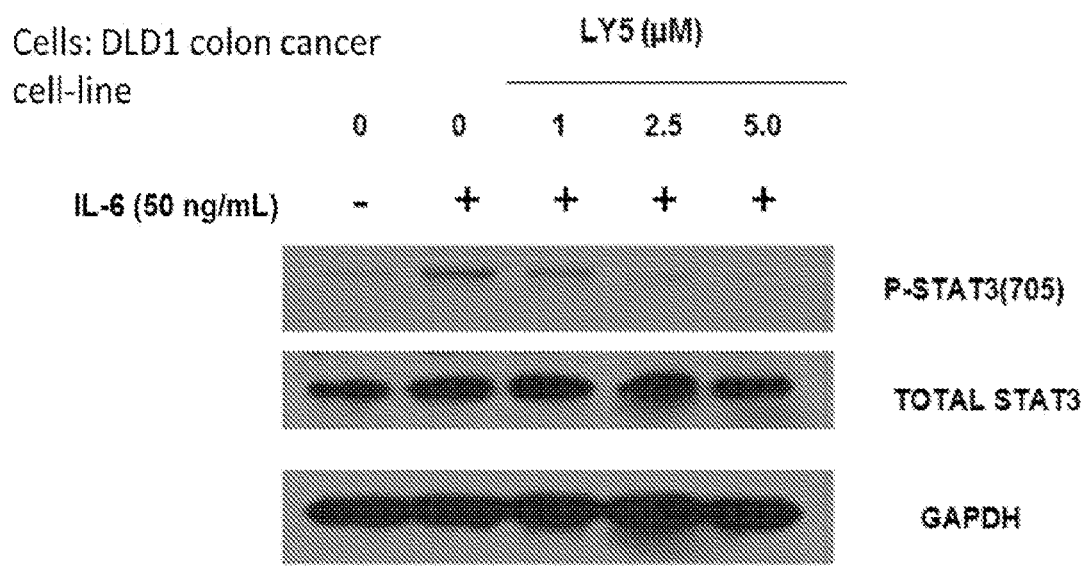

FIG. 25 shows that compound LY-5 inhibits IL-6 induced STAT3 phosphorylation. DLD1 colon cancer cell lines were serum-starved for 24 h, then left treated or un-treated with LY-5 (0-5 μM) for 2 h, followed by stimulation by IL-6 (50 ng/mL). The cells were harvested at 30 minutes and analyzed by Western blot assays.

Figure 26:
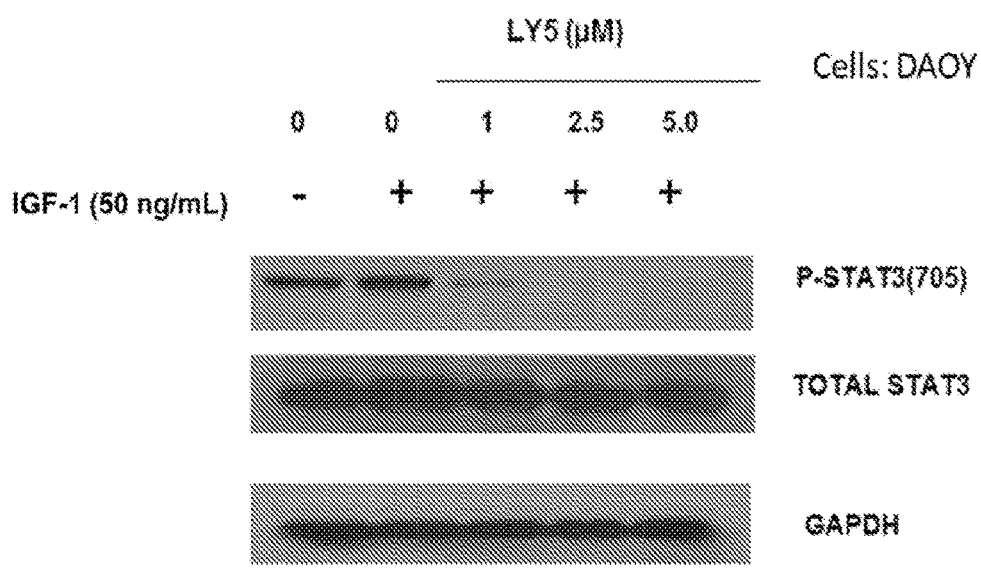

FIG. 26 shows that compound LY-5 inhibits IGF-1 induced STAT3 phosphorylation at Y705. DAOY cancer cell lines were serum-starved for 24 h, then left treated or un-treated with LY-5 (0-5 μM) for 2 h, followed by stimulation by IGF-6 (50 ng/mL). The cells were harvested at 30 minutes and analyzed by Western blot assays.

Figure 27:
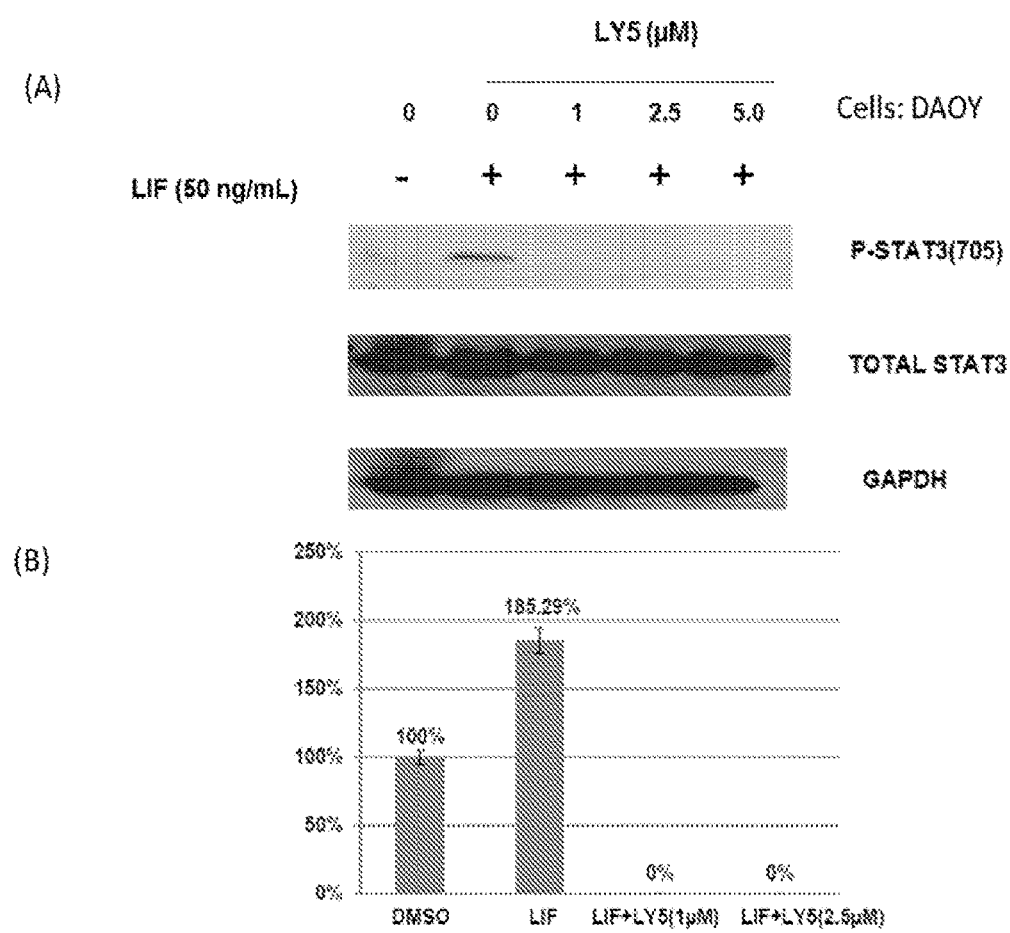

FIG. 27 shows that compound LY-5 inhibits LIF induced STAT3 phosphorylation at Y705. DAOY cancer cell lines were serum-starved for 24 h, then left treated or un-treated with LY-5 (0-5 μM) for 2 h, followed by stimulation by LIF (50 ng/mL). The cells were harvested at 30 minutes and analyzed by Western blot assays.

Figure 28:
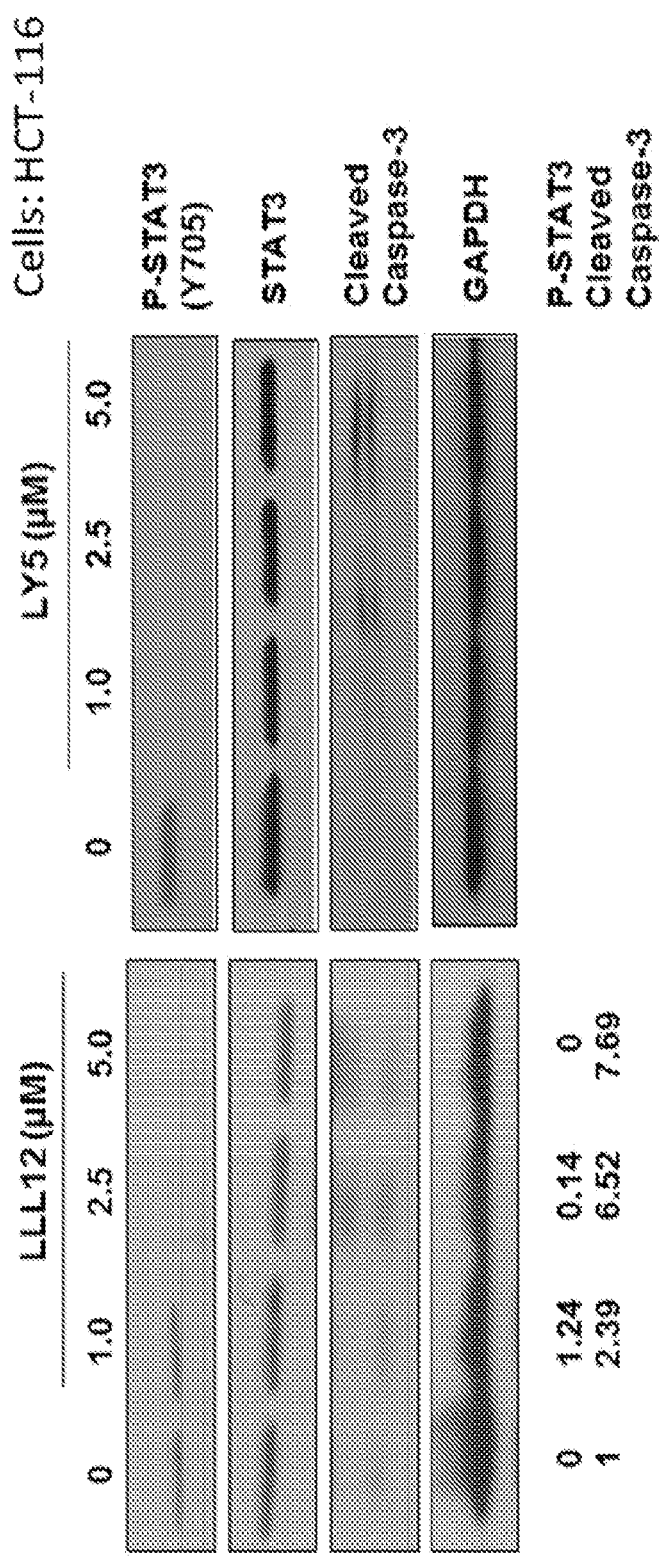

FIG. 28 shows that compound LY-5 inhibits constitutive STAT3 phosphorylation at Y705 and is more potent than LLL12. Human colon carcinoma cell line HCT-116 was treated with LY-5 (0-5 μM) or LLL12 (0-5 μM) for 2 h, then whole-cell extracts were prepared and phosphor-STAT3 was detected by Western blot assay, revealing a larger decrease in STAT3 phosphorylation by LY-5 compared to LLL12.

Figure 29:
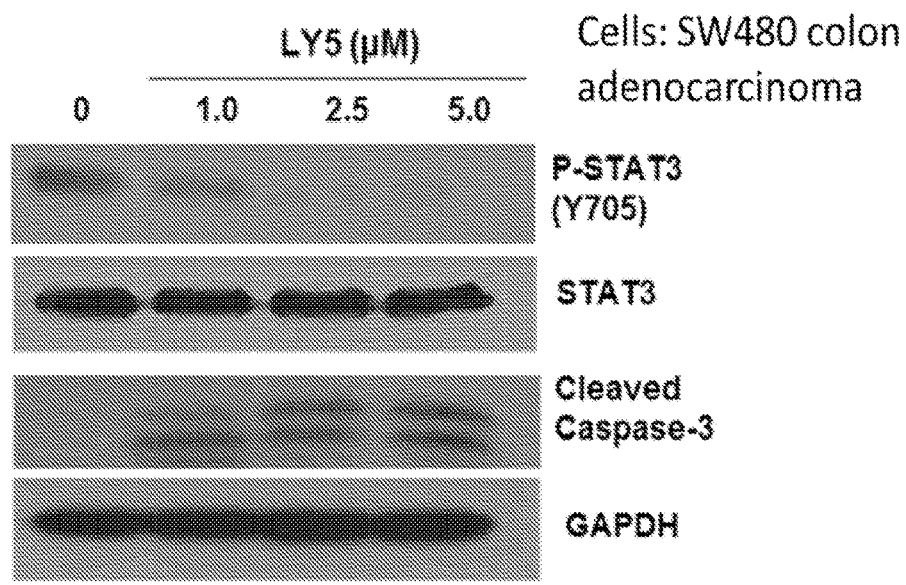

FIG. 29 shows that compound LY-5 inhibits constitutive STAT3 phosphorylation at Y705. Human colon adenocarcinoma cell line SW480 was treated with LY-5 (0-5 μM) for 2 h, then whole-cell extracts were prepared and phospho- STAT3 was detected by Western blot assay, revealing a decrease in STAT3 phosphorylation.

Figure 30:
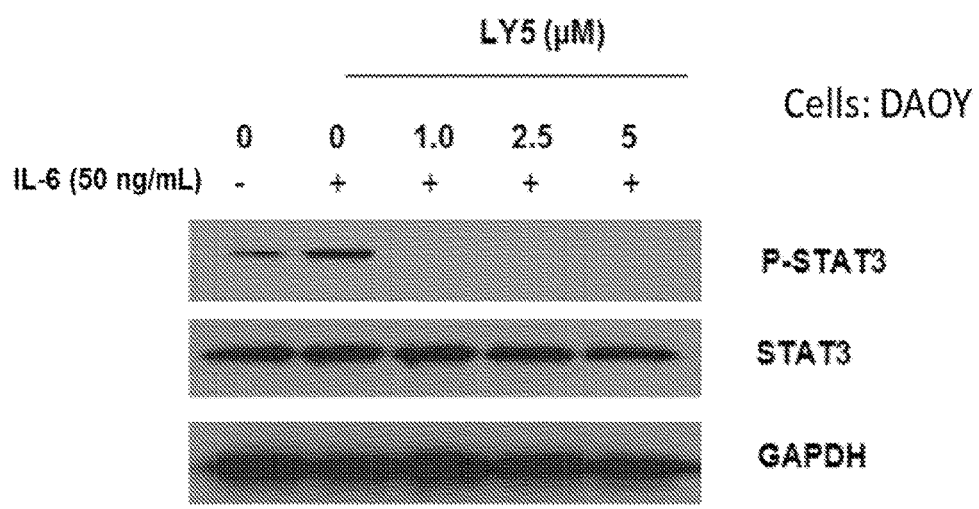

FIG. 30 shows that compound LY-5 inhibits IL-6 induced STAT3 phosphorylation at Y705. DAOY cancer cell lines were serum-starved for 24 h, then left treated or un-treated with LY-5 (0-5 µM) for 2 h, followed by stimulation by IL-6 (50 ng/mL). The cells were harvested at 30 min and analyzed by Western blot assays.

Figure 31:
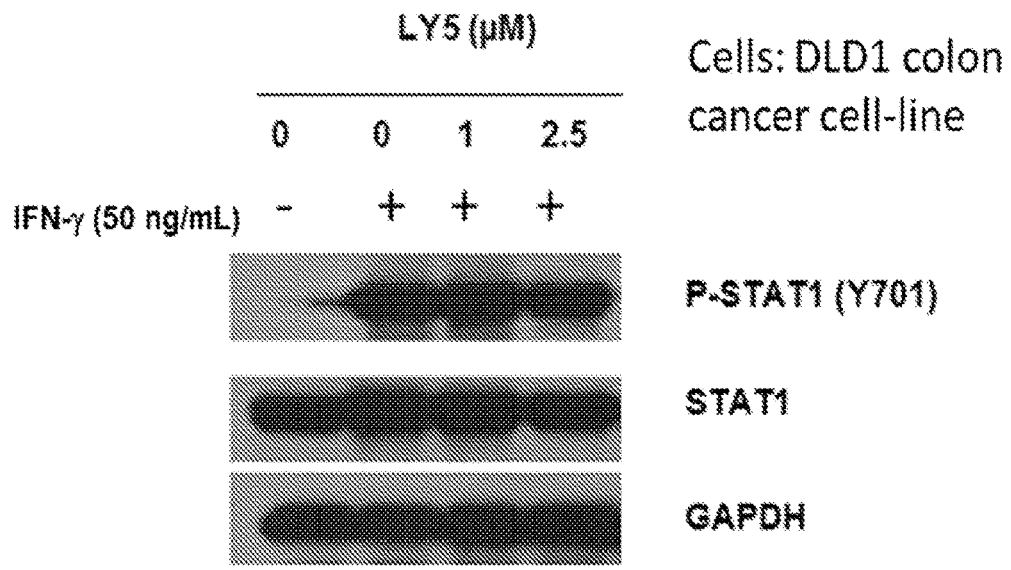

FIG. 31 shows that compound LY-5 does not inhibit IFN-γ induced STAT3 phosphorylation at Y701. DLD1 colon cancer cell lines were serum-starved 24 h, then left treated or un-treated with LY-5 (0-2.5 µM) for 2 h, followed by stimulation by IFN-γ (50 ng/mL). The cells were harvested at 30 minutes and analyzed by Western blot assays.

Figure 32:
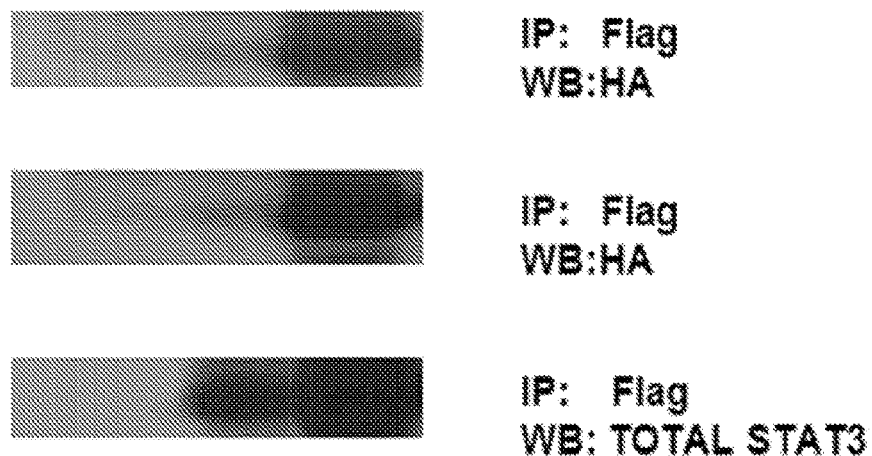
Figure 33:
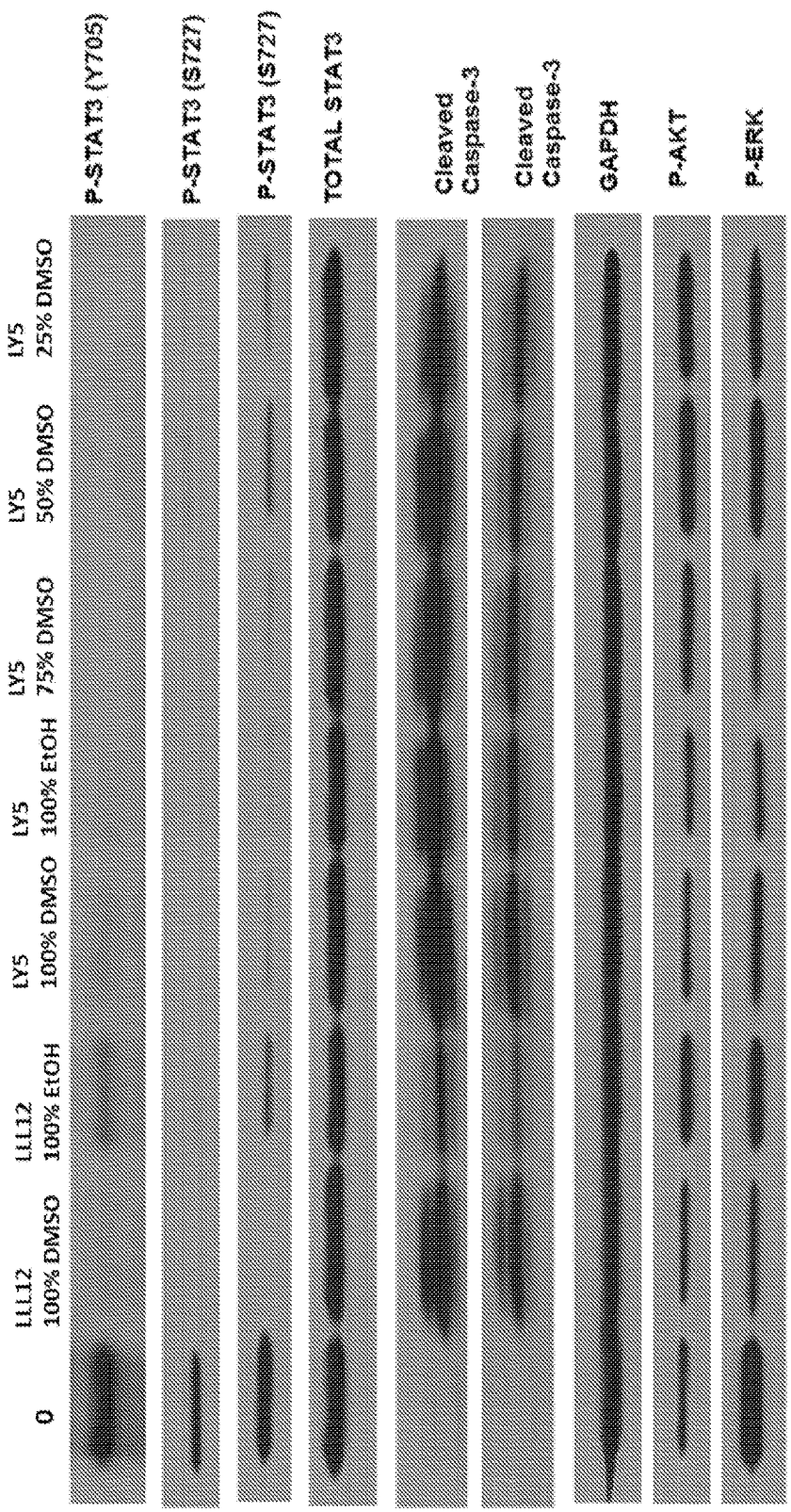

FIG. 32 shows that compound LY-5 inhibits STAT3 dimerization. HeLa cell lines were transfected with two expressing vectors, (1) flag epitope tagged STAT3 and (2) HA flag epitope tagged STAT3 and analyzed by Western blot assays, a decrease in STAT3 dimerization FIG. 33 shows representative pertaining to the effect LLL12 in either DMSO (100%) or ethanol (100%) and compound LY-5 in varying concentration of DMSO (25-100%) or ethanol (100%) on STAT3 phosphorylation at Y705 and S727. Human Rhabdomyosarcoma cell line RH30 was treated with LY-5 (5 µM in 25-100% DMSO or 5 µM EtOH) or LLL12 (5 µM DMSO or 5 µM EtOH) for 2 h, then whole-cell extracts were prepared and phospho-STAT3 was detected by Western blot assay, revealing a decrease in STAT3 phosphorylation at Y705 and S727.

Figure 34:
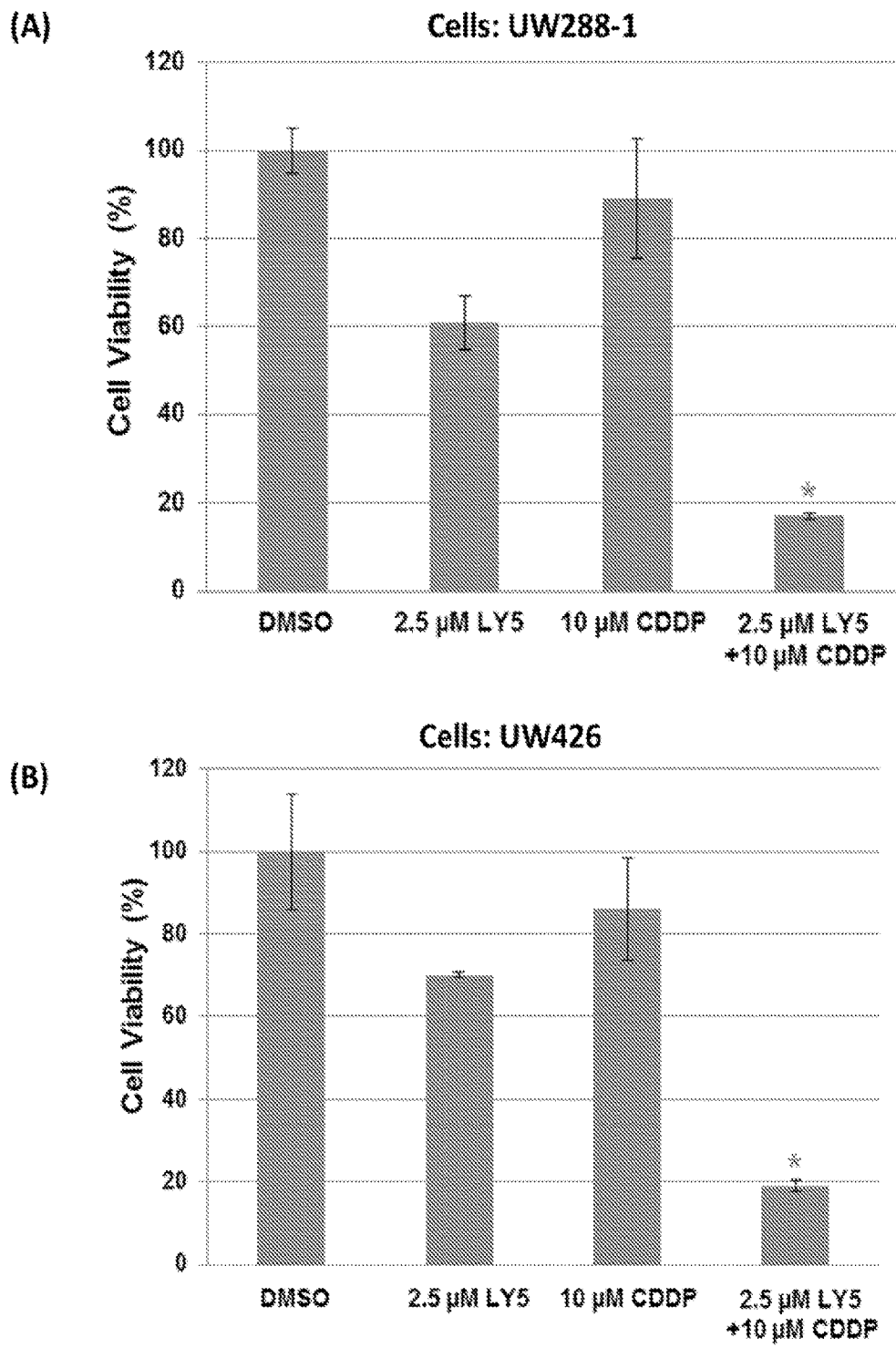

FIG. 34 shows representative data for the effect of LY-5 in combination with cisplatin (CDDP) on cell viability. Human medulloblastoma cell lines UW288-1 (A) and UW426 (B) were treated with LY-5 (2.5 µM), CDDP (10 µM) or LY-5+CDDP (2.5 µM+10 µM) for 2 h, and then cell viability assessed using an MTT-based cell proliferation assay. The absorbance was read at 595 nm, and cell viability normalized to the absorbance reading for the control cells (DMSO treated).

Figure 35:
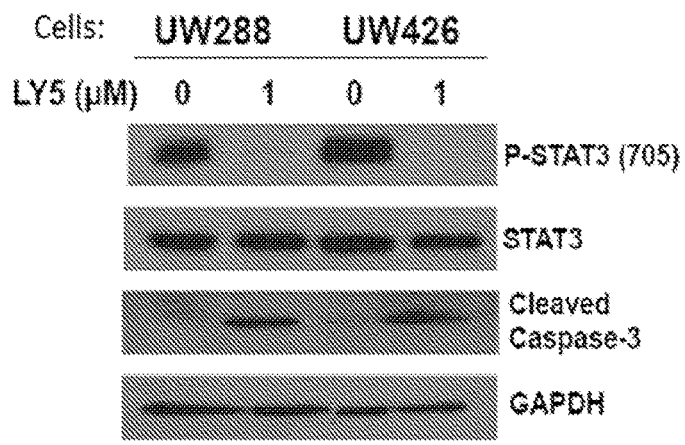

FIG. 35 shows that compound LY-5 inhibits constitutive STAT3 phosphorylation at Y705. Medulloblastoma cell lines UW288-1 and UW426 were treated with LY-5 (0-1 µM) for 2 h, then whole-cell extracts were prepared and phospho-STAT3 was detected by Western blot assay, revealing a decrease in STAT3 phosphorylation. Cleaved Caspase-3 was also detected by Western blot assay, revealing apoptosis in the medulloblastoma cells. The inhibition of STAT3 phosphorylation by LY-5 seems to be consistent with the induction of apoptosis as evidenced by the presence of cleaved caspase 3.

Figure 36:
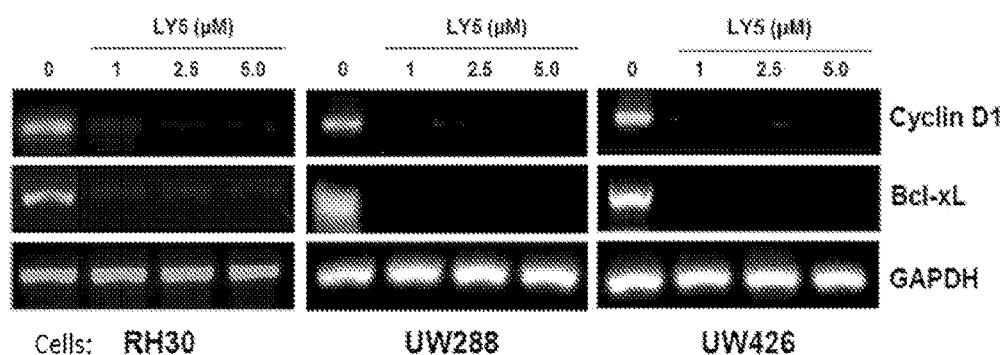

FIG. 36 shows that compound LY-5 inhibits STAT3 downstream targeted gene expression of Bcl-xL and cyclinD1. Medulloblastoma cell lines UW288-1 and UW426 were treated with LY-5 (0-5 µM) for 20 h, then whole-cell extracts were prepared and gene expression was detected by Western blot assay, revealing a decrease in gene expression of Bcl-xL and cyclinD1.

Figure 37:
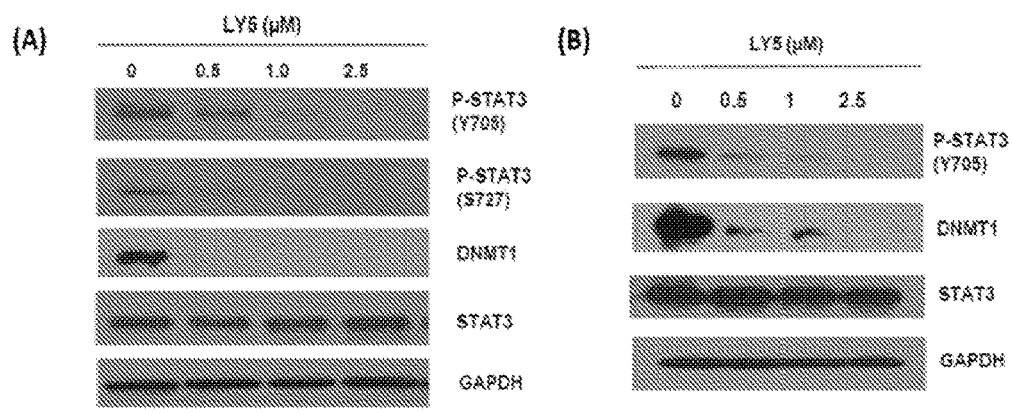

FIG. 37 shows that compound LY-5 inhibits P-STAT3 and gene expression of STAT3 downstream targeted gene DNMT1. Rhabdomyosarcoma cell lines RH30 and RD2 were treated with LY-5 (0-2.5 µM) for 2 h, then whole-cell extracts were prepared, and then phospho-STAT3, acetyl-STAT3, and DNMT1 was detected by Western blot assay, revealing a decrease in STAT3 phosphorylation and DNMT1 gene expression.

FIG. 38 shows that compound LY-5 inhibits P-STAT3, acetyl-STAT3, and gene expression of STAT3 downstream targeted gene DNMT1. Medulloblastoma cell lines UW288-1 and UW426 were treated with LY-5 (0-5 µM) for 2 h, then whole-cell extracts were prepared, then phospho-STAT3, acetyl-STAT3, and DNMT1 was detected by Western blot assay, revealing a decrease in STAT3 phosphorylation and DNMT1 gene expression.

FIG. 39 shows that compound LY-5 inhibits P-STAT3 in human osteosarcoma cells. Human osteosarcoma cell line OS-17 was treated with LY-5 (0-5 µM) for 2 h, then whole-cell extracts were prepared, and then phospho-STAT3, was detected by Western blot assay, revealing a decrease in STAT3 phosphorylation.

FIG. 40 shows that compound LY-5 inhibits P-STAT3 and cancer lipid metabolism genes SREBP1 and SREBP2. HeLa human cervical cells. Human osteosarcoma cell line OS-17 was treated with LY-5 (0-5 µM) for 2 h, then whole-cell extracts were prepared, and then phospho-STAT3 and SREBP1 and SREBP2 gene expression was detected by Western blot assay, revealing a decrease in STAT3 phosphorylation and a decrease in gene expression of SREBP1 and SREBP2.

Figure 41:
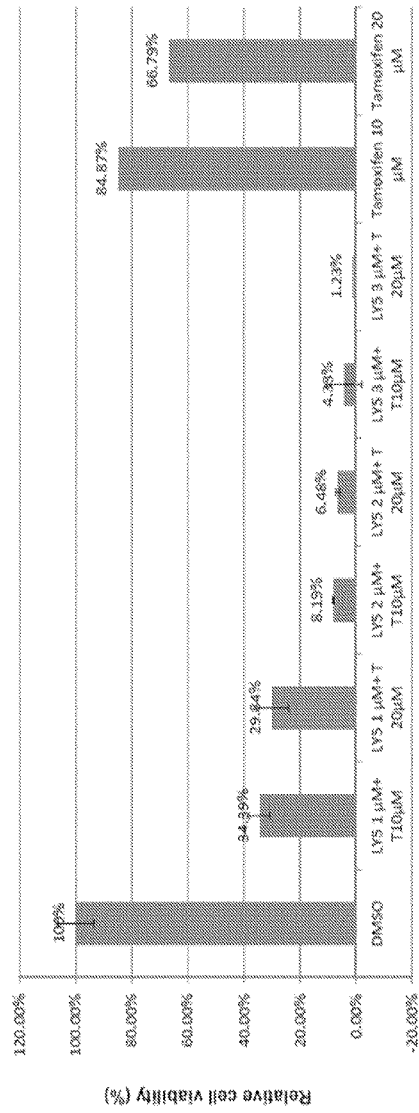

FIG. 41 shows representative data for the effect of LY-5 in combination with tamoxifen (T) on cell viability. Human breast cancer cell line MDA-MB-231 (ER−/PR−/HER2−) was treated with LY-5+T (1 µM+10 µM), LY-5+T (1 µM+20 µM), LY-5+T (2 µM+10 µM), LY-5+T (2 µM+20 µM), LY-5+T (3 µM+10 µM), LY-5+T (3 µM+20 µM), T (10 µM), or T (20 µM) for 2 h, and then cell viability assessed using an MTT-based cell proliferation assay. The absorbance was read at 595 nm, and cell viability normalized to the absorbance reading for the control cells (DMSO treated).

Figure 42:
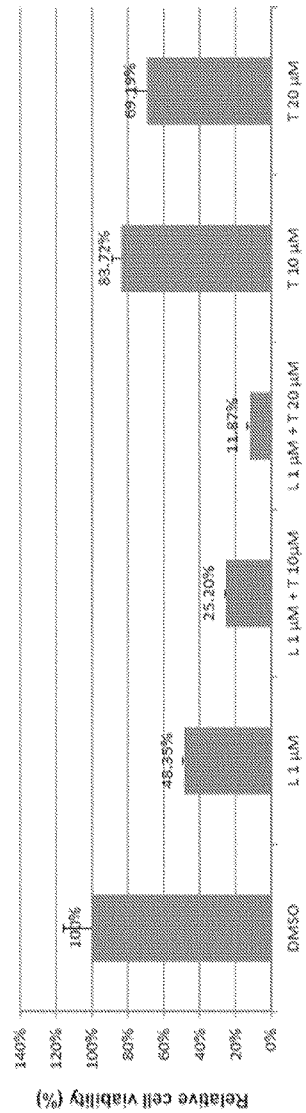

FIG. 42 shows representative data for the effect of LY-5 (L) in combination with tamoxifen (T) on cell viability. Human breast cancer cell line MDA-MB-468 (ER−/PR−/HER2−) was treated with L (1 µM), L+T (1 µM+10 µM), L+T (1 µM+20 µM), T (10 µM), or T (20 µM) for 2 h, and then cell viability assessed using an MTT-based cell proliferation assay. The absorbance was read at 595 nm, and cell viability normalized to the absorbance reading for the control cells (DMSO treated).

Figure 43:
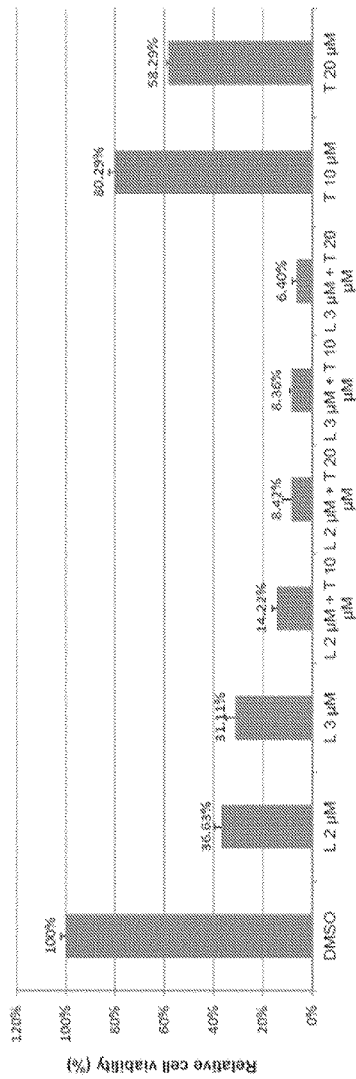

FIG. 43 shows representative data for the effect of LY-5 (L) in combination with tamoxifen (T) on cell viability. Human breast cancer cell line SUM159 (ER−/PR−/HER2−) was treated with L (2 µM), L (3 µM), L+T (2 µM+10 µM), L+T (2 µM+20 µM), L+T (3 µM+10 µM), L+T (3 µM+20 µM), T (10 µM), or T (20 µM) for 2 h, and then cell viability assessed using an MTT-based cell proliferation assay. The absorbance was read at 595 nm, and cell viability normalized to the absorbance reading for the control cells (DMSO treated).

Figure 44:
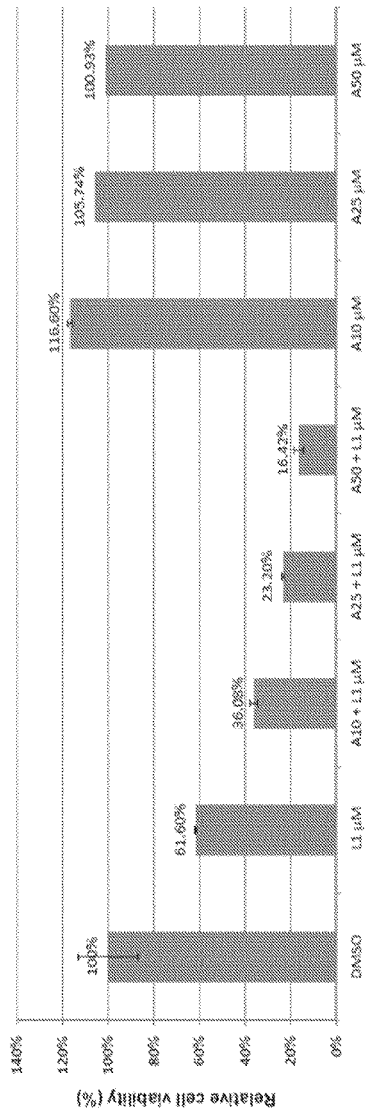

FIG. 44 shows representative data for the effect of LY-5 (L) in combination with MEK1/2 inhibitor AZD6244 (A) on cell viability. Human colon cancer cell line SW480 was treated with L (1 µM), L+A (1 µM+10 µM), L+A (1 µM+25 µM), L+A (1 µM+50 µM), A (10 µM), A (25 µM), or A (50 µM) for 2 h, and then cell viability assessed using an MTT-based cell proliferation assay. The absorbance was read at 595 nm, and cell viability normalized to the absorbance reading for the control cells (DMSO treated).

Figure 45:
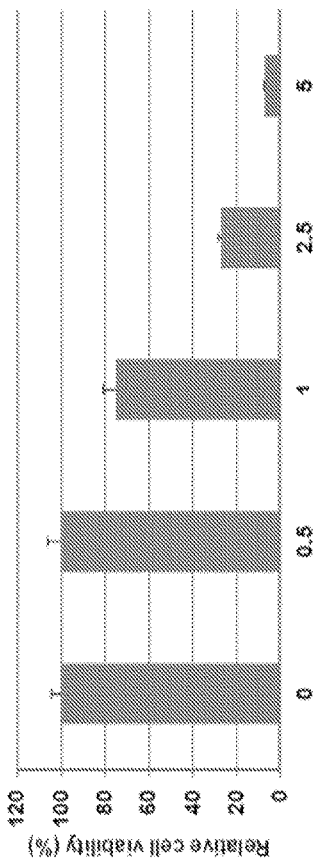

FIG. 45 shows representative data for the effect of LY-5 on cell viability. Human pancreatic cancer cell line MIA-PaCa-2 was treated with LY-5 (0-5 µM) for 2 h, and then cell viability assessed using an MTT-based cell proliferation assay. The absorbance was read at 595 nm, and cell viability normalized to the absorbance reading for the control cells (vehicle treated).

Figure 46:
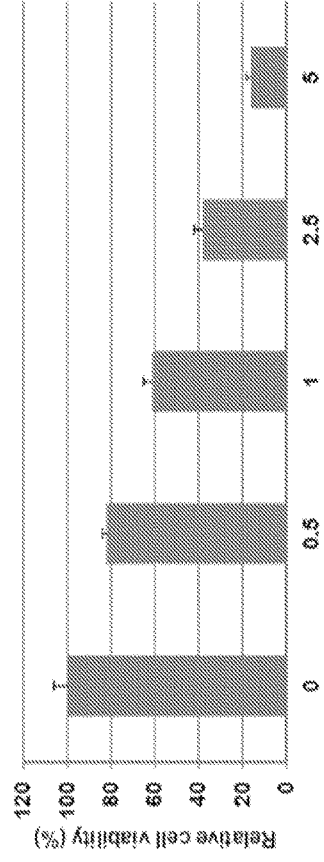

FIG. 46 shows representative data for the effect of LY-5 on cell viability. Human pancreatic cancer cell line PANC-1 was treated with LY-5 (0-5 µM) for 2 h, and then cell viability assessed using an MTT-based cell proliferation assay. The absorbance was read at 595 nm, and cell viability normalized to the absorbance reading for the control cells (vehicle treated).

Figure 47:
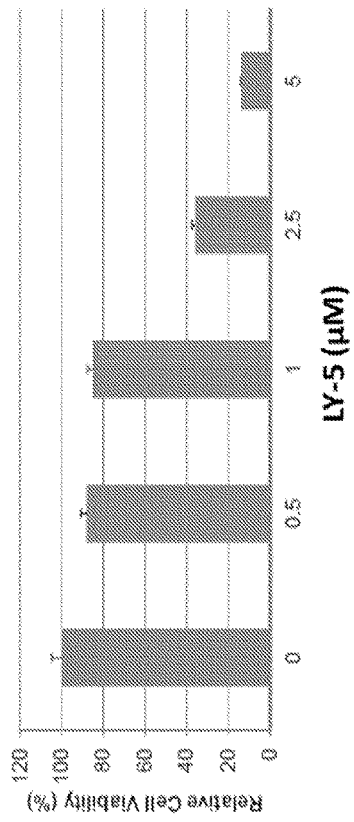

FIG. 47 shows representative data for the effect of LY-5 on cell viability. Human pancreatic cancer cell line ASPC-1 was treated with LY-5 (0-5 µM) for 2 h, and then cell viability assessed using an MTT-based cell proliferation assay. The absorbance was read at 595 nm, and cell viability normalized to the absorbance reading for the control cells (vehicle treated).

Figure 48:
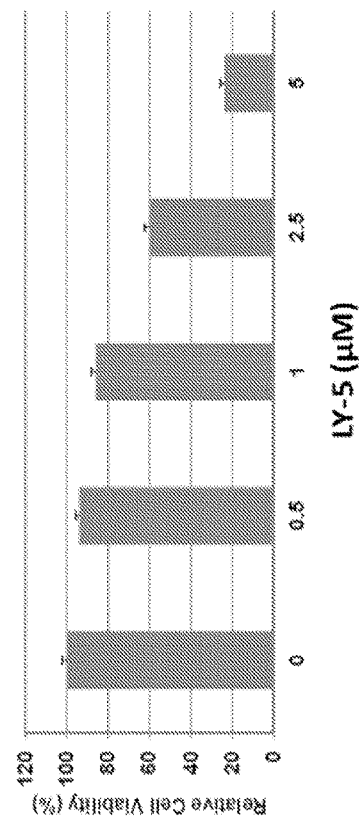

FIG. 48 shows representative data for the effect of LY-5 on cell viability. Human pancreatic cancer cell line HPAC-1 was treated with LY-5 (0-5 µM) for 2 h, and then cell viability assessed using an MTT-based cell proliferation assay. The absorbance was read at 595 nm, and cell viability normalized to the absorbance reading for the control cells (vehicle treated).

Figure 49:
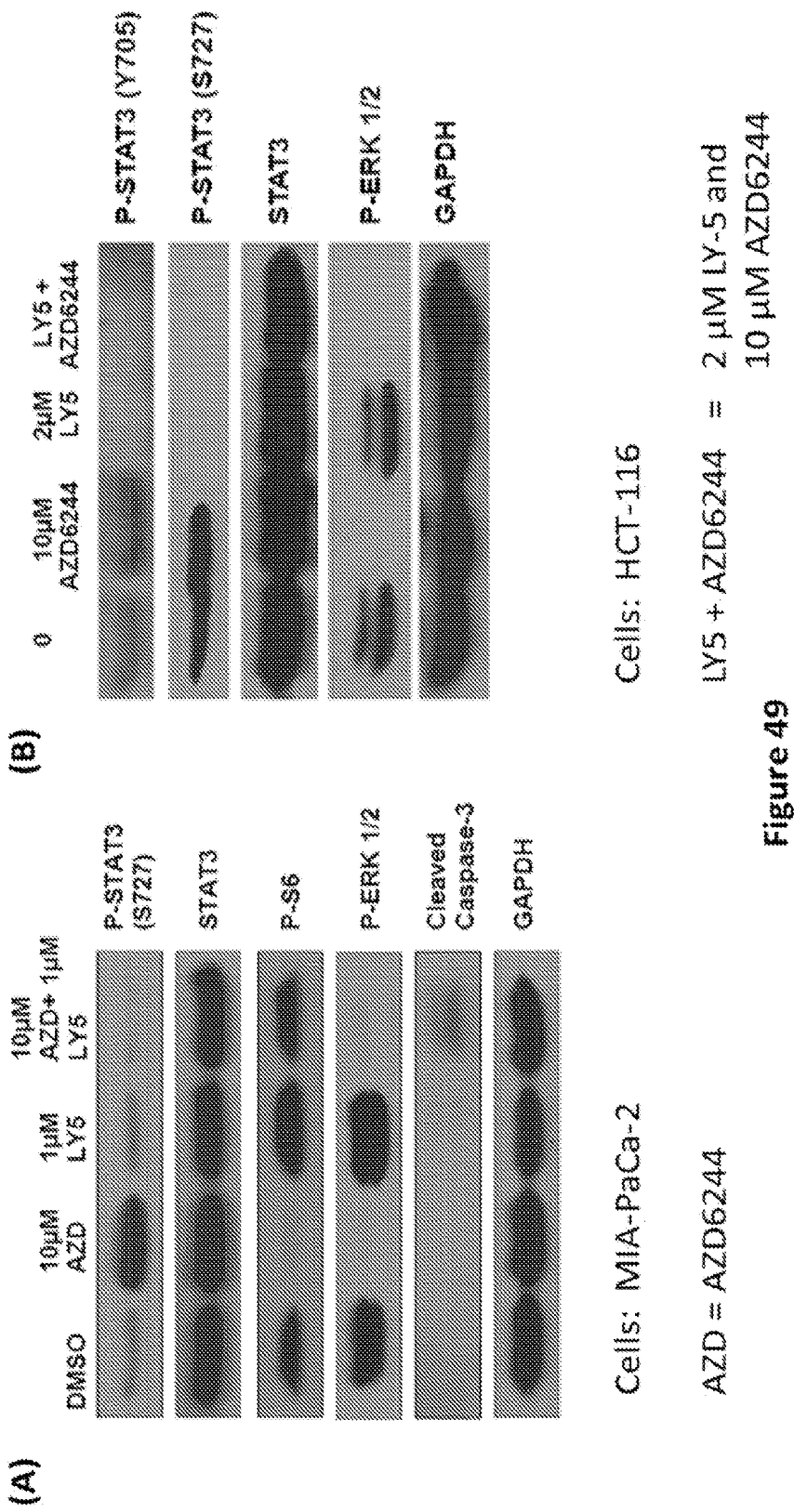

FIG. 49 shows that compound LY-5 (LY5) inhibits P-STAT3 induced by MEK inhibitor AZD6244 (AZD). In FIG. 49(A), Human pancreatic cancer cell line MIA-PaCa-2 was treated with LY5 (1 µM), AZD (10 µM), or LY5+AZD (1 µM+10 µM) for 2 h, then whole-cell extracts were prepared, and then phospho-STAT3 was detected by Western blot assay, revealing a decrease in STAT3 phosphorylation in the LY5+AZD (1 µM+10 µM) treated cells. In FIG. 49(B), Human colon cancer cell line HCT-116 was treated with LY5 (2 µM), AZD6244 (10 µM), or LY5+AZD6244 (5 µM+10 µM) for 2 h, then whole-cell extracts were prepared, and then phospho-STAT3 was detected by Western blot assay, revealing a decrease in STAT3 phosphorylation in the LY5+AZD6244 (5 µM+10 µM) treated cells.

Figure 50:
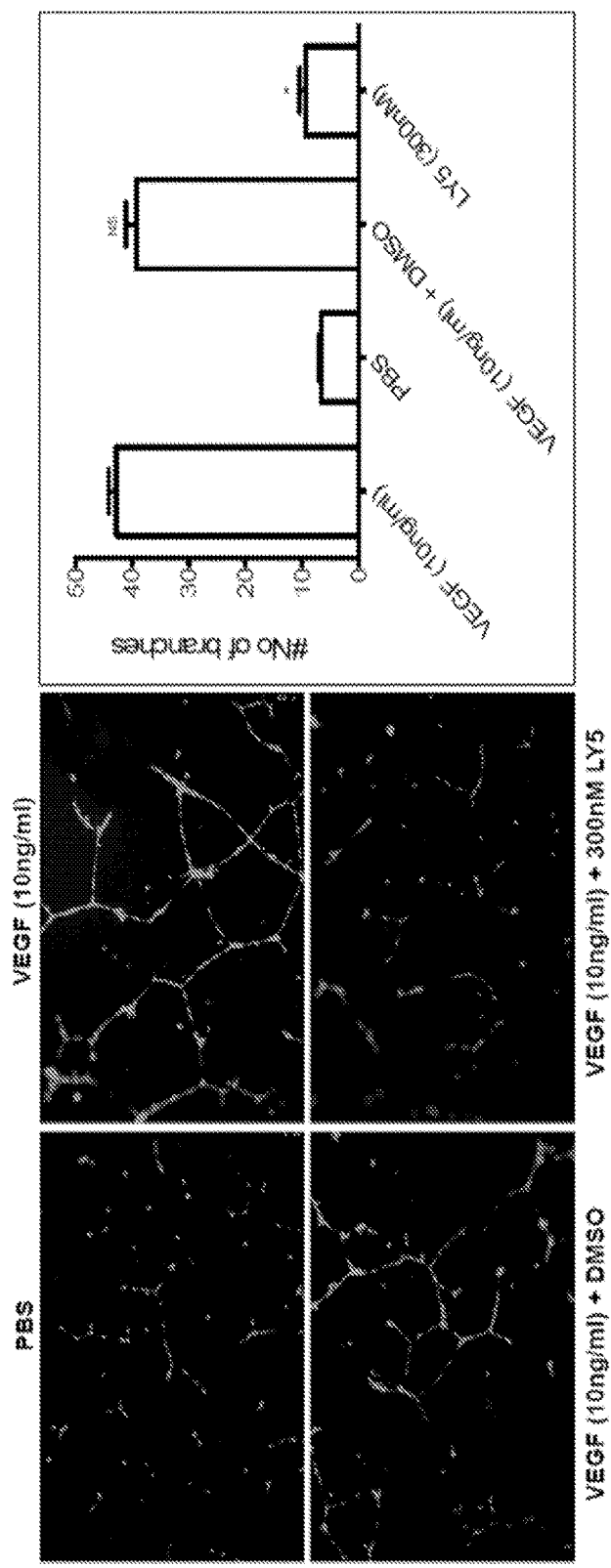

FIG. 50 shows that compound LY-5 inhibits VEGF induced HUVEC tube formation and spheroid formation. Human umbilical vein endothelial cells (HUVEC) were stimulated with VEGF in the absence or presence of LY-5 (300 nM), and number of endothelial vascular branches were determined using an in vitro angiogenesis assay after CalcinM staining, revealing reduce HUVEC tube formation and VEGF-induced sprouting from preformed spheroids.

Figure 51:
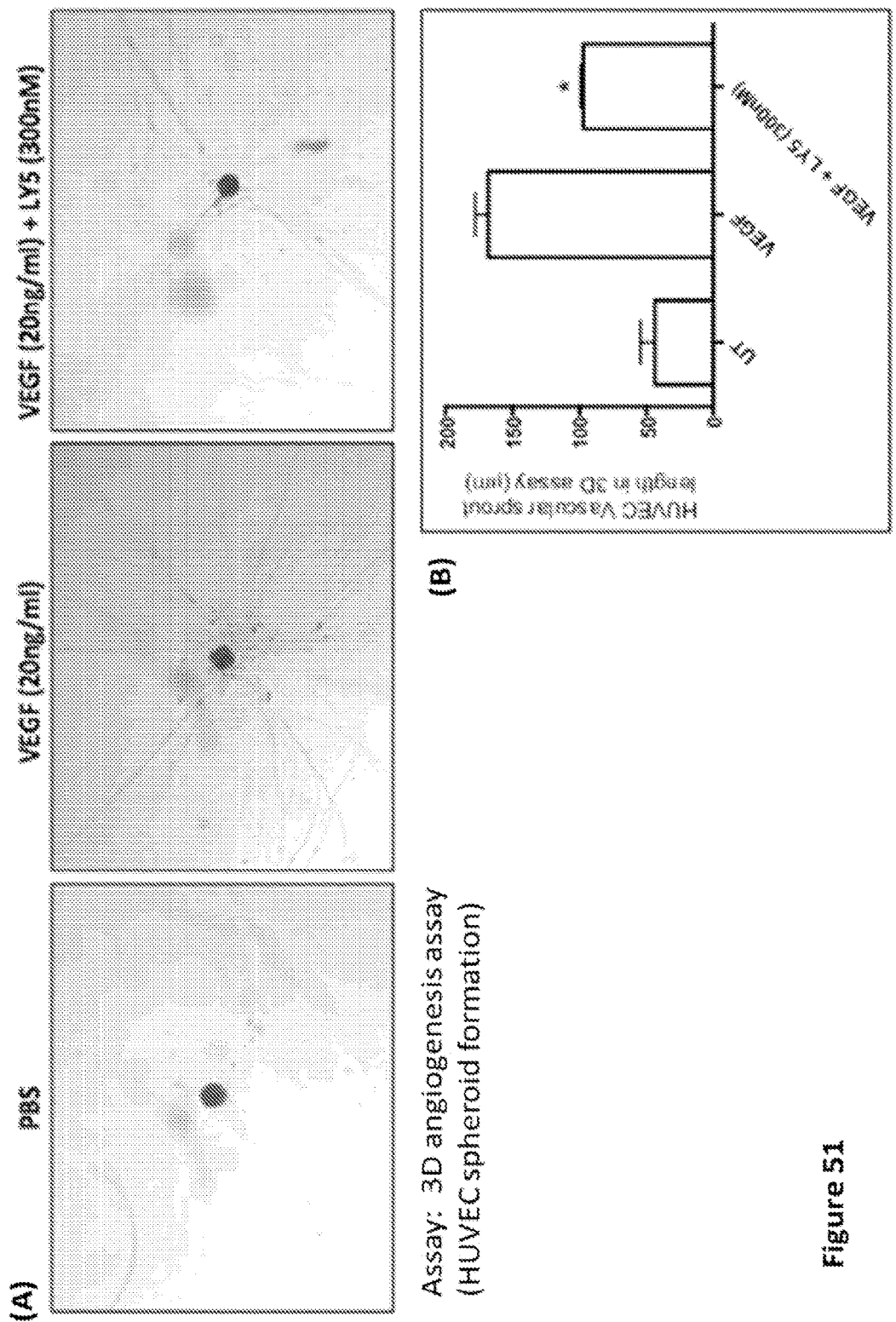

FIG. 51 shows that compound LY-5 inhibits VEGF induced HUVEC tube formation. HUVECs were stimulated with VEGF in the absence or presence of LY-5 (300 nM), and length endothelial vascular sprouts were determined using 3D in vitro angiogenesis assay, revealing reduce HUVEC vascular sprout length.

Figure 52:
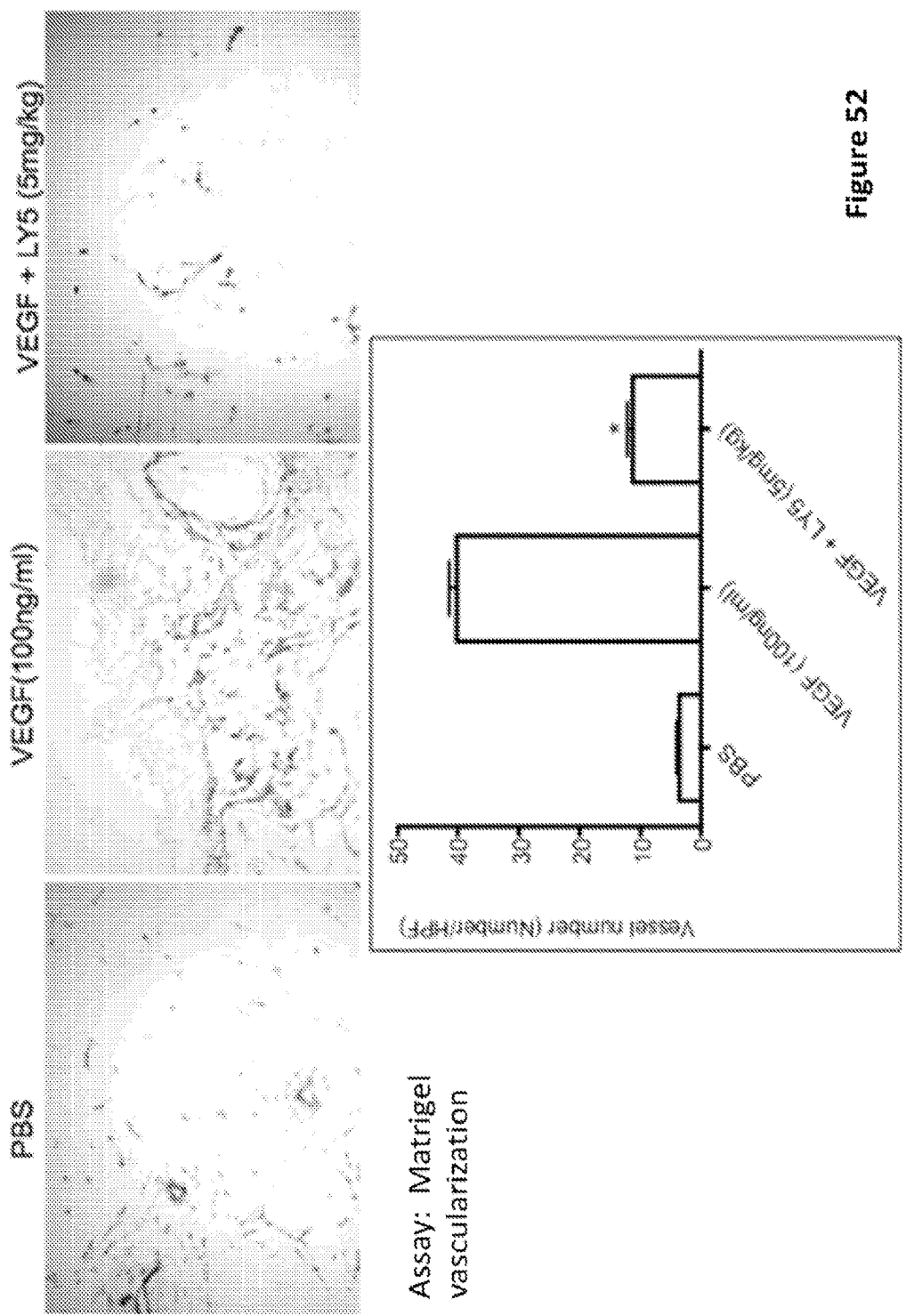

FIG. 52 shows that compound LY-5 inhibits angiogenesis in mice. Matrigel plugs containing with PBS, or VEGF (100 ng/ml) were implanted subcutaneously in mice that were or were not treated with LY5 (5 mg/kg daily) The Matrigel plugs were excised on day 7, fixed with formalin and 5 µm sections were stained with H&E, Messon Trichrome and CD34 staining, and numbers of CD34 positive vessels in HPF (magnification, 200×) were counted, revealing a decrease in number of vessels.

Figure 53:
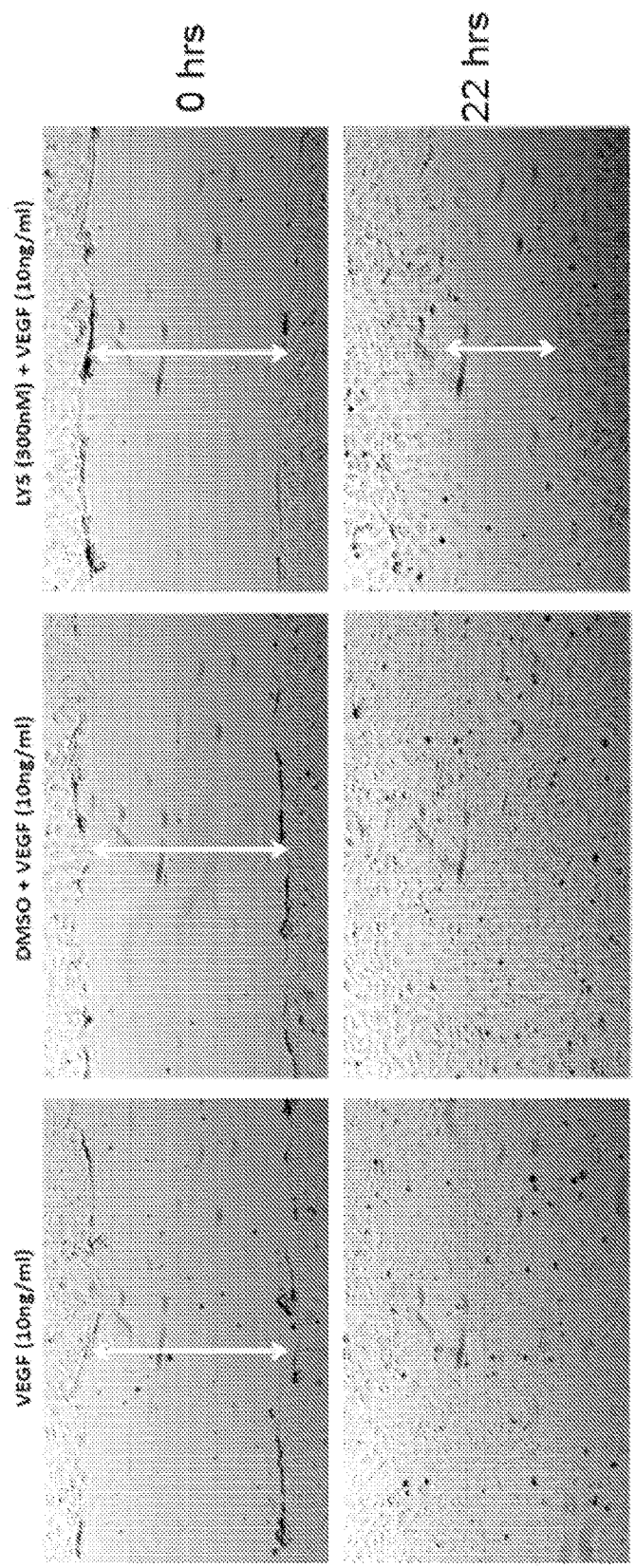

FIG. 53 shows that compound LY-5 inhibits VEGF induced HUVEC cell migration. Human umbilical vein endothelial cells (HUVEC) were incubated with medium containing VEGF (10 ng/ml)) with or without LY5 (300 nM) for 24 h, and width was photographed at different time intervals (0 and 22 h) with a magnification of 40× with a microscopic camera system, revealing decreased cell migration.

Figure 54:
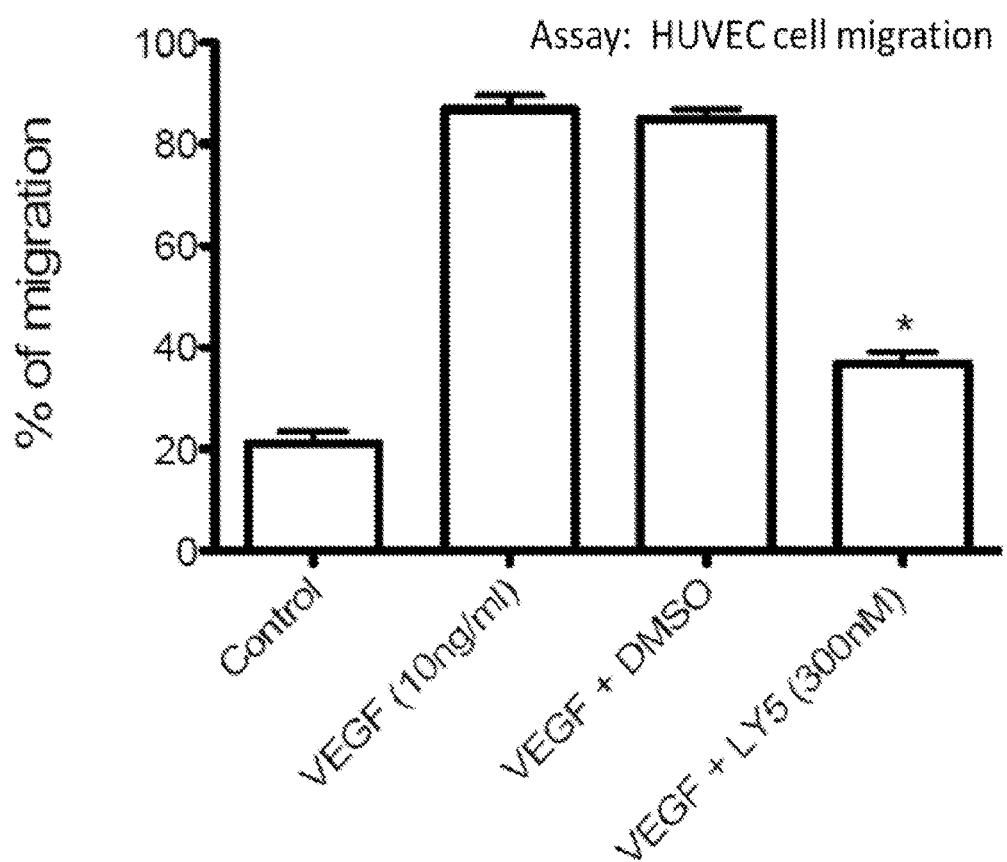

FIG. 54 shows representative data that compound LY-5 inhibits angiogenesis in mice. Human umbilical vein endothelial cells (HUVEC) were incubated with medium containing VEGF (10 ng/ml) with or without LY5 (300 nM), and migration was quantified using the ratio of the migrated cells over the total cells, revealing a decreased percentage of migration.

Figure 55:
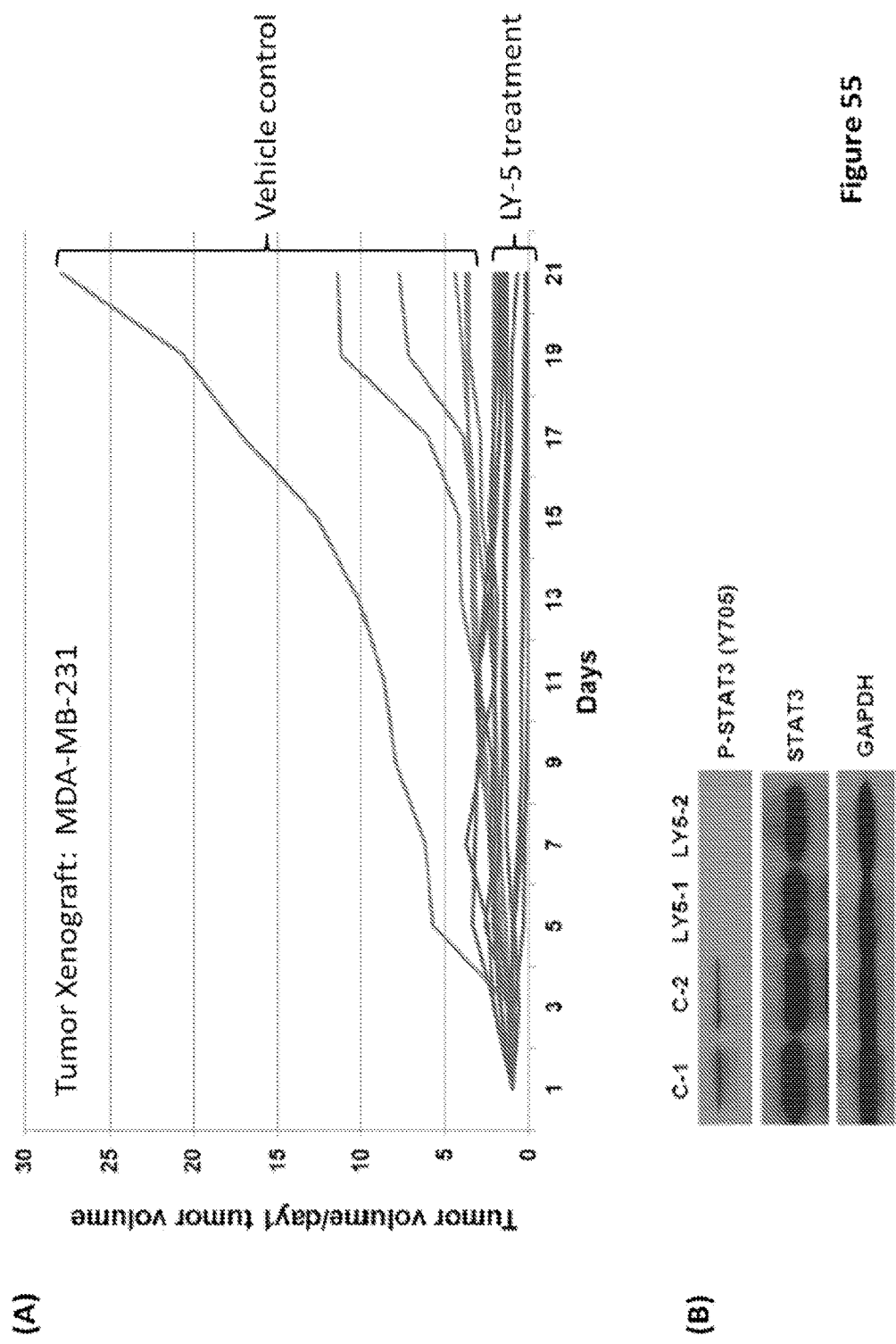

FIG. 55 shows data for the inhibition of STAT3 phosphorylation and breast xenograft tumor growth by oral administration. After tumor development, mice were treated with oral injection of LY5 (5 mg/kg) for 21 days, and growth of tumors was determined from sacrificed mice by measuring length (L) and width (W) of the tumor every other day with a caliper, revealing decreased tumor growth. Western Blot was also conducted on tumor tissue homogenates to measure the expression of STAT3 phosphorylation, revealing a decrease in STAT3 phosphorylation.

Figure 56:
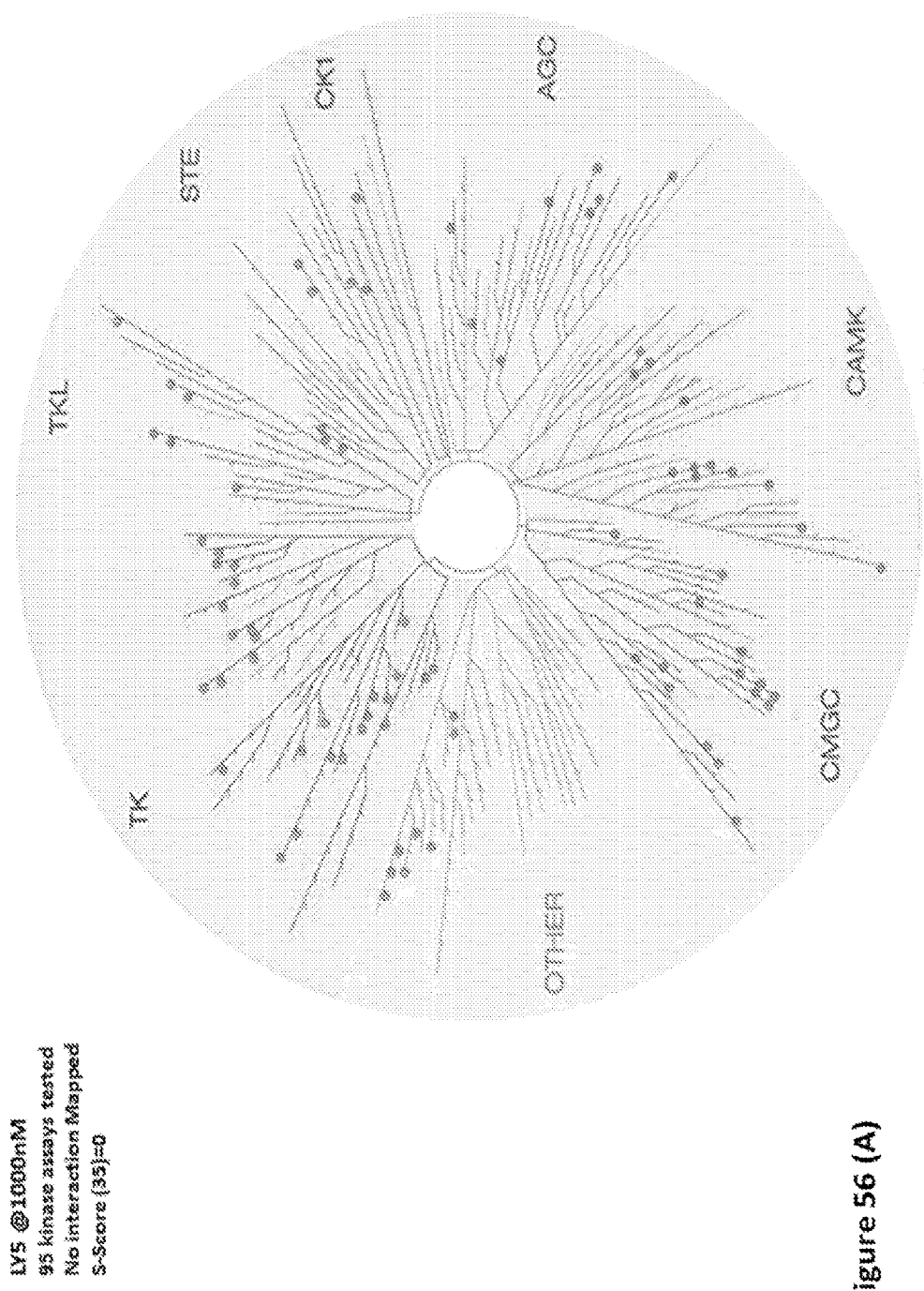
Figure 56:
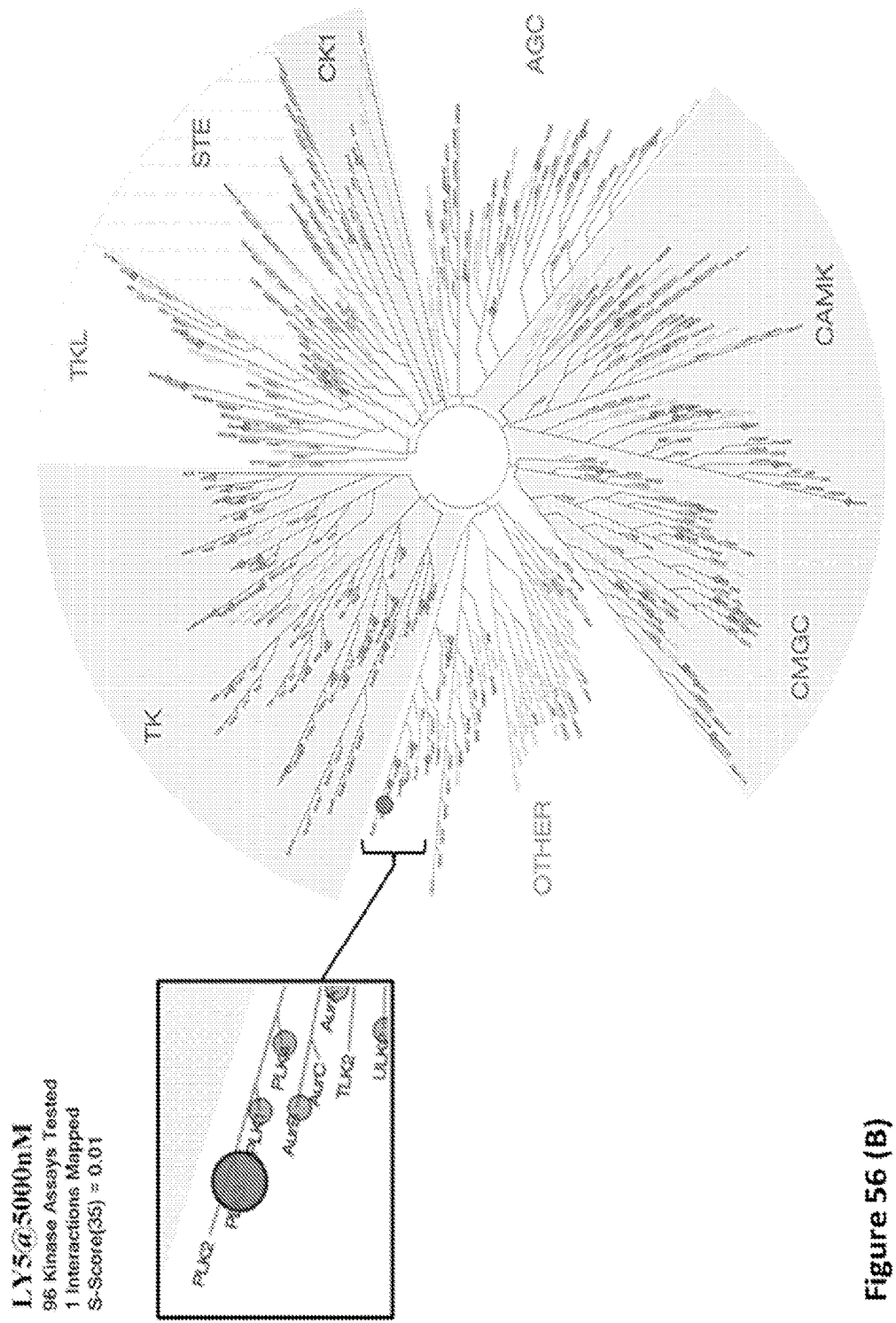

FIG. 56 shows representative data of the effect of compound LY-5 on kinase activities. The effects of LY-5 on 96 additional human protein or lipid kinase activities were interrogated using kinase profiler assay at 1 µM (A) or 5 µM (B) drug concentration, revealing LY-5 exhibits no apparent inhibitory binding either directly (isosterically) or indirectly (allosterically) to the active sites of these 96 kinases at a 1 µM drug concentration, a drug concentration that effectively inhibits P-STAT3 in cancer cells.

Figure 57:
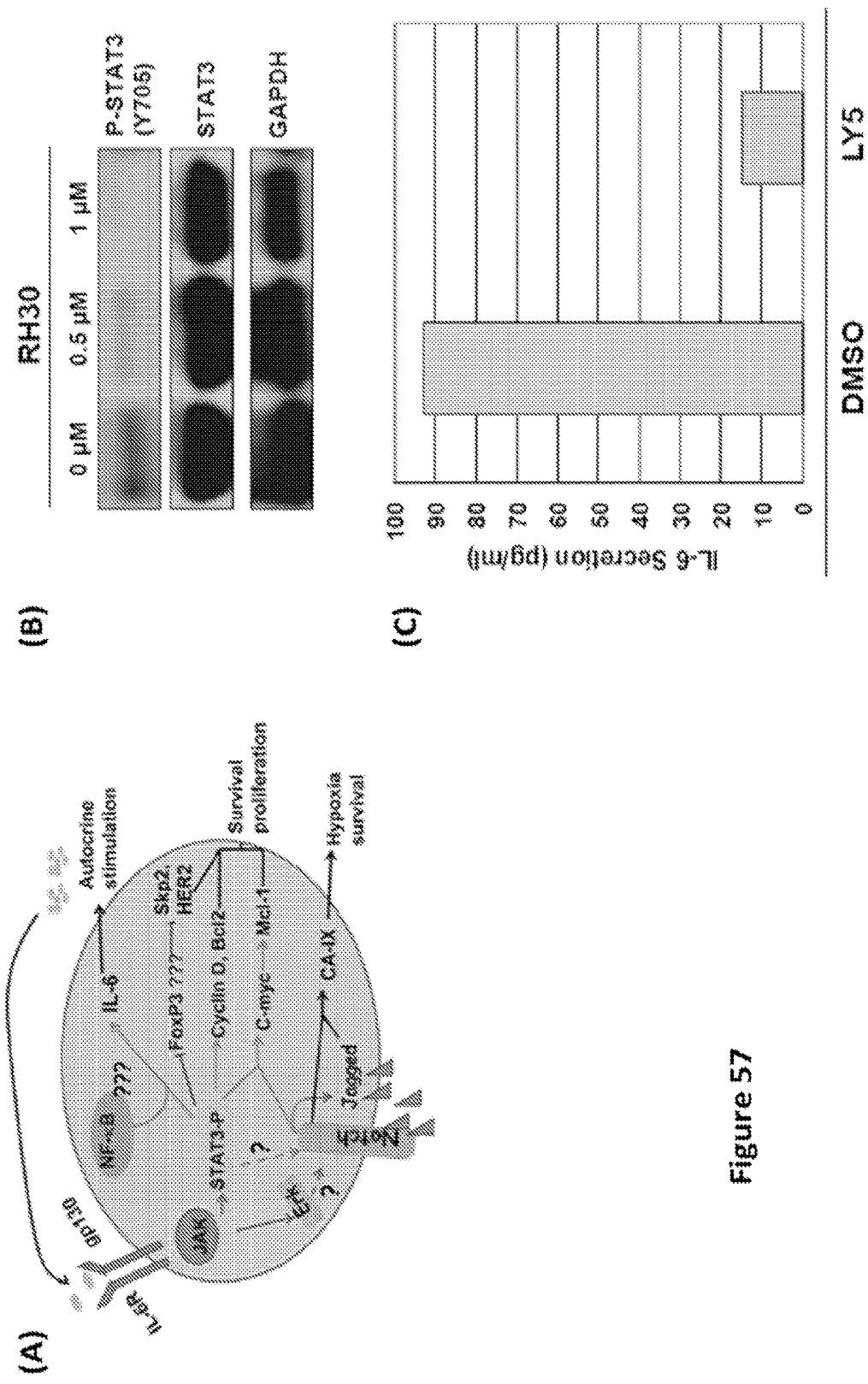

FIG. 57 shows that compound LY-5 reduces constitutive STAT3 phosphorylation at Y705 and IL-6 levels. FIG. 57(A) shows as schematic representation of IL-6 mediated STAT3 activation. In FIG. 57(B), rhabdomyosarcoma cell line RH30 were treated with LY-5 (0-1 µM) for 2 h, then whole-cell extracts were prepared and phospho-STAT3 was detected by Western blot assay, revealing a decrease in STAT3 phosphorylation. FIG. 57(C) shows representative data showing that compound LY-5 can decrease IL-6 secretion, which is understood to activate STAT3.

Figure 58:
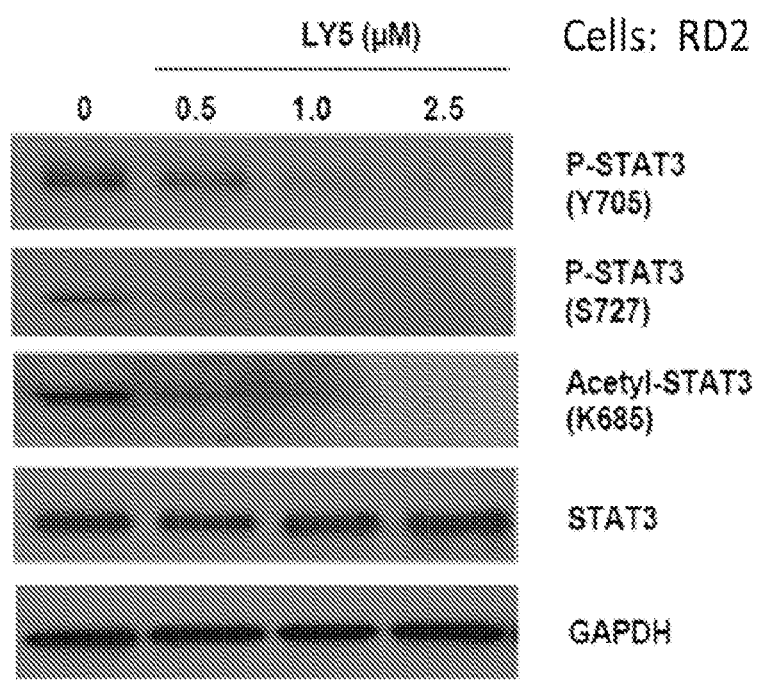

FIG. 58 shows that compound LY-5 inhibits P-STAT3 and acetyl-STAT3. Rhabdomyosarcoma cell line RD2 was treated with LY-5 (0-2.5 µM) for 2 h, then whole-cell extracts were prepared, then phospho-STAT3 and acetyl-STAT3 was detected by Western blot assay, revealing a decrease in STAT3 phosphorylation and acetyl-STAT3.

Figure 59:
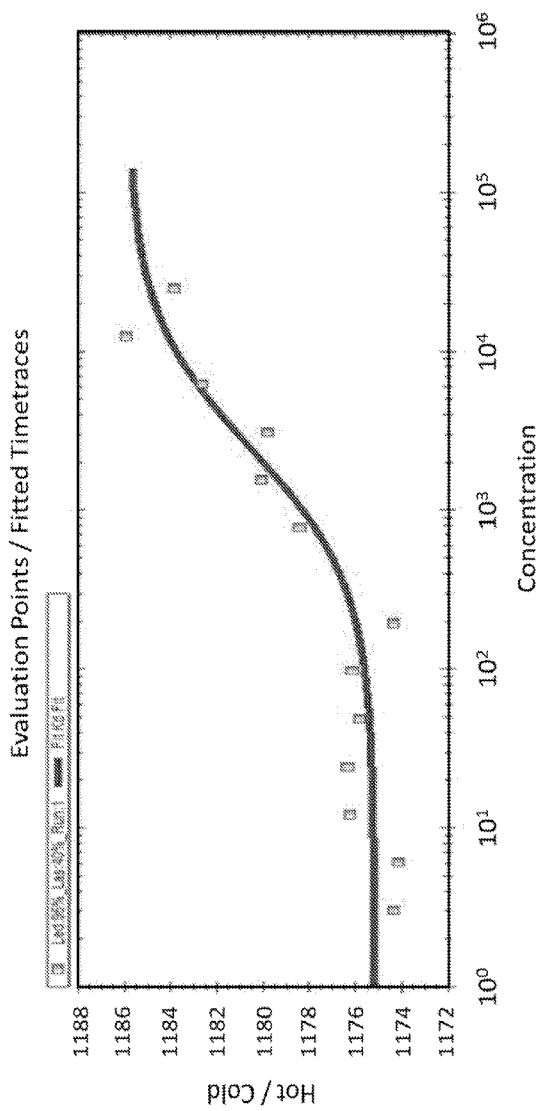

FIG. 59 shows representative data of compound LY-17 binding affinity for STAT3. The STAT3 binding affinity of LY-17 was determined using a microscale thermophoresis (MST) assay using changes in the hydration shell, charge or size of molecules and by measuring changes of the mobility of molecules in microscopic temperature gradients, revealing a binding interaction between LY-17 and STAT3.

Figure 60:

FIG. 60 shows representative data for the inhibition of 96 human protein or lipid kinase activities at 1 µM or 5 µM concentration of LY-5. The data show that LY-5 exhibits no apparent activity against this panel of kinases, except for some activity against PLK3 at 5 µM.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

A. Definitions

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

As used herein, the term "STAT" and "signal transducer and activator of transcription" can be used interchangeably, and refer to a protein family comprising at least the following members: STAT1, 2, 3, 4, 5a, 5b, and 6. The STAT family of proteins are latent cytoplasmic transcription factors that mediate cellular responses to cytokines, growth factors, and other polypeptide ligands.

As used herein, the terms "STAT3," "signal transducer and activator of transcription 3 (acute-phase response)," and "signal transducer and activator of transcription 3" can be used interchangeably and refer to a transcription factor encoded by a gene designated in human as the STAT3 gene, which has a human gene map locus of 17q21 and described by Entrez Gene cytogenetic band: 17q21.31; Ensembl cytogenetic band: 17q21.2; and, HGNC cytogenetic band: 17q21. The term STAT3 refers to a human protein that has 770 amino acids and has a molecular weight of about 88,068 Da. The term is inclusive of splice isoforms or variants, and also inclusive of that protein referred to by such alternative designations as: APRF, MGC16063, Acute-phase response factor, DNA-binding protein APRF, HIES as used by those skilled in the art to that protein encoded by human gene STAT3. The term is also inclusive of the non-human ortholog or homolog thereof.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects. In some aspects of the disclosed methods, the subject has been diagnosed with a need for treatment of one or more oncological disorders or cancers prior to the administering step. In some aspects of the disclosed method, the subject has been diagnosed with a need for inhibition or negative modulation of STAT3 prior to the administering step. In some aspects of the disclosed method, the subject has been diagnosed with a need for treatment of one or more oncological disorders or cancers associated with STAT3 dysfunction prior to the administering step.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with a disorder treatable by STAT3 inhibition" means having been subjected to a physical examination by a person of skill, for example, a physician, and found to have a condition that can be diagnosed or treated by a compound or composition that can inhibit or negatively modulate STAT3. As a further example, "diagnosed with a need for inhibition of STAT3" refers to having been subjected to a physical examination by a person of skill, for example, a physician, and found to have a condition characterized by a dysfunction in STAT3 activity. Such a diagnosis can be in reference to a disorder, such as an oncological disorder or disease, cancer and/or disorder of uncontrolled cellular proliferation and the like, as discussed herein. For example, the term "diagnosed with a need for inhibition of STAT3 activity" refers to having been subjected to a physical examination by a person of skill, for example, a physician, and found to have a condition that can be diagnosed or treated by inhibition of STAT3 activity. For example, "diagnosed with a need for modulation of STAT3 activity" means having been subjected to a physical examination by a person of skill, for example, a physician, and found to have a condition that can be diagnosed or treated by modulation of STAT3 activity, e.g. negative modulation. For example, "diagnosed with a need for treatment of one or more disorder of uncontrolled cellular proliferation associated with STAT3 dysfunction" means having been subjected to a physical examination by a person of skill, for example, a physician, and found to have one or disorders of uncontrolled cellular proliferation, e.g. a cancer, associated with STAT3 dysfunction.

As used herein, the phrase "identified to be in need of treatment for a disorder," or the like, refers to selection of a subject based upon need for treatment of the disorder. For example, a subject can be identified as having a need for treatment of a disorder (e.g., a disorder related to STAT3 activity) based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" as used herein refers to bringing a disclosed compound and a cell, target STAT3 protein, or other biological entity together in such a manner that the compound can affect the activity of the target (e.g., spliceosome, cell, etc.), either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "$EC_{50}$," is intended to refer to the concentration of a substance (e.g., a compound or a drug) that is required for 50% agonism or activation of a biological process, or component of a process, including a protein, subunit, organelle, ribonucleoprotein, etc. In one aspect, an $EC_{50}$ can refer to the concentration of a substance that is required for 50% agonism or activation in vivo, as further defined elsewhere herein. In a further aspect, $EC_{50}$ refers to the concentration of agonist or activator that provokes a response halfway between the baseline and maximum response.

As used herein, "$IC_{50}$," is intended to refer to the concentration of a substance (e.g., a compound or a drug) that is required for 50% inhibition of a biological process, or component of a process, including a protein, subunit, organelle, ribonucleoprotein, etc. In some contexts, an $IC_{50}$ can refer to the plasma concentration of a substance that is required for 50% inhibition in vivo, as further defined elsewhere herein. More commonly, $IC_{50}$ refers to the half maximal (50%) inhibitory concentration (IC) of a substance required to inhibit a process or activity in vitro.

As used herein, "STAT3 $IC_{50}$" refers to the concentration of a substance (e.g., a compound or a drug) that is required for 50% inhibition of a STAT3 activity. In some contexts, an $IC_{50}$ can refer to the plasma concentration of a substance that is required for 50% inhibition of an in vivo activity or process as further defined elsewhere herein, e.g. tumor growth in an animal or human. In other contexts, STAT3 $IC_{50}$ refers the half maximal (50%) inhibitory concentration (IC) of a substance or compound required to inhibit a process or activity an in vitro context, e.g. a cell-free or cell-based assay. For example, the STAT3 $IC_{50}$ can be in the context of the half-maximal concentration required to inhibit cell growth. As discussed below, the response is measured in a cell-line with aberrant STAT3 activity. Alternatively, the response is measured in a cell-line with persistently active STAT3. The response can be determined using a cell-line derived from a human breast cancer, human pancreatic cancer, and human prostate cancer. For example, the response can be measured in a cell-line selected from MDA-MB-231, Panc-1, and DU-145. Cell-lines transfected with specific genes can also be used. For example, the response can be measured in a cell-line transfected with v-Src. Alternatively, the cell-line transfected with v-Src is a permanent cell-line. In some cases, the STAT3 $IC_{50}$ is the half-maximal concentration required to inhibit STAT3 activity in a cell-free assay, e.g. an electrophoretic mobility shift assay ("EMSA"). Alternatively, the STAT3 $IC_{50}$ is the half-maximal concentration required to inhibit cell-growth, cell viability or cell migration activity.

As used herein, the term "STAT3 $K_D$" refers to the binding affinity of a compound or substance for the STAT3 determined in an in vitro assay. The $K_D$ of a substance for a protein can be determined by a variety of methods known to one skilled in the art, e.g. equilibrium dialysis, analytical ultracentrifugation, microscale thermophoresis, and surface plasmon resonance ("SPR") analysis. As typically used herein, STAT3 $K_D$ is determined by microscale thermophoresis using purified STAT3 protein.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —$OCH_2CH_2O$— units in the polyester, regardless of whether ethylene glycol was used to prepare the polyester. Similarly, a sebacic acid residue in a polyester refers to one or more —$CO(CH_2)_8CO$— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula —$(CH_2)_a$—, where "a" is an integer of from 2 to 500.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$-$OA^2$ or —$OA^1$-$(OA^2)_a$-$OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound.

Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula —$NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)$A^1$ or —C(O)O$A^1$, where $A^1$ can be alkyl, cycloalkyl, alkenyl, cycloalkenyl, alkynyl, cycloalkynyl, aryl, or heteroaryl group as described herein. The term "polyester" as used herein is represented by the formula -($A^1$O(O)C-$A^2$-C(O)O)$_a$— or -($A^1$O(O)C-$A^2$-OC(O))$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, an alkyl, cycloalkyl, alkenyl, cycloalkenyl, alkynyl, cycloalkynyl, aryl, or heteroaryl group described herein. The term "polyether" as used herein is represented by the formula -($A^1$O-$A^2$O)$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "halide" as used herein refers to the halogens fluorine, chlorine, bromine, and iodine.

The term "heterocycle," as used herein refers to single and multi-cyclic aromatic or non-aromatic ring systems in which at least one of the ring members is other than carbon. Heterocycle includes azetidine, dioxane, furan, imidazole, isothiazole, isoxazole, morpholine, oxazole, oxazole, including, 1,2,3-oxadiazole, 1,2,5-oxadiazole and 1,3,4-oxadiazole, piperazine, piperidine, pyrazine, pyrazole, pyridazine, pyridine, pyrimidine, pyrrole, pyrrolidine, tetrahydrofuran, tetrahydropyran, tetrazine, including 1,2,4,5-tetrazine, tetrazole, including 1,2,3,4-tetrazole and 1,2,4,5-tetrazole, thiadiazole, including, 1,2,3-thiadiazole, 1,2,5-thiadiazole, and 1,3,4-thiadiazole, thiazole, thiophene, triazine, including 1,3,5-triazine and 1,2,4-triazine, triazole, including, 1,2,3-triazole, 1,3,4-triazole, and the like.

The term "hydroxyl" as used herein is represented by the formula —OH.

The term "ketone" as used herein is represented by the formula $A^1$C(O)$A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" as used herein is represented by the formula —$N_3$.

The term "nitro" as used herein is represented by the formula —$NO_2$.

The term "nitrile" as used herein is represented by the formula —CN.

The term "silyl" as used herein is represented by the formula —Si$A^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —S(O)$A^1$, —S(O)$_2$A1, —OS(O)$_2$A1, or —OS(O)$_2$O$A^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —S(O)$_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula $A^1$S(O)$_2$A2, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH=CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR—, SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched alkylene)O—N(R°)$_2$; or —(C$_{1-4}$ straight or branched alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^●$, -(haloR$^●$), —(CH$_2$)$_{0-2}$OH, —(CH$_2$)$_{0-2}$OR$^●$, —(CH$_2$)$_{0-2}$CH(OR$^●$)$_2$; —O(haloR$^●$), —CN, —N$_3$, —(CH$_2$)$_{0-2}$C(O)R$^●$, —(CH$_2$)$_{0-2}$C(O)OH, —(CH$_2$)$_{0-2}$C(O)OR$^●$, —(CH$_2$)$_{0-2}$SR$^●$, —(CH$_2$)$_{0-2}$SH, —(CH$_2$)$_{0-2}$NH$_2$, —(CH$_2$)$_{0-2}$NHR$^●$, —(CH$_2$)$_{0-2}$NR$^●$$_2$, —NO$_2$, —SiR$^●$$_3$, —OSiR$^●$$_3$, —C(O)SR$^●$, —(C$_{1-4}$ straight or branched alkylene)C(O)OR$^●$, or —SSR$^●$ wherein each R$^●$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_1$-6 aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^●$, -(haloR$^●$), —OH, —OR$^●$, —O(haloR$^●$), —CN, —C(O)OH, —C(O)OR$^●$, —NH$_2$, —NHR$^●$, —NR$^●$$_2$, or —NO$_2$, wherein each R$^●$ is unsubstituted or where preceded by "halo" is substituted only with one or more halogens, and is independently C1-4 aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^†$, —NR$^†$$_2$, —C(O)R$^†$, —C(O)OR$^†$, —C(O)C(O)R$^†$, —C(O)CH$_2$C(O)R$^†$, —S(O)$_2$R$^†$, —S(O)$_2$NR$^†$$_2$, —C(S)NR$^†$$_2$, —C(NH)NR$^†$$_2$, or —N(R$^†$)S(O)$_2$R$^†$; wherein each R$^†$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R† are independently halogen, —R●, -(haloR●), —OH, —OR●, —O(haloR●), —CN, —C(O)OH, —C(O)OR●, —NH$_2$, —NHR●, —NR●$_2$, or —NO$_2$, wherein each R● is unsubstituted or where preceded by "halo" is substituted only with one or more halogens, and is independently $C_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, brosylate, and halides.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure given by the formula:

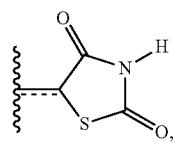

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5,6,7,8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

Compounds described herein comprise atoms in both their natural isotopic abundance and in non-natural abundance. The disclosed compounds can be isotopically-labelled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of the present invention and prodrugs thereof can generally be prepared by carrying out the procedures below, by substituting a readily available isotopically labelled reagent for a non-isotopically labelled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvate or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

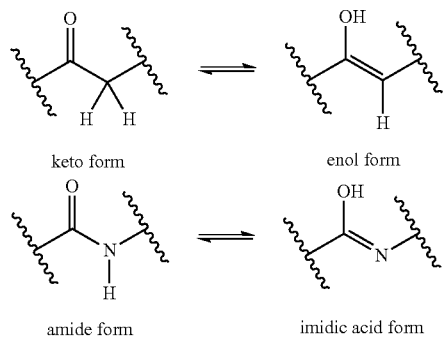

keto form    enol form amide form    imidic acid form

Likewise, amides with an N-hydrogen can exist in an equilibrium of the amide form and the imidic acid form. Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

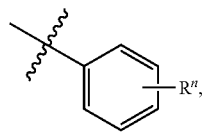

which is understood to be equivalent to a formula:

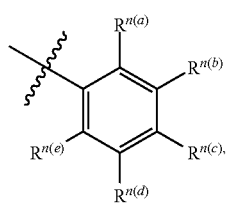

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds can not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. Compounds

To block phosphorylation and dimerization processes, STAT3 inhibitors should compete with the native phosphotyrosine (pTyr) peptide by binding to the STAT3 SH2 domain (FIG. 9). In one aspect, the compounds disclosed herein can compete with the native phosphotyrosine (pTyr) peptide by binding to the STAT3 SH2 domain.

Fragment-based drug design (FBDD) has emerged as a new strategy for drug discovery in the past decade. FBDD as a design-intensive method is superior to the resource-intensive conventional drug discovery methods, such as high-throughput screening and combinatorial chemistry (Hajduk, P. J. and Greer, J. Nat. Rev. Drug Discov. 2007, 6, 211-219). Conventional FBDD has made some improvement on efficiency and cost-effectiveness in drug design and several drug candidates designed by this methodology are currently under clinical trials.

In one aspect, the invention relates to compounds useful as inhibitors of STAT. In a further aspect, the disclosed compounds and products of disclosed methods of making are modulators of STAT activity. In various aspects, the present invention relates to compounds that bind to a STAT protein and negatively modulate STAT activity. In a further aspect, the disclosed compounds exhibit inhibition of STAT activity. The compounds can, in one aspect, exhibit subtype selectivity. In a further aspect, the compounds exhibit selectivity for the STAT3 member of the STAT protein family. In a yet further aspect, the compounds exhibit selectivity for the STAT5 members of the STAT protein family.

In one aspect, the compounds of the invention are useful in the treatment of a disorder of uncontrolled cellular proliferation associated with STAT dysfunction and other diseases in which a STAT protein is involved, as further described herein. In a further aspect, the STAT is STAT3. In a still further aspect, the compounds are useful in the treatment of a disorder of uncontrolled cellular proliferation or other disorder associated with a STAT3 dysfunction. In a yet further aspect, the compounds are useful in the treatment of a disorder of uncontrolled cellular proliferation or other disorder associated with a STAT5 dysfunction.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Structure

In one aspect, the invention relates to a compound having a structure represented by a formula:

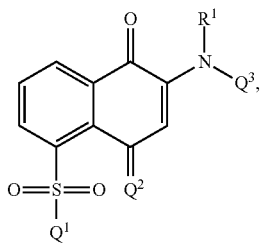

wherein $R^1$ is selected from hydrogen and C1-C3 alkyl; wherein $Q^1$ is —$NR^{2a}R^{2b}$ and wherein $Q^2$ is O; or wherein $Q^1$ and $Q^2$ are together N; wherein each of $R^{2a}$ and $R^{2b}$, when present, is independently selected from hydrogen and C1-C3 alkyl; wherein $Q^3$ is selected from —(C1-C6)-$Ar^1$, $Ar^1$, —(C1-C6)-$Cy^1$, and $Cy^1$; wherein $Ar^1$, when present, is selected from phenyl, naphthyl, monocyclic heteroaryl, and bicyclic heteroaryl; and wherein $Ar^1$ is substituted with 0, 1, 2, or 3 groups independently selected from halogen, —CN, —OH, —$NH_2$, —$NO_2$, C1-C6 alkyl, C1-C6 monohaloalkyl, C1-C6 polyhaloalkyl, C1-C6 hydroxyalkyl, C1-C6 monoalkylamino, C1-C6 dialkylamino, —(C1-C6)$NR^{4a}R^{4b}$, —(C1-C6)-(C=O)$R^3$, —(C1-C6)-(C=O)$OR^3$, —(C1-C6)(C=O)$NR^{4a}R^{4b}$, —(C1-C6)-$Ar^2$, $Ar^2$, —(C1-C6)-$Cy^2$, $Cy^2$, and —$S(O)_nNR^{5a}R^{5b}$; wherein n is 0, 1, or 2; wherein each $R^3$, when present, is independently selected from hydrogen, C1-C6 alkyl, C1-C6 monohaloalkyl, C1-C6 polyhaloalkyl, C1-C6 hydroxyalkyl, and C1-C6 aminoalkyl; wherein each of $R^{4a}$ and $R^{4b}$, when present, is independently selected from hydrogen, C1-C6 alkyl, C1-C6 monohaloalkyl, C1-C6 polyhaloalkyl, C1-C6 hydroxyalkyl, and C1-C6 aminoalkyl; wherein each of $R^{5a}$ and $R^{5b}$ when present, is independently selected from hydrogen, C1-C6 alkyl, C1-C6 monohaloalkyl, C1-C6 polyhaloalkyl, C1-C6 hydroxyalkyl, C1-C6 aminoalkyl, and —(C=O)$NR^{6a}R^{6b}$; wherein each of $R^{6a}$ and $R^{6b}$, when present, is independently selected from hydrogen and C1-C6 alkyl; wherein each $Ar^2$, when present, is independently selected from is phenyl and monocyclic heteroaryl; and wherein $Ar^2$ is substituted with 0, 1, 2, or 3 groups independently selected from halogen, —CN, —OH, —$NH_2$, —$NO_2$, C1-C6 alkyl, C1-C6 monohaloalkyl, C1-C6 polyhaloalkyl, C1-C6 hydroxyalkyl, C1-C6 aminoalkyl, C1-C6 monoalkylamino, and C1-C6 dialkylamino; wherein each $Cy^2$, when present, is independently selected from C3-C8 cycloalkyl and C2-C7 heterocycloalkyl; and wherein $Cy^2$ is substituted with 0, 1, 2, or 3 groups independently selected from halogen, —CN, —OH, —$NH_2$, —$NO_2$, C1-C6 alkyl, C1-C6 monohaloalkyl, C1-C6 polyhaloalkyl, C1-C6 hydroxyalkyl, C1-C6 aminoalkyl, C1-C6 monoalkylamino, C1-C6 dialkylamino, —(C=O)$R^7$, —(C=O)$OR^7$, —(C=O)$NR^{8a}R^{8b}$, —(C=O)—(C1-C6 alkyl)$Ar^3$, —(C=O)—O—(C1-C6 alkyl)$Ar^3$, and —(C=O)—$NR^{8a}$—(C1-C6 alkyl)$Ar^3$; wherein each $R^7$, when present, is independently selected from hydrogen, C1-C6 alkyl, C1-C6 monohaloalkyl, and C1-C6 polyhaloalkyl; wherein each of $R^{8a}$ and $R^{8b}$, when present, is independently selected from hydrogen, C1-C6 alkyl, C1-C6 monohaloalkyl, and C1-C6 polyhaloalkyl; wherein each $Ar^3$, when present, is independently selected from phenyl and monocyclic heteroaryl substituted with 0, 1, 2, or 3 groups independently selected from halogen, —CN, —OH, —$NH_2$, —$NO_2$, C1-C6 alkyl, C1-C6 monohaloalkyl, and C1-C6 polyhaloalkyl; wherein $Cy^1$, when present, is selected from C3-C8 cycloalkyl and C2-C7 heterocycloalkyl; and wherein $Cy^2$ is substituted with 0, 1, 2, or 3 groups independently selected from halogen, —CN, —OH, —$NH_2$, —$NO_2$, C1-C6 alkyl, C1-C6 monohaloalkyl, C1-C6 polyhaloalkyl, C1-C6 hydroxyalkyl, C1-C6 monoalkylamino, C1-C6 dialkylamino, —(C1-C6)$NR^{4a}R^{4b}$, —(C1-C6)-(C=O)$R^3$, —(C1-C6)-(C=O)$OR^3$, —(C1-C6)-(C=O)$NR^{4a}R^{4b}$, —(C1-C6)-$Ar^2$, $Ar^2$, —(C1-C6)-$Cy^2$, $Cy^2$, and —$S(O)_nNR^{5a}R^{5b}$; or a pharmaceutically acceptable salt, solvate, or polymorph thereof.

In a further aspect, the compound has a structure represented by a formula:

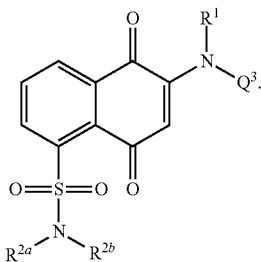

In a further aspect, the compound has a structure represented by a formula:

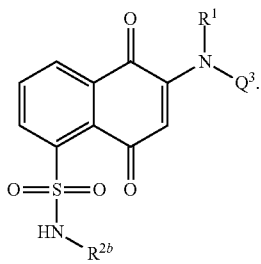

In a further aspect, the compound has a structure represented by a formula:

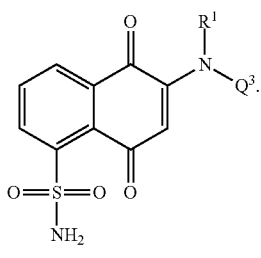

In a further aspect, the compound has a structure represented by a formula:

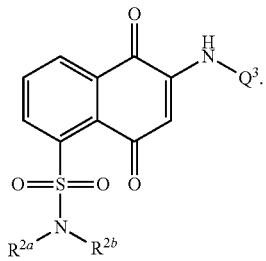

In a further aspect, the compound has a structure represented by a formula:

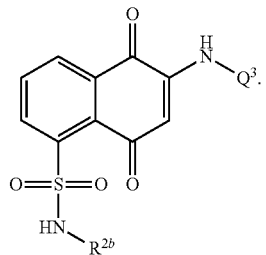

In a further aspect, the compound has a structure represented by a formula:

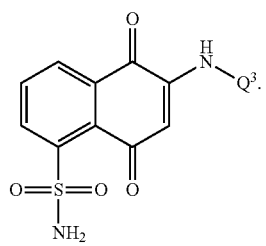

In a further aspect, the compound has a structure represented by a formula:

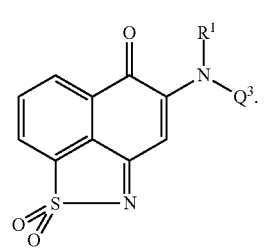

In a further aspect, the compound has a structure represented by a formula:

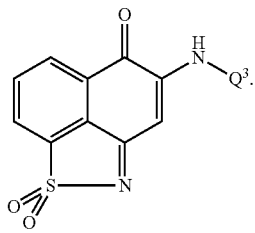

In a further aspect, the compound has a structure represented by a formula:

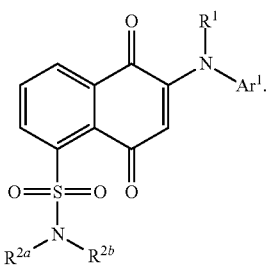

In a further aspect, the compound has a structure represented by a formula:

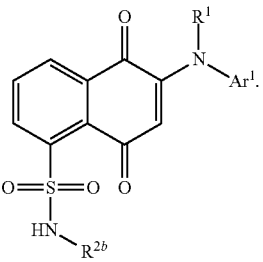

In a further aspect, the compound has a structure represented by a formula:

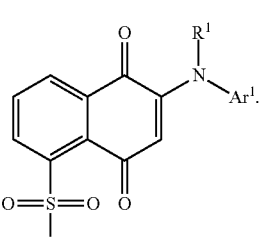

In a further aspect, the compound has a structure represented by a formula:

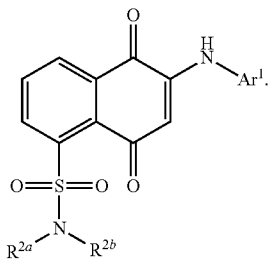

In a further aspect, the compound has a structure represented by a formula:

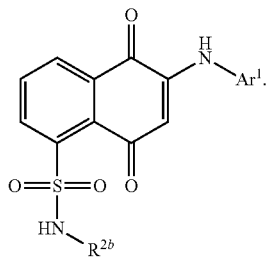

In a further aspect, the compound has a structure represented by a formula:

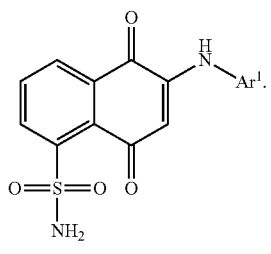

In a further aspect, the compound has a structure represented by a formula:

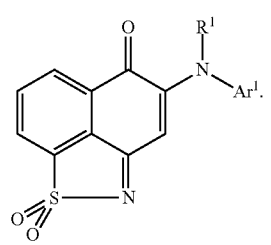

In a further aspect, the compound has a structure represented by a formula:

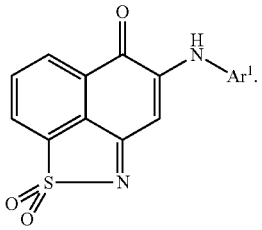

In a further aspect, the compound has a structure represented by a formula:

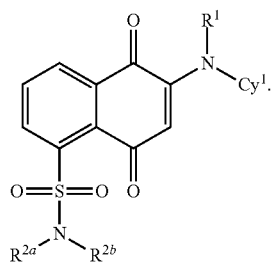

In a further aspect, the compound has a structure represented by a formula:

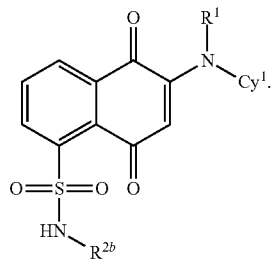

In a further aspect, the compound has a structure represented by a formula:

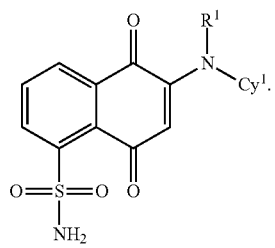

In a further aspect, the compound has a structure represented by a formula:

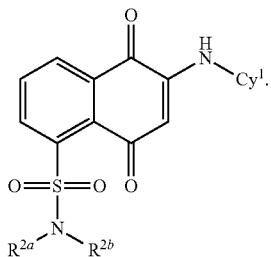

In a further aspect, the compound has a structure represented by a formula:

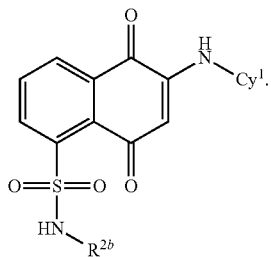

In a further aspect, the compound has a structure represented by a formula:

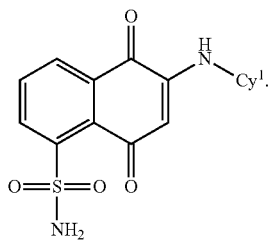

In a further aspect, the compound has a structure represented by a formula:

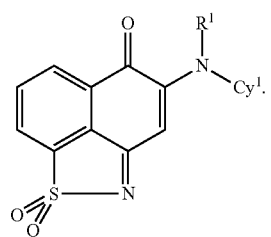

In a further aspect, the compound has a structure represented by a formula:

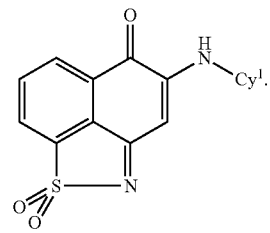

In a further aspect, the compound has a structure represented by a formula:

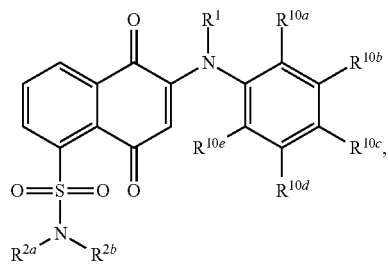

wherein each of $R^{10a}$, $R^{10b}$, $R^{10c}$, $R^{10d}$, and $R^{10e}$ is independently selected from hydrogen, halogen, —CN, —OH, —NH$_2$, —NO$_2$, C1-C6 alkyl, C1-C6 monohaloalkyl, C1-C6 polyhaloalkyl, C1-C6 hydroxyalkyl, C1-C6 monoalkylamino, C1-C6 dialkylamino, —(C1-C6)NR$^{4a}$R$^{4b}$, —(C1-C6)-(C=O)R$^3$, —(C1-C6)-(C=O)OR$^3$, —(C1-C6)-(C=O)NR$^{4a}$R$^{4b}$, —(C1-C6)-Ar$^2$, Ar$^2$, —(C1-C6)-Cy$^2$, Cy$^2$, and —S(O)$_n$NR$^{5a}$R$^{5b}$, provided that at least two of $R^{10a}$, $R^{10b}$, $R^{10c}$, $R^{10d}$, and $R^{10e}$ are hydrogen.

In a further aspect, the compound has a structure represented by a formula:

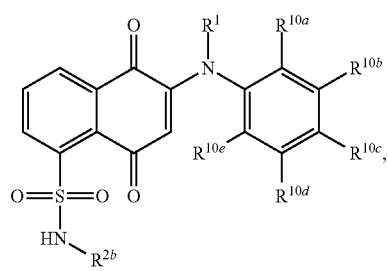

wherein each of $R^{10a}$, $R^{10b}$, $R^{10c}$, $R^{10d}$, and $R^{10e}$ is independently selected from hydrogen, halogen, —CN, —OH, —NH$_2$, —NO$_2$, C1-C6 alkyl, C1-C6 monohaloalkyl, C1-C6 polyhaloalkyl, C1-C6 hydroxyalkyl, C1-C6 monoalkylamino, C1-C6 dialkylamino, —(C1-C6)NR$^{4a}$R$^{4b}$, —(C1-C6)-(C=O)R$^3$, —(C1-C6)-(C=O)OR$^3$, —(C1-C6)-(C=O)NR$^{4a}$R$^{4b}$, —(C1-C6)-Ar$^2$, Ar$^2$, —(C1-C6)-Cy$^2$, Cy$^2$, and —S(O)$_n$NR$^{5a}$R$^{5b}$, provided that at least two of $R^{10a}$, $R^{10b}$, $R^{10c}$, $R^{10d}$, and $R^{10e}$ are hydrogen.

In a further aspect, the compound has a structure represented by a formula:

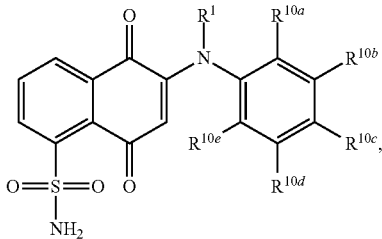

wherein each of $R^{10a}$, $R^{10b}$, $R^{10c}$, $R^{10d}$, and $R^{10e}$ is independently selected from hydrogen, halogen, —CN, —OH, —NH$_2$, —NO$_2$, C1-C6 alkyl, C1-C6 monohaloalkyl, C1-C6 polyhaloalkyl, C1-C6 hydroxyalkyl, C1-C6 monoalkylamino, C1-C6 dialkylamino, —(C1-C6)NR$^{4a}$R$^{4b}$, —(C1-C6)-(C=O)R$^3$, —(C1-C6)-(C=O)OR$^3$, —(C1-C6)-(C=O)NR$^{4a}$R$^{4b}$, —(C1-C6)-Ar$^2$, Ar$^2$, —(C1-C6)-Cy$^2$, Cy$^2$, and —S(O)$_n$NR$^{5a}$R$^{5b}$, provided that at least two of $R^{10a}$, $R^{10b}$, $R^{10c}$, $R^{10d}$, and $R^{10e}$ are hydrogen.

In a further aspect, the compound has a structure represented by a formula:

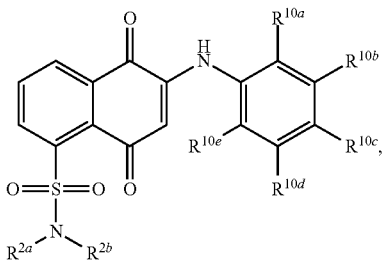

wherein each of $R^{10a}$, $R^{10b}$, $R^{10c}$, $R^{10d}$, and $R^{10e}$ is independently selected from hydrogen, halogen, —CN, —OH, —NH$_2$, —NO$_2$, C1-C6 alkyl, C1-C6 monohaloalkyl, C1-C6 polyhaloalkyl, C1-C6 hydroxyalkyl, C1-C6 monoalkylamino, C1-C6 dialkylamino, —(C1-C6)NR$^{4a}$R$^{4b}$, —(C1-C6)-(C=O)R$^3$, —(C1-C6)-(C=O)OR$^3$, —(C1-C6)-(C=O)NR$^{4a}$R$^{4b}$, —(C1-C6)-Ar$^2$, Ar$^2$, —(C1-C6)-Cy$^2$, Cy$^2$, and —S(O)$_n$NR$^{5a}$R$^{5b}$, provided that at least two of $R^{10a}$, $R^{10b}$, $R^{10c}$, $R^{10d}$, and $R^{10e}$ are hydrogen.

In a further aspect, the compound has a structure represented by a formula:

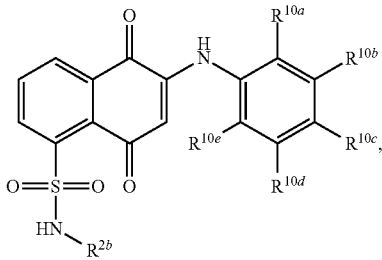

wherein each of $R^{10a}$, $R^{10b}$, $R^{10c}$, $R^{10d}$, and $R^{10e}$ is independently selected from hydrogen, halogen, —CN, —OH, —NH$_2$, —NO$_2$, C1-C6 alkyl, C1-C6 monohaloalkyl, C1-C6 polyhaloalkyl, C1-C6 hydroxyalkyl, C1-C6 monoalkylamino, C1-C6 dialkylamino, —(C1-C6)NR$^{4a}$R$^{4b}$, —(C1-C6)-(C=O)R$^3$, —(C1-C6)-(C=O)OR$^3$, —(C1-C6)-(C=O)NR$^{4a}$R$^{4b}$, —(C1-C6)-Ar$^2$, Ar$^2$, —(C1-C6)-Cy$^2$, Cy$^2$, and —S(O)$_n$NR$^{5a}$R$^{5b}$, provided that at least two of $R^{10a}$, $R^{10b}$, $R^{10c}$, $R^{10d}$, and $R^{10e}$ are hydrogen.

In a further aspect, the compound has a structure represented by a formula:

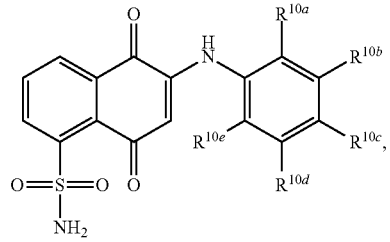

wherein each of $R^{10a}$, $R^{10b}$, $R^{10c}$, $R^{10d}$, and $R^{10e}$ is independently selected from hydrogen, halogen, —CN, —OH, —NH$_2$, —NO$_2$, C1-C6 alkyl, C1-C6 monohaloalkyl, C1-C6 polyhaloalkyl, C1-C6 hydroxyalkyl, C1-C6 monoalkylamino, C1-C6 dialkylamino, —(C1-C6)NR$^{4a}$R$^{4b}$, —(C1-C6)-(C=O)R$^3$, —(C1-C6)-(C=O)OR$^3$, —(C1-C6)-(C=O)NR$^{4a}$R$^{4b}$, —(C1-C6)-Ar$^2$, Ar$^2$, —(C1-C6)-Cy$^2$, Cy$^2$, and —S(O)$_n$NR$^{5a}$R$^{5b}$, provided that at least two of $R^{10a}$, $R^{10b}$, $R^{10c}$, $R^{10d}$, and $R^{10e}$ are hydrogen.

In a further aspect, the compound has a structure represented by a formula:

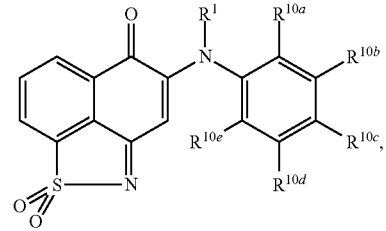

wherein each of $R^{10a}$, $R^{10b}$, $R^{10c}$, $R^{10d}$, and $R^{10e}$ is independently selected from hydrogen, halogen, —CN, —OH, —NH$_2$, —NO$_2$, C1-C6 alkyl, C1-C6 monohaloalkyl, C1-C6 polyhaloalkyl, C1-C6 hydroxyalkyl, C1-C6 monoalkylamino, C1-C6 dialkylamino, —(C1-C6)NR$^{4a}$R$^{4b}$, —(C1-C6)-(C=O)R$^3$, —(C1-C6)-(C=O)OR$^3$, —(C1-C6)-(C=O)NR$^{4a}$R$^{4b}$, —(C1-C6)-Ar$^2$, Ar$^2$, —(C1-C6)-Cy$^2$, Cy$^2$, and —S(O)$_n$NR$^{5a}$R$^{5b}$, provided that at least two of $R^{10a}$, $R^{10b}$, $R^{10c}$, $R^{10d}$, and $R^{10e}$ are hydrogen.

In a further aspect, the compound has a structure represented by a formula:

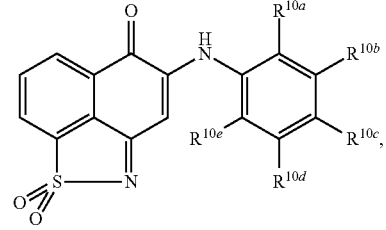

wherein each of $R^{10a}$, $R^{10b}$, $R^{10c}$, $R^{10d}$, and $R^{10e}$ is independently selected from hydrogen, halogen, —CN, —OH, —NH$_2$, —NO$_2$, C1-C6 alkyl, C1-C6 monohaloalkyl, C1-C6 polyhaloalkyl, C1-C6 hydroxyalkyl, C1-C6 monoalkylamino, C1-C6 dialkylamino, —(C1-C6)NR$^{4a}$R$^{4b}$, —(C1-C6)-(C=O)R$^3$, —(C1-C6)-(C=O)OR$^3$, —(C1-C6)-(C=O)NR$^{4a}$R$^{4b}$, —(C1-C6)-Ar$^2$, Ar$^2$, —(C1-C6)-Cy$^2$, Cy$^2$, and —S(O)$_n$NR$^{5a}$R$^{5b}$, provided that at least two of $R^{10a}$, $R^{10b}$, $R^{10c}$, $R^{10d}$, and $R^{10e}$ are hydrogen.

In a further aspect, the compound has a structure represented by a formula:

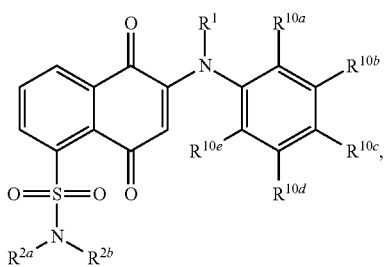

wherein each of $R^{10a}$, $R^{10b}$, $R^{10c}$, $R^{10d}$, and $R^{10e}$ is independently selected from hydrogen, —F, —Cl, —CN, —OH, —NH$_2$, —NO$_2$, methyl, —CF$_3$, —CHF$_2$, —CH$_2$F, C1-C6 hydroxyalkyl, C1-C6 monoalkylamino, C1-C6 dialkylamino, —(C1-C6)NR$^{4a}$R$^{4b}$, —(C1-C6)-(C=O)OH, Cy$^2$, and —S(O)$_n$NR$^{5a}$R$^{5b}$, provided that at least three of $R^{10a}$, $R^{10b}$, $R^{10c}$, $R^{10d}$, and $R^{10e}$ are hydrogen.

In a further aspect, the compound has a structure represented by a formula:

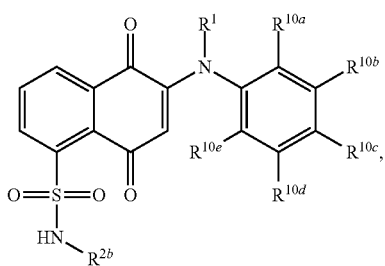

wherein each of $R^{10a}$, $R^{10b}$, $R^{10c}$, $R^{10d}$, and $R^{10e}$ is independently selected from hydrogen, —F, —Cl, —CN, —OH, —NH$_2$, —NO$_2$, methyl, —CF$_3$, —CHF$_2$, —CH$_2$F, C1-C6 hydroxyalkyl, C1-C6 monoalkylamino, C1-C6 dialkylamino, —(C1-C6)NR$^{4a}$R$^{4b}$, —(C1-C6)-(C=O)OH, Cy$^2$, and —S(O)$_n$NR$^{5a}$R$^{5b}$, provided that at least three of $R^{10a}$, $R^{10b}$, $R^{10c}$, $R^{10d}$, and $R^{10e}$ are hydrogen.

In a further aspect, the compound has a structure represented by a formula:

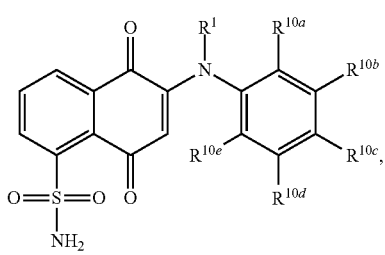

wherein each of $R^{10a}$, $R^{10b}$, $R^{10c}$, $R^{10d}$, and $R^{10e}$ is independently selected from hydrogen, —F, —Cl, —CN, —OH, —NH$_2$, —NO$_2$, methyl, —CF$_3$, —CHF$_2$, —CH$_2$F, C1-C6 hydroxyalkyl, C1-C6 monoalkylamino, C1-C6 dialkylamino, —(C1-C6)NR$^{4a}$R$^{4b}$, —(C1-C6)-(C=O)OH, Cy$^2$, and —S(O)$_n$NR$^{5a}$R$^{5b}$, provided that at least three of $R^{10a}$, $R^{10b}$, $R^{10c}$, $R^{10d}$, and $R^{10e}$ are hydrogen.

In a further aspect, the compound has a structure represented by a formula:

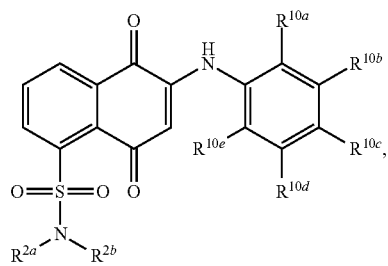

wherein each of $R^{10a}$, $R^{10b}$, $R^{10c}$, $R^{10d}$, and $R^{10e}$ is independently selected from hydrogen, —F, —Cl, —CN, —OH, —NH$_2$, —NO$_2$, methyl, —CF$_3$, —CHF$_2$, —CH$_2$F, C1-C6 hydroxyalkyl, C1-C6 monoalkylamino, C1-C6 dialkylamino, —(C1-C6)NR$^{4a}$R$^{4b}$, —(C1-C6)-(C=O)OH, Cy$^2$, and —S(O)$_n$NR$^{5a}$R$^{5b}$, provided that at least three of $R^{10a}$, $R^{10b}$, $R^{10c}$, $R^{10d}$, and $R^{10e}$ are hydrogen.

In a further aspect, the compound has a structure represented by a formula:

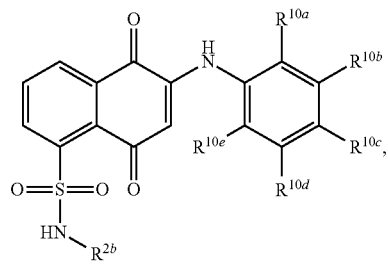

wherein each of $R^{10a}$, $R^{10b}$, $R^{10c}$, $R^{10d}$, and $R^{10e}$ is independently selected from hydrogen, —F, —Cl, —CN, —OH, —NH$_2$, —NO$_2$, methyl, —CF$_3$, —CHF$_2$, —CH$_2$F, C1-C6 hydroxyalkyl, C1-C6 monoalkylamino, C1-C6 dialkylamino, —(C1-C6)NR$^{4a}$R$^{4b}$, —(C1-C6)-(C=O)OH, Cy$^2$, and —S(O)$_n$NR$^{5a}$R$^{5b}$, provided that at least three of $R^{10a}$, $R^{10b}$, $R^{10c}$, $R^{10d}$, and $R^{10e}$ are hydrogen.

In a further aspect, the compound has a structure represented by a formula:

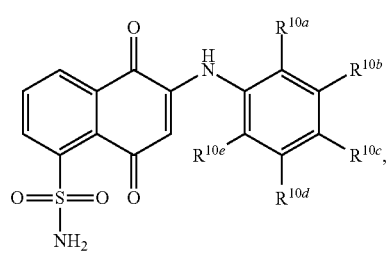

wherein each of $R^{10a}$, $R^{10b}$, $R^{10c}$, $R^{10d}$, and $R^{10e}$ is independently selected from hydrogen, —F, —Cl, —CN, —OH, —NH$_2$, —NO$_2$, methyl, —CF$_3$, —CHF$_2$, —CH$_2$F, C1-C6 hydroxyalkyl, C1-C6 monoalkylamino, C1-C6 dialkylamino, —(C1-C6)NR$^{4a}$R$^{4b}$, —(C1-C6)-(C=O)OH, Cy$^2$, and —S(O)$_n$NR$^{5a}$R$^{5b}$, provided that at least three of $R^{10a}$, $R^{10b}$, $R^{10c}$, $R^{10d}$, and $R^{10e}$ are hydrogen.

In a further aspect, the compound has a structure represented by a formula:

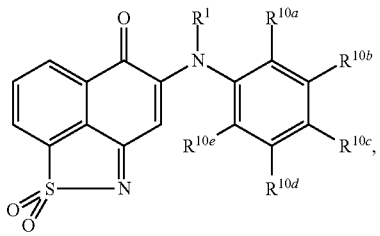

wherein each of $R^{10a}$, $R^{10b}$, $R^{10c}$, $R^{10d}$, and $R^{10e}$ is independently selected from hydrogen, —F, —Cl, —CN, —OH, —NH$_2$, —NO$_2$, methyl, —CF$_3$, —CHF$_2$, —CH$_2$F, C1-C6 hydroxyalkyl, C1-C6 monoalkylamino, C1-C6 dialkylamino, —(C1-C6)NR$^{4a}$R$^{4b}$, —(C1-C6)-(C=O)OH, Cy$^2$, and —S(O)$_n$NR$^{5a}$R$^{5b}$, provided that at least three of $R^{10a}$, $R^{10b}$, $R^{10c}$, $R^{10d}$, and $R^{10e}$ are hydrogen.

In a further aspect, the compound has a structure represented by a formula:

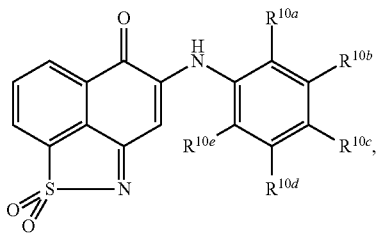

wherein each of $R^{10a}$, $R^{10b}$, $R^{10c}$, $R^{10d}$, and $R^{10e}$ is independently selected from hydrogen, —F, —Cl, —CN, —OH, —NH$_2$, —NO$_2$, methyl, —CF$_3$, —CHF$_2$, —CH$_2$F, C1-C6 hydroxyalkyl, C1-C6 monoalkylamino, C1-C6 dialkylamino, —(C1-C6)NR$^{4a}$R$^{4b}$, —(C1-C6)-(C=O)OH, Cy$^2$, and —S(O)$_n$NR$^{5a}$R$^{5b}$, provided that at least three of $R^{10a}$, $R^{10b}$, $R^{10c}$, $R^{10d}$, and $R^{10e}$ are hydrogen.

In a further aspect, the compound has a structure represented by a formula:

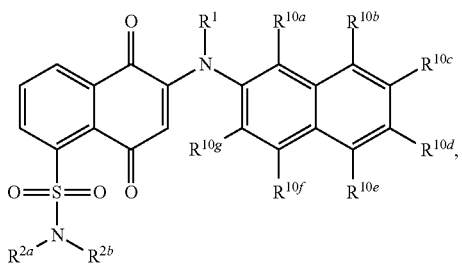

wherein each of $R^{10a}$, $R^{10b}$, $R^{10c}$, $R^{10d}$, $R^{10e}$, $R^{10f}$, and $R^{10g}$ is independently selected from hydrogen, halogen, —CN, —OH, —NH$_2$, —NO$_2$, C1-C6 alkyl, C1-C6 monohaloalkyl, C1-C6 polyhaloalkyl, C1-C6 hydroxyalkyl, C1-C6 monoalkylamino, C1-C6 dialkylamino, —(C1-C6)NR$^{4a}$R$^{4b}$, —(C1-C6)-(C=O)R$^3$, —(C1-C6)(C=O)OR$^3$, —(C1-C6)-(C=O)NR$^{4a}$R$^{4b}$, —(C1-C6)-Ar$^2$, Ar$^2$, —(C1-C6)-Cy$^2$, Cy$^2$, and —S(O)$_n$NR$^{5a}$R$^{5b}$, provided that at least four of $R^{10a}$, $R^{10b}$, $R^{10c}$, $R^{10d}$, $R^{10e}$, $R^{10f}$, and $R^{10g}$ are hydrogen.

In a further aspect, the compound has a structure represented by a formula:

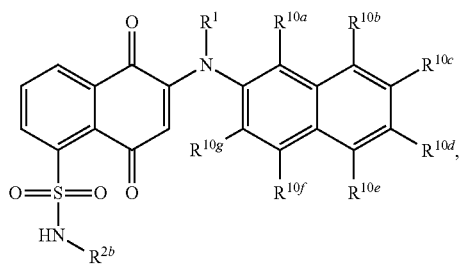

wherein each of $R^{10a}$, $R^{10b}$, $R^{10c}$, $R^{10d}$, $R^{10e}$, $R^{10f}$, and $R^{10g}$ is independently selected from hydrogen, halogen, —CN, —OH, —NH$_2$, —NO$_2$, C1-C6 alkyl, C1-C6 monohaloalkyl, C1-C6 polyhaloalkyl, C1-C6 hydroxyalkyl, C1-C6 monoalkylamino, C1-C6 dialkylamino, —(C1-C6)NR$^{4a}$R$^{4b}$, —(C1-C6)-(C=O)R$^3$, —(C1-C6)-(C=O)OR$^3$, —(C1-C6)-(C=O)NR$^{4a}$R$^{4b}$, —(C1-C6)-Ar$^2$, Ar$^2$, —(C1-C6)-Cy$^2$, Cy$^2$, and —S(O)$_n$NR$^{5a}$R$^{5b}$, provided that at least four of $R^{10a}$, $R^{10b}$, $R^{10c}$, $R^{10d}$, $R^{10e}$, $R^{10f}$, and $R^{10g}$ are hydrogen.

In a further aspect, the compound has a structure represented by a formula:

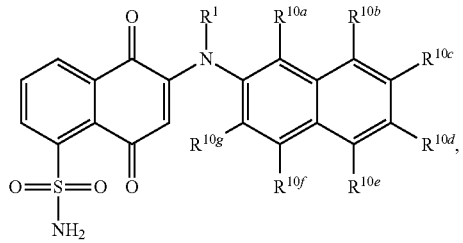

wherein each of $R^{10a}$, $R^{10b}$, $R^{10c}$, $R^{10d}$, $R^{10e}$, $R^{10f}$, and $R^{10g}$ is independently selected from hydrogen, halogen, —CN, —OH, —NH$_2$, —NO$_2$, C1-C6 alkyl, C1-C6 monohaloalkyl, C1-C6 polyhaloalkyl, C1-C6 hydroxyalkyl, C1-C6 monoalkylamino, C1-C6 dialkylamino, —(C1-C6)NR$^{4a}$R$^{4b}$, —(C1-C6)-(C=O)R$^3$, —(C1-C6)-(C=O)OR$^3$, —(C1-C6)-(C=O)NR$^{4a}$R$^{4b}$, —(C1-C6)-Ar$^2$, Ar$^2$, —(C1-C6)-Cy$^2$, Cy$^2$, and —S(O)$_n$NR$^{5a}$R$^{5b}$, provided that at least four of $R^{10a}$, $R^{10b}$, $R^{10c}$, $R^{10d}$, $R^{10e}$, $R^{10f}$, and $R^{10g}$ are hydrogen.

In a further aspect, the compound has a structure represented by a formula:

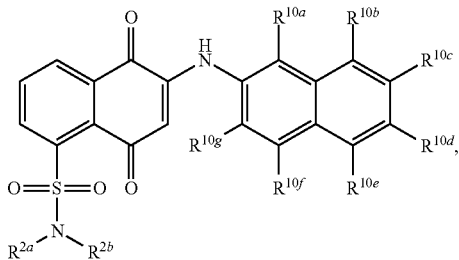

wherein each of $R^{10a}$, $R^{10b}$, $R^{10c}$, $R^{10d}$, $R^{10e}$, $R^{10f}$, and $R^{10g}$ is independently selected from hydrogen, halogen, —CN, —OH, —NH$_2$, —NO$_2$, C1-C6 alkyl, C1-C6 monohaloalkyl, C1-C6 polyhaloalkyl, C1-C6 hydroxyalkyl, C1-C6 monoalkylamino, C1-C6 dialkylamino, —(C1-C6)NR$^{4a}$R$^{4b}$, —(C1-C6)-(C=O)R$^3$, —(C1-C6)-(C=O)OR$^3$, —(C1-C6)-(C=O)NR$^{4a}$R$^{4b}$, —(C1-C6)-Ar$^2$, Ar$^2$, —(C1-C6)-Cy$^2$, Cy$^2$, and —S(O)$_n$NR$^{5a}$R$^{5b}$, provided that at least four of $R^{10a}$, $R^{10b}$, $R^{10c}$, $R^{10d}$, $R^{10e}$, $R^{10f}$, and $R^{10g}$ are hydrogen.

In a further aspect, the compound has a structure represented by a formula:

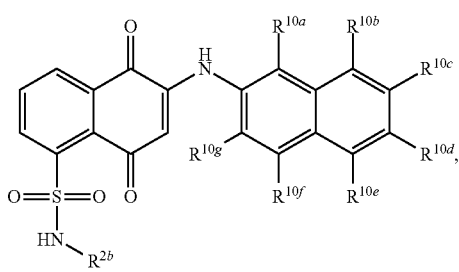

wherein each of $R^{10a}$, $R^{10b}$, $R^{10c}$, $R^{10d}$, $R^{10e}$, $R^{10f}$, and $R^{10g}$ is independently selected from hydrogen, halogen, —CN, —OH, —NH$_2$, —NO$_2$, C1-C6 alkyl, C1-C6 monohaloalkyl, C1-C6 polyhaloalkyl, C1-C6 hydroxyalkyl, C1-C6 monoalkylamino, C1-C6 dialkylamino, —(C1-C6)NR$^{4a}$R$^{4b}$, —(C1-C6)-(C=O)R$^3$, —(C1-C6)-(C=O)OR$^3$, —(C1-C6)-(C=O)NR$^{4a}$R$^{4b}$, —(C1-C6)-Ar$^2$, Ar$^2$, —(C1-C6)-Cy$^2$, Cy$^2$, and —S(O)$_n$NR$^{5a}$R$^{5b}$, provided that at least four of $R^{10a}$, $R^{10b}$, $R^{10c}$, $R^{10d}$, $R^{10e}$, $R^{10f}$, and $R^{10g}$ are hydrogen.

In a further aspect, the compound has a structure represented by a formula:

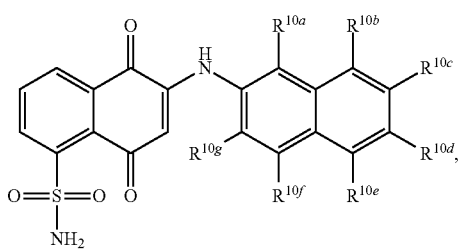

wherein each of $R^{10a}$, $R^{10b}$, $R^{10c}$, $R^{10d}$, $R^{10e}$, $R^{10f}$, and $R^{10g}$ is independently selected from hydrogen, halogen, —CN, —OH, —NH$_2$, —NO$_2$, C1-C6 alkyl, C1-C6 monohaloalkyl, C1-C6 polyhaloalkyl, C1-C6 hydroxyalkyl, C1-C6 monoalkylamino, C1-C6 dialkylamino, —(C1-C6)NR$^{4a}$R$^{4b}$, —(C1-C6)-(C=O)R$^3$, —(C1-C6)-(C=O)OR$^3$, —(C1-C6)-(C=O)NR$^{4a}$R$^{4b}$, —(C1-C6)-Ar$^2$, Ar$^2$, —(C1-C6)-Cy$^2$, Cy$^2$, and —S(O)$_n$NR$^{5a}$R$^{5b}$, provided that at least four of $R^{10a}$, $R^{10b}$, $R^{10c}$, $R^{10d}$, $R^{10e}$, $R^{10f}$, and $R^{10g}$ are hydrogen.

In a further aspect, the compound has a structure represented by a formula:

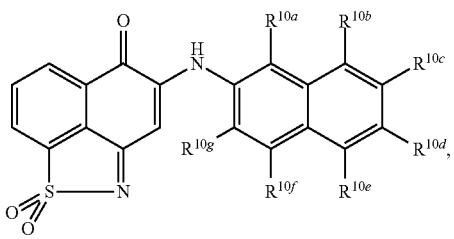

wherein each of $R^{10a}$, $R^{10b}$, $R^{10c}$, $R^{10d}$, $R^{10e}$, $R^{10f}$, and $R^{10g}$ is independently selected from hydrogen, halogen, —CN, —OH, —NH$_2$, —NO$_2$, C1-C6 alkyl, C1-C6 monohaloalkyl, C1-C6 polyhaloalkyl, C1-C6 hydroxyalkyl, C1-C6 monoalkylamino, C1-C6 dialkylamino, —(C1-C6)NR$^{4a}$R$^{4b}$, —(C1-C6)-(C=O)R$^3$, —(C1-C6)(C=O)OR$^3$, —(C1-C6)-(C=O)NR$^{4a}$R$^{4b}$, —(C1-C6)-Ar$^2$, Ar$^2$, —(C1-C6)-Cy$^2$, Cy$^2$, and —S(O)$_n$NR$^{5a}$R$^{5b}$, provided that at least four of $R^{10a}$, $R^{10b}$, $R^{10c}$, $R^{10d}$, $R^{10e}$, $R^{10f}$, and $R^{10g}$ are hydrogen.

In a further aspect, the compound has a structure represented by a formula:

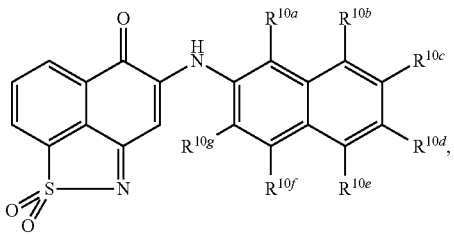

wherein each of $R^{10a}$, $R^{10b}$, $R^{10c}$, $R^{10d}$, $R^{10e}$, $R^{10f}$, and $R^{10g}$ is independently selected from hydrogen, halogen, —CN, —OH, —NH$_2$, —NO$_2$, C1-C6 alkyl, C1-C6 monohaloalkyl, C1-C6 polyhaloalkyl, C1-C6 hydroxyalkyl, C1-C6 monoalkylamino, C1-C6 dialkylamino, —(C1-C6)NR$^{4a}$R$^{4b}$, —(C1-C6)-(C=O)R$^3$, —(C1-C6)-(C=O)OR$^3$, —(C1-C6)-(C=O)NR$^{4a}$R$^{4b}$, —(C1-C6)-Ar$^2$, Ar$^2$, —(C1-C6)-Cy$^2$, Cy$^2$, and —S(O)$_n$NR$^{5a}$R$^{5b}$, provided that at least four of $R^{1a}$, $R^{10b}$, $R^{10c}$, $R^{10d}$, $R^{10e}$, $R^{10f}$, and $R^{10g}$ are hydrogen.

In a further aspect, the compound has a structure represented by a formula:

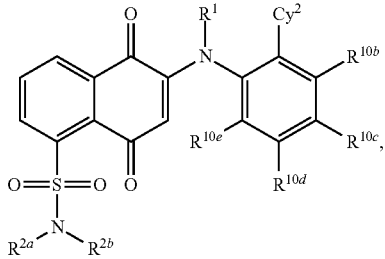

wherein each of $R^{10a}$, $R^{10b}$, $R^{10c}$, $R^{10d}$, and $R^{10e}$ is independently selected from hydrogen, halogen, —CN, —OH, —NH$_2$, —NO$_2$, C1-C6 alkyl, C1-C6 monohaloalkyl, C1-C6 polyhaloalkyl, C1-C6 hydroxyalkyl, C1-C6 monoalkylamino, C1-C6 dialkylamino, —(C1-C6)NR$^{4a}$R$^{4b}$, —(C1-C6)-(C=O)R$^3$, —(C1-C6)-(C=O)OR$^3$, —(C1-C6)-(C=O)NR$^{4a}$R$^{4b}$, —(C1-C6)-Ar$^2$, Ar$^2$, —(C1-C6)-Cy$^2$, Cy$^2$, and —S(O)$_n$NR$^{5a}$R$^{5b}$, provided that at least two of R$^{10a}$, R$^{10b}$, R$^{10c}$, R$^{10d}$, and R$^{10e}$ are hydrogen.

In a further aspect, the compound has a structure represented by a formula:

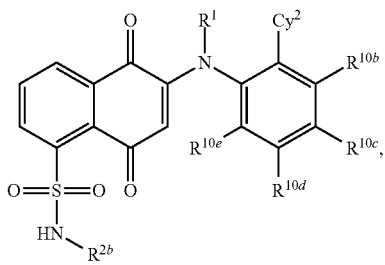

wherein each of R$^{10a}$, R$^{10b}$, R$^{10c}$, R$^{10d}$, and R$^{10e}$ is independently selected from hydrogen, halogen, —CN, —OH, —NH$_2$, —NO$_2$, C1-C6 alkyl, C1-C6 monohaloalkyl, C1-C6 polyhaloalkyl, C1-C6 hydroxyalkyl, C1-C6 monoalkylamino, C1-C6 dialkylamino, —(C1-C6)NR$^{4a}$R$^{4b}$, —(C1-C6)-(C=O)R$^3$, —(C1-C6)-(C=O)OR$^3$, —(C1-C6)-(C=O)NR$^{4a}$R$^{4b}$, —(C1-C6)-Ar$^2$, Ar$^2$, —(C1-C6)-Cy$^2$, Cy$^2$, and —S(O)$_n$NR$^{5a}$R$^{5b}$, provided that at least two of R$^{10a}$, R$^{10b}$, R$^{10c}$, R$^{10d}$, and R$^{10e}$ are hydrogen.

In a further aspect, the compound has a structure represented by a formula:

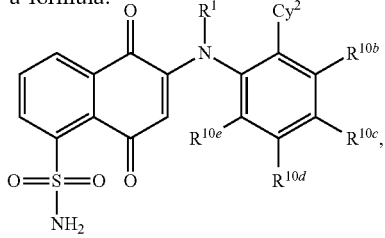

wherein each of R$^{10a}$, R$^{10b}$, R$^{10c}$, R$^{10d}$, and R$^{10e}$ is independently selected from hydrogen, halogen, —CN, —OH, —NH$_2$, —NO$_2$, C1-C6 alkyl, C1-C6 monohaloalkyl, C1-C6 polyhaloalkyl, C1-C6 hydroxyalkyl, C1-C6 monoalkylamino, C1-C6 dialkylamino, —(C1-C6)NR$^{4a}$R$^{4b}$, —(C1-C6)-(C=O)R$^3$, —(C1-C6)-(C=O)OR$^3$, —(C1-C6)-(C=O)NR$^{4a}$R$^{4b}$, —(C1-C6)-Ar$^2$, Ar$^2$, —(C1-C6)-Cy$^2$, Cy$^2$, and —S(O)$_n$NR$^{5a}$R$^{5b}$, provided that at least two of R$^{10a}$, R$^{10b}$, R$^{10c}$, R$^{10d}$, and R$^{10e}$ are hydrogen.

In a further aspect, the compound has a structure represented by a formula:

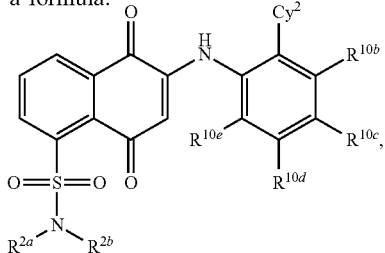

wherein each of R$^{10a}$, R$^{10b}$, R$^{10c}$, R$^{10d}$, and R$^{10e}$ is independently selected from hydrogen, halogen, —CN, —OH, —NH$_2$, —NO$_2$, C1-C6 alkyl, C1-C6 monohaloalkyl, C1-C6 polyhaloalkyl, C1-C6 hydroxyalkyl, C1-C6 monoalkylamino, C1-C6 dialkylamino, —(C1-C6)NR$^{4a}$R$^{4b}$, —(C1-C6)-(C=O)R$^3$, —(C1-C6)-(C=O)OR$^3$, —(C1-C6)-(C=O)NR$^{4a}$R$^{4b}$, —(C1-C6)-Ar$^2$, Ar$^2$, —(C1-C6)-Cy$^2$, Cy$^2$, and —S(O)$_n$NR$^{5a}$R$^{5b}$, provided that at least two of R$^{10a}$, R$^{10b}$, R$^{10c}$, R$^{10d}$, and R$^{10e}$ are hydrogen.

In a further aspect, the compound has a structure represented by a formula:

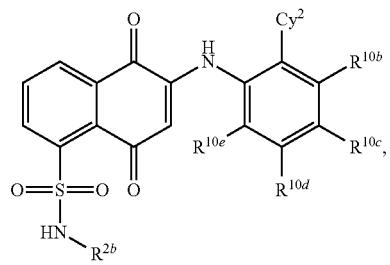

wherein each of R$^{10a}$, R$^{10b}$, R$^{10c}$, R$^{10d}$, and R$^{10e}$ is independently selected from hydrogen, halogen, —CN, —OH, —NH$_2$, —NO$_2$, C1-C6 alkyl, C1-C6 monohaloalkyl, C1-C6 polyhaloalkyl, C1-C6 hydroxyalkyl, C1-C6 monoalkylamino, C1-C6 dialkylamino, —(C1-C6)NR$^{4a}$R$^{4b}$, —(C1-C6)-(C=O)R$^3$, —(C1-C6)-(C=O)OR$^3$, —(C1-C6)-(C=O)NR$^{4a}$R$^{4b}$, —(C1-C6)-Ar$^2$, Ar$^2$, —(C1-C6)-Cy$^2$, Cy$^2$, and —S(O)$_n$NR$^{5a}$R$^{5b}$, provided that at least two of R$^{10a}$, R$^{10b}$, R$^{10c}$, R$^{10d}$, and R$^{10e}$ are hydrogen.

In a further aspect, the compound has a structure represented by a formula:

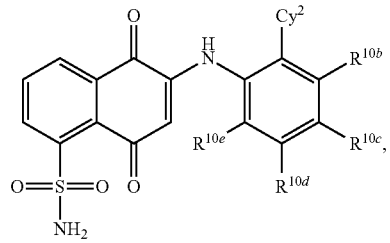

wherein each of R$^{10a}$, R$^{10b}$, R$^{10c}$, R$^{10d}$, and R$^{10e}$ is independently selected from hydrogen, halogen, —CN, —OH, —NH$_2$, —NO$_2$, C1-C6 alkyl, C1-C6 monohaloalkyl, C1-C6 polyhaloalkyl, C1-C6 hydroxyalkyl, C1-C6 monoalkylamino, C1-C6 dialkylamino, —(C1-C6)NR$^{4a}$R$^{4b}$, —(C1-C6)-(C=O)R$^3$, —(C1-C6)-(C=O)OR$^3$, —(C1-C6)-(C=O)NR$^{4a}$R$^{4b}$, —(C1-C6)-Ar$^2$, Ar$^2$, —(C1-C6)-Cy$^2$, Cy$^2$, and —S(O)$_n$NR$^{5a}$R$^{5b}$, provided that at least two of R$^{10a}$, R$^{10b}$, R$^{10c}$, R$^{10d}$, and R$^{10e}$ are hydrogen.

In a further aspect, the compound has a structure represented by a formula:

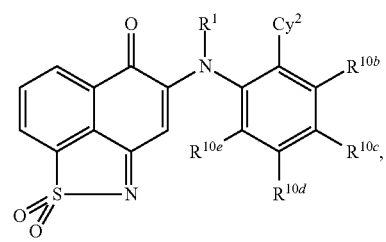

wherein each of $R^{10a}$, $R^{10b}$, $R^{10c}$, $R^{10d}$, and $R^{10e}$ is independently selected from hydrogen, halogen, —CN, —OH, —NH$_2$, —NO$_2$, C1-C6 alkyl, C1-C6 monohaloalkyl, C1-C6 polyhaloalkyl, C1-C6 hydroxyalkyl, C1-C6 monoalkylamino, C1-C6 dialkylamino, —(C1-C6)NR$^{4a}$R$^{4b}$, —(C1-C6)-(C=O)R$^3$, —(C1-C6)-(C=O)OR$^3$, —(C1-C6)-(C=O)NR$^{4a}$R$^{4b}$, —(C1-C6)-Ar$^2$, Ar$^2$, —(C1-C6)-Cy$^2$, Cy$^2$, and —S(O)$_n$NR$^{5a}$R$^{5b}$, provided that at least two of $R^{10a}$, $R^{10b}$, $R^{10c}$, $R^{10d}$, and $R^{10e}$ are hydrogen.

In a further aspect, the compound has a structure represented by a formula:

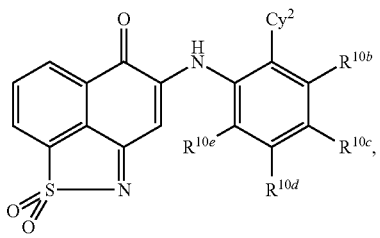

wherein each of $R^{10a}$, $R^{10b}$, $R^{10c}$, $R^{10d}$, and $R^{10e}$ is independently selected from hydrogen, halogen, —CN, —OH, —NH$_2$, —NO$_2$, C1-C6 alkyl, C1-C6 monohaloalkyl, C1-C6 polyhaloalkyl, C1-C6 hydroxyalkyl, C1-C6 monoalkylamino, C1-C6 dialkylamino, —(C1-C6)NR$^{4a}$R$^{4b}$, —(C1-C6)-(C=O)R$^3$, —(C1-C6)-(C=O)OR$^3$, —(C1-C6)-(C=O)NR$^{4a}$R$^{4b}$, —(C1-C6)-Ar$^2$, Ar$^2$, —(C1-C6)-Cy$^2$, Cy$^2$, and —S(O)$_n$NR$^{5a}$R$^{5b}$, provided that at least two of $R^{10a}$, $R^{10b}$, $R^{10c}$, $R^{10d}$, and $R^{10e}$ are hydrogen.

In a further aspect, the compound has a structure represented by a formula:

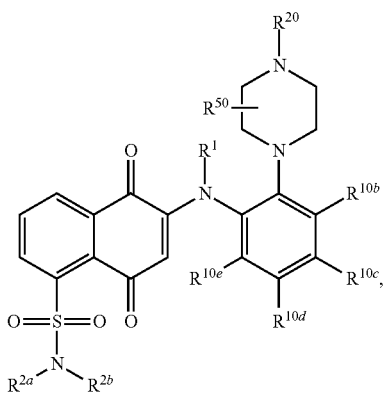

wherein each of $R^{10a}$, $R^{10b}$, $R^{10c}$, $R^{10d}$, and $R^{10e}$ is independently selected from hydrogen, halogen, —CN, —OH, —NH$_2$, —NO$_2$, C1-C6 alkyl, C1-C6 monohaloalkyl, C1-C6 polyhaloalkyl, C1-C6 hydroxyalkyl, C1-C6 monoalkylamino, C1-C6 dialkylamino, —(C1-C6)NR$^{4a}$R$^{4b}$, —(C1-C6)-(C=O)R$^3$, —(C1-C6)-(C=O)OR$^3$, —(C1-C6)-(C=O)NR$^{4a}$R$^{4b}$, —(C1-C6)-Ar$^2$, Ar$^2$, —(C1-C6)-Cy$^2$, Cy$^2$, and —S(O)$_n$NR$^{5a}$R$^{5b}$, provided that at least two of $R^{10a}$, $R^{10b}$, $R^{10c}$, $R^{10d}$, and $R^{10e}$ are hydrogen; wherein each $R^{50}$ is independently selected from hydrogen, halogen, —CN, —OH, —NH$_2$, —NO$_2$, C1-C6 alkyl, C1-C6 monohaloalkyl, C1-C6 polyhaloalkyl, C1-C6 hydroxyalkyl, C1-C6 aminoalkyl, C1-C6 monoalkylamino, C1-C6 dialkylamino, —(C=O)R, —(C=O)OR$^7$, —(C=O)NR$^{5a}$R$^{8b}$, —(C=O)—(C1-C6 alkyl)Ar$^3$, —(C=O)—O—(C1-C6 alkyl)Ar$^3$, and —(C=O)—NR$^{8a}$—(C1-C6 alkyl)Ar$^3$, provided that at least six of $R^{50}$ are hydrogen; and wherein $R^{20}$ is selected from hydrogen, C1-C6 alkyl, C1-C6 monohaloalkyl, C1-C6 polyhaloalkyl, C1-C6 hydroxyalkyl, C1-C6 aminoalkyl, C1-C6 monoalkylamino, C1-C6 dialkylamino, —(C=O)R, —(C=O)OR, —(C=O)NR$^{8a}$R$^{8b}$, —(C=O)—(C1-C6 alkyl)Ar$^3$, —(C=O)—O—(C1-C6 alkyl)Ar$^3$, and —(C=O)—NR$^{8a}$—(C1-C6 alkyl)Ar$^3$.

For clarity, a structure or moiety of a compound can be represented by a formula such as:

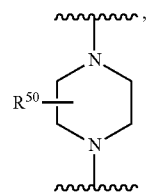

is understood to be equivalent to a formula:

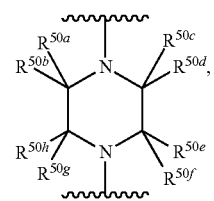

that is, $R^{50}$ is understood to represent, in this case, eight independent substituents, $R^{50a}$, $R^{50b}$ $R^{50c}$, $R^{50d}$, $R^{50e}$, $R^{50f}$, $R^{50g}$, and $R^{50h}$. Thus, if it is stated that "each $R^{50}$ is independently selected from," it is meant that, in this context, each of $R^{50a}$, $R^{50b}$, $R^{50c}$, $R^{50d}$, $R^{50e}$, $R^{50f}$, $R^{50g}$ and $R^{50h}$ can be independently defined. For example, if in one instance $R^{50a}$ is halogen, then $R^{50b}$, $R^{50c}$, $R^{50d}$, $R^{50e}$, $R^{50f}$, $R^{50g}$, and $R^{50h}$ are not necessarily halogen in that instance.

In a further aspect, the compound has a structure represented by a formula:

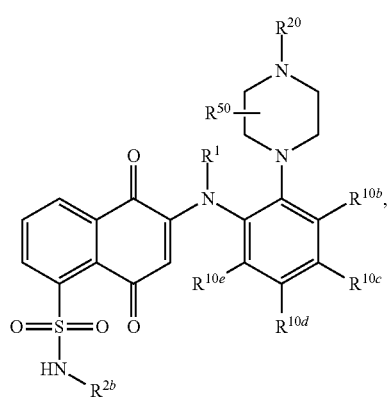

wherein each of $R^{10a}$, $R^{10b}$, $R^{10c}$, $R^{10d}$, and $R^{10e}$ is independently selected from hydrogen, halogen, —CN, —OH, —NH$_2$, —NO$_2$, C1-C6 alkyl, C1-C6 monohaloalkyl, C1-C6 polyhaloalkyl, C1-C6 hydroxyalkyl, C1-C6 monoalkylamino, C1-C6 dialkylamino, —(C1-C6)NR$^{4a}$R$^{4b}$, —(C1-C6)-(C=O)R$^3$, —(C1-C6)-(C=O)OR$^3$, —(C1-C6)-

(C=O)NR$^{4a}$R$^{4b}$, —(C1-C6)-Ar$^2$, Ar$^2$, —(C1-C6)-Cy$^2$, Cy$^2$, and —S(O)$_n$NR$^{5a}$R$^{5b}$, provided that at least two of R$^{10a}$, R$^{10b}$, R$^{10c}$, R$^{10d}$, and R$^{10e}$ are hydrogen; wherein each R$^{50}$ is independently selected from hydrogen, halogen, —CN, —OH, —NH$_2$, —NO$_2$, C1-C6 alkyl, C1-C6 monohaloalkyl, C1-C6 polyhaloalkyl, C1-C6 hydroxyalkyl, C1-C6 aminoalkyl, C1-C6 monoalkylamino, C1-C6 dialkylamino, —(C=O)R$^7$, —(C=O)OR$^7$, —(C=O)NR$^{8a}$R$^{8b}$, —(C=O)—(C1-C6 alkyl)Ar$^3$, —(C=O)—O—(C1-C6 alkyl)Ar$^3$, and —(C=O)—NR$^{8a}$—(C1-C6 alkyl)Ar$^3$, provided that at least six of R$^{50}$ are hydrogen; and wherein R$^{20}$ is selected from hydrogen, C1-C6 alkyl, C1-C6 monohaloalkyl, C1-C6 polyhaloalkyl, C1-C6 hydroxyalkyl, C1-C6 aminoalkyl, C1-C6 monoalkylamino, C1-C6 dialkylamino, —(C=O)R$^7$, —(C=O)OR$^7$, —(C=O)NR$^{8a}$R$^{8b}$, —(C=O)—(C1-C6 alkyl)Ar$^3$, —(C=O)—O—(C1-C6 alkyl)Ar$^3$, and —(C=O)—NR$^{8a}$—(C1-C6 alkyl)Ar$^3$.

In a further aspect, the compound has a structure represented by a formula:

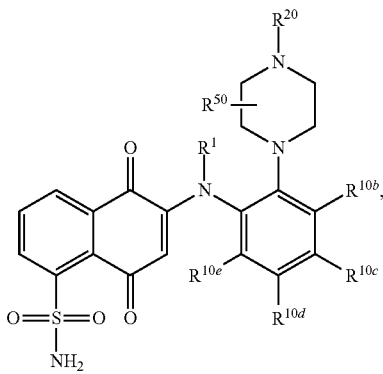

wherein each of R$^{10a}$, R$^{10b}$, R$^{10c}$, R$^{10d}$, and R$^{10e}$ is independently selected from hydrogen, halogen, —CN, —OH, —NH$_2$, —NO$_2$, C1-C6 alkyl, C1-C6 monohaloalkyl, C1-C6 polyhaloalkyl, C1-C6 hydroxyalkyl, C1-C6 monoalkylamino, C1-C6 dialkylamino, —(C1-C6)NR$^{4a}$R$^{4b}$, —(C1-C6)-(C=O)R$^3$, —(C1-C6)-(C=O)OR$^3$, —(C1-C6)-(C=O)NR$^{4a}$R$^{4b}$, —(C1-C6)-Ar$^2$, Ar$^2$, —(C1-C6)-Cy$^2$, Cy$^2$, and —S(O)$_n$NR$^{5a}$R$^{5b}$, provided that at least two of R$^{10a}$, R$^{10b}$, R$^{10c}$, R$^{10d}$, and R$^{10e}$ are hydrogen; wherein each R$^{50}$ is independently selected from hydrogen, halogen, —CN, —OH, —NH$_2$, —NO$_2$, C1-C6 alkyl, C1-C6 monohaloalkyl, C1-C6 polyhaloalkyl, C1-C6 hydroxyalkyl, C1-C6 aminoalkyl, C1-C6 monoalkylamino, C1-C6 dialkylamino, —(C=O)R, —(C=O)OR$^7$, —(C=O)NR$^{8a}$R$^{8b}$, —(C=O)—(C1-C6 alkyl)Ar$^3$, —(C=O)—O—(C1-C6 alkyl)Ar$^3$, and —(C=O)—NR$^{8a}$—(C1-C6 alkyl)Ar$^3$, provided that at least six of R$^{50}$ are hydrogen; and wherein R$^{20}$ is selected from hydrogen, C1-C6 alkyl, C1-C6 monohaloalkyl, C1-C6 polyhaloalkyl, C1-C6 hydroxyalkyl, C1-C6 aminoalkyl, C1-C6 monoalkylamino, C1-C6 dialkylamino, —(C=O)R$^7$, —(C=O)OR$^7$, —(C=O)NR$^{8a}$R$^{8b}$, —(C=O)—(C1-C6 alkyl)Ar$^3$, —(C=O)—O—(C1-C6 alkyl)Ar$^3$, and —(C=O)—NR$^{8a}$—(C1-C6 alkyl)Ar$^3$.

In a further aspect, the compound has a structure represented by a formula:

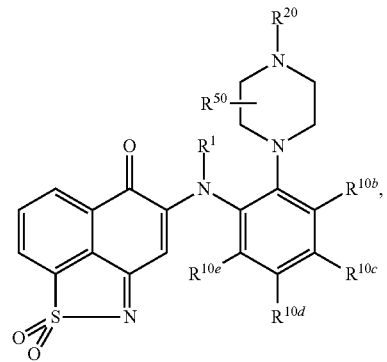

wherein each of R$^{10a}$, R$^{10b}$, R$^{10c}$, R$^{10d}$, and R$^{10e}$ is independently selected from hydrogen, halogen, —CN, —OH, —NH$_2$, —NO$_2$, C1-C6 alkyl, C1-C6 monohaloalkyl, C1-C6 polyhaloalkyl, C1-C6 hydroxyalkyl, C1-C6 monoalkylamino, C1-C6 dialkylamino, —(C1-C6)NR$^{4a}$R$^{4b}$, —(C1-C6)-(C=O)R$^3$, —(C1-C6)-(C=O)OR$^3$, —(C1-C6)-(C=O)NR$^{4a}$R$^{4b}$, —(C1-C6)-Ar$^2$, Ar$^2$, —(C1-C6)-Cy$^2$, Cy$^2$, and —S(O)$_n$NR$^{5a}$R$^{5b}$, provided that at least two of R$^{10a}$, R$^{10b}$, R$^{10c}$, R$^{10d}$, and R$^{10e}$ are hydrogen; wherein each R$^{50}$ is independently selected from hydrogen, halogen, —CN, —OH, —NH$_2$, —NO$_2$, C1-C6 alkyl, C1-C6 monohaloalkyl, C1-C6 polyhaloalkyl, C1-C6 hydroxyalkyl, C1-C6 aminoalkyl, C1-C6 monoalkylamino, C1-C6 dialkylamino, —(C=O)R$^7$, —(C=O)OR$^7$, —(C=O)NR$^{8a}$R$^{8b}$, —(C=O)—(C1-C6 alkyl)Ar$^3$, —(C=O)—O—(C1-C6 alkyl)Ar$^3$, and —(C=O)—NR$^{8a}$—(C1-C6 alkyl)Ar$^3$, provided that at least six of R$^{50}$ are hydrogen; and wherein R$^{20}$ is selected from hydrogen, C1-C6 alkyl, C1-C6 monohaloalkyl, C1-C6 polyhaloalkyl, C1-C6 hydroxyalkyl, C1-C6 aminoalkyl, C1-C6 monoalkylamino, C1-C6 dialkylamino, —(C=O)R$^7$, —(C=O)OR$^7$, —(C=O)NR$^{8a}$R$^{8b}$, —(C=O)—(C1-C6 alkyl)Ar$^3$, —(C=O)—O—(C1-C6 alkyl)Ar$^3$, and —(C=O)—NR$^{8a}$—(C1-C6 alkyl)Ar$^3$.

In a further aspect, the compound has a structure represented by a formula:

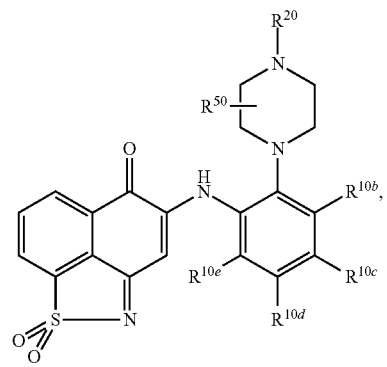

wherein each of R$^{10a}$, R$^{10b}$, R$^{10c}$, R$^{10d}$, and R$^{10e}$ is independently selected from hydrogen, halogen, —CN, —OH, —NH$_2$, —NO$_2$, C1-C6 alkyl, C1-C6 monohaloalkyl, C1-C6 polyhaloalkyl, C1-C6 hydroxyalkyl, C1-C6 monoalkylamino, C1-C6 dialkylamino, —(C1-C6)NR$^{4a}$R$^{4b}$, —(C1-C6)-(C=O)R$^3$, —(C1-C6)-(C=O)OR$^3$, —(C1-C6)-(C=O)NR$^{4a}$R$^{4b}$, —(C1-C6)-Ar$^2$, Ar$^2$, —(C1-C6)-Cy$^2$, Cy$^2$, and —S(O)$_n$NR$^{5a}$R$^{5b}$, provided that at least two of R$^{10a}$, R$^{10b}$, R$^{10c}$, R$^{10d}$, and R$^{10e}$ are hydrogen; wherein each R$^{50}$ is independently selected from hydrogen, halogen, —CN, —OH, —NH$_2$, —NO$_2$, C1-C6 alkyl, C1-C6 monohaloalkyl, C1-C6 polyhaloalkyl, C1-C6 hydroxyalkyl, C1-C6 aminoalkyl, C1-C6 monoalkylamino, C1-C6 dialkylamino, —(C=O)R$^7$, —(C=O)OR$^7$, —(C=O)NR$^{8a}$R$^{8b}$, —(C=O)—(C1-C6 alkyl)Ar$^3$, —(C=O)—O—(C1-C6 alkyl)Ar$^3$, and —(C=O)—NR$^{8a}$—(C1-C6 alkyl)Ar$^3$, provided that at least six of R$^{50}$ are hydrogen; and wherein R$^{20}$ is selected from hydrogen, C1-C6 alkyl, C1-C6 monohaloalkyl, C1-C6 polyhaloalkyl, C1-C6 hydroxyalkyl, C1-C6 aminoalkyl, C1-C6 monoalkylamino, C1-C6 dialkylamino, —(C=O)R$^7$, —(C=O)OR$^7$, —(C=O)NR$^{8a}$R$^{8b}$, —(C=O)—(C1-C6 alkyl)Ar$^3$, —(C=O)—O—(C1-C6 alkyl)Ar$^3$, and —(C=O)—NR$^{8a}$—(C1-C6 alkyl)Ar$^3$.

a. $Q^1$, $Q^2$, and $Q^3$ Groups

In one aspect, $Q^1$ is —NR$^{2a}$R$^{2b}$. In a further aspect, $Q^1$ is selected from —NH$_2$, —NHCH$_3$, and —N(CH$_3$)$_2$. In a further aspect, $Q^1$ is —NH$_2$. In a further aspect, $Q^1$ is —NHCH$_3$. In a further aspect, $Q^1$ is —N(CH$_3$)$_2$.

In one aspect $Q^2$ is O. In a further aspect, $Q^1$ and $Q^2$ are together N.

In one aspect, $Q^3$ is selected from —(C1-C6)-Ar$^1$ and Ar$^1$. In a further aspect, $Q^3$ is selected from —(C1-C6)-Cy$^1$ and Cy$^1$. In a further aspect, $Q^3$ is selected from Ar$^1$ and Cy$^1$. In a further aspect, $Q^3$ is selected from —(C1-C6)-Ar$^1$ and —(C1-C6)-Cy$^1$. In a further aspect, $Q^3$ is Ar$^1$. In a further aspect, $Q^3$ is —(C1-C6)-Ar$^1$. In a further aspect, $Q^3$ is —(CH$_2$)—Ar$^1$. In a further aspect, $Q^3$ is —(CH$_2$)$_2$—Ar$^1$. In a further aspect, $Q^3$ is —(CH$_2$)$_3$—Ar$^1$. In a further aspect, $Q^3$ is —(CH(CH$_3$))—Ar$^1$. In a further aspect, $Q^3$ is Cy$^1$. In a further aspect, $Q^3$ is —(C1-C6)-Cy$^1$. In a further aspect, $Q^3$ is —(CH$_2$)—Cy$^1$. In a further aspect, $Q^3$ is —(CH$_2$)$_2$-Cy$^1$. In a further aspect, $Q^3$ is —(CH$_2$)$_3$-Cy$^1$. In a further aspect, $Q^3$ is —(CH(CH$_3$))-Cy$^1$.

b. Ar$^1$ Groups

In one aspect, Ar$^1$, when present, is phenyl and is substituted with 0, 1, 2, or 3 groups independently selected from halogen, —CN, —OH, —NH$_2$, —NO$_2$, C1-C6 alkyl, C1-C6 monohaloalkyl, C1-C6 polyhaloalkyl, C1-C6 hydroxyalkyl, C1-C6 aminoalkyl, C1-C6 monoalkylamino, C1-C6 dialkylamino, —(C1-C6)NR$^{4a}$R$^{4b}$, —(C1-C6)-(C=O)R$^3$, —(C1-C6)-(C=O)OR$^3$, —(C1-C6)-(C=O)NR$^{4a}$R$^{4b}$, —(C1-C6)-Ar$^2$, Ar$^2$, —(C1-C6)-Cy$^2$, Cy$^2$, and —S(O)$_n$NR$^{5a}$R$^{5b}$. In a further aspect, Ar$^1$, when present, is naphthyl and is substituted with 0, 1, 2, or 3 groups independently selected from halogen, —CN, —OH, —NH$_2$, —NO$_2$, C1-C6 alkyl, C1-C6 monohaloalkyl, C1-C6 polyhaloalkyl, C1-C6 hydroxyalkyl, C1-C6 aminoalkyl, C1-C6 monoalkylamino, C1-C6 dialkylamino, —(C1-C6)NR$^{4a}$R$^{4b}$, —(C1-C6)-(C=O)R$^3$, —(C1-C6)-(C=O)OR$^3$, —(C1-C6)-(C=O)NR$^{4a}$R$^{4b}$, —(C1-C6)-Ar$^2$, Ar$^2$, —(C1-C6)-Cy$^2$, Cy$^2$, and —S(O)$_n$NR$^{5a}$R$^{5b}$. In a further aspect, Ar$^1$, when present, is a monocyclic heterocycle and is substituted with 0, 1, 2, or 3 groups independently selected from halogen, —CN, —OH, —NH$_2$, —NO$_2$, C1-C6 alkyl, C1-C6 monohaloalkyl, C1-C6 polyhaloalkyl, C1-C6 hydroxyalkyl, C1-C6 aminoalkyl, C1-C6 monoalkylamino, C1-C6 dialkylamino, —(C1-C6)NR$^{4a}$R$^{4b}$, —(C1-C6)-(C=O)R$^3$, —(C1-C6)-(C=O)OR$^3$, —(C1-C6)-(C=O)NR$^{4a}$R$^{4b}$, —(C1-C6)-Ar$^2$, Ar$^2$, —(C1-C6)-Cy$^2$, Cy$^2$, and —S(O)$_n$NR$^{5a}$R$^{5b}$. In a further aspect, Ar$^1$, when present, is pyridinyl and is substituted with 0, 1, 2, or 3 groups independently selected from halogen, —CN, —OH, —NH$_2$, —NO$_2$, C1-C6 alkyl, C1-C6 monohaloalkyl, C1-C6 polyhaloalkyl, C1-C6 hydroxyalkyl, C1-C6 aminoalkyl, C1-C6 monoalkylamino, C1-C6 dialkylamino, —(C1-C6)NR$^{4a}$R$^{4b}$, —(C1-C6)-(C=O)R$^3$, —(C1-C6)-(C=O)OR$^3$, —(C1-C6)-(C=O)NR$^{4a}$R$^{4b}$, —(C1-C6)-Ar$^2$, Ar$^2$, —(C1-C6)-Cy$^2$, Cy$^2$, and —S(O)$_n$NR$^{5a}$R$^{5b}$. In a further aspect, Ar$^1$, when present, is pyrimidinyl and is substituted with 0, 1, 2, or 3 groups independently selected from halogen, —CN, —OH, —NH$_2$, —NO$_2$, C1-C6 alkyl, C1-C6 monohaloalkyl, C1-C6 polyhaloalkyl, C1-C6 hydroxyalkyl, C1-C6 aminoalkyl, C1-C6 monoalkylamino, C1-C6 dialkylamino, —(C1-C6)NR$^{4a}$R$^{4b}$, —(C1-C6)-(C=O)R$^3$, —(C1-C6)-(C=O)OR$^3$, —(C1-C6)-(C=O)NR$^{4a}$R$^{4b}$, —(C1-C6)-Ar$^2$, Ar$^2$, —(C1-C6)-Cy$^2$, Cy$^2$, and —S(O)$_n$NR$^{5a}$R$^{5b}$. In a further aspect, Ar$^1$, when present, is pyrazinyl and is substituted with 0, 1, 2, or 3 groups independently selected from halogen, —CN, —OH, —NH$_2$, —NO$_2$, C1-C6 alkyl, C1-C6 monohaloalkyl, C1-C6 polyhaloalkyl, C1-C6 hydroxyalkyl, C1-C6 aminoalkyl, C1-C6 monoalkylamino, C1-C6 dialkylamino, —(C1-C6)NR$^{4a}$R$^{4b}$, —(C1-C6)-(C=O)R$^3$, —(C1-C6)-(C=O)OR$^3$, —(C1-C6)-(C=O)NR$^{4a}$R$^{4b}$, —(C1-C6)-Ar$^2$, Ar$^2$, —(C1-C6)-Cy$^2$, Cy$^2$, and —S(O)$_n$NR$^{5a}$R$^{5b}$. In a further aspect, Ar$^1$, when present, is pyridazinyl and is substituted with 0, 1, 2, or 3 groups independently selected from halogen, —CN, —OH, —NH$_2$, —NO$_2$, C1-C6 alkyl, C1-C6 monohaloalkyl, C1-C6 polyhaloalkyl, C1-C6 hydroxyalkyl, C1-C6 aminoalkyl, C1-C6 monoalkylamino, C1-C6 dialkylamino, —(C1-C6)NR$^{4a}$R$^{4b}$, —(C1-C6)-(C=O)R$^3$, —(C1-C6)-(C=O)OR$^3$, —(C1-C6)-(C=O)NR$^{4a}$R$^{4b}$, —(C1-C6)-Ar$^2$, Ar$^2$, —(C1-C6)-Cy$^2$, Cy$^2$, and —S(O)$_n$NR$^{5a}$R$^{5b}$.

In one aspect, Ar$^1$ is unsubstituted.

In one aspect, Ar$^1$ is substituted with 0, 1, 2, or 3 groups independently selected from —F, —Cl, —CN, —OH, —NH$_2$, —NO$_2$, C1-C3 alkyl, C1-C3 monohaloalkyl, C1-C3 polyhaloalkyl, C1-C3 hydroxyalkyl, C1-C3 aminoalkyl, C1-C3 monoalkylamino, C1-C3 dialkylamino, —(C1-C3)NR$^{4a}$R$^{4b}$, —(C1-C3)-(C=O)R$^3$, —(C1-C3)-(C=O)OR$^3$, —(C1-C3)-(C=O)NR$^{4a}$R$^{4b}$, —(C1-C3)-Ar$^2$, Ar$^2$, —(C1-C3)-Cy$^2$, Cy$^2$, and —S(O)$_n$NR$^{5a}$R$^{5b}$. In a further aspect, Ar$^1$ is substituted with 0, 1, 2, or 3 groups independently selected from —F, —Cl, —CN, —OH, —NH$_2$, —NO$_2$, methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)CH$_2$CH$_3$, and —N(CH$_3$)(CH$_2$)$_2$CH$_3$. In a further aspect, Ar$^1$ is substituted with 0, 1, 2, or 3 groups independently selected from methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$. —NHCH$_3$, and —N(CH$_3$)$_2$. In a further aspect, Ar$^1$ is substituted with 0, 1, 2, or 3 groups independently selected from methyl, —CH$_2$F, —CHF$_2$, —CF$_3$, —NHCH$_3$, and —N(CH$_3$)$_2$. In a further aspect, Ar$^1$ is substituted with 0, 1, 2, or 3 groups independently selected from —F, —Cl, —CN, —OH, —NH$_2$, —NO$_2$, —CH$_2$OH, —(CH$_2$)$_2$OH, —(CH$_2$)$_3$OH, —(CH$_2$)$_4$OH, —(CH$_2$)$_5$OH, —(CH$_2$)$_6$OH, —(CHOH)CH$_3$, —(CHOH)CH$_2$CH$_3$, —(CHOH)(CH$_2$)$_2$CH$_3$, —(CHOH)(CH$_2$)$_3$CH$_3$, —(CHOH)(CH$_2$)$_4$CH$_3$, —CH$_2$(CHOH)CH$_3$, —CH$_2$(CHOH)CH$_2$CH$_3$, —CH$_2$(CHOH)(CH$_2$)$_2$CH$_3$, —CH$_2$(CHOH)(CH$_2$)$_3$CH$_3$, —(CH$_2$)$_2$(CHOH)CH$_3$, —(CH$_2$)$_3$(CHOH)CH$_3$, —(CH$_2$)$_4$(CHOH)CH$_3$, —(CHOH)CH(CH$_3$)$_2$, —(CHOH)C(CH$_3$)$_3$, —CH₂NH₂, —(CH₂)₂NH₂, —(CH₂)₃NH₂, —(CH₂)₄NH₂, —(CH₂)₅NH₂, —(CH₂)₆NH₂, —(CHNH₂)CH₃, —(CHNH₂)CH₂CH₃, —(CHNH₂)(CH₂)₂CH₃, —(CHNH₂)(CH₂)₃CH₃, —(CHNH₂)(CH₂)₄CH₃, —CH₂(CHNH₂)CH₃, —CH₂(CHNH₂)CH₂CH₃, —CH₂(CHNH₂)(CH₂)₂CH₃, —CH₂(CHNH₂)(CH₂)₃CH₃, —(CH₂)₂(CHNH₂)CH₃, —(CH₂)₂(CHNH₂)CH₂CH₃, —(CH₂)₂(CHNH₂)(CH₂)₂CH₃, —(CH₂)₃(CHNH₂)CH₃, —(CH₂)₃(CHNH₂)CH₂CH₃, —(CH₂)₄(CHNH₂)CH₃, —(CHNH₂)CH(CH₃)₂, and —(CHNH₂)C(CH₃)₃. In a further aspect, $Ar^1$ is substituted with 0, 1, 2, or 3 groups independently selected from —F, —Cl, —CN, —OH, —NH₂, —NO₂, —CH₂OH, —(CH₂)₂OH, —(CH₂)₃OH, —(CH₂)₄OH, —(CHOH)CH₃, —(CHOH)CH₂CH₃, —(CHOH)(CH₂)₂CH₃, —CH₂(CHOH)CH₃, —CH₂(CHOH)CH₂CH₃, —(CH₂)₂(CHOH)CH₃, —(CHOH)CH(CH₃)₂, —CH₂NH₂, —(CH₂)₂NH₂, —(CH₂)₃NH₂, —(CH₂)₄NH₂, —(CHNH₂)CH₃, —(CHNH₂)CH₂CH₃, —(CHNH₂)(CH₂)₂CH₃, —CH₂(CHNH₂)CH₃, —CH₂(CHNH₂)CH₂CH₃, —(CH₂)₂(CHNH₂)CH₃, and —(CHNH₂)CH(CH₃)₂. In a further aspect, $Ar^1$ is substituted with 0, 1, 2, or 3 groups independently selected from —F, —Cl, —CN, —OH, —NH₂, —NO₂, —CH₂OH, —(CH₂)₂OH, —(CHOH)CH₃, —CH₂NH₂, —(CH₂)₂NH₂, and —(CHNH₂)CH₃. In a further aspect, $Ar^1$ is substituted with 0, 1, 2, or 3 groups independently selected from —F, —Cl, —CN, —OH, —NH₂, —NO₂, —CH₂OH, and —CH₂NH₂. In a further aspect, $Ar^1$ is substituted with 0, 1, 2, or 3 groups independently selected from halogen, —CN, —OH, —NH₂, —NO₂, —(C1-C6)-(C=O)$R^3$, —(C1-C6)-(C=O)O$R^3$, —(C1-C6)-(C=O)N$R^{4a}R^{4b}$, —(C1-C6)-$Ar^2$, $Ar^2$, —(C1-C6)-$Cy^2$, $Cy^2$, and —S(O)$_n$N$R^{5a}R^{5b}$. In a further aspect, $Ar^1$ is substituted with 0, 1, 2, or 3 groups independently selected from halogen, —CN, —OH, —NH₂, —NO₂, —(C1-C3)-(C=O)$R^3$, —(C1-C3)-(C=O)O$R^3$, —(C1-C3)-(C=O)N$R^{4a}R^{4b}$, —(C1-C3)-$Ar^2$, $Ar^2$, —(C1-C3)-$Cy^2$, $Cy^2$, and —S(O)$_n$N$R^{5a}R^{5b}$. In a further aspect, $Ar^1$ is substituted with 0, 1, 2, or 3 groups independently selected from —F, —Cl, —CN, —OH, —NH₂, —NO₂, —(C1-C3)-(C=O)$R^3$, —(C1-C3)-(C=O)O$R^3$, —(C1-C3)-(C=O)N$R^{4a}R^{4b}$, —(C1-C3)-$Ar^2$, $Ar^2$, —(C1-C3)-$Cy^2$, $Cy^2$, and —S(O)$_n$N$R^{5a}R^{5b}$. In a further aspect, $Ar^1$ is substituted with 0, 1, 2, or 3 groups independently selected from —F, —Cl, —CN, —OH, —NH₂, —NO₂, —(C=O)H, —(C=O)CH₃, —(C=O)OH, —(C=O)OCH₃, —(C=O)NH₂, —(C=O)NHCH₃, —(C=O)N(CH₃)₂, phenyl, —(CH₂)-phenyl, —(CH₂)₂-phenyl, —(CH₂)₃-phenyl, cyclohexyl, —(CH₂)-cyclohexyl, —(CH₂)₂-cyclohexyl, —(CH₂)₃-cyclohexyl, —(S=O)NH₂, —(S=O)NHCH₃, —(S=O)N(CH₃)₂—SO₂NH₂, —SO₂NHCH₃, and —SO₂N(CH₃)₂. In a further aspect, $Ar^1$ is substituted with 0, 1, 2, or 3 groups independently selected from halogen, —CN, —OH, —NH₂, —NO₂, C1-C3 alkyl, C1-C3 monohaloalkyl, C1-C3 polyhaloalkyl, C1-C3 hydroxyalkyl, C1-C3 aminoalkyl, C1-C3 monoalkylamino, C1-C3 dialkylamino, —(C1-C6)-(C=O)$R^3$, —(C1-C6)-(C=O)O$R^3$, —(C1-C6)-(C=O)N$R^{4a}R^{4b}$, —(C1-C6)-$Ar^2$, $Ar^2$, —(C1-C6)-$Cy^2$, $Cy^2$, and —S(O)$_n$N$R^{5a}R^{5b}$. In a further aspect, $Ar^1$ is substituted with 0, 1, 2, or 3 groups independently selected from halogen, —CN, —OH, —NH₂, —NO₂, methyl, ethyl, —CH₂F, —CH₂Cl, —CH₂CH₂F, —CH₂CH₂Cl, —CHF₂, —CF₃, —CHCl₂, —CCl₃, —CH₂CHF₂, —CH₂CF₃. —NHCH₃, —N(CH₃)₂, —CH₂OH, —(CH₂)₂OH, —(CHOH)CH₃, —CH₂NH₂, —(CH₂)₂NH₂, —(CHNH₂)CH₃, —(C1-C3)-(C=O)$R^3$, —(C1-C3)-(C=O)O$R^3$, —(C1-C3)-(C=O)N$R^{4a}R^{4b}$, —(C1-C3)-$Ar^2$, $Ar^2$, —(C1-C3)-$Cy^2$, $Cy^2$, and —S(O)$_n$N$R^{5a}R^{5b}$. In a further aspect, $Ar^1$ is substituted with 0, 1, 2, or 3 groups independently selected from —F, —Cl, —CN, —OH, —NH₂, —NO₂, methyl, ethyl, —CH₂F, —CH₂Cl, —CH₂CH₂F, —CH₂CH₂Cl, —CHF₂, —CF₃, —CHCl₂, —CCl₃, —CH₂CHF₂, —CH₂CF₃. —NHCH₃, —N(CH₃)₂, —CH₂OH, —(CH₂)₂OH, —(CHOH)CH₃, —CH₂NH₂, —(CH₂)₂NH₂, —(CHNH₂)CH₃, —(C=O)H, —(C=O)CH₃, —(C=O)OH, —(C=O)OCH₃, —(C=O)NH₂, —(C=O)NHCH₃, —(C=O)N(CH₃)₂, phenyl, —(CH₂)-phenyl, —(CH₂)₂-phenyl, —(CH₂)₃-phenyl, cyclohexyl, —(CH₂)-cyclohexyl, —(CH₂)₂-cyclohexyl, —(CH₂)₃-cyclohexyl, —(S=O)NH₂, —(S=O)NHCH₃, —(S=O)N(CH₃)₂—SO₂NH₂, —SO₂NHCH₃, and —SO₂N(CH₃)₂.

c. $Ar^2$ Group

In a further aspect, $Ar^2$, when present, is phenyl and is substituted with 0, 1, 2, or 3 groups independently selected from halogen, —CN, —OH, —NH₂, —NO₂, C1-C6 alkyl, C1-C6 monohaloalkyl, C1-C6 polyhaloalkyl, C1-C6 hydroxyalkyl, C1-C6 aminoalkyl, C1-C6 monoalkylamino, and C1-C6 dialkylamino. In a further aspect, $Ar^2$, when present, is a monocyclic heteroaryl and is substituted with 0, 1, 2, or 3 groups independently selected from halogen, —CN, —OH, —NH₂, —NO₂, C1-C6 alkyl, C1-C6 monohaloalkyl, C1-C6 polyhaloalkyl, C1-C6 hydroxyalkyl, C1-C6 aminoalkyl, C1-C6 monoalkylamino, and C1-C6 dialkylamino. In a further aspect, $Ar^2$, when present, is pyridinyl and is substituted with 0, 1, 2, or 3 groups independently selected from halogen, —CN, —OH, —NH₂, —NO₂, C1-C6 alkyl, C1-C6 monohaloalkyl, C1-C6 polyhaloalkyl, C1-C6 hydroxyalkyl, C1-C6 aminoalkyl, C1-C6 monoalkylamino, and C1-C6 dialkylamino. In a further aspect, $Ar^2$, when present, is pyrimidinyl and is substituted with 0, 1, 2, or 3 groups independently selected from halogen, —CN, —OH, —NH₂, —NO₂, C1-C6 alkyl, C1-C6 monohaloalkyl, C1-C6 polyhaloalkyl, C1-C6 hydroxyalkyl, C1-C6 aminoalkyl, C1-C6 monoalkylamino, and C1-C6 dialkylamino. In a further aspect, $Ar^2$, when present, is pyrazinyl and is substituted with 0, 1, 2, or 3 groups independently selected from halogen, —CN, —OH, —NH₂, —NO₂, C1-C6 alkyl, C1-C6 monohaloalkyl, C1-C6 polyhaloalkyl, C1-C6 hydroxyalkyl, C1-C6 aminoalkyl, C1-C6 monoalkylamino, and C1-C6 dialkylamino. In a further aspect, $Ar^2$, when present, is pyridazinyl and is substituted with 0, 1, 2, or 3 groups independently selected from halogen, —CN, —OH, —NH₂, —NO₂, C1-C6 alkyl, C1-C6 monohaloalkyl, C1-C6 polyhaloalkyl, C1-C6 hydroxyalkyl, C1-C6 aminoalkyl, C1-C6 monoalkylamino, and C1-C6 dialkylamino.

In one aspect, $Ar^2$ is unsubstituted.

In one aspect, $Ar^2$ is substituted with 0, 1, 2, or 3 groups independently selected from —F, —Cl, —CN, —OH, —NH₂, —NO₂, C1-C3 alkyl, C1-C3 monohaloalkyl, C1-C3 polyhaloalkyl, C1-C3 hydroxyalkyl, C1-C3 aminoalkyl, C1-C3 monoalkylamino, and C1-C3 dialkylamino. In a further aspect, $Ar^2$ is substituted with 0, 1, 2, or 3 groups independently selected from —F, —Cl, —CN, —OH, —NH₂, —NO₂, methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl, —CH₂F, —CH₂Cl, —CH₂Br, —CH₂I, —CH₂CH₂F, —CH₂CH₂Cl, —CH₂CH₂Br, —CH₂CH₂I, —(CH₂)₂CH₂F, —$(CH_2)_2CH_2Cl$, —$(CH_2)_2CH_2Br$, —$(CH_2)_2CH_2I$, —$CHF_2$, —$CF_3$, —$CHCl_2$, —$CCl_3$, —$CHBr_2$, —$CBr_3$, —$CHI_2$, —$CI_3$, —$CH_2CHF_2$, —$CH_2CF_3$, —$CH_2CHCl_2$, —$CH_2CCl_3$, —$CH_2CHBr_2$, —$CH_2CBr_3$, —$CH_2CHI_2$, —$CH_2CI_3$, —$(CH_2)_2CHF_2$, —$(CH_2)_2CF_3$, —$(CH_2)_2CHCl_2$, —$(CH_2)_2CCl_3$, —$(CH_2)_2CHBr_2$, —$(CH_2)_2CBr_3$, —$(CH_2)_2CHI_2$, —$(CH_2)_2CI_3$, —$NHCH_3$, —$NHCH_2CH_3$, —$NH(CH_2)_2CH_3$, —$NHCH(CH_3)_2$, —$N(CH_3)_2$, —$N(CH_3)CH_2CH_3$, and —$N(CH_3)(CH_2)_2CH_3$. In a further aspect, $Ar^2$ is substituted with 0, 1, 2, or 3 groups independently selected from methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$. —$NHCH_3$, and —$N(CH_3)_2$. In a further aspect, $Ar^2$ is substituted with 0, 1, 2, or 3 groups independently selected from methyl, —$CH_2F$, —$CHF_2$, —$CF_3$, —$NHCH_3$, and —$N(CH_3)_2$. In a further aspect, $Ar^2$ is substituted with 0, 1, 2, or 3 groups independently selected from —F, —Cl, —CN, —OH, —$NH_2$, —$NO_2$, —$CH_2OH$, —$(CH_2)_2OH$, —$(CH_2)_3OH$, —$(CH_2)_4OH$, —$(CH_2)_5OH$, —$(CH_2)_6OH$, —$(CHOH)CH_3$, —$(CHOH)CH_2CH_3$, —$(CHOH)(CH_2)_2CH_3$, —$(CHOH)(CH_2)_3CH_3$, —$(CHOH)(CH_2)_4CH_3$, —$CH_2(CHOH)CH_3$, —$CH_2(CHOH)CH_2CH_3$, —$CH_2(CHOH)(CH_2)_2CH_3$, —$CH_2(CHOH)(CH_2)_3CH_3$, —$(CH_2)_2(CHOH)CH_3$, —$(CH_2)_3(CHOH)CH_3$, —$(CH_2)_4(CHOH)CH_3$, —$(CHOH)CH(CH_3)_2$, —$(CHOH)C(CH_3)_3$, —$CH_2NH_2$, —$(CH_2)_2NH_2$, —$(CH_2)_3NH_2$, —$(CH_2)_4NH_2$, —$(CH_2)_5NH_2$, —$(CH_2)_6NH_2$, —$(CHNH_2)CH_3$, —$(CHNH_2)CH_2CH_3$, —$(CHNH_2)(CH_2)_2CH_3$, —$(CHNH_2)(CH_2)_3CH_3$, —$(CHNH_2)(CH_2)_4CH_3$, —$CH_2(CHNH_2)CH_3$, —$CH_2(CHNH_2)CH_2CH_3$, —$CH_2(CHNH_2)(CH_2)_2CH_3$, —$CH_2(CHNH_2)(CH_2)_3CH_3$, —$(CH_2)_2(CHNH_2)CH_3$, —$(CH_2)_3(CHNH_2)CH_3$, —$(CH_2)_4(CHNH_2)CH_3$, —$(CHNH_2)CH(CH_3)_2$, and —$(CHNH_2)C(CH_3)_3$. In a further aspect, $Ar^2$ is substituted with 0, 1, 2, or 3 groups independently selected from —F, —Cl, —CN, —OH, —$NH_2$, —$NO_2$, —$CH_2OH$, —$(CH_2)_2OH$, —$(CH_2)_3OH$, —$(CH_2)_4OH$, —$(CHOH)CH_3$, —$(CHOH)CH_2CH_3$, —$(CHOH)(CH_2)_2CH_3$, —$CH_2(CHOH)CH_3$, —$CH_2(CHOH)CH_2CH_3$, —$(CH_2)_2(CHOH)CH_3$, —$(CHOH)CH(CH_3)_2$, —$CH_2NH_2$, —$(CH_2)_2NH_2$, —$(CH_2)_3NH_2$, —$(CH_2)_4NH_2$, —$(CHNH_2)CH_3$, —$(CHNH_2)CH_2CH_3$, —$(CHNH_2)(CH_2)_2CH_3$, —$CH_2(CHNH_2)CH_3$, —$CH_2(CHNH_2)CH_2CH_3$, —$(CH_2)_2(CHNH_2)CH_3$, and —$(CHNH_2)CH(CH_3)_2$. In a further aspect, $Ar^2$ is substituted with 0, 1, 2, or 3 groups independently selected from —F, —Cl, —CN, —OH, —$NH_2$, —$NO_2$, —$CH_2OH$, —$(CH_2)_2OH$, —$(CHOH)CH_3$, —$CH_2NH_2$, —$(CH_2)_2NH_2$, and —$(CHNH_2)CH_3$. In a further aspect, $Ar^2$ is substituted with 0, 1, 2, or 3 groups independently selected from —F, —Cl, —CN, —OH, —$NH_2$, —$NO_2$, —$CH_2OH$, —$(CH_2)_2OH$, —$(CHOH)CH_3$, —$CH_2NH_2$, —$(CH_2)_2NH_2$, and —$(CHNH_2)CH_3$. In a further aspect, $Ar^2$ is substituted with 0, 1, 2, or 3 groups independently selected from —F, —Cl, —CN, —OH, —$NH_2$, —$NO_2$, —$CH_2OH$, and —$CH_2NH_2$.

d. $Ar^3$

In one aspect, $Ar^3$, when present, is phenyl and is substituted with 0, 1, 2, or 3 groups independently selected from halogen, —CN, —OH, —$NH_2$, —$NO_2$, C1-C6 alkyl, C1-C6 monohaloalkyl, and C1-C6 polyhaloalkyl. In a further aspect, $Ar^3$, when present, is a monocyclic heterocycle and is substituted with 0, 1, 2, or 3 groups independently selected from halogen, —CN, —OH, —$NH_2$, —$NO_2$, C1-C6 alkyl, C1-C6 monohaloalkyl, and C1-C6 polyhaloalkyl. In a further aspect, $Ar^3$, when present, is pyridinyl and is substituted with 0, 1, 2, or 3 groups independently selected from halogen, —CN, —OH, —$NH_2$, —$NO_2$, C1-C6 alkyl, C1-C6 monohaloalkyl, and C1-C6 polyhaloalkyl. In a further aspect, $Ar^3$, when present, is pyrimidinyl and is substituted with 0, 1, 2, or 3 groups independently selected from halogen, —CN, —OH, —$NH_2$, —$NO_2$, C1-C6 alkyl, C1-C6 monohaloalkyl, and C1-C6 polyhaloalkyl. In a further aspect, $Ar^3$, when present, is pyrazinyl and is substituted with 0, 1, 2, or 3 groups independently selected from halogen, —CN, —OH, —$NH_2$, —$NO_2$, C1-C6 alkyl, C1-C6 monohaloalkyl, and C1-C6 polyhaloalkyl. In a further aspect, $Ar^3$, when present, is pyridazinyl and is substituted with 0, 1, 2, or 3 groups independently selected from halogen, —CN, —OH, —$NH_2$, —$NO_2$, C1-C6 alkyl, C1-C6 monohaloalkyl, and C1-C6 polyhaloalkyl.

In one aspect, $Ar^3$ is unsubstituted.

In one aspect, $Ar^3$ is substituted with 0, 1, 2, or 3 groups independently selected from —F, —Cl, —CN, —OH, —$NH_2$, —$NO_2$, C1-C3 alkyl, C1-C3 monohaloalkyl, and C1-C3 polyhaloalkyl. In a further aspect, $Ar^3$ is substituted with 0, 1, 2, or 3 groups independently selected from —F, —Cl, —CN, —OH, —$NH_2$, —$NO_2$, methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl, —$CH_2F$, —$CH_2Cl$, —$CH_2Br$, —$CH_2I$, —$CH_2CH_2F$, —$CH_2CH_2Cl$, —$CH_2CH_2Br$, —$CH_2CH_2I$, —$(CH_2)_2CH_2F$, —$(CH_2)_2CH_2Cl$, —$(CH_2)_2CH_2Br$, —$(CH_2)_2CH_2I$, —$CHF_2$, —$CF_3$, —$CHCl_2$, —$CCl_3$, —$CHBr_2$, —$CBr_3$, —$CHI_2$, —$CI_3$, —$CH_2CHF_2$, —$CH_2CF_3$, —$CH_2CHCl_2$, —$CH_2CCl_3$, —$CH_2CHBr_2$, —$CH_2CBr_3$, —$CH_2CHI_2$, —$CH_2CI_3$, —$(CH_2)_2CHF_2$, —$(CH_2)_2CF_3$, —$(CH_2)_2CHCl_2$, —$(CH_2)_2CCl_3$, —$(CH_2)_2CHBr_2$, —$(CH_2)_2CBr_3$, —$(CH_2)_2CHI_2$, and —$(CH_2)_2CI_3$. In a further aspect, $Ar^3$ is substituted with 0, 1, 2, or 3 groups independently selected from methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, and —$CH_2CF_3$. In a further aspect, $Ar^3$ is substituted with 0, 1, 2, or 3 groups independently selected from methyl, —$CH_2F$, —$CHF_2$, and —$CF_3$.

e. $Cy^1$ Groups

In one aspect, $Cy^1$, when present, is C3-C8 cycloalkyl and is substituted with 0, 1, 2, or 3 groups independently selected from halogen, —CN, —OH, —$NH_2$, —$NO_2$, C1-C6 alkyl, C1-C6 monohaloalkyl, C1-C6 polyhaloalkyl, C1-C6 hydroxyalkyl, C1-C6 aminoalkyl, C1-C6 monoalkylamino, C1-C6 dialkylamino, —(C1-C6)$NR^{4a}R^{4b}$, —(C1-C6)-(C=O)$R^3$, —(C1-C6)-(C=O)$OR^3$, —(C1-C6)-(C=O)$NR^{4a}R^{4b}$, —(C1-C6)-$Ar^2$, $Cy^2$, —(C1-C6)-$Cy^2$, $Cy^2$, and —$S(O)_nNR^{5a}R^{5b}$. In a further aspect, $Cy^1$, when present, is cyclohexyl and is substituted with 0, 1, 2, or 3 groups independently selected from halogen, —CN, —OH, —$NH_2$, —$NO_2$, C1-C6 alkyl, C1-C6 monohaloalkyl, C1-C6 polyhaloalkyl, C1-C6 hydroxyalkyl, C1-C6 aminoalkyl, C1-C6 monoalkylamino, C1-C6 dialkylamino, —(C1-C6)$NR^{4a}R^{4b}$, —(C1-C6)-(C=O)$R^3$, —(C1-C6)-(C=O)$OR^3$, —(C1-C6)-(C=O)$NR^{4a}R^{4b}$, —(C1-C6)-$Ar^2$, $Cy^2$, —(C1-C6)-$Cy^2$, $Cy^2$, and —$S(O)_nNR^{5a}R^{5b}$. In a further aspect, $Cy^1$, when present, is a C2-C7 heterocycloalkyl and is substituted with 0, 1, 2, or 3 groups independently selected from halogen, —CN, —OH, —$NH_2$, —$NO_2$, C1-C6 alkyl, C1-C6 monohaloalkyl, C1-C6 polyhaloalkyl, C1-C6 hydroxyalkyl, C1-C6 aminoalkyl, C1-C6 monoalkylamino, C1-C6 dialkylamino, —(C1-C6)$NR^{4a}R^{4b}$, —(C1-C6)-(C=O)$R^3$, —(C1-C6)-(C=O)$OR^3$, —(C1-C6)-(C=O)$NR^{4a}R^{4b}$, —(C1-C6)-$Ar^2$, $Cy^2$, —(C1-C6)-$Cy^2$, $Cy^2$, and —$S(O)_nNR^{5a}R^{5b}$. In a further aspect, $Cy^1$, when present, is piperidinyl and is substituted with 0, 1, 2, or 3 groups independently selected from halogen, —CN, —OH, —$NH_2$, —$NO_2$, C1-C6 alkyl, C1-C6 monohaloalkyl, C1-C6 polyhaloalkyl, C1-C6 hydroxyalkyl, C1-C6 aminoalkyl, C1-C6 monoalkylamino, C1-C6 dialkylamino, —(C1-C6)NR$^{4a}$R$^{4b}$, —(C1-C6)-(C=O)R$^3$, —(C1-C6)-(C=O)OR$^3$, —(C1-C6)-(C=O)NR$^{4a}$R$^{4b}$, —(C1-C6)-Ar$^2$, Cy$^2$, —(C1-C6)-Cy$^2$, Cy$^2$, and —S(O)$_n$NR$^{5a}$R$^{5b}$. In a further aspect, Cy$^1$, when present, is piperazinyl and is substituted with 0, 1, 2, or 3 groups independently selected from halogen, —CN, —OH, —NH$_2$, —NO$_2$, C1-C6 alkyl, C1-C6 monohaloalkyl, C1-C6 polyhaloalkyl, C1-C6 hydroxyalkyl, C1-C6 aminoalkyl, C1-C6 monoalkylamino, C1-C6 dialkylamino, —(C1-C6)NR$^{4a}$R$^{4b}$, —(C1-C6)-(C=O)R$^3$, —(C1-C6)-(C=O)OR$^3$, —(C1-C6)(C=O)NR$^{4a}$R$^{4b}$, —(C1-C6)-Ar$^2$, Cy$^2$, —(C1-C6)-Cy$^2$, Cy$^2$, and —S(O)$_n$NR$^{5a}$R$^{5b}$. In a further aspect, Cy$^1$, when present, is morpholinyl and is substituted with 0, 1, 2, or 3 groups independently selected from halogen, —CN, —OH, —NH$_2$, —NO$_2$, C1-C6 alkyl, C1-C6 monohaloalkyl, C1-C6 polyhaloalkyl, C1-C6 hydroxyalkyl, C1-C6 aminoalkyl, C1-C6 monoalkylamino, C1-C6 dialkylamino, —(C1-C6)NR$^{4a}$R$^{4b}$, —(C1-C6)-(C=O)R$^3$, —(C1-C6)-(C=O)OR$^3$, —(C1-C6)-(C=O)NR$^{4a}$R$^{4b}$, —(C1-C6)-Ar$^2$, Cy$^2$, —(C1-C6)-Cy$^2$, Cy$^2$, and —S(O)$_n$NR$^{5a}$R$^{5b}$. In a further aspect, Cy$^1$, when present, is pyrrolidinyl and is substituted with 0, 1, 2, or 3 groups independently selected from halogen, —CN, —OH, —NH$_2$, —NO$_2$, C1-C6 alkyl, C1-C6 monohaloalkyl, C1-C6 polyhaloalkyl, C1-C6 hydroxyalkyl, C1-C6 aminoalkyl, C1-C6 monoalkylamino, C1-C6 dialkylamino, —(C1-C6)NR$^{4a}$R$^{4b}$, —(C1-C6)-(C=O)R$^3$, —(C1-C6)-(C=O)OR$^3$, —(C1-C6)-(C=O)NR$^{4a}$R$^{4b}$, —(C1-C6)-Ar$^2$, Cy$^2$, —(C1-C6)-Cy$^2$, Cy$^2$, and —S(O)$_n$NR$^{5a}$R$^{5b}$.

In one aspect, Cy$^1$ is unsubstituted.

In a further aspect, Cy$^1$ is substituted with 0, 1, 2, or 3 groups independently selected from —F, —Cl, —CN, —OH, —NH$_2$, —NO$_2$, C1-C3 alkyl, C1-C3 monohaloalkyl, C1-C3 polyhaloalkyl, C1-C3 hydroxyalkyl, C1-C3 aminoalkyl, C1-C3 monoalkylamino, C1-C3 dialkylamino, —(C1-C3)NR$^{4a}$R$^{4b}$, —(C1-C3)-(C=O)R$^3$, —(C1-C3)-(C=O)OR$^3$, —(C1-C3)-(C=O)NR$^{4a}$R$^{4b}$, —(C1-C3)-Ar$^2$, Cy$^2$, —(C1-C3)-Cy$^2$, Cy$^2$, and —S(O)$_n$NR$^{5a}$R$^{5b}$. In a further aspect, Cy$^1$ is substituted with 0, 1, 2, or 3 groups independently selected from —F, —Cl, —CN, —OH, —NH$_2$, —NO$_2$, methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)CH$_2$CH$_3$, and —N(CH$_3$)(CH$_2$)$_2$CH$_3$. In a further aspect, Cy$^1$ is substituted with 0, 1, 2, or 3 groups independently selected from methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$. —NHCH$_3$, and —N(CH$_3$)$_2$. In a further aspect, Cy$^1$ is substituted with 0, 1, 2, or 3 groups independently selected from methyl, —CH$_2$F, —CHF$_2$, —CF$_3$, —NHCH$_3$, and —N(CH$_3$)$_2$. In a further aspect, Cy$^1$ is substituted with 0, 1, 2, or 3 groups independently selected from —F, —Cl, —CN, —OH, —NH$_2$, —NO$_2$, —CH$_2$OH, —(CH$_2$)$_2$OH, —(CH$_2$)$_3$OH, —(CH$_2$)$_4$OH, —(CH$_2$)$_5$OH, —(CH$_2$)$_6$OH, —(CHOH)CH$_3$, —(CHOH)CH$_2$CH$_3$, —(CHOH)(CH$_2$)$_2$CH$_3$, —(CHOH)(CH$_2$)$_3$CH$_3$, —(CHOH)(CH$_2$)$_4$CH$_3$, —CH$_2$(CHOH)CH$_3$, —CH$_2$(CHOH)CH$_2$CH$_3$, —CH$_2$(CHOH)(CH$_2$)$_2$CH$_3$, —CH$_2$(CHOH)(CH$_2$)$_3$CH$_3$, —(CH$_2$)$_2$(CHOH)CH$_3$, —(CH$_2$)$_3$(CHOH)CH$_3$, —(CH$_2$)$_4$(CHOH)CH$_3$, —(CHOH)CH(CH$_3$)$_2$, —(CHOH)C(CH$_3$)$_3$, —CH$_2$NH$_2$, —(CH$_2$)$_2$NH$_2$, —(CH$_2$)$_3$NH$_2$, —(CH$_2$)$_4$NH$_2$, —(CH$_2$)$_5$NH$_2$, —(CH$_2$)$_6$NH$_2$, —(CHNH$_2$)CH$_3$, —(CHNH$_2$)CH$_2$CH$_3$, —(CHNH$_2$)(CH$_2$)$_2$CH$_3$, —(CHNH$_2$)(CH$_2$)$_3$CH$_3$, —(CHNH$_2$)(CH$_2$)$_4$CH$_3$, —CH$_2$(CHNH$_2$)CH$_3$, —CH$_2$(CHNH$_2$)CH$_2$CH$_3$, —CH$_2$(CHNH$_2$)(CH$_2$)$_2$CH$_3$, —CH$_2$(CHNH$_2$)(CH$_2$)$_3$CH$_3$, —(CH$_2$)$_2$(CHNH$_2$)CH$_3$, —(CH$_2$)$_3$(CHNH$_2$)CH$_3$, —(CH$_2$)$_4$(CHNH$_2$)CH$_3$, —(CHNH$_2$)CH(CH$_3$)$_2$, and —(CHNH$_2$)C(CH$_3$)$_3$. In a further aspect, Cy$^1$ is substituted with 0, 1, 2, or 3 groups independently selected from —F, —Cl, —CN, —OH, —NH$_2$, —NO$_2$, —CH$_2$OH, —(CH$_2$)$_2$OH, —(CH$_2$)$_3$OH, —(CH$_2$)$_4$OH, —(CHOH)CH$_3$, —(CHOH)CH$_2$CH$_3$, —(CHOH)(CH$_2$)$_2$CH$_3$, —CH$_2$(CHOH)CH$_3$, —CH$_2$(CHOH)CH$_2$CH$_3$, —(CH$_2$)$_2$(CHOH)CH$_3$, —(CHOH)CH(CH$_3$)$_2$, —CH$_2$NH$_2$, —(CH$_2$)$_2$NH$_2$, —(CH$_2$)$_3$NH$_2$, —(CH$_2$)$_4$NH$_2$, —(CHNH$_2$)CH$_3$, —(CHNH$_2$)CH$_2$CH$_3$, —(CHNH$_2$)(CH$_2$)$_2$CH$_3$, —CH$_2$(CHNH$_2$)CH$_3$, —CH$_2$(CHNH$_2$)CH$_2$CH$_3$, —(CH$_2$)$_2$(CHNH$_2$)CH$_3$, and —(CHNH$_2$)CH(CH$_3$)$_2$. In a further aspect, Cy$^1$ is substituted with 0, 1, 2, or 3 groups independently selected from —F, —Cl, —CN, —OH, —NH$_2$, —NO$_2$, —CH$_2$OH, —(CH$_2$)$_2$OH, —(CHOH)CH$_3$, —CH$_2$NH$_2$, —(CH$_2$)$_2$NH$_2$, and —(CHNH$_2$)CH$_3$. In a further aspect, Cy$^1$ is substituted with 0, 1, 2, or 3 groups independently selected from —F, —Cl, —CN, —OH, —NH$_2$, —NO$_2$, —CH$_2$OH, and —CH$_2$NH$_2$. In a further aspect, Cy$^1$ is substituted with 0, 1, 2, or 3 groups independently selected from halogen, —CN, —OH, —NH$_2$, —NO$_2$, —(C1-C6)-(C=O)R$^3$, —(C1-C6)-(C=O)OR$^3$, —(C1-C6)-(C=O)NR$^{4a}$R$^{4b}$, —(C1-C6)-Ar$^2$, Cy$^2$, —(C1-C6)-Cy$^2$, Cy$^2$, and —S(O)$_n$NR$^{5a}$R$^{5b}$. In a further aspect, Cy$^1$ is substituted with 0, 1, 2, or 3 groups independently selected from halogen, —CN, —OH, —NH$_2$, —NO$_2$, —(C1-C3)-(C=O)R$^3$, —(C1-C3)-(C=O)OR$^3$, —(C1-C3)-(C=O)NR$^{4a}$R$^{4b}$, —(C1-C3)-Ar$^2$, Cy$^2$, —(C1-C3)-Cy$^2$, Cy$^2$, and —S(O)$_n$NR$^{5a}$R$^{5b}$.

f. Cy$^2$

In one aspect, Cy$^2$, when present, is C3-C8 cycloalkyl and is substituted with 0, 1, 2, or 3 groups independently selected from halogen, —CN, —OH, —NH$_2$, —NO$_2$, C1-C6 alkyl, C1-C6 monohaloalkyl, C1-C6 polyhaloalkyl, C1-C6 hydroxyalkyl, C1-C6 aminoalkyl, C1-C6 monoalkylamino, C1-C6 dialkylamino, —(C=O)R$^7$, —(C=O)OR$^7$, —(C=O)NR$^{8a}$R$^{8b}$, —(C=O)—(C1-C6 alkyl)-Ar$^3$, —(C=O)—O—(C1-C6 alkyl)-Ar$^3$, and —(C=O)—NR$^a$—(C1-C6 alkyl)-Ar$^3$. In a further aspect, Cy$^2$, when present, is cyclohexyl and is substituted with 0, 1, 2, or 3 groups independently selected from halogen, —CN, —OH, —NH$_2$, —NO$_2$, C1-C6 alkyl, C1-C6 monohaloalkyl, C1-C6 polyhaloalkyl, C1-C6 hydroxyalkyl, C1-C6 aminoalkyl, C1-C6 monoalkylamino, C1-C6 dialkylamino, —(C=O)R$^7$, —(C=O)OR$^7$, —(C=O)NR$^{8a}$R$^{8b}$, —(C=O)—(C1-C6 alkyl)-Ar$^3$, —(C=O)—O—(C1-C6 alkyl)-Ar$^3$, and —(C=O)—NR$^{8a}$—(C1-C6 alkyl)-Ar$^3$. In a further aspect, Cy$^2$, when present, is a C2-C7 heterocycloalkyl and is substituted with 0, 1, 2, or 3 groups independently selected from halogen, —CN, —OH, —NH$_2$, —NO$_2$, C1-C6 alkyl, C1-C6 monohaloalkyl, C1-C6 polyhaloalkyl, C1-C6 hydroxyalkyl, C1-C6 aminoalkyl, C1-C6 monoalkylamino, C1-C6 dialkylamino, —(C=O)R$^7$, —(C=O)OR$^7$, —(C=O)NR$^{8a}$R$^{8b}$, —(C=O)—(C1-C6 alkyl)-Ar$^3$, —(C=O)—O—(C1-C6 alkyl)-Ar$^3$, and —(C=O)—NR$^{8a}$—(C1-C6 alkyl)-Ar$^3$. In a further aspect, Cy$^2$, when present, is piperidinyl and is substituted with 0, 1, 2, or 3 groups independently selected from halogen, —CN, —OH, —NH$_2$, —NO$_2$, C1-C6 alkyl, C1-C6 monohaloalkyl, C1-C6 polyhaloalkyl, C1-C6 hydroxyalkyl, C1-C6 aminoalkyl, C1-C6 monoalkylamino, C1-C6 dialkylamino, —(C=O) R$^7$, —(C=O)OR$^7$, —(C=O)NR$^{8a}$R$^{8b}$, —(C=O)—(C1-C6 alkyl)-Ar$^3$, —(C=O)—O—(C1-C6 alkyl)-Ar$^3$, and —(C=O)—NR$^{8a}$—(C1-C6 alkyl)-Ar$^3$. In a further aspect, Cy$^2$, when present, is piperazinyl and is substituted with 0, 1, 2, or 3 groups independently selected from halogen, —CN, —OH, —NH$_2$, —NO$_2$, C1-C6 alkyl, C1-C6 monohaloalkyl, C1-C6 polyhaloalkyl, C1-C6 hydroxyalkyl, C1-C6 aminoalkyl, C1-C6 monoalkylamino, C1-C6 dialkylamino, —(C=O)R$^7$, —(C=O)OR$^7$, —(C=O)NR$^{8a}$R$^{8b}$, —(C=O)—(C1-C6 alkyl)-Ar$^3$, —(C=O)—O—(C1-C6 alkyl)-Ar$^3$, and —(C=O)—NR$^a$—(C1-C6 alkyl)-Ar$^3$. In a further aspect, Cy$^2$, when present, is morpholinyl and is substituted with 0, 1, 2, or 3 groups independently selected from halogen, —CN, —OH, —NH$_2$, —NO$_2$, C1-C6 alkyl, C1-C6 monohaloalkyl, C1-C6 polyhaloalkyl, C1-C6 hydroxyalkyl, C1-C6 aminoalkyl, C1-C6 monoalkylamino, C1-C6 dialkylamino, —(C=O)R$^7$, —(C=O)OR$^7$, —(C=O)NR$^{8a}$R$^{8b}$, —(C=O)—(C1-C6 alkyl)-Ar$^3$, —(C=O)—O—(C1-C6 alkyl)-Ar$^3$, and —(C=O)—NR$^{8a}$—(C1-C6 alkyl)-Ar$^3$. In a further aspect, Cy$^2$, when present, is pyrrolidinyl and is substituted with 0, 1, 2, or 3 groups independently selected from halogen, —CN, —OH, —NH$_2$, —NO$_2$, C1-C6 alkyl, C1-C6 monohaloalkyl, C1-C6 polyhaloalkyl, C1-C6 hydroxyalkyl, C1-C6 aminoalkyl, C1-C6 monoalkylamino, C1-C6 dialkylamino, —(C=O) R$^7$, —(C=O)OR$^7$, —(C=O)NR$^{8a}$R$^{8b}$, —(C=O)—(C1-C6 alkyl)-Ar$^3$, —(C=O)—O—(C1-C6 alkyl)-Ar$^3$, and —(C=O)—NR$^{8a}$—(C1-C6 alkyl)-Ar$^3$.

In one aspect, Cy$^2$ is unsubstituted.

In a further aspect, Cy$^2$ is substituted with 0, 1, 2, or 3 groups independently selected from —F, —Cl, —CN, —OH, —NH$_2$, —NO$_2$, C1-C3 alkyl, C1-C3 monohaloalkyl, C1-C3 polyhaloalkyl, C1-C3 hydroxyalkyl, C1-C3 aminoalkyl, C1-C3 monoalkylamino, C1-C3 dialkylamino, —(C=O)R$^7$, —(C=O)OR$^7$, —(C=O)NR$^{8a}$R$^{8b}$, —(C=O)—(C1-C3 alkyl)-Ar$^3$, —(C=O)—O—(C1-C3 alkyl)-Ar$^3$, and —(C=O)—NR$^{8a}$—(C1-C3 alkyl)-Ar$^3$. In a further aspect, Cy$^2$ is substituted with 0, 1, 2, or 3 groups independently selected from —F, —Cl, —CN, —OH, —NH$_2$, —NO$_2$, methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$) CH$_2$CH$_3$, and —N(CH$_3$)(CH$_2$)$_2$CH$_3$. In a further aspect, Cy$^2$ is substituted with 0, 1, 2, or 3 groups independently selected from methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$. —NHCH$_3$, and —N(CH$_3$)$_2$. In a further aspect, Cy$^2$ is substituted with 0, 1, 2, or 3 groups independently selected from methyl, —CH$_2$F, —CHF$_2$, —CF$_3$, —NHCH$_3$, and —N(CH$_3$)$_2$. In a further aspect, Cy$^2$ is substituted with 0, 1, 2, or 3 groups independently selected from —F, —Cl, —CN, —OH, —NH$_2$, —NO$_2$, —CH$_2$OH, —(CH$_2$)$_2$OH, —(CH$_2$)$_3$OH, —(CH$_2$)$_4$OH, —(CH$_2$)$_5$OH, —(CH$_2$)$_6$OH, —(CHOH)CH$_3$, —(CHOH)CH$_2$CH$_3$, —(CHOH)(CH$_2$)$_2$CH$_3$, —(CHOH)(CH$_2$)$_3$CH$_3$, —(CHOH) (CH$_2$)$_4$CH$_3$, —CH$_2$(CHOH)CH$_3$, —CH$_2$(CHOH)CH$_2$CH$_3$, —CH$_2$(CHOH)(CH$_2$)$_2$CH$_3$, —CH$_2$(CHOH)(CH$_2$)$_3$CH$_3$, —(CH$_2$)$_2$(CHOH)CH$_3$, —(CH$_2$)$_3$(CHOH)CH$_3$, —(CH$_2$)$_4$ (CHOH)CH$_3$, —(CHOH)CH(CH$_3$)$_2$, —(CHOH)C(CH$_3$)$_3$, —CH$_2$NH$_2$, —(CH$_2$)$_2$NH$_2$, —(CH$_2$)$_3$NH$_2$, —(CH$_2$)$_4$NH$_2$, —(CH$_2$)$_5$NH$_2$, —(CH$_2$)$_6$NH$_2$, —(CHNH$_2$)CH$_3$, —(CHNH$_2$)CH$_2$CH$_3$, —(CHNH$_2$)(CH$_2$)$_2$CH$_3$, —(CHNH$_2$) (CH$_2$)$_3$CH$_3$, —(CHNH$_2$)(CH$_2$)$_4$CH$_3$, —CH$_2$(CHNH$_2$)CH$_3$, —CH$_2$(CHNH$_2$)CH$_2$CH$_3$, —CH$_2$(CHNH$_2$)(CH$_2$)$_2$CH$_3$, —CH$_2$(CHNH$_2$)(CH$_2$)$_3$CH$_3$, —(CH$_2$)$_2$(CHNH$_2$)CH$_3$, —(CH$_2$)$_3$(CHNH$_2$)CH$_3$, —(CH$_2$)$_4$(CHNH$_2$)CH$_3$, —(CHNH$_2$)CH(CH$_3$)$_2$, and —(CHNH$_2$)C(CH$_3$)$_3$. In a further aspect, Cy$^2$ is substituted with 0, 1, 2, or 3 groups independently selected from —F, —Cl, —CN, —OH, —NH$_2$, —NO$_2$, —CH$_2$OH, —(CH$_2$)$_2$OH, —(CH$_2$)$_3$OH, —(CH$_2$)$_4$OH, —(CHOH)CH$_3$, —(CHOH)CH$_2$CH$_3$, —(CHOH)(CH$_2$)$_2$CH$_3$, —CH$_2$(CHOH)CH$_3$, —CH$_2$ (CHOH)CH$_2$CH$_3$, —(CH$_2$)$_2$(CHOH)CH$_3$, —(CHOH)CH (CH$_3$)$_2$, —CH$_2$NH$_2$, —(CH$_2$)$_2$NH$_2$, —(CH$_2$)$_3$NH$_2$, —(CH$_2$)$_4$NH$_2$, —(CHNH$_2$)CH$_3$, —(CHNH$_2$)CH$_2$CH$_3$, —(CHNH$_2$)(CH$_2$)$_2$CH$_3$, —CH$_2$(CHNH$_2$)CH$_3$, —CH$_2$ (CHNH$_2$)CH$_2$CH$_3$, —(CH$_2$)$_2$(CHNH$_2$)CH$_3$, and —(CHNH$_2$)CH(CH$_3$)$_2$. In a further aspect, Cy$^2$ is substituted with 0, 1, 2, or 3 groups independently selected from —F, —Cl, —CN, —OH, —NH$_2$, —NO$_2$, —CH$_2$OH, —(CH$_2$)$_2$OH, —(CHOH)CH$_3$, —CH$_2$NH$_2$, —(CH$_2$)$_2$NH$_2$, and —(CHNH$_2$)CH$_3$. In a further aspect, Cy$^2$ is substituted with 0, 1, 2, or 3 groups independently selected from —F, —Cl, —CN, —OH, —NH$_2$, —NO$_2$, —CH$_2$OH, and —CH$_2$NH$_2$. In a further aspect, Cy$^2$ is substituted with 0, 1, 2, or 3 groups independently selected from halogen, —CN, —OH, —NH$_2$, —NO$_2$, C1-C6 alkyl, C1-C6 monohaloalkyl, C1-C6 polyhaloalkyl, C1-C6 hydroxyalkyl, C1-C6 aminoalkyl, C1-C6 monoalkylamino, C1-C6 dialkylamino, —(C=O)R$^7$, —(C=O)OR$^7$, —(C=O)NR$^{8a}$R$^{8b}$, —(C=O)—(C1-C6 alkyl)-Ar$^3$, —(C=O)—O—(C1-C6 alkyl)-Ar$^3$, and —(C=O)—NR$^{8a}$—(C1-C6 alkyl)-Ar$^3$. In a further aspect, Cy$^2$ is substituted with 0, 1, 2, or 3 groups independently selected from halogen, —CN, —OH, —NH$_2$, —NO$_2$, C1-C3 alkyl, C1-C3 monohaloalkyl, C1-C3 polyhaloalkyl, C1-C3 hydroxyalkyl, C1-C3 aminoalkyl, C1-C3 monoalkylamino, C1-C3 dialkylamino, —(C=O)R, —(C=O)OR$^7$, —(C=O)NR$^{8a}$R$^{8b}$, —(C=O)—(C1-C3 alkyl)-Ar$^3$, —(C=O)—O—(C1-C3 alkyl)-Ar$^3$, and —(C=O)—NR$^{8a}$—(C1-C3 alkyl)-Ar$^3$. In a further aspect, Cy$^2$ is substituted with 0, 1, 2, or 3 groups independently selected from —F, —Cl, —CN, —OH, —NH$_2$, —NO$_2$, C1-C3 alkyl, C1-C3 monohaloalkyl, C1-C3 polyhaloalkyl, C1-C3 hydroxyalkyl, C1-C3 aminoalkyl, C1-C3 monoalkylamino, C1-C3 dialkylamino, —(C=O)R$^7$, —(C=O)OR$^7$, —(C=O)NR$^{8a}$R$^{8b}$, —(C=O)—(C1-C3 alkyl)-Ar$^3$, —(C=O)—O—(C1-C3 alkyl)-Ar$^3$, and —(C=O)— NR$^{8a}$—(C1-C3 alkyl)-Ar$^3$. In a further aspect, Cy$^2$ is substituted with 0, 1, 2, or 3 groups independently selected from —F, —Cl, —CN, —OH, —NH$_2$, —NO$_2$, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$. —NHCH$_3$, —N(CH$_3$)$_2$, —CH$_2$OH, —(CH$_2$)$_2$OH, —(CHOH)CH$_3$, —CH$_2$NH$_2$, —(CH$_2$)$_2$NH$_2$, —(CHNH$_2$) CH$_3$, —(C=O)R$^7$, —(C=O)OR$^7$, —(C=O)NR$^{8a}$R$^{8b}$, —(C=O)—(C1-C3 alkyl)-Ar$^3$, —(C=O)—O—(C1-C3 alkyl)-Ar$^3$, and —(C=O)—NR$^{8a}$—(C1-C3 alkyl)-Ar$^3$. In a further aspect, Cy$^2$ is substituted with 0, 1, 2, or 3 groups independently selected from —F, —Cl, —CN, —OH, —NH$_2$, —NO$_2$, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$. —NHCH$_3$, —N(CH$_3$)$_2$, —CH$_2$OH, —(CH$_2$)$_2$OH, —(CHOH)CH$_3$, —CH$_2$NH$_2$, —(CH$_2$)$_2$NH$_2$, —(CHNH$_2$)CH$_3$, —(C=O)H, —(C=O)CH$_3$, —(C=O)OH, —(C=O)OCH$_3$, —(C=O)NH$_2$, —(C=O)NHCH$_3$, —(C=O)N(CH$_3$)$_2$, —(C=O)—(CH$_2$)-phenyl, —(C=O)—O—(CH$_2$)-phenyl, —(C=O)—NH—(CH$_2$)-phenyl, —(C=O)—(CH$_2$)$_2$-phenyl, —(C=O)—O—(CH$_2$)$_2$-phenyl, —(C=O)—NH—(CH$_2$)$_2$-phenyl, —(C=O)—(CH$_2$)$_3$-phenyl, —(C=O)—O—(CH$_2$)$_3$-phenyl, and —(C=O)—NH—(CH$_2$)$_3$-phenyl.

g. R$^1$ Groups

In one aspect, R$^1$ is hydrogen. In a further aspect, R$^1$ is selected from hydrogen, methyl, and ethyl. In a further aspect, R$^1$ is selected from hydrogen and methyl. In a further aspect, R$^1$ is selected from methyl, ethyl, propyl, and isopropyl.

h. R$^{2a}$ and R$^{2b}$ Groups

In one aspect, R$^{2a}$ and R$^{2b}$, when present, is hydrogen. In a further aspect, R$^{2a}$ and R$^{2b}$, when present, is methyl. In a further aspect, R$^{2a}$ and R$^{2b}$, when present, is ethyl. In a further aspect, R$^{2a}$ and R$^{2b}$, when present, is independently selected from hydrogen, methyl, and ethyl. In a further aspect, R$^{2a}$ and R$^{2b}$, when present, is independently selected from hydrogen and methyl. In a further aspect, R$^{2a}$, when present, is hydrogen and R$^{2b}$, when present, is selected from hydrogen, methyl, ethyl, propyl, and isopropyl. In a further aspect, R$^{2a}$, when present, is hydrogen and R$^{2b}$, when present, is selected from hydrogen, hydrogen, methyl, and ethyl. In a further aspect, R$^{2a}$, when present, is hydrogen and R$^{2b}$, when present, is selected from hydrogen and methyl.

i. R$^3$ Groups

In one aspect, each R$^3$, when present, is hydrogen. In a further aspect, each R$^3$, when present, is methyl. In a further aspect, each R$^3$, when present, is independently selected from hydrogen and C1-C6 alkyl. In a further aspect, each R$^3$, when present, is independently selected from hydrogen and C1-C3 alkyl. In a further aspect, each R$^3$, when present, is independently selected from hydrogen, methyl, ethyl, propyl, isopropyl, tert-butyl, sec-butyl, isobutyl, neopentyl, isopentyl, sec-pentyl, tert-pentyl, 3,3-dimethylbutan-2-yl, and 2,3-dimethylbutan-2-yl. In a further aspect, each R$^3$, when present, is independently selected from hydrogen, methyl, ethyl, propyl, and isopropyl. In a further aspect, each R$^3$, when present, is independently selected from hydrogen, methyl, and ethyl. In a further aspect, each R$^3$, when present, is independently selected from hydrogen and methyl. In a further aspect, each R$^3$ is independently selected from hydrogen, C1-C6 alkyl, C1-C6 monohaloalkyl, C1-C6 polyhaloalkyl. In a further aspect, each R$^3$ is independently selected from hydrogen, C1-C3 alkyl, C1-C3 monohaloalkyl, C1-C3 polyhaloalkyl. In a further aspect, each R$^3$, when present, is independently selected from hydrogen, methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, and —(CH$_2$)$_2$CI$_3$. In a further aspect, each R$^3$, when present, is independently selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, and —CH$_2$CF$_3$. In a further aspect, each R$^3$, when present, is independently selected from hydrogen, methyl, —CH$_2$F, —CHF$_2$, and —CF$_3$. In a further aspect, each R$^3$, when present, is independently selected from hydrogen, C1-C6 hydroxyalkyl, and C1-C6 aminoalkyl. In a further aspect, each R$^3$, when present, is independently selected from hydrogen, C1-C3 hydroxyalkyl, and C1-C3 aminoalkyl. In a further aspect, each R$^3$, when present, is independently selected from —CH$_2$OH, —(CH$_2$)$_2$OH, —(CH$_2$)$_3$OH, —(CH$_2$)$_4$OH, —(CH$_2$)$_5$OH, —(CH$_2$)$_6$OH, —(CHOH)CH$_3$, —(CHOH)CH$_2$CH$_3$, —(CHOH)(CH$_2$)$_2$CH$_3$, —(CHOH)(CH$_2$)$_3$CH$_3$, —(CHOH)(CH$_2$)$_4$CH$_3$, —CH$_2$(CHOH)CH$_3$, —CH$_2$(CHOH)CH$_2$CH$_3$, —CH$_2$(CHOH)(CH$_2$)$_2$CH$_3$, —CH$_2$(CHOH)(CH$_2$)$_3$CH$_3$, —(CH$_2$)$_2$(CHOH)CH$_3$, —(CH$_2$)$_3$(CHOH)CH$_3$, —(CH$_2$)$_4$(CHOH)CH$_3$, —(CHOH)CH(CH$_3$)$_2$, —(CHOH)C(CH$_3$)$_3$, —CH$_2$NH$_2$, —(CH$_2$)$_2$NH$_2$, —(CH$_2$)$_3$NH$_2$, —(CH$_2$)$_4$NH$_2$, —(CH$_2$)$_5$NH$_2$, —(CH$_2$)$_6$NH$_2$, —(CHNH$_2$)CH$_3$, —(CHNH$_2$)CH$_2$CH$_3$, —(CHNH$_2$)(CH$_2$)$_2$CH$_3$, —(CHNH$_2$)(CH$_2$)$_3$CH$_3$, —(CHNH$_2$)(CH$_2$)$_4$CH$_3$, —CH$_2$(CHNH$_2$)CH$_3$, —CH$_2$(CHNH$_2$)CH$_2$CH$_3$, —CH$_2$(CHNH$_2$)(CH$_2$)$_2$CH$_3$, —CH$_2$(CHNH$_2$)(CH$_2$)$_3$CH$_3$, —(CH$_2$)$_2$(CHNH$_2$)CH$_3$, —(CH$_2$)$_3$(CHNH$_2$)CH$_3$, —(CH$_2$)$_4$(CHNH$_2$)CH$_3$, —(CHNH$_2$)CH(CH$_3$)$_2$, and —(CHNH$_2$)C(CH$_3$)$_3$. In a further aspect, each R$^3$, when present, is independently selected from —CH$_2$OH, —(CH$_2$)$_2$OH, —(CH$_2$)$_3$OH, —(CH$_2$)$_4$OH, —(CHOH)CH$_3$, —(CHOH)CH$_2$CH$_3$, —(CHOH)(CH$_2$)$_2$CH$_3$, —CH$_2$(CHOH)CH$_3$, —CH$_2$(CHOH)CH$_2$CH$_3$, —(CH$_2$)$_2$(CHOH)CH$_3$, —(CHOH)CH(CH$_3$)$_2$, —CH$_2$NH$_2$, —(CH$_2$)$_2$NH$_2$, —(CH$_2$)$_3$NH$_2$, —(CH$_2$)$_4$NH$_2$, —(CHNH$_2$)CH$_3$, —(CHNH$_2$)CH$_2$CH$_3$, —(CHNH$_2$)(CH$_2$)$_2$CH$_3$, —CH$_2$(CHNH$_2$)CH$_3$, —CH$_2$(CHNH$_2$)CH$_2$CH$_3$, —(CH$_2$)$_2$(CHNH$_2$)CH$_3$, and —(CHNH$_2$)CH(CH$_3$)$_2$. In a further aspect, each R$^3$, when present, is independently selected from —CH$_2$OH, —(CH$_2$)$_2$OH, —(CHOH)CH$_3$, —CH$_2$NH$_2$, —(CH$_2$)$_2$NH$_2$, and —(CHNH$_2$)CH$_3$. In a further aspect, each R$^3$, when present, is independently selected from —CH$_2$OH and —CH$_2$NH$_2$. In a further aspect, each R$^3$, when present, is independently selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$OH, —(CH$_2$)$_2$OH, —(CHOH)CH$_3$, —CH$_2$NH$_2$, —(CH$_2$)$_2$NH$_2$, and —(CHNH$_2$)CH$_3$.

j. R$^{4a}$ and R$^{4b}$ Groups

In one aspect, each of R$^{4a}$ and R$^{4b}$, when present, is hydrogen. In a further aspect, each of R$^{4a}$ and R$^{4b}$, when present, is methyl. In a further aspect, each of R$^{4a}$ and R$^{4b}$, when present, is independently selected from hydrogen and C1-C6 alkyl. In a further aspect, each of R$^{4a}$ and R$^{4b}$, when present, is independently selected from hydrogen and C1-C3 alkyl. In a further aspect, each of R$^{4a}$ and R$^{4b}$, when present, is independently selected from hydrogen, methyl, ethyl, propyl, isopropyl, tert-butyl, sec-butyl, isobutyl, neopentyl, isopentyl, sec-pentyl, tert-pentyl, 3,3-dimethylbutan-2-yl, and 2,3-dimethylbutan-2-yl. In a further aspect, each of R$^{4a}$ and R$^{4b}$, when present, is independently selected from hydrogen, methyl, ethyl, propyl, and isopropyl. In a further aspect, each of R$^{4a}$ and R$^{4b}$, when present, is independently selected from hydrogen, methyl, and ethyl. In a further aspect, each of R$^{4a}$ and R$^{4b}$, when present, is independently selected from hydrogen and methyl. In a further aspect, each of R$^{4a}$ and R$^{4b}$, when present, is independently selected from hydrogen, C1-C6 alkyl, C1-C6 monohaloalkyl, C1-C6 polyhaloalkyl. In a further aspect, each of R$^{4a}$ and R$^{4b}$, when present, is independently selected from hydrogen, C1-C3 alkyl, C1-C3 monohaloalkyl, C1-C3 polyhaloalkyl. In a further aspect, each of $R^{4a}$ and $R^{4b}$, when present, is independently selected from hydrogen, methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, and —(CH$_2$)$_2$CI$_3$. In a further aspect, each of $R^{4a}$ and $R^{4b}$, when present, is independently selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, and —CH$_2$CF$_3$. In a further aspect, each of $R^{4a}$ and $R^{4b}$, when present, is independently selected from hydrogen, methyl, —CH$_2$F, —CHF$_2$, and —CF$_3$. In a further aspect, each of $R^{4a}$ and $R^{4b}$, when present, is independently selected from hydrogen, C1-C6 hydroxyalkyl, and C1-C6 aminoalkyl. In a further aspect, each of $R^{4a}$ and $R^{4b}$, when present, is independently selected from hydrogen, C1-C3 hydroxyalkyl, and C1-C3 aminoalkyl. In a further aspect, each of $R^{4a}$ and $R^{4b}$, when present, is independently selected from —CH$_2$OH, —(CH$_2$)$_2$OH, —(CH$_2$)$_3$OH, —(CH$_2$)$_4$OH, —(CH$_2$)$_5$OH, —(CH$_2$)$_6$OH, —(CHOH)CH$_3$, —(CHOH)CH$_2$CH$_3$, —(CHOH)(CH$_2$)$_2$CH$_3$, —(CHOH)(CH$_2$)$_3$CH$_3$, —(CHOH)(CH$_2$)$_4$CH$_3$, —CH$_2$(CHOH)CH$_3$, —CH$_2$(CHOH)CH$_2$CH$_3$, —CH$_2$(CHOH)(CH$_2$)$_2$CH$_3$, —CH$_2$(CHOH)(CH$_2$)$_3$CH$_3$, —(CH$_2$)$_2$(CHOH)CH$_3$, —(CH$_2$)$_3$(CHOH)CH$_3$, —(CH$_2$)$_4$(CHOH)CH$_3$, —(CHOH)CH(CH$_3$)$_2$, —(CHOH)C(CH$_3$)$_3$, —CH$_2$NH$_2$, —(CH$_2$)$_2$NH$_2$, —(CH$_2$)$_3$NH$_2$, —(CH$_2$)$_4$NH$_2$, —(CH$_2$)$_5$NH$_2$, —(CH$_2$)$_6$NH$_2$, —(CHNH$_2$)CH$_3$, —(CHNH$_2$)CH$_2$CH$_3$, —(CHNH$_2$)(CH$_2$)$_2$CH$_3$, —(CHNH$_2$)(CH$_2$)$_3$CH$_3$, —(CHNH$_2$)(CH$_2$)$_4$CH$_3$, —CH$_2$(CHNH$_2$)CH$_3$, —CH$_2$(CHNH$_2$)CH$_2$CH$_3$, —CH$_2$(CHNH$_2$)(CH$_2$)$_2$CH$_3$, —CH$_2$(CHNH$_2$)(CH$_2$)$_3$CH$_3$, —(CH$_2$)$_2$(CHNH$_2$)CH$_3$, —(CH$_2$)$_3$(CHNH$_2$)CH$_3$, —(CH$_2$)$_4$(CHNH$_2$)CH$_3$, —(CHNH$_2$)CH(CH$_3$)$_2$, and —(CHNH$_2$)C(CH$_3$)$_3$. In a further aspect, each of $R^{4a}$ and $R^{4b}$, when present, is independently selected from —CH$_2$OH, —(CH$_2$)$_2$OH, —(CH$_2$)$_3$OH, —(CH$_2$)$_4$OH, —(CHOH)CH$_3$, —(CHOH)CH$_2$CH$_3$, —(CHOH)(CH$_2$)$_2$CH$_3$, —CH$_2$(CHOH)CH$_3$, —CH$_2$(CHOH)CH$_2$CH$_3$, —(CH$_2$)$_2$(CHOH)CH$_3$, —(CHOH)CH(CH$_3$)$_2$, —CH$_2$NH$_2$, —(CH$_2$)$_2$NH$_2$, —(CH$_2$)$_3$NH$_2$, —(CH$_2$)$_4$NH$_2$, —(CHNH$_2$)CH$_3$, —(CHNH$_2$)CH$_2$CH$_3$, —(CHNH$_2$)(CH$_2$)$_2$CH$_3$, —CH$_2$(CHNH$_2$)CH$_3$, —CH$_2$(CHNH$_2$)CH$_2$CH$_3$, —(CH$_2$)$_2$(CHNH$_2$)CH$_3$, and —(CHNH$_2$)CH(CH$_3$)$_2$. In a further aspect, each of $R^{4a}$ and $R^{4b}$, when present, is independently selected from —CH$_2$OH, —(CH$_2$)$_2$OH, —(CHOH)CH$_3$, —CH$_2$NH$_2$, —(CH$_2$)$_2$NH$_2$, and —(CHNH$_2$)CH$_3$. In a further aspect, each of $R^{4a}$ and $R^{4b}$, when present, is independently selected from —CH$_2$OH and —CH$_2$NH$_2$. In a further aspect, each of $R^{4a}$ and $R^{4b}$, when present, is independently selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$OH, —(CH$_2$)$_2$OH, —(CHOH)CH$_3$, —CH$_2$NH$_2$, —(CH$_2$)$_2$NH$_2$, and —(CHNH$_2$)CH$_3$. In a further aspect, $R^{4a}$, when present, is hydrogen and $R^{4b}$, when present, is selected from hydrogen and C1-C6 alkyl. In a further aspect, $R^{4a}$, when present, is hydrogen and $R^{4b}$, when present, is selected from hydrogen and C1-C3 alkyl. In a further aspect, $R^{4a}$, when present, is hydrogen and $R^{4b}$, when present, is selected from hydrogen, methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl, and 2,3-dimethylbutan-2-yl. In a further aspect, $R^{4a}$, when present, is hydrogen and $R^{4b}$, when present, is selected from hydrogen, methyl, ethyl, propyl, and isopropyl. In a further aspect, $R^{4a}$, when present, is hydrogen and $R^{4b}$, when present, is selected from hydrogen, methyl, and ethyl. In a further aspect, $R^{4a}$, when present, is hydrogen and $R^{4b}$, when present, is selected from hydrogen and methyl. In a further aspect, $R^{4a}$, when present, is hydrogen and $R^{4b}$, when present, is selected from hydrogen, C1-C6 alkyl, C1-C6 monohaloalkyl, C1-C6 polyhaloalkyl. In a further aspect, $R^{4a}$, when present, is hydrogen and $R^{4b}$, when present, is selected from hydrogen, C1-C3 alkyl, C1-C3 monohaloalkyl, C1-C3 polyhaloalkyl. In a further aspect, $R^{4a}$, when present, is hydrogen and $R^{4b}$, when present, is selected from hydrogen, methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, and —(CH$_2$)$_2$CI$_3$. In a further aspect, $R^{4a}$, when present, is hydrogen and $R^{4b}$, when present, is selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, and —CH$_2$CF$_3$. In a further aspect, $R^{4a}$, when present, is hydrogen and $R^{4b}$, when present, is selected from hydrogen, methyl, —CH$_2$F, —CHF$_2$, and —CF$_3$. In a further aspect, $R^{4a}$, when present, is hydrogen and $R^{4b}$, when present, is selected from hydrogen, C1-C6 hydroxyalkyl, and C1-C6 aminoalkyl. In a further aspect, $R^{4a}$, when present, is hydrogen and $R^{4b}$, when present, is selected from hydrogen, C1-C3 hydroxyalkyl, and C1-C3 aminoalkyl. In a further aspect, $R^{4a}$, when present, is hydrogen and $R^{4b}$, when present, is selected from —CH$_2$OH, —(CH$_2$)$_2$OH, —(CH$_2$)$_3$OH, —(CH$_2$)$_4$OH, —(CH$_2$)$_5$OH, —(CH$_2$)$_6$OH, —(CHOH)CH$_3$, —(CHOH)CH$_2$CH$_3$, —(CHOH)(CH$_2$)$_2$CH$_3$, —(CHOH)(CH$_2$)$_3$CH$_3$, —(CHOH)(CH$_2$)$_4$CH$_3$, —CH$_2$(CHOH)CH$_3$, —CH$_2$(CHOH)CH$_2$CH$_3$, —CH$_2$(CHOH)(CH$_2$)$_2$CH$_3$, —CH$_2$(CHOH)(CH$_2$)$_3$CH$_3$, —(CH$_2$)$_2$(CHOH)CH$_3$, —(CH$_2$)$_3$(CHOH)CH$_3$, —(CH$_2$)$_4$(CHOH)CH$_3$, —(CHOH)CH(CH$_3$)$_2$, —(CHOH)C(CH$_3$)$_3$, —CH$_2$NH$_2$, —(CH$_2$)$_2$NH$_2$, —(CH$_2$)$_3$NH$_2$, —(CH$_2$)$_4$NH$_2$, —(CH$_2$)$_5$NH$_2$, —(CH$_2$)$_6$NH$_2$, —(CHNH$_2$)CH$_3$, —(CHNH$_2$)CH$_2$CH$_3$, —(CHNH$_2$)(CH$_2$)$_2$CH$_3$, —(CHNH$_2$)(CH$_2$)$_3$CH$_3$, —(CHNH$_2$)(CH$_2$)$_4$CH$_3$, —CH$_2$(CHNH$_2$)CH$_3$, —CH$_2$(CHNH$_2$)CH$_2$CH$_3$, —CH$_2$(CHNH$_2$)(CH$_2$)$_2$CH$_3$, —CH$_2$(CHNH$_2$)(CH$_2$)$_3$CH$_3$, —(CH$_2$)$_2$(CHNH$_2$)CH$_3$, —(CH$_2$)$_3$(CHNH$_2$)CH$_3$, —(CH$_2$)$_4$(CHNH$_2$)CH$_3$, —(CHNH$_2$)CH(CH$_3$)$_2$, and —(CHNH$_2$)C(CH$_3$)$_3$. In a further aspect, $R^{4a}$, when present, is hydrogen and $R^{4b}$, when present, is selected from —CH$_2$OH, —(CH$_2$)$_2$OH, —(CH$_2$)$_3$OH, —(CH$_2$)$_4$OH, —(CHOH)CH$_3$, —(CHOH)CH$_2$CH$_3$, —(CHOH)(CH$_2$)$_2$CH$_3$, —CH$_2$(CHOH)CH$_3$, —CH$_2$(CHOH)CH$_2$CH$_3$, —(CH$_2$)$_2$(CHOH)CH$_3$, —(CHOH)CH(CH$_3$)$_2$, —CH$_2$NH$_2$, —(CH$_2$)$_2$NH$_2$, —(CH$_2$)$_3$NH$_2$, —(CH$_2$)$_4$NH$_2$, —(CHNH$_2$)CH$_3$, —(CHNH$_2$)CH$_2$CH$_3$, —(CHNH$_2$)(CH$_2$)$_2$CH$_3$, —CH$_2$(CHNH$_2$)CH$_3$, —CH$_2$(CHNH$_2$)CH$_2$CH$_3$, —(CH$_2$)$_2$ (CHNH$_2$)CH$_3$, and —(CHNH$_2$)CH(CH$_3$)$_2$. In a further aspect, R$^{4a}$, when present, is hydrogen and R$^{4b}$, when present, is selected from —CH$_2$OH, —(CH$_2$)$_2$OH, —(CHOH)CH$_3$, —CH$_2$NH$_2$, —(CH$_2$)$_2$NH$_2$, and —(CHNH$_2$)CH$_3$. In a further aspect, R$^{4a}$, when present, is hydrogen and R$^{4b}$, when present, is selected from —CH$_2$OH and —CH$_2$NH$_2$. In a further aspect, R$^{4a}$, when present, is hydrogen and R$^{4b}$, when present, is selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$OH, —(CH$_2$)$_2$OH, —(CHOH)CH$_3$, —CH$_2$NH$_2$, —(CH$_2$)$_2$NH$_2$, and —(CHNH$_2$)CH$_3$.

k. R$^{5a}$ and R$^{5b}$ Groups

In one aspect, each of R$^{5a}$ and R$^{5b}$, when present, is hydrogen. In a further aspect, each of R$^{5a}$ and R$^{5b}$, when present, is methyl. In a further aspect, each of R$^{5a}$ and R$^{5b}$, when present, is independently selected from hydrogen and C1-C6 alkyl. In a further aspect, each of R$^{5a}$ and R$^{5b}$, when present, is independently selected from hydrogen and C1-C3 alkyl. In a further aspect, each of R$^{5a}$ and R$^{5b}$, when present, is independently selected from hydrogen, methyl, ethyl, propyl, isopropyl, tert-butyl, sec-butyl, isobutyl, neopentyl, isopentyl, sec-pentyl, tert-pentyl, 3,3-dimethylbutan-2-yl, and 2,3-dimethylbutan-2-yl. In a further aspect, each of R$^{5a}$ and R$^{5b}$, when present, is independently selected from hydrogen, methyl, ethyl, propyl, and isopropyl. In a further aspect, each of R$^{5a}$ and R$^{5b}$, when present, is independently selected from hydrogen, methyl, and ethyl. In a further aspect, each of R$^{5a}$ and R$^{5b}$, when present, is independently selected from hydrogen and methyl. In a further aspect, each of R$^{5a}$ and R$^{5b}$, when present, is independently selected from hydrogen, C1-C6 alkyl, C1-C6 monohaloalkyl, C1-C6 polyhaloalkyl. In a further aspect, each of R$^{5a}$ and R$^{5b}$, when present, is independently selected from hydrogen, C1-C3 alkyl, C1-C3 monohaloalkyl, C1-C3 polyhaloalkyl. In a further aspect, each of R$^{5a}$ and R$^{5b}$, when present, is independently selected from hydrogen, methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, and —(CH$_2$)$_2$CI$_3$. In a further aspect, each of R$^{5a}$ and R$^{5b}$, when present, is independently selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, and —CH$_2$CF$_3$. In a further aspect, each of R$^{5a}$ and R$^{5b}$, when present, is independently selected from hydrogen, methyl, —CH$_2$F, —CHF$_2$, and —CF$_3$. In a further aspect, each of R$^{5a}$ and R$^{5b}$, when present, is independently selected from hydrogen, C1-C6 hydroxyalkyl, and C1-C6 aminoalkyl. In a further aspect, each of R$^{5a}$ and R$^{5b}$, when present, is independently selected from hydrogen, C1-C3 hydroxyalkyl, and C1-C3 aminoalkyl. In a further aspect, each of R$^{5a}$ and R$^{5b}$, when present, is independently selected from —CH$_2$OH, —(CH$_2$)$_2$OH, —(CH$_2$)$_3$OH, —(CH$_2$)$_4$OH, —(CH$_2$)$_5$OH, —(CH$_2$)$_6$OH, —(CHOH)CH$_3$, —(CHOH)CH$_2$CH$_3$, —(CHOH)(CH$_2$)$_2$CH$_3$, —(CHOH)(CH$_2$)$_3$CH$_3$, —(CHOH)(CH$_2$)$_4$CH$_3$, —CH$_2$(CHOH)CH$_3$, —CH$_2$(CHOH)CH$_2$CH$_3$, —CH$_2$(CHOH)(CH$_2$)$_2$CH$_3$, —CH$_2$(CHOH)(CH$_2$)$_3$CH$_3$, —(CH$_2$)$_2$(CHOH)CH$_3$, —(CH$_2$)$_3$(CHOH)CH$_3$, —(CH$_2$)$_4$(CHOH)CH$_3$, —(CHOH)CH(CH$_3$)$_2$, —(CHOH)C(CH$_3$)$_3$, —CH$_2$NH$_2$, —(CH$_2$)$_2$NH$_2$, —(CH$_2$)$_3$NH$_2$, —(CH$_2$)$_4$NH$_2$, —(CH$_2$)$_5$NH$_2$, —(CH$_2$)$_6$NH$_2$, —(CHNH$_2$)CH$_3$, —(CHNH$_2$)CH$_2$CH$_3$, —(CHNH$_2$)(CH$_2$)$_2$CH$_3$, —(CHNH$_2$)(CH$_2$)$_3$CH$_3$, —(CHNH$_2$)(CH$_2$)$_4$CH$_3$, —CH$_2$(CHNH$_2$)CH$_3$, —CH$_2$(CHNH$_2$)CH$_2$CH$_3$, —CH$_2$(CHNH$_2$)(CH$_2$)$_2$CH$_3$, —CH$_2$(CHNH$_2$)(CH$_2$)$_3$CH$_3$, —(CH$_2$)$_2$(CHNH$_2$)CH$_3$, —(CH$_2$)$_3$(CHNH$_2$)CH$_3$, —(CH$_2$)$_4$(CHNH$_2$)CH$_3$, —(CHNH$_2$)CH(CH$_3$)$_2$, and —(CHNH$_2$)C(CH$_3$)$_3$. In a further aspect, each of R$^{5a}$ and R$^{5b}$, when present, is independently selected from —CH$_2$OH, —(CH$_2$)$_2$OH, —(CH$_2$)$_3$OH, —(CH$_2$)$_4$OH, —(CHOH)CH$_3$, —(CHOH)CH$_2$CH$_3$, —(CHOH)(CH$_2$)$_2$CH$_3$, —CH$_2$(CHOH)CH$_3$, —CH$_2$(CHOH)CH$_2$CH$_3$, —(CH$_2$)$_2$(CHOH)CH$_3$, —(CHOH)CH(CH$_3$)$_2$, —CH$_2$NH$_2$, —(CH$_2$)$_2$NH$_2$, —(CH$_2$)$_3$NH$_2$, —(CH$_2$)$_4$NH$_2$, —(CHNH$_2$)CH$_3$, —(CHNH$_2$)CH$_2$CH$_3$, —(CHNH$_2$)(CH$_2$)$_2$CH$_3$, —CH$_2$(CHNH$_2$)CH$_3$, —CH$_2$(CHNH$_2$)CH$_2$CH$_3$, —(CH$_2$)$_2$(CHNH$_2$)CH$_3$, and —(CHNH$_2$)CH(CH$_3$)$_2$. In a further aspect, each of R$^{5a}$ and R$^{5b}$, when present, is independently selected from —CH$_2$OH, —(CH$_2$)$_2$OH, —(CHOH)CH$_3$, —CH$_2$NH$_2$, —(CH$_2$)$_2$NH$_2$, and —(CHNH$_2$)CH$_3$. In a further aspect, each of R$^{5a}$ and R$^{5b}$, when present, is independently selected from —CH$_2$OH and —CH$_2$NH$_2$. In a further aspect, each of R$^{5a}$ and R$^{5b}$, when present, is independently selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$OH, —(CH$_2$)$_2$OH, —(CHOH)CH$_3$, —CH$_2$NH$_2$, —(CH$_2$)$_2$NH$_2$, —(CHNH$_2$)CH$_3$, —(C=O)NH$_2$, —(C=O)NHCH$_3$, and —(C=O)N(CH$_3$)$_2$. In a further aspect, each of R$^{5a}$ and R$^{5b}$, when present, is independently selected from hydrogen and —(C=O)NR$^{6a}$R$^{6b}$. In a further aspect, each of R$^{5a}$ and R$^{5b}$, when present, is independently selected from hydrogen, —(C=O)N(CH$_2$CH$_3$)((CH$_2$)$_2$CH$_3$), —(C=O)N(CH$_2$CH$_3$)$_2$, —(C=O)N(CH$_3$)(CH$_2$)$_2$CH$_3$, —(C=O)N(CH$_3$)CH(CH$_3$)$_2$, —(C=O)N(CH$_3$)CH$_2$CH$_3$, —(C=O)NH$_2$, —(C=O)NHCH$_3$, and —(C=O)N(CH$_3$)$_2$. In a further aspect, each of R$^{5a}$ and R$^{5b}$, when present, is independently selected from hydrogen, —(C=O)N(CH$_2$CH$_3$)$_2$, —(C=O)N(CH$_3$)CH$_2$CH$_3$, —(C=O)NH$_2$, —(C=O)NHCH$_3$, and —(C=O)N(CH$_3$)$_2$. In a further aspect, each of R$^{5a}$ and R$^{5b}$, when present, is independently selected from hydrogen, —(C=O)NH$_2$, —(C=O)NHCH$_3$, and —(C=O)N(CH$_3$)$_2$. In a further aspect, R$^{5a}$, when present, is hydrogen and R$^{5b}$, when present, is selected from hydrogen and C1-C6 alkyl. In a further aspect, R$^{5a}$, when present, is hydrogen and R$^{5b}$, when present, is selected from hydrogen and C1-C3 alkyl. In a further aspect, R$^{5a}$, when present, is hydrogen and R$^{5b}$, when present, is selected from hydrogen, methyl, ethyl, propyl, isopropyl, tert-butyl, sec-butyl, isobutyl, neopentyl, isopentyl, sec-pentyl, tert-pentyl, 3,3-dimethylbutan-2-yl, and 2,3-dimethylbutan-2-yl. In a further aspect, R$^{5a}$, when present, is hydrogen and R$^{5b}$, when present, is selected from hydrogen, methyl, ethyl, propyl, and isopropyl. In a further aspect, R$^{5a}$, when present, is hydrogen and R$^{5b}$, when present, is selected from hydrogen, methyl, and ethyl. In a further aspect, R$^{5a}$, when present, is hydrogen and R$^{5b}$, when present, is selected from hydrogen and methyl. In a further aspect, R$^{5a}$, when present, is hydrogen and R$^{5b}$, when present, is selected from hydrogen, C1-C6 alkyl, C1-C6 monohaloalkyl, C1-C6 polyhaloalkyl. In a further aspect, R$^{5a}$ when present, is hydrogen and R$^{5b}$, when present, is selected from hydrogen, C1-C3 alkyl, C1-C3 monohaloalkyl, C1-C3 polyhaloalkyl. In a further aspect, R$^{5a}$, when present, is hydrogen and R$^{5b}$, when present, is selected from hydrogen, methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, and —(CH$_2$)$_2$CI$_3$. In a further aspect, R$^{5a}$, when present, is hydrogen and R$^{5b}$ when present, is selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, and —CH$_2$CF$_3$. In a further aspect, R$^{5a}$, when present, is hydrogen and R$^{5b}$, when present, is selected from hydrogen, methyl, —CH$_2$F, —CHF$_2$, and —CF$_3$. In a further aspect, R$^{5a}$, when present, is hydrogen and R$^{5b}$, when present, is selected from hydrogen, C1-C6 hydroxyalkyl, and C1-C6 aminoalkyl. In a further aspect, R$^{5a}$, when present, is hydrogen and R$^{5b}$, when present, is selected from hydrogen, C1-C3 hydroxyalkyl, and C1-C3 aminoalkyl. In a further aspect, R$^{5a}$, when present, is hydrogen and R$^{5b}$, when present, is selected from —CH$_2$OH, —(CH$_2$)$_2$OH, —(CH$_2$)$_3$OH, —(CH$_2$)$_4$OH, —(CH$_2$)$_5$OH, —(CH$_2$)$_6$OH, —(CHOH)CH$_3$, —(CHOH)CH$_2$CH$_3$, —(CHOH)(CH$_2$)$_2$CH$_3$, —(CHOH)(CH$_2$)$_3$CH$_3$, —(CHOH)(CH$_2$)$_4$CH$_3$, —CH$_2$(CHOH)CH$_3$, —CH$_2$(CHOH)CH$_2$CH$_3$, —CH$_2$(CHOH)(CH$_2$)$_2$CH$_3$, —CH$_2$(CHOH)(CH$_2$)$_3$CH$_3$, —(CH$_2$)$_2$(CHOH)CH$_3$, —(CH$_2$)$_3$(CHOH)CH$_3$, —(CH$_2$)$_4$(CHOH)CH$_3$, —(CHOH)CH(CH$_3$)$_2$, —(CHOH)C(CH$_3$)$_3$, —CH$_2$NH$_2$, —(CH$_2$)$_2$NH$_2$, —(CH$_2$)$_3$NH$_2$, —(CH$_2$)$_4$NH$_2$, —(CH$_2$)$_5$NH$_2$, —(CH$_2$)$_6$NH$_2$, —(CHNH$_2$)CH$_3$, —(CHNH$_2$)CH$_2$CH$_3$, —(CHNH$_2$)(CH$_2$)$_2$CH$_3$, —(CHNH$_2$)(CH$_2$)$_3$CH$_3$, —(CHNH$_2$)(CH$_2$)$_4$CH$_3$, —CH$_2$(CHNH$_2$)CH$_3$, —CH$_2$(CHNH$_2$)CH$_2$CH$_3$, —CH$_2$(CHNH$_2$)(CH$_2$)$_2$CH$_3$, —CH$_2$(CHNH$_2$)(CH$_2$)$_3$CH$_3$, —(CH$_2$)$_2$(CHNH$_2$)CH$_3$, —(CH$_2$)$_3$(CHNH$_2$)CH$_3$, —(CH$_2$)$_4$(CHNH$_2$)CH$_3$, —(CHNH$_2$)CH(CH$_3$)$_2$, and —(CHNH$_2$)C(CH$_3$)$_3$. In a further aspect, R$^{5a}$, when present, is hydrogen and R$^{5b}$, when present, is selected from —CH$_2$OH, —(CH$_2$)$_2$OH, —(CH$_2$)$_3$OH, —(CH$_2$)$_4$OH, —(CHOH)CH$_3$, —(CHOH)CH$_2$CH$_3$, —(CHOH)(CH$_2$)$_2$CH$_3$, —CH$_2$(CHOH)CH$_3$, —CH$_2$(CHOH)CH$_2$CH$_3$, —(CH$_2$)$_2$(CHOH)CH$_3$, —(CHOH)CH(CH$_3$)$_2$, —CH$_2$NH$_2$, —(CH$_2$)$_2$NH$_2$, —(CH$_2$)$_3$NH$_2$, —(CH$_2$)$_4$NH$_2$, —(CHNH$_2$)CH$_3$, —(CHNH$_2$)CH$_2$CH$_3$, —(CHNH$_2$)(CH$_2$)$_2$CH$_3$, —CH$_2$(CHNH$_2$)CH$_3$, —CH$_2$(CHNH$_2$)CH$_2$CH$_3$, —(CH$_2$)$_2$(CHNH$_2$)CH$_3$, and —(CHNH$_2$)CH(CH$_3$)$_2$. In a further aspect, R$^{5a}$, when present, is hydrogen and R$^{5b}$, when present, is selected from —CH$_2$OH, —(CH$_2$)$_2$OH, —(CHOH)CH$_3$, —CH$_2$NH$_2$, —(CH$_2$)$_2$NH$_2$, and —(CHNH$_2$)CH$_3$. In a further aspect, R$^{5a}$, when present, is hydrogen and R$^{5b}$, when present, is selected from —CH$_2$OH and —CH$_2$NH$_2$. In a further aspect, R$^{5s}$, when present, is hydrogen and R$^{5b}$, when present, is selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$OH, —(CH$_2$)$_2$OH, —(CHOH)CH$_3$, —CH$_2$NH$_2$, —(CH$_2$)$_2$NH$_2$, —(CHNH$_2$)CH$_3$, —(C=O)NH$_2$, —(C=O)NHCH$_3$, and —(C=O)N(CH$_3$)$_2$. In a further aspect, R$^{5a}$, when present, is hydrogen and R$^{5b}$, when present, is selected from hydrogen and —(C=O)NR$^{6a}$R$^{6b}$. In a further aspect, R$^{5a}$, when present, is hydrogen and R$^{5b}$, when present, is selected from hydrogen, —(C=O)N(CH$_2$CH$_3$)((CH$_2$)$_2$CH$_3$), —(C=O)N(CH$_2$CH$_3$)$_2$, —(C=O)N(CH$_3$)(CH$_2$)$_2$CH$_3$, —(C=O)N(CH$_3$)CH(CH$_3$)$_2$, —(C=O)N(CH$_3$)CH$_2$CH$_3$, —(C=O)NH$_2$, —(C=O)NHCH$_3$, and —(C=O)N(CH$_3$)$_2$. In a further aspect, R$^{50a}$, when present, is hydrogen and R$^{5b}$, when present, is selected from hydrogen, —(C=O)N(CH$_2$CH$_3$)$_2$, —(C=O)N(CH$_3$)CH$_2$CH$_3$, —(C=O)NH$_2$, —(C=O)NHCH$_3$, and —(C=O)N(CH$_3$)$_2$. In a further aspect, R$^{5a}$, when present, is hydrogen and R$^{5b}$, when present, is selected from hydrogen, —(C=O)NH$_2$, —(C=O)NHCH$_3$, and —(C=O)N(CH$_3$)$_2$.

l. R$^{6a}$ and R$^{6b}$ Groups

In one aspect, each of R$^{6a}$ and R$^{6b}$, when present, is hydrogen. In a further aspect, each of R$^{6a}$ and R$^{6b}$, when present, is methyl. In a further aspect, each of R$^{6a}$ and R$^{6b}$, when present, is ethyl. In a further aspect, each of R$^{6a}$ and R$^{6b}$, when present, is independently selected from hydrogen, methyl, ethyl, propyl, isopropyl, tert-butyl, sec-butyl, isobutyl, neopentyl, isopentyl, sec-pentyl, tert-pentyl, 3,3-dimethylbutan-2-yl, and 2,3-dimethylbutan-2-yl. In a further aspect, each of R$^{6a}$ and R$^{6b}$, when present, is independently selected from hydrogen, methyl, ethyl, propyl, isopropyl, tert-butyl, sec-butyl, isobutyl, and tert-butyl. In a further aspect, each of R$^{6a}$ and R$^{6b}$, when present, is independently selected from hydrogen, methyl, ethyl, propyl, and isopropyl. In a further aspect, each of R$^{6a}$ and R$^{6b}$, when present, is independently selected from hydrogen, methyl, and ethyl. In a further aspect, each of R$^{6a}$ and R$^{6b}$, when present, is independently selected from hydrogen and methyl. In a further aspect, R$^{6a}$, when present, is hydrogen, and R$^{6b}$, when present, is selected from hydrogen, methyl, ethyl, propyl, isopropyl, tert-butyl, sec-butyl, isobutyl, neopentyl, isopentyl, sec-pentyl, tert-pentyl, 3,3-dimethylbutan-2-yl, and 2,3-dimethylbutan-2-yl. In a further aspect, R$^{6a}$, when present, is hydrogen, and R$^{6b}$, when present, is selected from hydrogen, methyl, ethyl, propyl, isopropyl, tert-butyl, sec-butyl, isobutyl, and tert-butyl. In a further aspect, R$^{6a}$, when present, is hydrogen, and R$^{6b}$, when present, is selected from hydrogen, methyl, ethyl, propyl, and isopropyl. In a further aspect, R$^{6a}$, when present, is hydrogen, and R$^{6b}$, when present, is selected from hydrogen, methyl, and ethyl. In a further aspect, R$^{6a}$, when present, is hydrogen, and R$^{6b}$, when present, is selected from hydrogen and methyl.

m. R$^7$ Groups

In one aspect, each R$^7$, when present, is hydrogen. In a further aspect, each R$^7$, when present, is methyl. In a further aspect, each R$^7$, when present, is independently selected from hydrogen and C1-C6 alkyl. In a further aspect, each R$^7$, when present, is independently selected from hydrogen and C1-C3 alkyl. In a further aspect, each R$^7$, when present, is independently selected from hydrogen, methyl, ethyl, propyl, isopropyl, tert-butyl, sec-butyl, isobutyl, neopentyl, isopentyl, sec-pentyl, tert-pentyl, 3,3-dimethylbutan-2-yl, and 2,3-dimethylbutan-2-yl. In a further aspect, each R$^7$, when present, is independently selected from hydrogen, methyl, ethyl, propyl, and isopropyl. In a further aspect, each R$^7$, when present, is independently selected from hydrogen, methyl, and ethyl. In a further aspect, each R$^7$, when present, is independently selected from hydrogen and methyl. In a further aspect, each R$^7$ is independently selected from hydrogen, C1-C3 alkyl, C1-C3 monohaloalkyl, C1-C3 polyhaloalkyl. In a further aspect, each R$^7$, when present, is independently selected from hydrogen, methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, and —(CH$_2$)$_2$CI$_3$. In a further aspect, each R$^7$, when present, is independently selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, and —CH$_2$CF$_3$. In a further aspect, each R$^7$, when present, is independently selected from hydrogen, methyl, —CH$_2$F, —CHF$_2$, and —CF$_3$.

n. R$^{8a}$ and R$^{8b}$ Groups

In one aspect, each of R$^{8a}$ and R$^{8b}$, when present, is hydrogen. In a further aspect, each of R$^{8a}$ and R$^{8b}$, when present, is methyl. In a further aspect, each of R$^{8a}$ and R$^{8b}$, when present, is independently selected from hydrogen and C1-C6 alkyl. In a further aspect, each of R$^{8a}$ and R$^{8b}$, when present, is independently selected from hydrogen and C1-C3 alkyl. In a further aspect, each of R$^{8a}$ and R$^{8b}$, when present, is independently selected from hydrogen, methyl, ethyl, propyl, isopropyl, tert-butyl, sec-butyl, isobutyl, neopentyl, isopentyl, sec-pentyl, tert-pentyl, 3,3-dimethylbutan-2-yl, and 2,3-dimethylbutan-2-yl. In a further aspect, each of R$^{8a}$ and R$^{8b}$, when present, is independently selected from hydrogen, methyl, ethyl, propyl, and isopropyl. In a further aspect, each of R$^{8a}$ and R$^{8b}$, when present, is independently selected from hydrogen, methyl, and ethyl. In a further aspect, each of R$^{8a}$ and R$^{8b}$, when present, is independently selected from hydrogen and methyl. In a further aspect, each of R$^{8a}$ and R$^{8b}$, when present, is independently selected from hydrogen, C1-C3 alkyl, C1-C3 monohaloalkyl, C1-C3 polyhaloalkyl. In a further aspect, each of R$^{8a}$ and R$^{8b}$, when present, is independently selected from hydrogen, methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, and —(CH$_2$)$_2$CI$_3$. In a further aspect, each of R$^{8a}$ and R$^{8b}$, when present, is independently selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, and —CH$_2$CF$_3$. In a further aspect, each of R$^{8a}$ and R$^{8b}$ when present, is independently selected from hydrogen, methyl, —CH$_2$F, —CHF$_2$, and —CF$_3$. In a further aspect, R$^{8a}$, when present, is hydrogen and R$^{8b}$, when present, is selected from hydrogen and C1-C6 alkyl. In a further aspect, R$^{8a}$, when present, is hydrogen and R$^{8b}$, when present, is selected from hydrogen and C1-C3 alkyl. In a further aspect, R$^{8a}$, when present, is hydrogen and R$^{8b}$, when present, is selected from hydrogen, methyl, ethyl, propyl, isopropyl, tert-butyl, sec-butyl, isobutyl, neopentyl, isopentyl, sec-pentyl, tert-pentyl, 3,3-dimethylbutan-2-yl, and 2,3-dimethylbutan-2-yl. In a further aspect, R$^{8a}$, when present, is hydrogen and R$^{8b}$, when present, is selected from hydrogen, methyl, ethyl, propyl, and isopropyl. In a further aspect, R$^{8a}$, when present, is hydrogen and R$^{8b}$, when present, is selected from hydrogen, methyl, and ethyl. In a further aspect, R$^{8a}$, when present, is hydrogen and R$^{8b}$, when present, is selected from hydrogen and methyl. In a further aspect, R$^{8a}$, when present, is hydrogen and R$^{8b}$, when present, is selected from hydrogen, C1-C6 alkyl, C1-C6 monohaloalkyl, C1-C6 polyhaloalkyl. In a further aspect, R$^{8a}$, when present, is hydrogen and R$^{8b}$, when present, is selected from hydrogen, C1-C3 alkyl, C1-C3 monohaloalkyl, C1-C3 polyhaloalkyl. In a further aspect, R$^{8a}$, when present, is hydrogen and R$^{8b}$, when present, is selected from hydrogen, methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, and —(CH$_2$)$_2$CI$_3$. In a further aspect, R$^{8a}$, when present, is hydrogen and R$^{8b}$, when present, is selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, and —CH$_2$CF$_3$. In a further aspect, R$^{8b}$, when present, is hydrogen and R$^{8b}$, when present, is selected from hydrogen, methyl, —CH$_2$F, —CHF$_2$, and —CF$_3$.

o. Halogen (X)

In one aspect, halogen is fluoro, chloro, bromo or iodo. In a still further aspect, halogen is fluoro, chloro, or bromo. In a yet further aspect, halogen is fluoro or chloro. In a further aspect, halogen is fluoro. In an even further aspect, halogen is chloro or bromo. In an even further aspect, halogen is chloro. In a yet further aspect, halogen is iodo. In a still further aspect, halogen is bromo.

It is also contemplated that pseudohalogens (e.g. triflate, mesylate, brosylate, etc.) can be used as leaving groups in place of halogens in certain aspects.

2. Example Compounds

In one aspect, a compound can be present as:

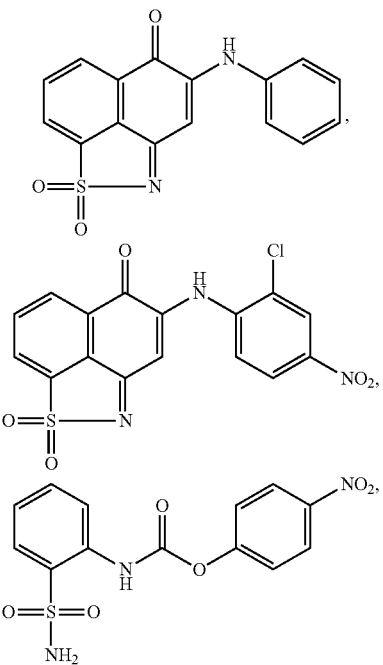

71
-continued
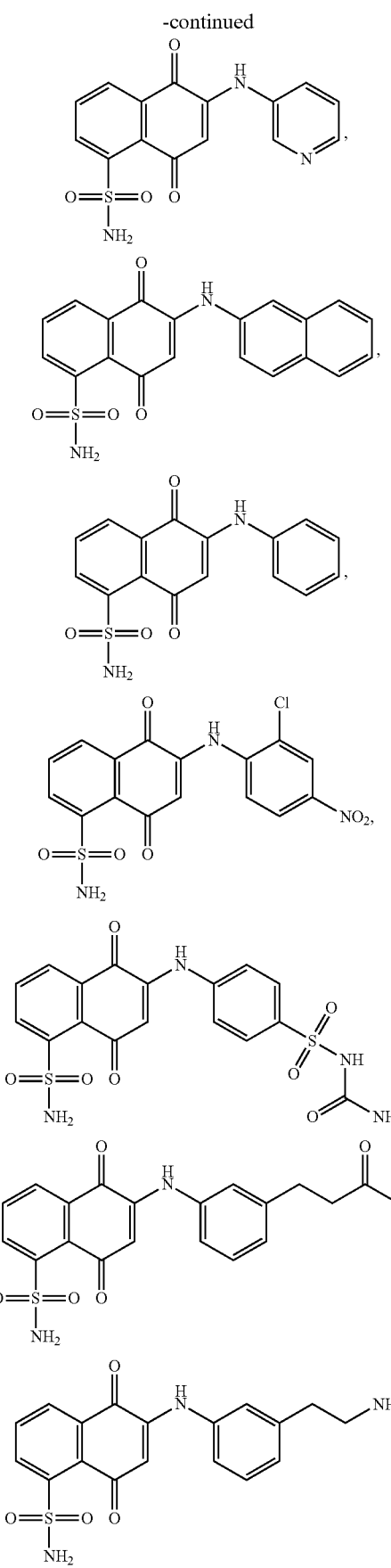
72
-continued
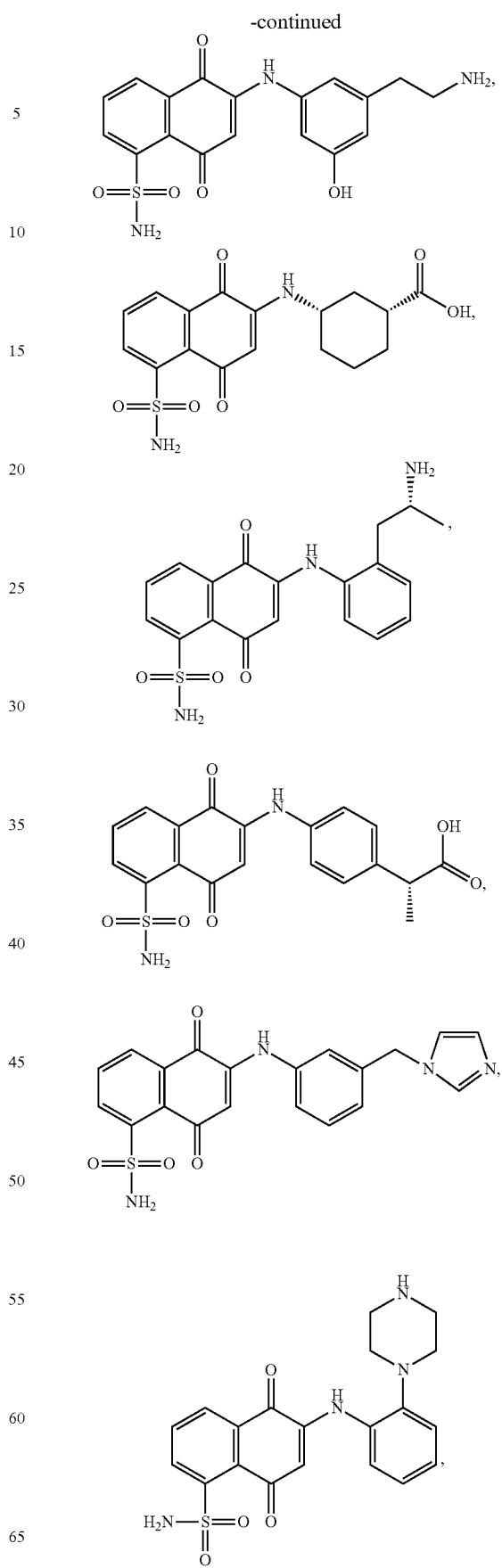

73
-continued
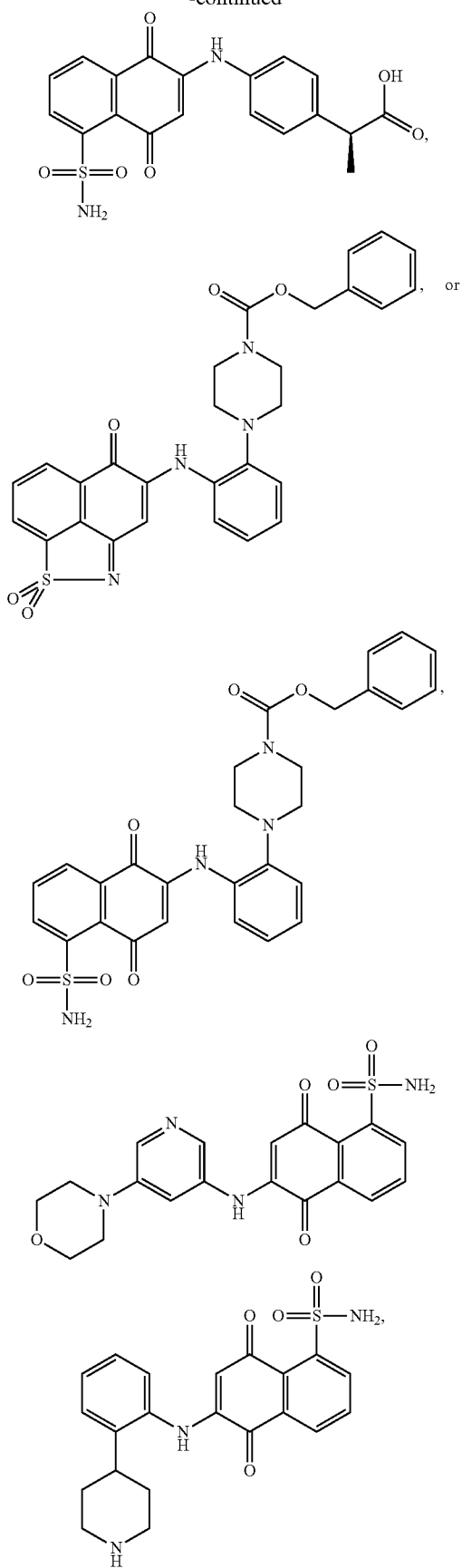
74
-continued
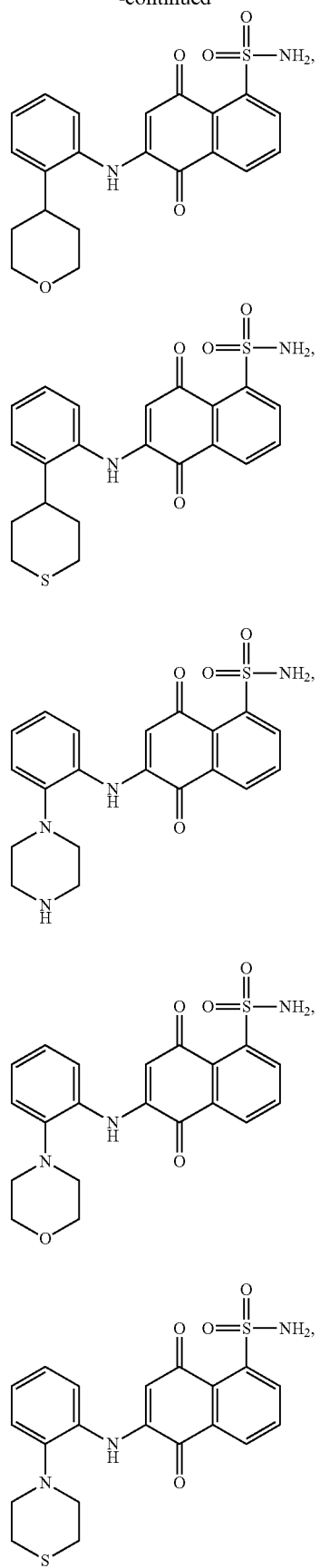

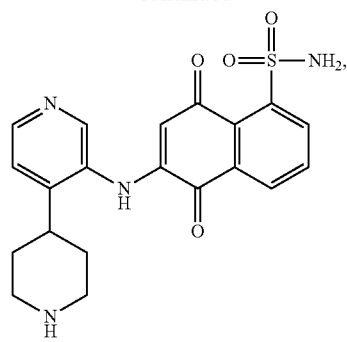
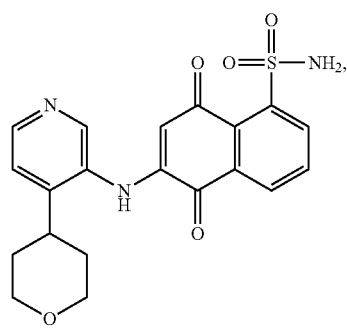
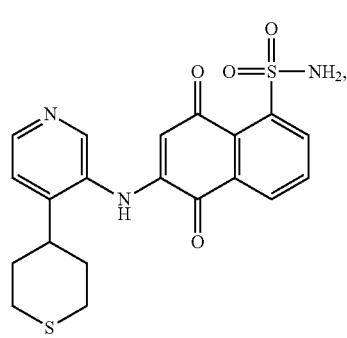
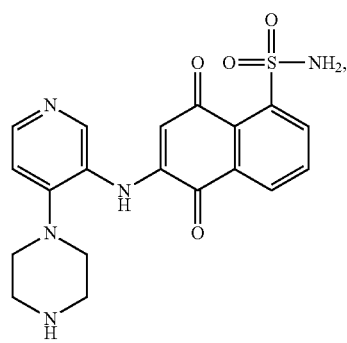
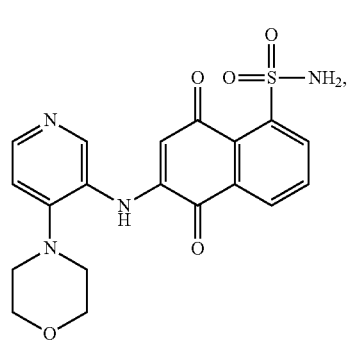
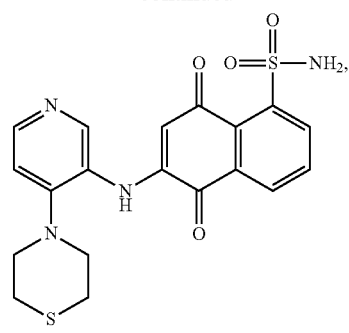
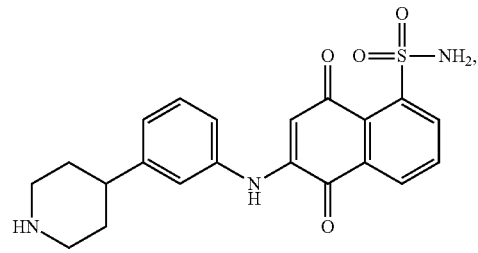
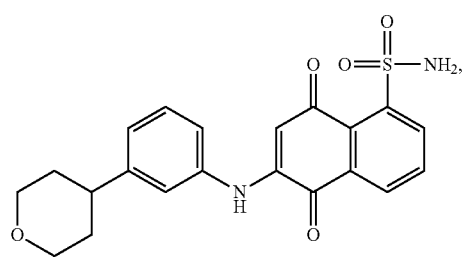
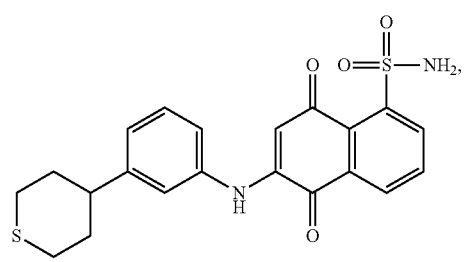
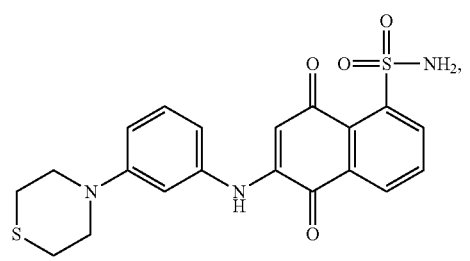
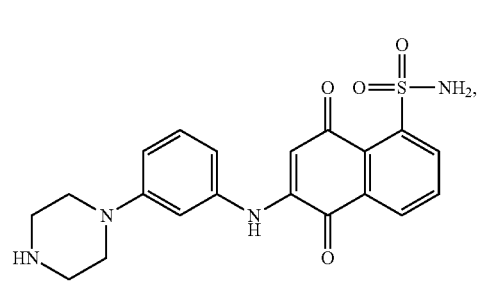

-continued
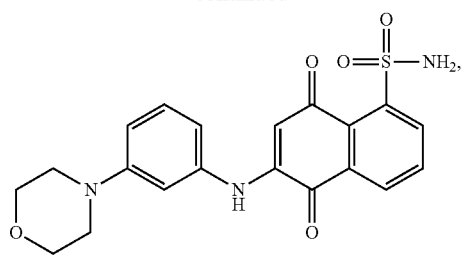
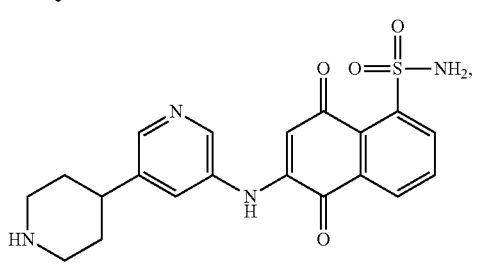
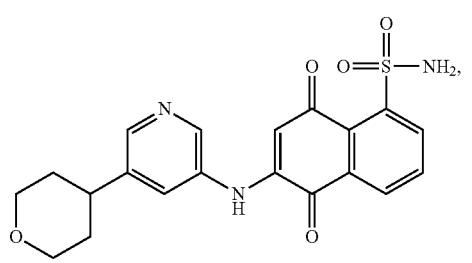
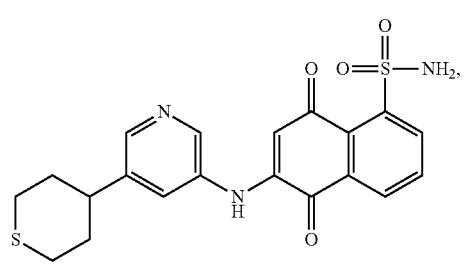
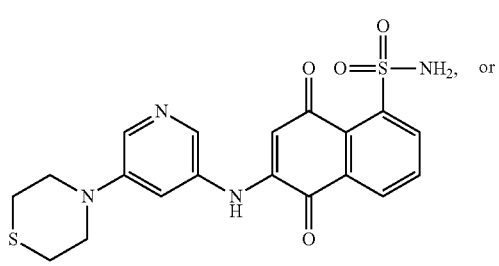
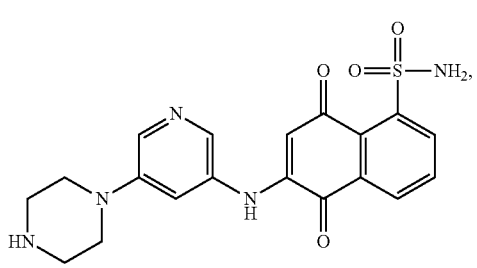
In one aspect, a compound can be present as:
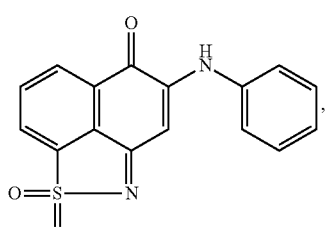
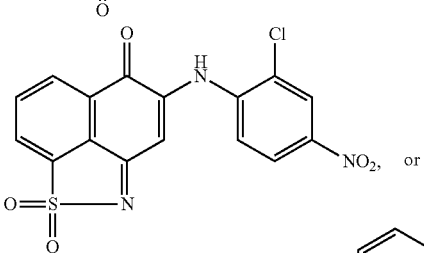
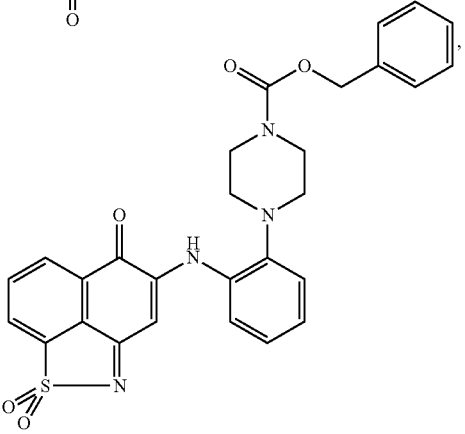
or a subgroup thereof.
In one aspect, a compound can be present as:
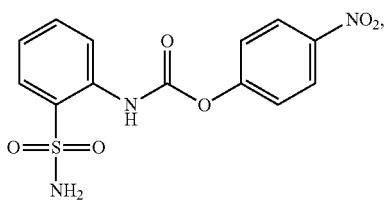
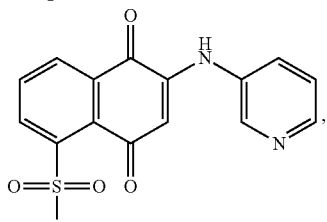
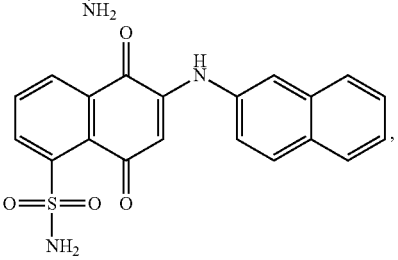

79
-continued
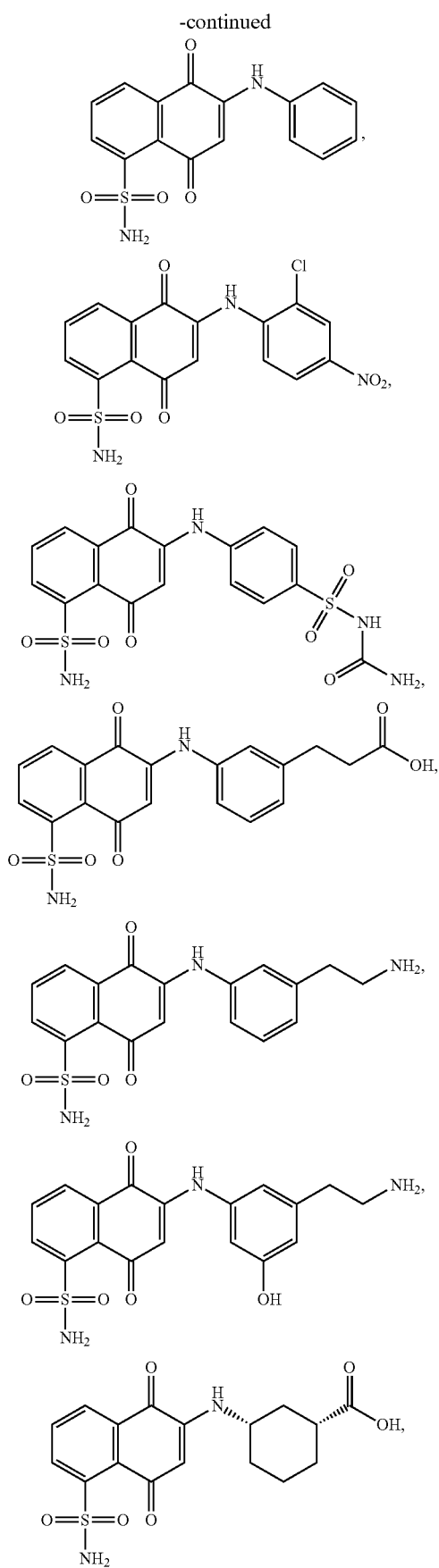
80
-continued
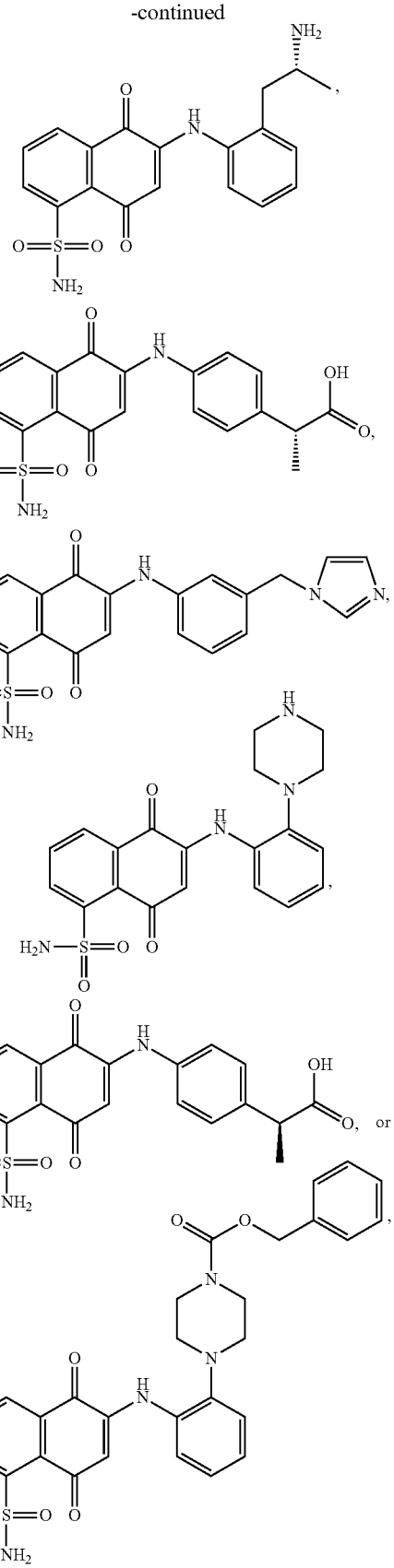
or a subgroup thereof.

In one aspect, a compound can be present as:
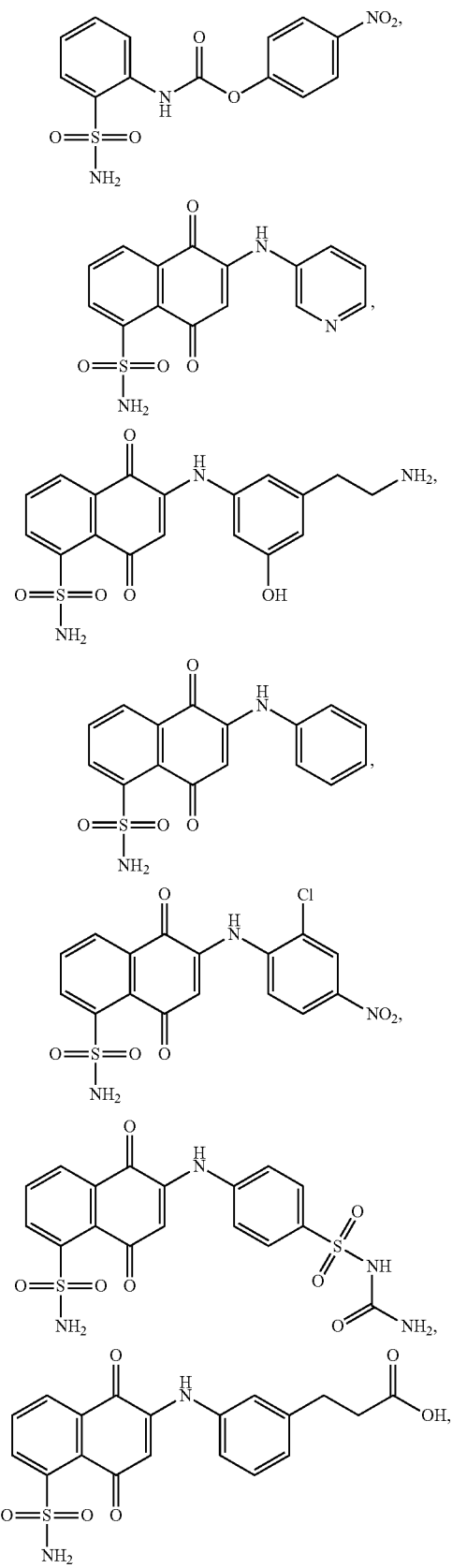
-continued
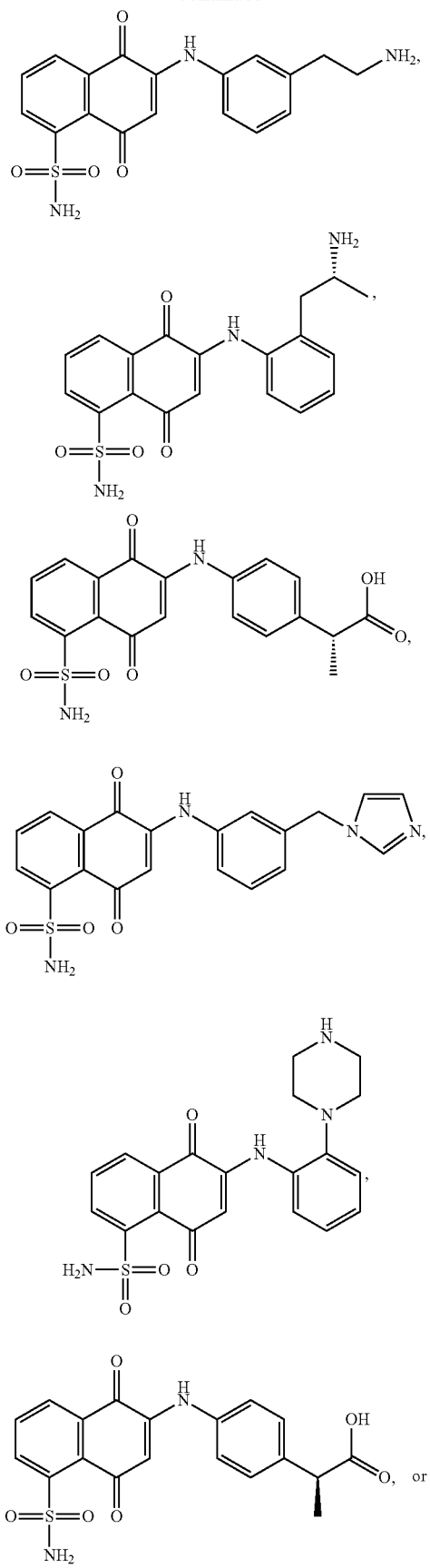

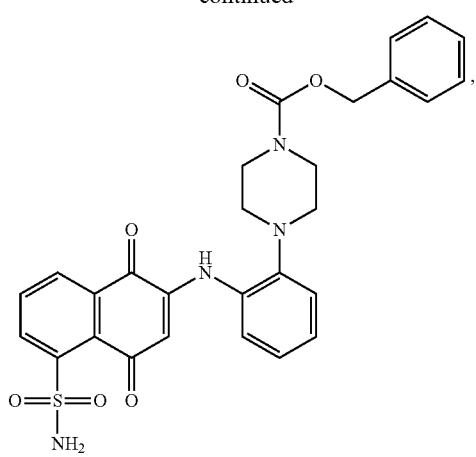
or a subgroup thereof.
In one aspect, a compound can be present as:
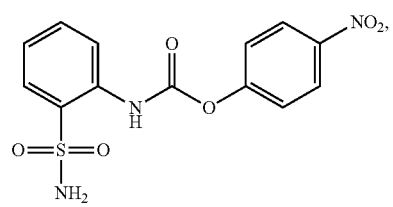
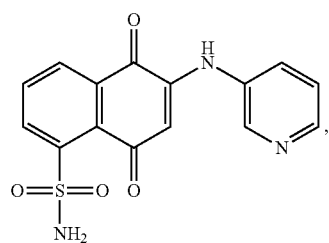
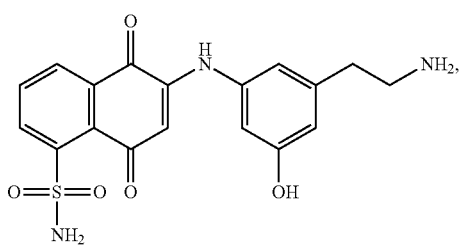
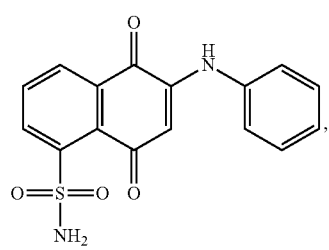
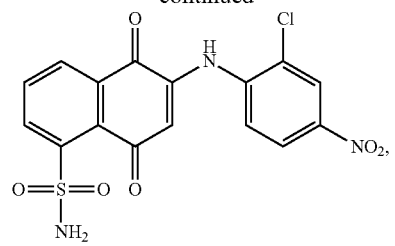
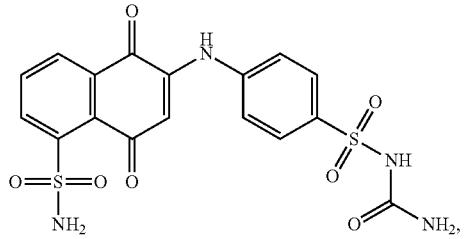
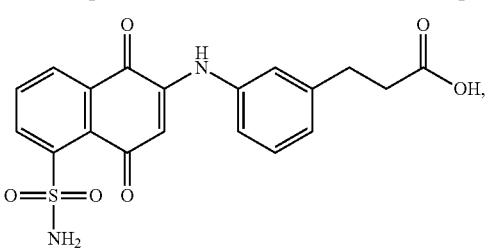
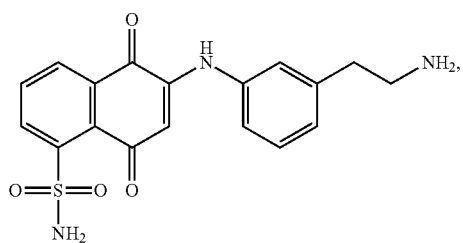
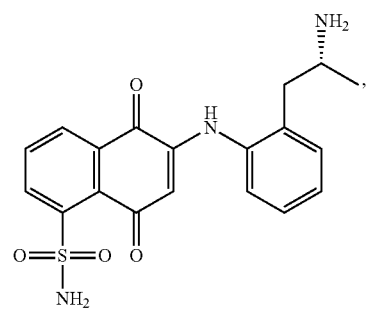
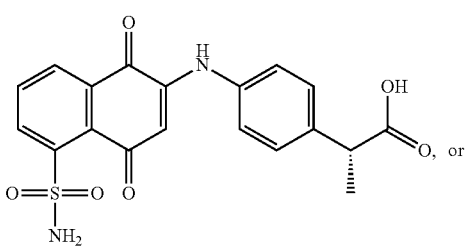

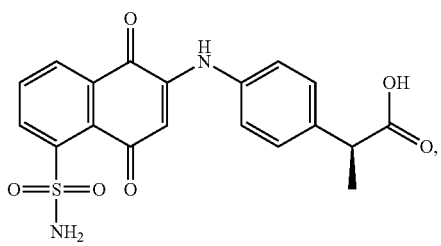
or a subgroup thereof.
In one aspect, a compound can be present as:
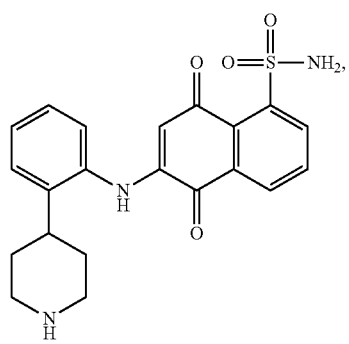
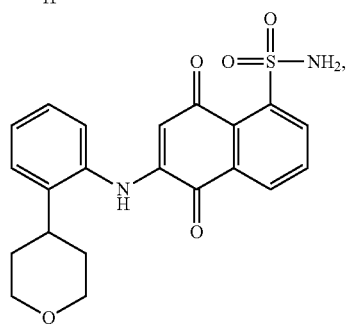
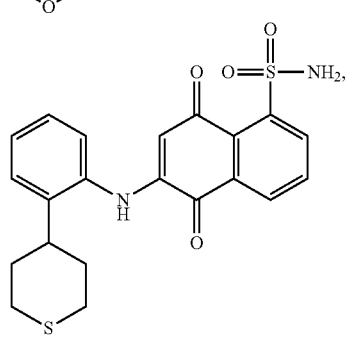
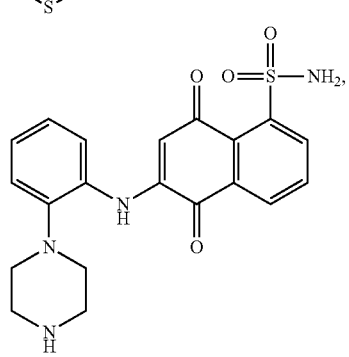
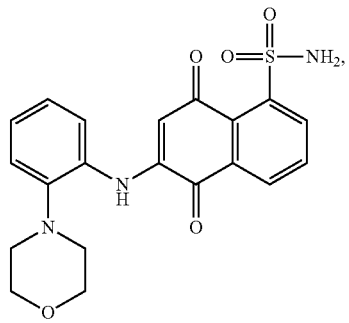
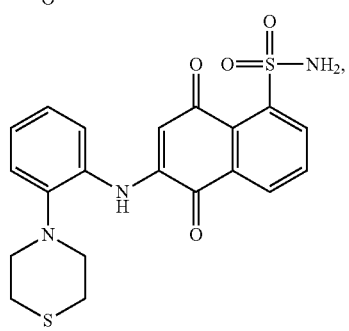
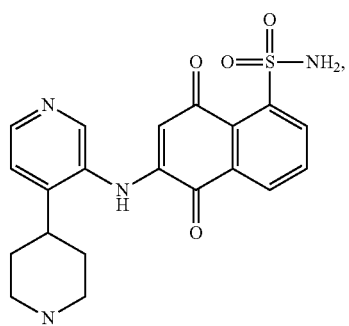
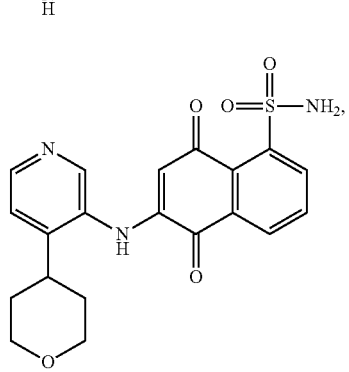
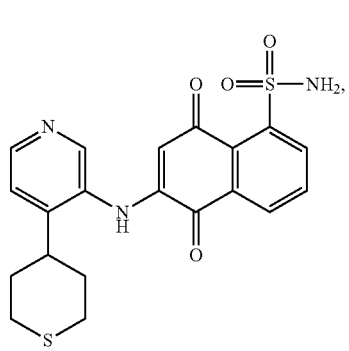

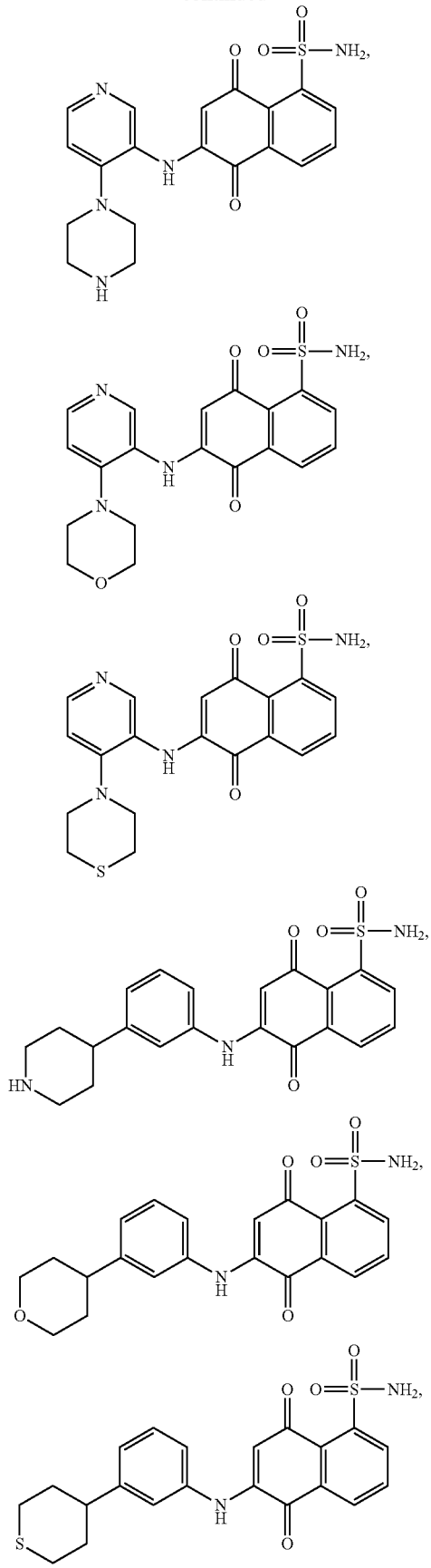
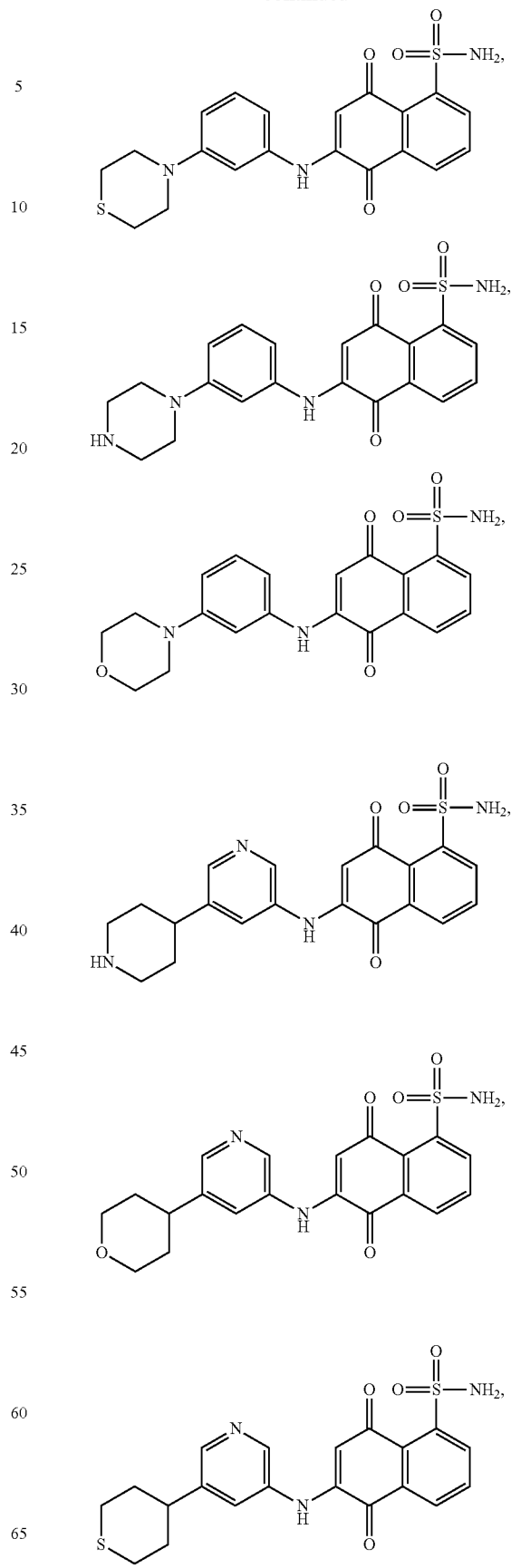

-continued

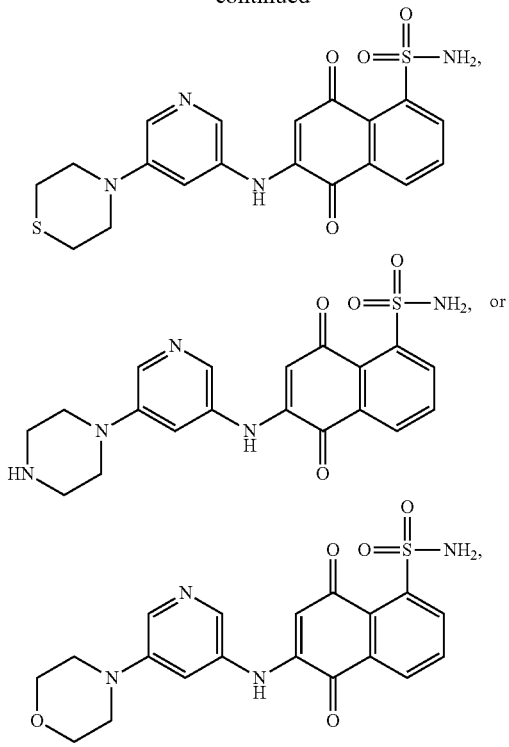

or a subgroup thereof.

In yet a further aspect, the compound produced exhibits STAT3 inhibition as described herein.

In a further aspect, the disclosed compounds are useful in therapeutics related to STAT3 dysfunction.

It is contemplated that one or more compounds can optionally be omitted from the disclosed invention.

3. STAT Inhibition

Generally, the disclosed compounds exhibit STAT inhibition, such as STAT3 inhibition.

In one aspect, the disclosed compounds exhibit STAT3 inhibition. Such inhibition can be useful in the treatment or prevention of diseases associated with STAT3 dysfunction, such as upregulation. Such diseases, treatment, and prevention For example, a compound can exhibit STAT3 with an $IC_{50}$ of less than about 10,000 nM, of less than about 5,000 nM. of less than about 1,000 nM, of less than about 500 nM, or of less than about 100 nM.

C. Modulation of Stat3 Activity

In one aspect, the disclosed compounds exhibit inhibition of STAT3 protein activity. In a yet further aspect, the disclosed compounds exhibit selective inhibition of STAT3 protein activity. In a still further aspect, the disclosed compounds prevent STAT3 protein dimerization. In a yet further aspect, the disclosed compounds exhibit disruption of preformed or existing STAT3 dimers. In a still further aspect, the disclosed compounds exhibit binding to the SH2 domain of STAT3.

Inhibition of STAT3 activity can be determined by a variety of both in vitro and in vivo methods known to one skilled in the art. For example, inhibition of STAT3 protein activity can be determined using a electrophoretic mobility shift assay ("EMSA"). In one aspect, the disclosed compounds exhibit inhibition of STAT3 protein activity with an $IC_{50}$ in an EMSA assay of less than about 300 µM, less than about 100 µM, less than about 50 µM, less than about 10 µM, less than about 1 µM, less than about 500 nM, or of less than about 100 nM.

In one aspect, the disclosed compounds are selective for STAT3. In a further aspect, selective inhibition of STAT3 activity is determined using an EMSA assay. In various further aspects, the compound inhibits STAT3 activity in a EMSA assay with an $IC_{50}$ less than the $IC_{50}$ for one or more of STAT1, STAT2, STAT4, STAT5a, STAT5b, or STAT6. That is, a disclosed compound can have selectivity for the STAT3 protein vis-à-vis one or more of STAT1, STAT2, STAT4, STAT5a, STAT5b, or STAT6 proteins. For example, in one aspect, a disclosed compound can inhibit STAT3 with an $IC_{50}$ of about 5-fold less than that for STAT1, of about 10-fold less than that for STAT1, of about 20-fold less than that for STAT1, of about 30-fold less than that for STAT1, or of about 50-fold less than that for STAT1. In a further aspect, a disclosed compound can inhibit STAT3 with an $IC_{50}$ of about 5-fold less than that for STAT2, of about 10-fold less than that for STAT2, of about 20-fold less than that for STAT2, of about 30-fold less than that for STAT2, or of about 50-fold less than that for STAT2. In a still further aspect, a disclosed compound can inhibit STAT3 with an $IC_{50}$ of about 5-fold less than that for STAT4, of about 10-fold less than that for STAT4, of about 20-fold less than that for STAT4, of about 30-fold less than that for STAT4, or of about 50-fold less than that for STAT4. In a yet further aspect, a disclosed compound can inhibit STAT3 with an $IC_{50}$ of about 5-fold less than that for STAT5a, of about 10-fold less than that for STAT5a, of about 20-fold less than that for STAT5a, of about 30-fold less than that for STAT5a, or of about 50-fold less than that for STAT5a. In an even further aspect, a disclosed compound can inhibit STAT3 with an $IC_{50}$ of about 5-fold less than that for STAT5b, of about 10-fold less than that for STAT5b, of about 20-fold less than that for STAT5b, of about 30-fold less than that for STAT5b, or of about 50-fold less than that for STAT5b. In a still further aspect, a disclosed compound can inhibit STAT3 with an $IC_{50}$ of about 5-fold less than that for STAT6, of about 10-fold less than that for STAT6, of about 20-fold less than that for STAT6, of about 30-fold less than that for STAT6, or of about 50-fold less than that for STAT6.

In various aspects, the disclosed compounds exhibit binding to a STAT protein. In a further aspect, the disclosed compounds exhibit binding to the SH2 domain of a STAT protein. In a still further aspect, the disclosed compounds exhibit binding to STAT3 protein. In a yet further aspect, the disclosed compounds exhibit binding to the SH2 domain of STAT3. The binding affinity of a disclosed compound for a STAT protein, e.g. STAT3 protein, can be determined by various methods known to one skilled in the art. For example, inhibition of STAT protein activity can be determined using a surface plasmon resonance ("SPR") assay. In one aspect, the disclosed compounds exhibit binding to STAT protein with a $K_D$ of less than about 50 µM, less than about 10 µM, less than about 1 µM, less than about 500 nM, or of less than about 100 nM. In a further aspect, the $K_D$ is determined using an SPR method. In a still further aspect, the binding is determined using STAT3 protein.

In various further aspects, the binding to STAT3 is selective. In a further aspect, the disclosed compounds exhibit a $K_D$ for STAT3 binding less than the $K_D$ for one or more of STAT1, STAT2, STAT4, STAT5a, STAT5b, or STAT6. That is, a disclosed compound can have selectivity for the STAT3 protein vis-à-vis one or more of STAT1, STAT2, STAT4, STAT5a, STAT5b, or STAT6 proteins. For example, in one aspect, a disclosed compound can bind STAT3 with a $K_D$ of about 5-fold less than that for STAT1, of about 10-fold less than that for STAT1, of about 20-fold less than that for STAT1, of about 30-fold less than that for STAT1, or of about 50-fold less than that for STAT1. In a further aspect, a disclosed compound can bind STAT3 with a $K_D$ of about 5-fold less than that for STAT2, of about 10-fold less than that for STAT2, of about 20-fold less than that for STAT2, of about 30-fold less than that for STAT2, or of about 50-fold less than that for STAT2. In a still further aspect, a disclosed compound can bind STAT3 with a $K_D$ of about 5-fold less than that for STAT4, of about 10-fold less than that for STAT4, of about 20-fold less than that for STAT4, of about 30-fold less than that for STAT4, or of about 50-fold less than that for STAT4. In a yet further aspect, a disclosed compound can bind STAT3 with a $K_D$ of about 5-fold less than that for STAT5a, of about 10-fold less than that for STAT5a, of about 20-fold less than that for STAT5a, of about 30-fold less than that for STAT5a, or of about 50-fold less than that for STAT5a. In an even further aspect, a disclosed compound can bind STAT3 with a $K_D$ of about 5-fold less than that for STAT5b, of about 10-fold less than that for STAT5b, of about 20-fold less than that for STAT5b, of about 30-fold less than that for STAT5b, or of about 50-fold less than that for STAT5b. In a still further aspect, a disclosed compound can bind STAT3 with a $K_D$ of about 5-fold less than that for STAT6, of about 10-fold less than that for STAT6, of about 20-fold less than that for STAT6, of about 30-fold less than that for STAT6, or of about 50-fold less than that for STAT6.

In a further aspect, the disclosed compounds exhibit inhibition of binding a reporter molecule to a STAT protein. In a further aspect, the disclosed compounds exhibit inhibition of binding of a reporter molecule to the SH2 domain of a STAT protein. In a still further aspect, the disclosed compounds exhibit inhibition of binding of a reporter molecule to the STAT3 protein. In a yet further aspect, the disclosed compounds exhibit inhibition of binding of a reporter molecule to the SH2 domain of STAT3. The inhibition of binding of a reporter molecule to a STAT protein, e.g. STAT3 protein, can by a disclosed compound can be determined by various methods known to one skilled in the art. For example, inhibition of a reporter molecule to STAT3 can be determined using a fluorescence polarization assay. In a further aspect, the compound exhibits inhibition with an $K_i$ of less than about 300 µM. In a still further aspect, the compound exhibits inhibition with an $K_i$ of less than about 100 µM. In a yet further aspect, the compound exhibits inhibition with an $K_i$ of less than about 50 µM. In an even further aspect, the compound exhibits inhibition with an $K_i$ of less than about 10 µM. In a still further aspect, the compound exhibits inhibition with an $K_i$ of less than about 1 µM. In an even further aspect, the compound exhibits inhibition with an $K_i$ of less than about 0.1 µM. In a still further aspect, the report molecule is a fluorescently labeled peptide. In a yet further aspect, the fluorescently-labeled reporter peptide is 5-carboxyfluorescein-GpYLPQTV-NH2.

Alternatively, the inhibition of STAT protein activity can be determined in a cell-based assay. There are a variety of cell-based assays that are suitable for determination of inhibition of STAT protein activity known to one skilled in the art. For example, cell growth inhibition or cell arrest can be determined using a cell, either a permanent cell-line or a primary cell culture that has a STAT protein with dysfunction activity. In a further aspect, the STAT protein is STAT3. In a yet further aspect, the STAT3 protein dysfunction is one wherein the STAT3 protein is has acquired a gain of function mutation. Alternatively, the STAT3 protein has a phenotype of persistent or constitutive activity. For example, the STAT3 protein can have a persistent or constitutive activity due to a dysfunction in an upstream regulatory protein. In a further aspect, the STAT3 protein is overexpressed.

In one aspect, the disclosed compounds and products of disclosed methods of making inhibit cell growth. In a still further aspect, the disclosed compounds and products of disclosed methods inhibit cell growth in an in vitro assay system. In an even further aspect, the in vitro assay system makes use of a cell-line derived from a from cancer or tumor selected from breast cancer, prostate cancer, and pancreatic cancer. In a yet further aspect, the cell-line is derived from a human source. In a yet further aspect, the disclosed compounds inhibit cell growth in a cell with a persistently active STAT3 protein. In an even further aspect, the cell-line has an activated STAT3 protein. In a still further aspect, the cell-line is selected from MDA-MB-231, MDA-468, Panc-1, DU145, OPM2, OCL-AML2, and A549. In an even further aspect, the cell-line is selected from DU-145, Panc-1, and MDA-MB-231. In a still further aspect, the inhibition of cell growth by the disclosed compounds is determined in a cell-line expressing v-Src. In an even further aspect, the cell-line is transformed with v-Src. In a yet further aspect, cell-line which is transformed in the NIH3T3 cell-line. In one aspect, the disclosed compounds exhibit inhibition of cell growth activity in an in vitro cell-based assay with an $IC_{50}$ of less than about 300 µM, less than about 100 µM, less than about 50 µM, less than about 10 µM, less than about 1 µM, less than about 500 nM, or of less than about 100 nM.

In one aspect, the disclosed compounds and products of disclosed methods of making inhibit cell migration. In a still further aspect, the disclosed compounds and products of disclosed methods inhibit cell migration in an in vitro assay system. In an even further aspect, the in vitro assay system makes use of a cell-line derived from a from cancer or tumor selected from breast cancer, prostate cancer, and pancreatic cancer. In a yet further aspect, the cell-line is derived from a human source. In a yet further aspect, the disclosed compounds inhibit cell growth in a cell with a persistently active STAT3 protein. In an even further aspect, the cell-line has an activated STAT3 protein. In a still further aspect, the cell-line is selected from MDA-MB-231, MDA-468, Panc-1, DU145, OPM2, OCL-AML2, and A549. In an even further aspect, the cell-line is selected from DU-145, Panc-1, and MDA-MB-231. In a still further aspect, the inhibition of cell migration by of the disclosed compound is determined in a cell-line expressing v-Src. In an even further aspect, the cell-line is transformed with v-Src. In a yet further aspect, cell-line which is transformed in the NIH3T3 cell-line. In one aspect, the disclosed compounds exhibit inhibition of cell migration in an in vitro cell-based assay with an $IC_{50}$ of less than about 300 µM, less than about 100 µM, less than about 50 µM, less than about 10 µM, less than about 1 PM, less than about 500 nM, or of less than about 100 nM.

Alternatively, the modulatory effects, e.g. inhibition, of the disclosed compounds can be determined using other types of cell-based assays, e.g. determination of the level of pY705STAT3 levels in cells following treatment with a disclosed compound and compared to the pY705STAT3 levels in control cells versus the unphosphorylated form of STAT3 in the same cell lysate. Determination of pY705STAT3 can be carried by immunoblots of cell lysates, e.g. whole-cell lysates, nuclear extracts, and cytosolic lysates. Other markers of STAT3 inhibition can be assessed in similar fashion, and include markers selected from the phosphorylated and unphosphorylated forms Shc, Jaks, Src, and Erk1/2. In a further aspect, the cellular marker determined by immunoblotting is selected from c-myc, cyclin D1, Bcl-xL, suvivin, and VEGF. In various further aspects, the effect of the disclosed compounds on the STAT3 transcriptional activity can be determined using a luciferase-based transcriptional reporter assay. Briefly, the appropriate cell-type, e.g. DU145, Panc-1, or MDA-MB-231, is transiently transfected with a plasmid, e.g. pLucTKS3 wherein expression of luciferase is STAT3-dependent, and compared to the expression of luciferase in a cell-line transiently transfected with a plasmid wherein the expression of luciferase is not dependent upon STAT3, e.g. pLucSRE.

D. Methods of Making the Compounds

In one aspect, the invention relates to methods of making compounds useful as inhibitors of STAT. In a further aspect, the products of disclosed methods of making are modulators of STAT activity. In a yet further aspect, the products of disclosed methods of making bind to a STAT protein and negatively modulate STAT activity. The compounds can, in one aspect, exhibit subtype selectivity. In a still further aspect, the products of disclosed methods of making exhibit selectivity for the STAT3 member of the STAT protein family.

The compounds of this invention can be prepared by employing reactions as shown in the following schemes, in addition to other standard manipulations that are known in the literature, exemplified in the experimental sections or clear to one skilled in the art. For clarity, examples having a single substituent are shown where multiple substituents are allowed under the definitions disclosed herein.

Reactions used to generate the compounds of this invention are prepared by employing reactions as shown in the following Reaction Schemes, in addition to other standard manipulations known in the literature or to one skilled in the art. The following examples are provided so that the invention might be more fully understood, are illustrative only, and should not be construed as limiting.

In one aspect, the disclosed compounds comprise the products of the synthetic methods described herein. In a further aspect, the disclosed compounds comprise a compound produced by a synthetic method described herein. In a still further aspect, the invention comprises a pharmaceutical composition comprising a therapeutically effective amount of the product of the disclosed methods and a pharmaceutically acceptable carrier. In a still further aspect, the invention comprises a method for manufacturing a medicament comprising combining at least one compound of any of disclosed compounds or at least one product of the disclosed methods with a pharmaceutically acceptable carrier or diluent.

In a further aspect, the compound produced is useful in the treatment of a disorder of uncontrolled cellular proliferation associated with STAT dysfunction and other diseases in which a STAT protein is involved, as further described herein. In a further aspect, the STAT protein is STAT3.

1. Route I

In one aspect, the disclosed compounds, substitutions and analogs thereof, of the present invention can be prepared as shown below.

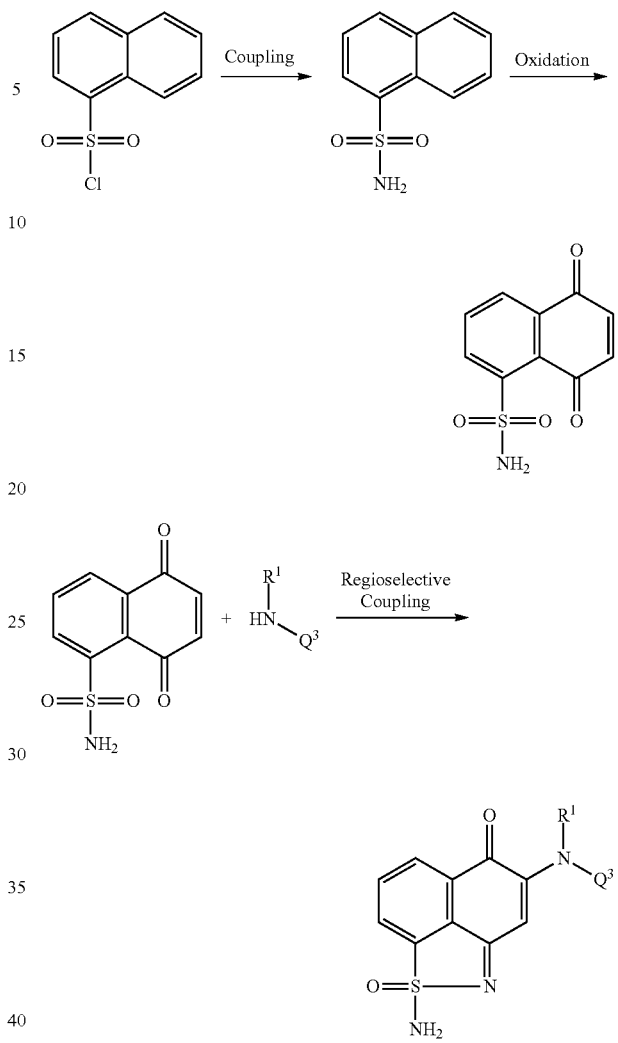

Compounds are represented in generic form, with substituents as noted in compound descriptions elsewhere herein. A more specific example is set forth below.

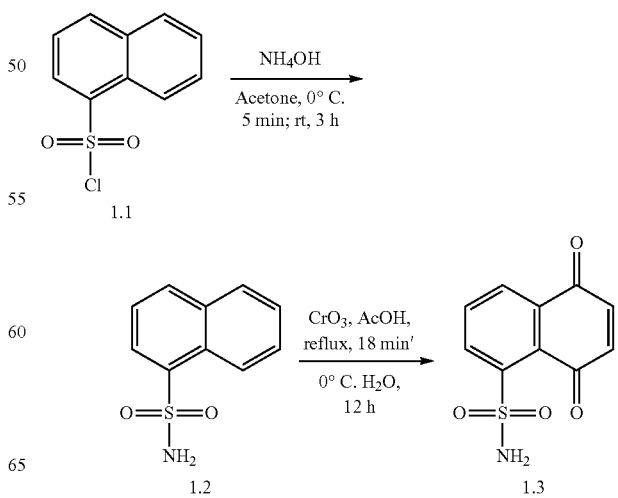

-continued

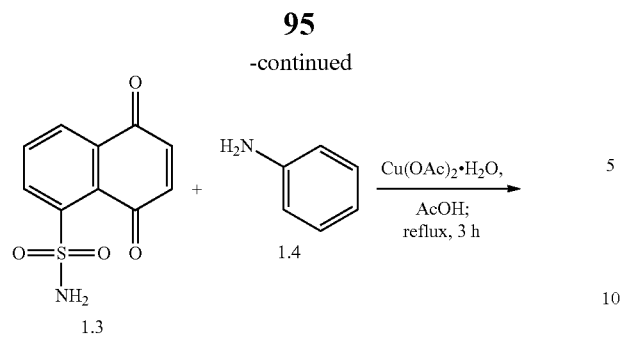

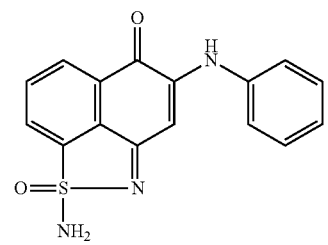

In various aspects, compounds of type 1.2 can be prepared starting with a compound of type 1.1, which is commercially available or prepared by methods known to one skilled in the art. Thus, a compound of type 1.2 can be prepared by a coupling reaction with a suitable amine, e.g. ammonium hydroxide as shown above. Appropriate amines are commercially available or can be prepared by methods known to one skilled in the art. The reaction is carried out at a suitable temperature, e.g. about −10-20° C., in a suitable solvent, e.g. acetone, for a period of time sufficient to complete the reaction, e.g. about 3-5 h. A compound of type 1.3 can be prepared by oxidation of a compound of type 1.2. For example, as shown above, such an oxidation reaction can be accomplished using a suitable oxidizing agent, e.g. chromium trioxide, and a suitable solvent, e.g. acetone, at an appropriate temperature, e.g. about 90-130° C., for a suitable period time, e.g. 5-30 min, before addition of a suitable protic polar solvent, e.g. water, at an appropriate temperature, e.g. −10-20° C., for a period of time sufficient to complete the reaction, e.g. about 8-16 h. A compound of type 1.5 can be prepared by reaction of a compound of type 1.3 and 1.4, which are commercially available or can be prepared by methods known to one skilled in the art. For example, as shown above, such a reaction can be accomplished using a suitable coupling agent, e.g. copper acetate monohydrate, with a suitable solvent, e.g. acetic acid, at a suitable temperature, e.g. 90-130° C., for a period of time sufficient to complete the reaction, e.g. about 2-4 h.

2. Route II

In one aspect, the disclosed compounds, substitutions and analogs thereof, of the present invention can be prepared as shown below.

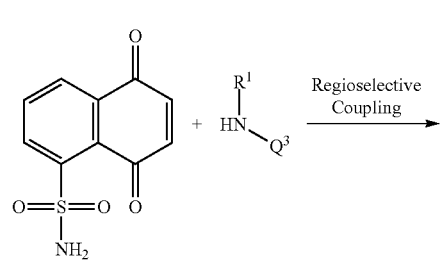

Compounds are represented in generic form, with substituents as noted in compound descriptions elsewhere herein. A more specific example is set forth below.

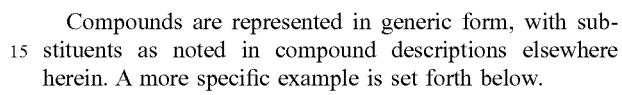

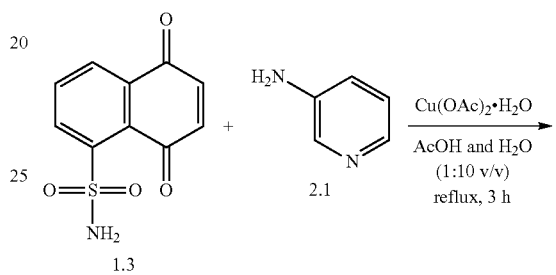

In various aspects, compounds of type 2.2 can be prepared by reaction of a compound of type 1.3 and 2.1, which are commercially available or prepared by methods known to one skilled in the art. For example, as shown above, such a reaction can be accomplished using a suitable coupling agent, e.g. copper acetate monohydrate, with a suitable solvent mixture, e.g. acetic acid and water, at a suitable concentration, e.g. 1:10 v/v of glacial acetic acid in water, at a suitable temperature, e.g. 90-130° C., for a period of time sufficient to complete the reaction, e.g. about 2-4 h.

Additional specific examples are set forth below.

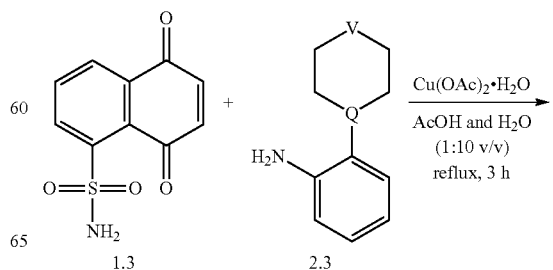

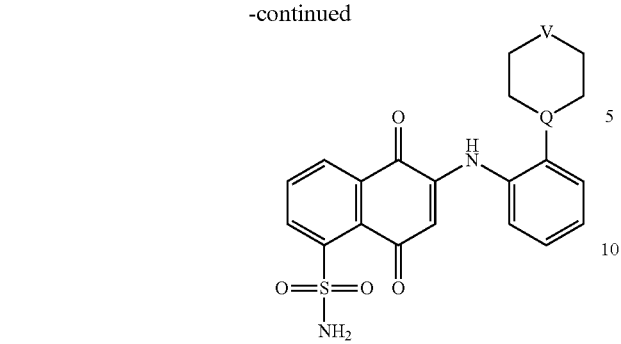
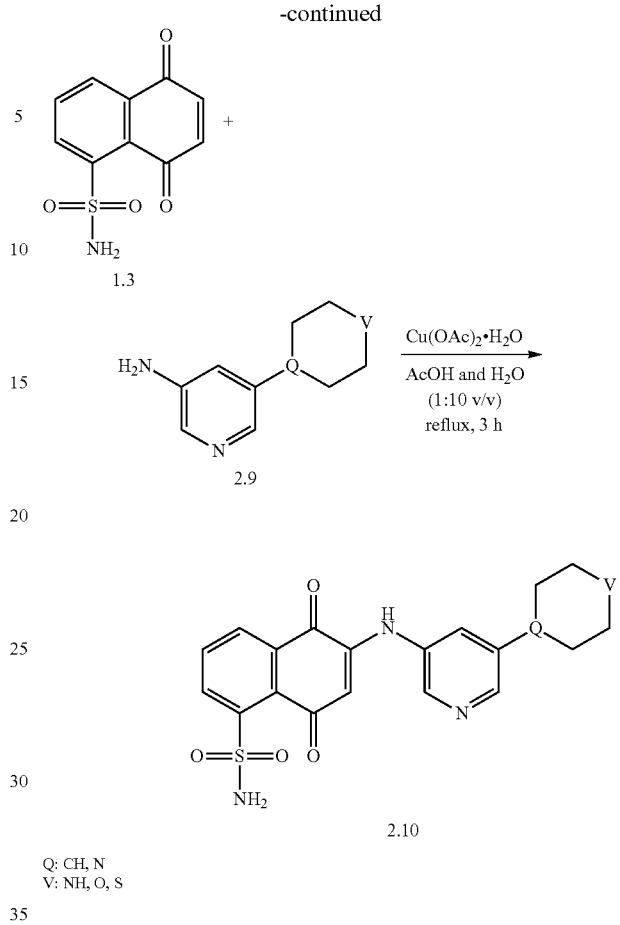

Q: CH, N
V: NH, O, S

In various aspects, compounds of types 2.4, 2.6, 2.8, and 2.10 can be prepared by reaction of a compound of type 1.3 with compounds of type, receptively, 2.3, 2.5, 2.7, and 2.9, which are commercially available or can be prepared by methods known to one skilled in the art. For example, as shown above, such a reaction can be accomplished using a suitable coupling agent, e.g. copper acetate monohydrate, with a suitable solvent mixture, e.g. acetic acid and water, at a suitable concentration, e.g. 1:10 v/v of glacial acetic acid in water, at a suitable temperature, e.g. 90-130° C., for a period of time sufficient to complete the reaction, e.g. about 2-4 h.

3. Route III

In one aspect, the disclosed compounds, substitutions and analogs thereof, of the present invention can be prepared as shown below.

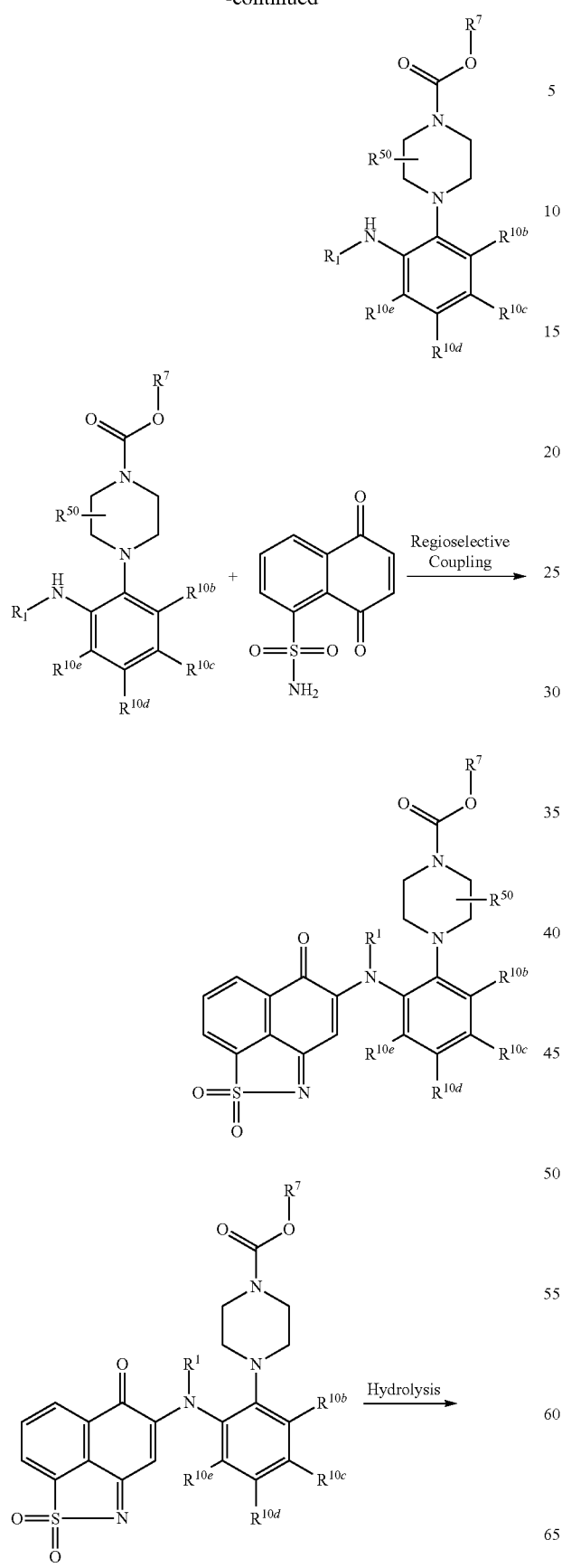
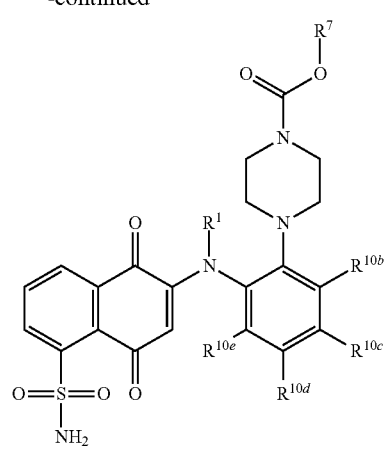
Compounds are represented in generic form, with substituents as noted in compound descriptions elsewhere herein. A more specific example is set forth below.
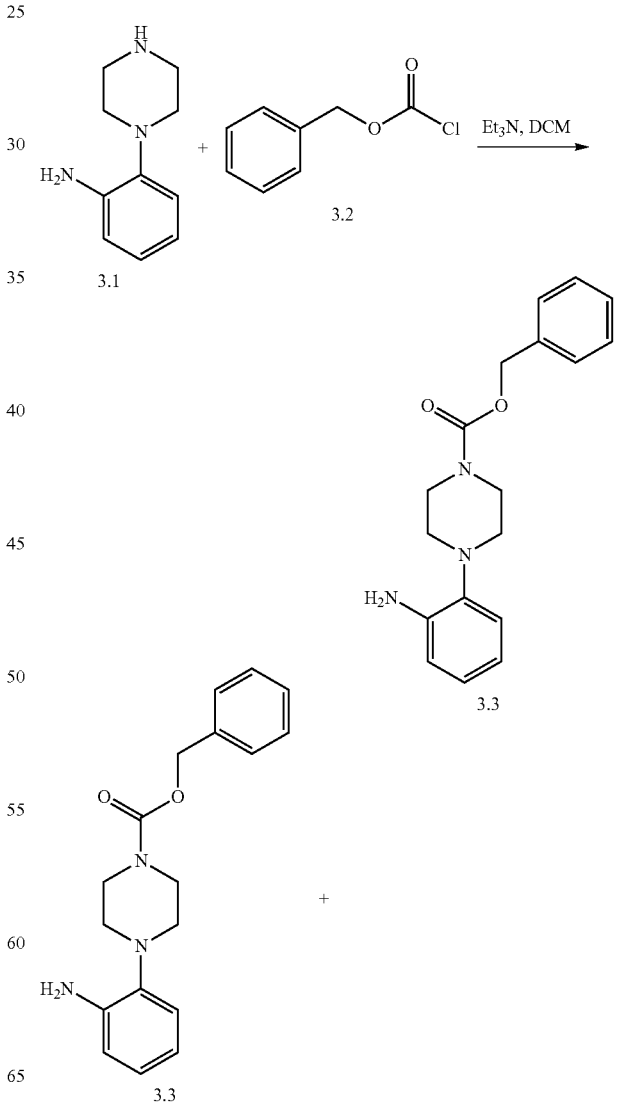

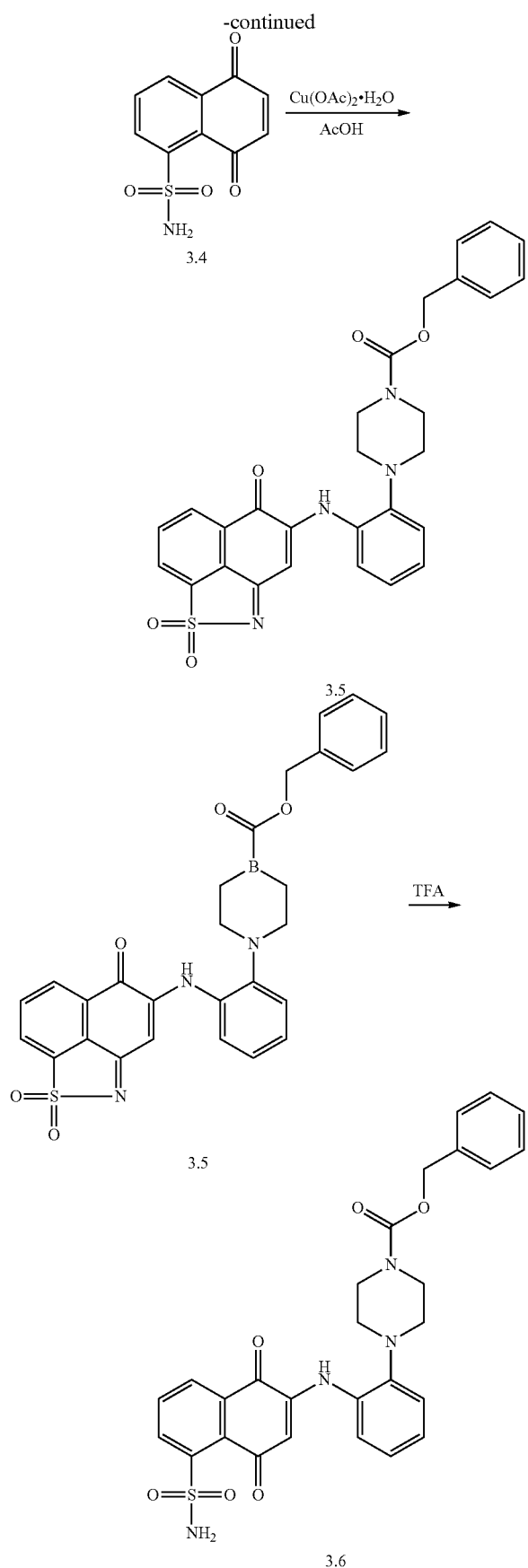

In various aspects, compounds of type 3.3 can be by reaction of a compound of type 3.1 and 3.2, which are commercially available or prepared by methods known to one skilled in the art. For example, as shown above, such a reaction can be accomplished using a suitable base, e.g. triethylamine, in a suitable solvent, e.g. dichloromethane. A compound of type 3.5 can be prepared by reaction of a compound of type 3.3 and 3.4, which is commercially available or prepared by methods known to one skilled in the art. For example, as shown above, such a reaction can be carried out using a suitable coupling agent, e.g. copper acetate monohydrate, with a suitable solvent, e.g. acetic acid. A compound of type 3.6 can be prepared by a hydrolysis reaction of a compound of type 3.5. For example, as shown above, such a reaction can be accomplished using a suitable acid, e.g. trifluoroacetic acid.

4. Chiral Resolution

The disclosed methods of making can provide compounds that can contain one or more asymmetric centers and, thus, potentially give rise to enantiomers and diastereomers. Unless stated to the contrary, the compounds prepared by the disclosed methods include all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included.

In one aspect, the disclosed methods of making can provide racemic or scalemic mixtures that can be resolved to pure or substantially pure enantiomers using chiral phase chromatography or other suitable methods known to one skilled in the art. As known to one skilled in the art, a variety specific columns and/or mobile phases can effect the desired resolution of enantiomers, and the specific choice can be determined by one skilled in the art. As known to one skilled in the art, chiral chromatography can be carried out in a variety of formats (e.g. SFC, HPLC, and SMB), and other formats can be used to obtain similar results. Moreover, other suitable methods known to one skilled in the art for the separation and isolation of individual enantiomers from a racemic or scalemic mixture can be used to isolate specific enantiomers as needed.

Thus, in one aspect, described herein are methods of making a compound comprising the steps of: (a) providing a compound having a structure represented by a formula 1.3 as shown above and reacting it with a compound having the formula $NH_2$—R. In a further aspect, aspect, the method comprises the steps of: (a) providing a compound having a structure represented by a formula:

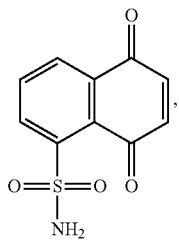 [SMILES: NS(=O)(=O)c1cccc2c1C(=O)C=CC2=O]

and reacting it with a compound having the formula $NHR^1Q^3$. In a still further aspect, the method comprises the steps of: (a) providing a compound having a structure represented by a formula:

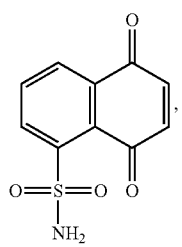 [SMILES: NS(=O)(=O)c1cccc2c1C(=O)C=CC2=O]

and reacting it with a compound having the formula NH₂Q³. In a yet further aspect, the prepared compound has a structure represented by the disclosed compounds herein.

In various further aspects, the prepared compound has a structure represented by a formula:

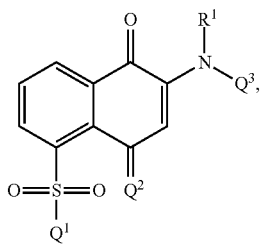

wherein $R^1$ is selected from hydrogen and C1-C3 alkyl; wherein $Q^1$ is —$NR^{2a}R^{2b}$ and wherein $Q^2$ is O; or wherein $Q^1$ and $Q^2$ are together N; wherein each of $R^{2a}$ and $R^{2b}$, when present, is independently selected from hydrogen and C1-C3 alkyl; wherein $Q^3$ is selected from —(C1-C6)-$Ar^1$, $Ar^1$, —(C1-C6)-$Cy^1$, and $Cy^1$; wherein $Ar^1$, when present, is selected from phenyl, naphthyl, monocyclic heteroaryl, and bicyclic heteroaryl; and wherein $Ar^1$ is substituted with 0, 1, 2, or 3 groups independently selected from halogen, —CN, —OH, —NH₂, —NO₂, C1-C6 alkyl, C1-C6 monohaloalkyl, C1-C6 polyhaloalkyl, C1-C6 hydroxyalkyl, C1-C6 monoalkylamino, C1-C6 dialkylamino, —(C1-C6)$NR^{4a}R^{4b}$, —(C1-C6)-(C=O)$R^3$, —(C1-C6)-(C=O)$OR^3$, —(C1-C6)-(C=O)$NR^{4a}R^{4b}$, —(C1-C6)-$Ar^2$, $Ar^2$, —(C1-C6)-$Cy^2$, $Cy^2$, and —$S(O)_nNR^{5a}R^{5b}$; wherein n is 0, 1, or 2; wherein each $R^3$, when present, is independently selected from hydrogen, C1-C6 alkyl, C1-C6 monohaloalkyl, C1-C6 polyhaloalkyl, C1-C6 hydroxyalkyl, and C1-C6 aminoalkyl; wherein each of $R^{4a}$ and $R^{4b}$, when present, is independently selected from hydrogen, C1-C6 alkyl, C1-C6 monohaloalkyl, C1-C6 polyhaloalkyl, C1-C6 hydroxyalkyl, and C1-C6 aminoalkyl; wherein each of $R^{5a}$ and $R^{5b}$ when present, is independently selected from hydrogen, C1-C6 alkyl, C1-C6 monohaloalkyl, C1-C6 polyhaloalkyl, C1-C6 hydroxyalkyl, C1-C6 aminoalkyl, and —(C=O)$NR^{6a}R^{6b}$; wherein each of $R^{6a}$ and $R^{6b}$, when present, is independently selected from hydrogen and C1-C6 alkyl; wherein each $Ar^2$, when present, is independently selected from is phenyl and monocyclic heteroaryl; and wherein $Ar^2$ is substituted with 0, 1, 2, or 3 groups independently selected from halogen, —CN, —OH, —NH₂, —NO₂, C1-C6 alkyl, C1-C6 monohaloalkyl, C1-C6 polyhaloalkyl, C1-C6 hydroxyalkyl, C1-C6 aminoalkyl, C1-C6 monoalkylamino, and C1-C6 dialkylamino; wherein each $Cy^2$, when present, is independently selected from C3-C8 cycloalkyl and C2-C7 heterocycloalkyl; and wherein $Cy^2$ is substituted with 0, 1, 2, or 3 groups independently selected from halogen, —CN, —OH, —NH₂, —NO₂, C1-C6 alkyl, C1-C6 monohaloalkyl, C1-C6 polyhaloalkyl, C1-C6 hydroxyalkyl, C1-C6 aminoalkyl, C1-C6 monoalkylamino, C1-C6 dialkylamino, —(C=O)$R^7$, —(C=O)$OR^7$, —(C=O)$NR^{8a}R^{8b}$, —(C=O)—(C1-C6 alkyl)$Ar^3$, —(C=O)—O—(C1-C6 alkyl)$Ar^3$, and —(C=O)—$NR^{8a}$—(C1-C6 alkyl)$Ar^3$; wherein each $R^7$, when present, is independently selected from hydrogen, C1-C6 alkyl, C1-C6 monohaloalkyl, and C1-C6 polyhaloalkyl; wherein each of $R^{8a}$ and $R^{8b}$, when present, is independently selected from hydrogen, C1-C6 alkyl, C1-C6 monohaloalkyl, and C1-C6 polyhaloalkyl; wherein each $Ar^3$, when present, is independently selected from phenyl and monocyclic heteroaryl substituted with 0, 1, 2, or 3 groups independently selected from halogen, —CN, —OH, —NH₂, —NO₂, C1-C6 alkyl, C1-C6 monohaloalkyl, and C1-C6 polyhaloalkyl; wherein $Cy^1$, when present, is selected from C3-C8 cycloalkyl and C2-C7 heterocycloalkyl; and wherein $Cy^2$ is substituted with 0, 1, 2, or 3 groups independently selected from halogen, —CN, —OH, —NH₂, —NO₂, C1-C6 alkyl, C1-C6 monohaloalkyl, C1-C6 polyhaloalkyl, C1-C6 hydroxyalkyl, C1-C6 monoalkylamino, C1-C6 dialkylamino, —(C1-C6)$NR^{4a}R^{4b}$, —(C1-C6)-(C=O)$R^3$, —(C1-C6)-(C=O)$OR^3$, —(C1-C6)-(C=O)$NR^{4a}R^{4b}$, —(C1-C6)-$Ar^2$, $Ar^2$, —(C1-C6)-$Cy^2$, $Cy^2$, and —$S(O)_nNR^{5a}R^{5b}$; or a pharmaceutically acceptable salt, solvate, or polymorph thereof.

In a further aspect, the compound produced by the disclosed methods exhibits inhibition of STAT with an IC₅₀ of less than about 10,000 nM, of less than about 5,000 nM. of less than about 1,000 nM, of less than about 500 nM, or of less than about 100 nM. In a still further aspect, the compound produced exhibits inhibition of growth in cancer cells, such as stromal cancer cells.

In a further aspect, the compound produced by the disclosed methods exhibits inhibition of STAT3 with an IC₅₀ of less than about 10,000 nM, of less than about 5,000 nM. of less than about 1,000 nM, of less than about 500 nM, or of less than about 100 nM. In a still further aspect, the compound produced exhibits inhibition of growth in cancer cells, such as stromal cancer cells.

Other specific examples of the syntheses described herein above are set forth in the Examples provided herein. It is contemplated that each disclosed method can further comprise additional steps, manipulations, and/or components. It is also contemplated that any one or more step, manipulation, and/or component can be optionally omitted from the invention. It is understood that a disclosed method can be used to provide the disclosed compounds. It is also understood that the products of the disclosed methods can be employed in the disclosed methods of using.

It is contemplated that each disclosed methods can further comprise additional steps, manipulations, and/or components. It is also contemplated that any one or more step, manipulation, and/or component can be optionally omitted from the invention. It is understood that a disclosed methods can be used to provide the disclosed compounds. It is also understood that the products of the disclosed methods can be employed in the disclosed methods of using.

E. Pharmaceutical Compositions

In one aspect, the invention relates pharmaceutical compositions comprising a therapeutically effective amount of a disclosed compound, or a pharmaceutically acceptable salt, solvate, or polymorph thereof, or a product of disclosed method of making, and a pharmaceutically acceptable carrier.

In one aspect, the compound exhibits inhibition of STAT3 activity. In a further aspect, the compound exhibits inhibition with an $IC_{50}$ of less than about 30 µM. In a further aspect, the compound exhibits inhibition with an $IC_{50}$ of less than about 10 µM. In a further aspect, the compound exhibits inhibition with an $IC_{50}$ of less than about 5 µM. In a further aspect, the compound exhibits inhibition with an $IC_{50}$ of less than about 1 µM. In a further aspect, the compound exhibits inhibition with an $IC_{50}$ of less than about 100 nM. In a further aspect, the compound exhibits inhibition with an $IC_{50}$ of less than about 50 nM. In a further aspect, the compound exhibits inhibition with an $IC_{50}$ of less than about 10 nM.

In a further aspect, the inhibition is inhibition of STAT3 activity. In a further aspect, the STAT3 activity is determined using a fluorescence polarization assay. In a further aspect, the inhibition is inhibition of cell growth. In a further aspect, cell growth is determined using an osteosarcoma cell-line. In a further aspect, the cell-line is selected from RD2, RH30, and U2OS cells.

In a further aspect, the pharmaceutical composition treats a disorder selected from psoriasis and pulmonary arterial hypertension.

In a further aspect, the pharmaceutical composition treats a disorder of uncontrolled cellular proliferation. In a still further aspect, the disorder of uncontrolled cellular proliferation is cancer. In a further aspect, the cancer is a solid tumor.

In a further aspect, the pharmaceutical composition treats a cancer is selected from a cancer of the head, neck, pancreas, brain, ovary, kidney, prostate, breast, lung, colon, bladder, and liver. In a still further aspect, the cancer is a melanoma, glioma, medulloblastoma, renal cell carcinoma, pancreatic adenocarcinoma, ovarian carcinoma, rhabdomyosarcoma, or osteosarcoma. In a yet further aspect, the cancer is selected from a cancer of the breast, ovary, prostate, head, neck, and kidney. In an even further aspect, the cancer is breast cancer. In a still further aspect, the cancer is pancreatic cancer.

In a further aspect, the pharmaceutical composition treats a brain cancer. In a still further aspect, the brain cancer is selected from a glioma, medulloblastoma, primitive neuroectodermal tumor (PNET), acoustic neuroma, glioma, meningioma, pituitary adenoma, schwannoma, CNS lymphoma, primitive neuroectodermal tumor, craniopharyngioma, chordoma, medulloblastoma, cerebral neuroblastoma, central neurocytoma, pineocytoma, pineoblastoma, atypical teratoid rhabdoid tumor, chondrosarcoma, chondroma, choroid plexus carcinoma, choroid plexus papilloma, craniopharyngioma, dysembryoplastic neuroepithelial tumor, gangliocytoma, germinoma, hemangioblastoma, hemangiopercytoma, and metastatic brain tumor. In a yet further aspect, the glioma is selected from ependymoma, astrocytoma, oligodendroglioma, and oligoastrocytoma. In an even further aspect, the glioma is selected from juvenile pilocytic astrocytoma, subependymal giant cell astrocytoma, ganglioglioma, subependymoma, pleomorphic xanthoastrocytom, anaplastic astrocytoma, glioblastoma multiforme, brain stem glioma, oligodendroglioma, ependymoma, oligoastrocytoma, cerebellar astrocytoma, desmoplastic infantile astrocytoma, subependymal giant cell astrocytoma, diffuse astrocytoma, mixed glioma, optic glioma, gliomatosis cerebri, multifocal gliomatous tumor, multicentric glioblastoma multiforme tumor, paraganglioma, and ganglioglioma.

In a further aspect, the pharmaceutical composition treats a hematological cancer. In a still further aspect, the hematological cancer is selected from acute myeloid leukemia (AML), acute lymphoblastic leukemia (ALL), chronic myeloid leukemia (CML), chronic lymphocytic leukemia (CLL), hairy cell leukemia, chronic myelomonocytic leukemia (CMML), juvenile myelomonocytic leukemia (JMML), megakaryocytic leukemia, and large granular lymphocyte leukemia. In a yet further aspect, the hematological cancer is selected from Hodgkin lymphoma, Non-Hodgkin lymphoma, EBV-related/Burkitt's lymphoma, cutaneous T-cell lymphoma, and anaplastic large T-cell lymphoma. In an even further aspect, the hematological cancer is selected from multiple myeloma, solitary myeloma, localized myeloma, and extramedullary myeloma.

In various aspects, the pharmaceutical composition is a combination therapy comprising a disclosed compound, or a pharmaceutically acceptable salt, solvate, or polymorph thereof, or a product of disclosed method of making, and a pharmaceutically acceptable carrier, and at least one other therapeutic agent. In a further aspect, the combination therapy is a fixed dose combination therapy in the form of a pill or tablet. In a still further aspect, the at least one other therapeutic agent of the combination therapy is an antineoplastic agent, anti-cancer agent, or agent that inhibits uncontrolled cellular proliferation. In a yet further aspect, the at least one other therapeutic agent is a MEK inhibitor. In an even further aspect, the MEK inhibitor is selected from dabrafenib, trametinib, cobimetinib (GDC-093), pimasertib, selumetinib, refametinib, ARRY-162, ARRY-300, RO4987655, RO5126766, WX-554, MEK162, MEK300, AZD8330, and AZD6244. In an even further aspect, the MEK inhibitor is selected from dabrafenib, trametinib, cobimetinib (GDC-093), pimasertib, selumetinib, and refametinib. In a still further aspect, the MEK inhibitor is selected from dabrafenib and trametinib.

In certain aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids", includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In the treatment conditions which require negative allosteric modulation of metabotropic glutamate receptor activity an appropriate dosage level will generally be about 0.01 to 500 mg per kg patient body weight per day and can be administered in single or multiple doses. Preferably, the dosage level will be about 0.1 to about 250 mg/kg per day; more preferably 0.5 to 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the form of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900 and 1000 milligrams of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response.

It is understood, however, that the specific dose level for any particular patient will depend upon a variety of factors. Such factors include the age, body weight, general health, sex, and diet of the patient. Other factors include the time and route of administration, rate of excretion, drug combination, and the type and severity of the particular disease undergoing therapy.

The present invention is further directed to a method for the manufacture of a medicament for modulating glutamate receptor activity (e.g., treatment of one or more neurological and/or psychiatric disorder associated with glutamate dysfunction) in mammals (e.g., humans) comprising combining one or more disclosed compounds, products, or compositions with a pharmaceutically acceptable carrier or diluent. Thus, in one aspect, the invention relates to a method for manufacturing a medicament comprising combining at least one disclosed compound or at least one disclosed product with a pharmaceutically acceptable carrier or diluent.

The disclosed pharmaceutical compositions can further comprise other therapeutically active compounds, which are usually applied in the treatment of the above mentioned pathological conditions.

It is understood that the disclosed compositions can be prepared from the disclosed compounds. It is also understood that the disclosed compositions can be employed in the disclosed methods of using.

F. Methods of Using the Compounds and Compositions

The disclosed compounds can be used as single agents or in combination with one or more other drugs in the treatment, prevention, control, amelioration or reduction of risk of the aforementioned diseases, disorders and conditions for which compounds of formula I or the other drugs have utility, where the combination of drugs together are safer or more effective than either drug alone. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound will be more efficacious than either as a single agent.

In one aspect, the subject compounds can be coadministered with 13-cis-Retinoic Acid, 2-CdA, 2-Chlorodeoxyadenosine, 5-Azacitidine, 5-Fluorouracil, 5-FU, 6-Mercaptopurine, 6-MP, 6-TG, 6-Thioguanine, Abraxane, ACCUTANE®, Actinomycin-D, ADRIAMYCIN®, ADRUCIL®, AFINITOR®, AGRYLIN®, ALA-CORT®, Aldesleukin, Alemtuzumab, ALIMTA, Alitretinoin, ALKABAN-AQ®, ALKERAN®, All-transretinoic Acid, Alpha Interferon, Altretamine, Amethopterin, Amifostine, Aminoglutethimide, Anagrelide, ANANDRON®, Anastrozole, Arabinosylcytosine, Ara-C, ARANESP®, AREDIA®, ARIMIDEX®, AROMASIN®, ARRANON®, Arsenic Trioxide, ARZERRA™, Asparaginase, ATRA, AVASTIN®, Azacitidine, BCG, BCNU, Bendamustine, Bevacizumab, Bexarotene, BEXXAR®, Bicalutamide, BiCNU, BLENOXANE®, Bleomycin, Bortezomib, Busulfan, BUSULFEX®, C225 Calcium Leucovorin, CAMPATH®, CAMPTOSAR®, Camptothecin-11, Capecitabine, CARAC™, Carboplatin, Carmustine, Carmustine Wafer, CASODEX®, CC-5013, CCI-779, CCNU, CDDP, CeeNU, CERUBIDINE®, Cetuximab, Chlorambucil, Cisplatin, Citrovorum Factor, Cladribine, Cortisone, COSMEGEN®, CPT-11, Cyclophosphamide, CYTADREN®, Cytarabine, Cytarabine Liposomal, CYTOSAR-U®, CYTOXAN®, Dacarbazine, Dacogen, Dactinomycin, Darbepoetin Alfa, Dasatinib, Daunomycin, Daunorubicin, Daunorubicin Hydrochloride, Daunorubicin Liposomal, DAUNOXOME®, Decadron, Decitabine, DELTA-CORTEF®, DELTASONE®, Denileukin Diftitox, DEPOCYT™, Dexamethasone, Dexamethasone AcetateDexamethasone Sodium PhosphateDexasone, Dexrazoxane, DHAD, DIC, Diodex, Docetaxel, DOXIL®, Doxorubicin, Doxorubicin Liposomal, DROXIA™, DTIC, DTIC-DOME®, DURALONE®, EFUDEX®, ELIGARD™, ELLENCE™, ELOXATIN™, ELSPAR®, EMCYT®, Epirubicin, Epoetin Alfa, Erbitux, Erlotinib, *Erwinia* L-asparaginase, Estramustine, ETHYOLETOPOPHOS®, Etoposide, Etoposide Phosphate, EULEXIN®, Everolimus, EVISTA®, Exemestane, FARESTON®, FASLODEX®, FEMARA®, Filgrastim, Floxuridine, FLUDARA®, Fludarabine, FLUOROPLEX®, Fluorouracil, Fluorouracil (cream), Fluoxymesterone, Flutamide, Folinic Acid, FUDR®, Fulvestrant, G-CSF, Gefitinib, Gemcitabine, Gemtuzumab ozogamicin, GEMZARGLEEVEC™, GLIADEL® Wafer, GM-CSF, Goserelin, Granulocyte-Colony Stimulating Factor, Granulocyte Macrophage Colony Stimulating Factor, HALOTESTIN®, HERCEPTIN®, Hexadrol, HEXALEN®, Hexamethylmelamine, HMM, HYCAMTIN®, HYDREA®, HYDROCORT ACETATE®. Hydrocortisone, Hydrocortisone Sodium Phosphate, Hydrocortisone Sodium Succinate, Hydrocortone Phosphate, Hydroxyurea, Ibritumomab, IBRITUMOMAB TIUXETANIDAMYCIN®, Idarubicin, IFEX®, IFN-alphalfosfamide, IL-11IL-2 Imatinib mesylate, Imidazole CarboxamideInterferon alfa, Interferon Alfa-2b (PEG Conjugate), Interleukin-2, Interleukin-11, INTRON A® (interferon alfa-2b) IRESSA®, Irinotecan, Isotretinoin, Ixabepilone, IXEMPRA™, K, Kidrolase (t), L, LANACORT®, Lapatinib, L-asparaginase, LCR, Lenalidomide, Letrozole, Leucovorin, Leukeran, LEUKINE™, Leuprolide, Leurocristine, LEUSTATIN™, Liposomal Ara-C, LIQUID PRED®, Lomustine, L-PAM, L-Sarcolysin, LUPRON®, LUPRON DEPOT®, M, MATULANE®, Maxidex, Mechlorethamine, Mechlorethamine Hydrochloride, MEDRALONE®, MEDROL®, MEGACE®, Megestrol, Megestrol Acetate, Melphalan, Mercaptopurine, Mesna, MESNEX™, Methotrexate, Methotrexate Sodium, Methylprednisolone, METICORTEN®, Mitomycin, Mitomycin-C, Mitoxantrone, M-PREDNISOL®, MTC, MTX, MUSTARGEN®, MUSTINEMUTAMYCIN®, MYLERAN®, MYLOCEL™, MYLOTARG®, N, NAVELBINE®, Nelarabine, NEOSAR®, NEULASTA™, NEUMEGA®, NEUPOGEN®, NEXAVAR®, NILANDRON®, Nilotinib, Nilutamide, NIPENT®, Nitrogen Mustard, NOVALDEX®, NOVANTRONE®, Nplate, O, Octreotide, Octreotide acetate, Ofatumumab, ONCOSPAR®, ONCOVIN®, ONTAK®, ONXAL™, Oprelvekin, ORAPRED®, ORASONE®, Oxaliplatin, P, Paclitaxel, Paclitaxel Protein-bound, Pamidronate, Panitumumab, PANRETIN®, PARAPLATIN®, Pazopanib, PEDIAPRED®, PEG Interferon, Pegaspargase, Pegfilgrastim, PEG-INTRON™, PEG-L-asparaginase, PEMETREXED, Pentostatin, Phenylalanine Mustard, PLATINOL®, PLATINOL-AQ®, Prednisolone, Prednisone, PRELONE®, Procarbazine, PROCRIT®, PROLEUKIN®, Prolifeprospan 20 with Carmustine Implant, PURINETHOL®, R, Raloxifene, REVLIMID®, RHEUMATREX®, RITUXAN®, Rituximab, ROFERON-A® (Interferon Alfa-2a) Romiplostim, RUBEX®, Rubidomycin hydrochloride, S, SANDOSTATIN®, SANDOSTATIN LAR®, Sargramostim, SOLU-CORTEF®, SOLU-MEDROL®, Sorafenib, SPRYCEL™, STI-571, Streptozocin, SU11248, Sunitinib, SUTENT®, T, Tamoxifen, TARCEVA®, TARGRETIN®, TASIGNA®, TAXOL®, TAXOTERE®, TEMODAR®, Temozolomide, Temsirolimus, Teniposide, TESPA, Thalidomide, THALOMID®, THERACYS®, Thioguanine, THIOGUANINE TABLOID®, Thiophosphoamide, THIOPLEX®, Thiotepa, TICE®, TOPOSAR®, Topotecan, Toremifene, TORISEL®, Tositumomab, Trastuzumab, TREANDA®, Tretinoin, TREXAL™, TRISENOX®, TSPA, TYKERB®, V, VCR, VECTIBIX™, VELBAN®, VELCADE®, VEPRESID®, VESANOID®, VIADUR™, VIDAZA®, Vinblastine, Vinblastine Sulfate, VINCASAR PFS®, Vincristine, Vinorelbine, Vinorelbine tartrate, VLB, VM-26, Vorinostat, Votrient, VP-16, VUMON®, X, XELODA®, ZANOSAR®, ZEVALIN™, ZINECARD®, ZOLADEX®, Zoledronic acid, Zolinza, ZOMETA®.

In another aspect, the subject compounds can be administered in combination with 13-cis-Retinoic Acid, 2-CdA, 2-Chlorodeoxyadenosine, 5-Azacitidine, 5-Fluorouracil, 5-FU, 6-Mercaptopurine, 6-MP, 6-TG, 6-Thioguanine, Abraxane, ACCUTANE®, Actinomycin-D, ADRIAMYCIN®, ADRUCIL®, AFINITOR®, AGRYLIN®, ALACORT®, Aldesleukin, Alemtuzumab, ALIMTA, Alitretinoin, ALKABAN-AQ®, ALKERAN®, All-transretinoic Acid. Alpha Interferon, Altretamine, Amethopterin, Amifostine, Aminoglutethimide, Anagrelide, ANANDRON®, Anastrozole, Arabinosylcytosine, Ara-C, ARANESP®, AREDIA®, ARIMIDEX®, AROMASIN®, ARRANON®, Arsenic Trioxide, ARZERRA™, Asparaginase, ATRA, AVASTIN®, Azacitidine, BCG, BCNU, Bendamustine, Bevacizumab, Bexarotene, BEXXAR®, Bicalutamide, BiCNU, BLENOXANE®, Bleomycin, Bortezomib, Busulfan, BUSULFEX®, C225 Calcium Leucovorin, CAMPATH®, Camptosar®, CAMPTOSAR®, Camptothecin-11, Capecitabine, CARAC™, Carboplatin, Carmustine, Carmustine Wafer, CASODEX®, CC-5013, CCI-779, CCNU, CDDP, CeeNU, CERUBIDINE®, Cetuximab, Chlorambucil, Cisplatin, Citrovorum Factor, Cladribine, Cortisone, COSMEGEN®, CPT-11, Cyclophosphamide, CYTADREN®, Cytarabine, Cytarabine Liposomal, CYTOSAR-U®, CYTOXAN®, Dacarbazine, Dacogen, Dactinomycin, Darbepoetin Alfa, Dasatinib, Daunomycin, Daunorubicin, Daunorubicin Hydrochloride, Daunorubicin Liposomal, DAUNOXOME®, Decadron, Decitabine, DELTA-CORTEF®, DELTASONE®, Denileukin Diftitox, DEPOCYT™, Dexamethasone, Dexamethasone AcetateDexamethasone Sodium PhosphateDexasone, Dexrazoxane, DHAD, DIC, Diodex, Docetaxel, DOXIL®, Doxorubicin, Doxorubicin Liposomal, DROXIA™, DTIC, DTIC-DOME®, DURALONE®, EFUDEX®, ELIGARD™, ELLENCE™, ELOXATIN™, ELSPAR®, EMCYT®, Epirubicin, Epoetin Alfa, Erbitux, Erlotinib, *Erwinia* L-asparaginase, Estramustine, ETHYOLETOPOPHOS®, Etoposide, Etoposide Phosphate, EULEXIN®, Everolimus, EVISTA®, Exemestane, FARESTON®, FASLODEX®, FEMARA®, Filgrastim, Floxuridine, FLUDARA®, Fludarabine, FLUOROPLEX®, Fluorouracil, Fluorouracil (cream), Fluoxymesterone, Flutamide, Folinic Acid, FUDR®, Fulvestrant, G-CSF. Gefitinib, Gemcitabine, Gemtuzumab ozogamicin, GEMZARGLEEVEC™, GLIADEL® Wafer, GM-CSF, Goserelin, Granulocyte-Colony Stimulating Factor, Granulocyte Macrophage Colony Stimulating Factor, HALOTESTIN®, HERCEPTIN®, Hexadrol, HEXALEN®, Hexamethylmelamine, HMM, HYCAMTIN®, HYDREA®, HYDROCORT ACETATE®, Hydrocortisone, Hydrocortisone Sodium Phosphate, Hydrocortisone Sodium Succinate, Hydrocortone Phosphate, Hydroxyurea, Ibritumomab, IBRITUMOMAB TIUXETANIDAMYCIN®, Idarubicin, IFEX®, IFN-alphalfosfamide, IL-11IL-2 Imatinib mesylate, Imidazole CarboxamideInterferon alfa, Interferon Alfa-2b (PEG Conjugate), Interleukin-2, Interleukin-11, INTRON A® (interferon alfa-2b) IRESSA®, Irinotecan, Isotretinoin, Ixabepilone, IXEMPRA™, K, Kidrolase (t), L, LANACORT®, Lapatinib, L-asparaginase, LCR, Lenalidomide, Letrozole, Leucovorin, Leukeran, LEUKINE™, Leuprolide, Leurocristine, LEUSTATIN™, Liposomal Ara-C, LIOUID PRED®, Lomustine, L-PAM, L-Sarcolysin, LUPRON®, LUPRON DEPOT®, M, MATULANE®, Maxidex, Mechlorethamine, Mechlorethamine Hydrochloride, MEDRALONE®, MEDROL®, MEGACE®, Megestrol, Megestrol Acetate, Melphalan, Mercaptopurine, Mesna, MESNEX™, Methotrexate, Methotrexate Sodium, Methylprednisolone, METICORTEN®, Mitomycin, Mitomycin-C, Mitoxantrone, M-PREDNISOL®, MTC, MTX, MUSTARGEN®, MUSTINEMUTAMYCIN®, MYLERAN®, MYLOCEL™, MYLOTARG®, NAVELBINE®, Nelarabine, NEOSAR®, NEULASTA™, NEUMEGA®, NEUPOGEN®, NEXAVAR®, NILANDRON®, Nilotinib, Nilutamide, NIPENT®, Nitrogen Mustard, NOVALDEX®, NOVANTRONE®, Nplate, O, Octreotide, Octreotide acetate, Ofatumumab, ONCOSPAR®, ONCOVIN®, ONTAK®, ONXAL™, Oprelvekin, ORAPRED®, ORASONE®, Oxaliplatin, P, Paclitaxel, Paclitaxel Protein-bound, Pamidronate, Panitumumab, PANRETIN®, PARAPLATIN®, Pazopanib, PEDIAPRED®, PEG Interferon, Pegaspargase, Pegfilgrastim, PEG-INTRON™, PEG-L-asparaginase, PEMETREXED, Pentostatin, Phenyl alanine Mustard, PLATINOL®, PLATINOL-AQ®, Prednisolone, Prednisone, PRELONE®, Procarbazine, PROCRIT®, PROLEUKIN®, Prolifeprospan 20 with Carmustine Implant, PURINETHOL®, R, Raloxifene, REVLIMID®, RHEUMATREX®, RITUXAN®, Rituximab, ROFERON-A® (Interferon Alfa-2a)Romiplostim, RUBEX®, Rubidomycin hydrochloride, S, SANDOSTATIN®, SANDOSTATIN LAR®, Sargramostim, SOLU-CORTEF®, SOLU-MEDROL®, Sorafenib, SPRYCEL™, STI-571, Streptozocin, SU11248, Sunitinib, SUTENT®, T, Tamoxifen, TARCEVA®, TARGRETIN®, TASIGNA®, TAXOL®, TAXOTERE®, TEMODAR®, Temozolomide, Temsirolimus, Teniposide, TESPA, Thalidomide, THALOMIID®, THERACYS®, Thioguanine, THIOGUANINE TABLOID®, Thiophosphoamide, THIOPLEX®, Thiotepa, TICE®, TOPOSAR®, Topotecan, Toremifene, TORISEL®, Tositumomab, Trastuzumab, TREANDA®, Tretinoin, TREXALL™, TRISENOX®, TSPA, TYKERB®, V, VCR, VECTIBIX™, VELBAN®, VELCADE®, VEPRESID®, VESANOID®, VIADUR™, VIDAZA®, Vinbiastine, Vinbiastine Sulfate, VINCASAR PFS®, Vincristine, Vinorelbine, Vinorelbine tartrate, VLB, VM-26, Vorinostat, Votrient, VP-16, VUMON®, X, XELODA®, Z, ZANOSAR®, ZEVALIN™, ZINECARD®, ZOLADEX®, Zoledronic acid, Zolinza, ZOMETA®.

In another aspect, the subject compound can be used in combination with 13-cis-Retinoic Acid, 2-CdA, 2-Chlorodeoxyadenosine, 5-Azacitidine, 5-Fluorouracil, 5-FU, 6-Mercaptopurine, 6-MP, 6-TG, 6-Thioguanine, Abraxane, ACCUTANE®, Actinomycin-D, ADRIAMYCIN®, ADRUCL®, AFINITOR®, AGRYLIN®, ALA-CORT®, Aldesleukin, Alemtuzumab, ALIMTA, Alitretinoin, ALKABAN-AQ®, ALKERAN®, All-transretinoic Acid, Alpha Interferon, Altretamine, Amethopterin, Amifostine, Aminoglutethimide, Anagrelide, ANANDRON®, Anastrozole, Arabinosylcytosine, Ara-C, ARANESP®, AREDIA®, ARIMIDEX®, AROMASIN®, ARRANON®, Arsenic Trioxide, ARZERRA™, Asparaginase, ATRA, AVASTIN®, Azacitidine, BCG, BCNU, Bendamustine, Bevacizumab, Bexarotene, BEXXAR®, Bicalutamide, BiCNU, BLENOXANE®, Bleomycin, Bortezomib, Busulfan, BUSULFEX®, C225 Calcium Leucovorin, CAMPATH®, CAMPTOSAR®, Camptothecin-11, Capecitabine, CARAC™, Carboplatin, Carmustine, Carmustine Wafer, CASODEX®, CC-5013, CCI-779, CCNU, CDDP, CeeNU, CERUBIDINE®, Cetuximab, Chlorambucil, Cisplatin, Citrovorum Factor, Cladribine, Cortisone, COSMEGEN®, CPT-11, Cyclophosphamide, CYTADREN®, Cytarabine, Cytarabine Liposomal, CYTOSAR-U®, CYTOXAN®, Dacarbazine, Dacogen, Dactinomycin, Darbepoetin Alfa, Dasatinib, Daunomycin, Daunorubicin, Daunorubicin Hydrochloride, Daunorubicin Liposomal, DAUNOXOME®, Decadron, Decitabine, DELTA-CORTEF®, DELTASONE®, Denileukin Diftitox, DEPOCYT™, Dexamethasone, Dexamethasone AcetateDexamethasone Sodium PhosphateDexasone, Dexrazoxane, DHAD, DIC, Diodex, Docetaxel, DOXIL®, Doxorubicin, Doxorubicin Liposomal, DROXIA™, DTIC, DTIC-DOME®, DURALONE®, EFUDEX®, ELIGARD™, ELLENCE™, ELOXATIN™, ELSPAR®, EMCYT®, Epirubicin, Epoetin Alfa, Erbitux, Erlotinib, *Erwinia* L-asparaginase, Estramustine, ETHYOLETOPOPHOS®, Etoposide, Etoposide Phosphate, EULEXIN®, Everolimus, EVISTA®, Exemestane, FARESTON®, FASLODEX®, FEMARA®, Filgrastim, Floxuridine, FLUDARA®, Fludarabine, FLUOROPLEX®, Fluorouracil, Fluorouracil (cream), Fluoxymesterone, Flutamide, Folinic Acid, FUDR®, Fulvestrant, G-CSF, Gefitinib, Gemcitabine, Gemtuzumab ozogamicin, GEMZARGLEEVEC™, GLIADEL® Wafer, GM-CSF, Goserelin, Granulocyte-Colony Stimulating Factor, Granulocyte Macrophage Colony Stimulating Factor, HALOTESTIN®, HERCEPTIN®, Hexadrol, HEXALEN®, Hexamethylmelamine, HMM, HYCAMTIN®, HYDREA®, HYDROCORT ACETATE®, Hydrocortisone, Hydrocortisone Sodium Phosphate, Hydrocortisone Sodium Succinate, Hydrocortone Phosphate, Hydroxyurea, Ibritumomab, IBRITUMOMAB TIUXETANIDAMYCIN®, Idarubicin, IFEX®, IFN-alphalfosfamide, IL-11IL-2 Imatinib mesylate, Imidazole CarboxamideInterferon alfa, Interferon Alfa-2b (PEG Conjugate), Interleukin-2, Interleukin-11, INTRON A® (interferon alfa-2b) IRESSA®, Irinotecan, Isotretinoin, Ixabepilone, IXEMPR™, Kidrolase (t), L, LANACORT®, Lapatinib, L-asparaginase, LCR, Lenalidomide, Letrozole, Leucovorin, Leukeran, LEUKINE™, Leuprolide, Leurocristine, LEUSTATIN™, Liposomal Ara-C, LIQUID PRED®, Lomustine, L-PAM, L-Sarcolysin, LUPRON®, LUPRON DEPOT®, M, MATULANE®, Maxidex, Mechlorethamine, Mechlorethamine Hydrochloride, MEDRALONE®, MEDROL®, MEGACE®, Megestrol, Megestrol Acetate, Melphalan, Mercaptopurine, Mesna, MESNEX™, Methotrexate, Methotrexate Sodium, Methylprednisolone, METICORTEN®, Mitomycin, Mitomycin-C, Mitoxantrone, M-PREDNISOL®, MTC, MTX, MUSTARGEN®, MUSTINEMUTAMYCIN®, MYLERAN®, MYLOCEL™, MYLOTARG®, NAVELBINE®, Nelarabine, NEOSAR®, NEULASTA™, NEUMEGA®, NEUPOGEN®, NEXAVAR®, NILANDRON®, Nilotinib, Nilutamide, NIPENT®, Nitrogen Mustard, NOVALDEX®, NOVANTRONE®, Nplate, O, Octreotide, Octreotide acetate, Ofatumumab, ONCOSPAR®, ONCOVIN®, ONTAK®, ONXAL™, Oprelvekin, ORAPRED®, ORASONE®, Oxaliplatin, P, Paclitaxel, Paclitaxel Proteinbound, Pamidronate, Panitumumab, PANRETIN®, PARAPLATIN®, Pazopanib, PEDIAPRED®, PEG Interferon, Pegaspargase, Pegfilgrastim, PEG-INTRON™, PEG-L-asparaginase, PEMETREXED, Pentostatin, Phenylalanine Mustard, PLATINOL®, PLATINOL-AQ®, Prednisolone, Prednisone, PRELONE®, Procarbazine, PROCRIT®, PROLEUKIN®, Prolifeprospan 20 with Carmustine Implant, PURINETHOL®, R, Raloxifene, REVLIMID®, RHEUMATREX®, RITUXAN®, Rituximab, ROFERON-A® (Interferon Alfa-2a)Romiplostim, RUBEX®, Rubidomycin hydrochloride, S, SANDOSTATIN®, SANDOSTATIN LAR®, Sargramostim, SOLU-CORTEF®, SOLU-MEDROL®, Sorafenib, SPRYCEL™, STI-571, Streptozocin, SU11248, Sunitinib, SUTENT®, T, Tamoxifen, TARCEVA®, TARGRETIN®, TASIGNA®, TAXOL®, TAXOTERE®, TEMODAR®, Temozolomide, Temsirolimus, Teniposide, TESPA, Thalidomide, THALOMID®, THERACYS®, Thioguanine, THIOGUANINE TABLOID®, Thiophosphoamide, THIOPLEX®, Thiotepa, TICE®, TOPOSAR®, Topotecan, Toremifene, TORISEL®, Tositumomab, Trastuzumab, TREANDA®, Tretinoin, TREXALL™, TRISENOX®, TSPA, TYKERB®, V, VCR, VECTIBIX™, VELBAN®, VELCADE®, VEPRESID®, VESANOID®, VIADUR™, VIDAZA®, Vinblastine, Vinblastine Sulfate, VINCASAR PFS®, Vincristine, Vinorelbine, Vinorelbine tartrate, VLB, VM-26, Vorinostat, Votrient, VP-16, VUMON®, X, XELODA®, Z, ZANOSAR®, ZEVALIN™, ZINECARD®, ZOLADEX®, Zoledronic acid, Zolinza, ZOMETA®.

The pharmaceutical compositions and methods of the present invention can further comprise other therapeutically active compounds as noted herein which are usually applied in the treatment of the above mentioned pathological conditions.

1. Treatment and Inhibition Methods

The compounds disclosed herein are useful for treating, preventing, ameliorating, controlling or reducing the risk of a variety of disorders of uncontrolled cellular proliferation associated with a STAT protein activity dysfunction. In a yet further aspect, the disorder of uncontrolled cellular proliferation is a cancer. In a still further aspect, the STAT protein activity dysfunction is that the STAT protein is persistently active. In a yet further aspect, the STAT protein is constitutively active. In an even further aspect, the STAT protein is overexpressed. In a still further aspect, the STAT protein is STAT3.

In one aspect, the invention relates to a method for the treatment of a disorder associated with a STAT protein activity dysfunction in a mammal comprising the step of administering to the mammal at least one disclosed compound or at least one disclosed product in a dosage and amount effective to treat the disorder in the mammal. In a further aspect, the mammal is a human. In a further aspect, the mammal has been diagnosed with a need for treatment of the disorder prior to the administering step. In a further aspect, the method further comprises the step of identifying a mammal in need of treatment of the disorder.

It is understood that cancer refer to or describe the physiological condition in mammals that is typically characterized by unregulated cell growth. The cancer may be multi-drug resistant (MDR) or drug-sensitive. Examples of cancer include but are not limited to, carcinoma, lymphoma, blastoma, sarcoma, and leukemia. More particular examples of such cancers include breast cancer, prostate cancer, colon cancer, squamous cell cancer, small-cell lung cancer, non-small cell lung cancer, gastrointestinal cancer, pancreatic cancer, cervical cancer, ovarian cancer, peritoneal cancer, liver cancer, e.g., hepatic carcinoma, bladder cancer, colorectal cancer, endometrial carcinoma, kidney cancer, and thyroid cancer.

In various aspects, further examples of cancers are basal cell carcinoma, biliary tract cancer; bone cancer; brain and CNS cancer; choriocarcinoma; connective tissue cancer; esophageal cancer; eye cancer; cancer of the head and neck; gastric cancer; intra-epithelial neoplasm; larynx cancer; lymphoma including Hodgkin's and Non-Hodgkin's lymphoma; melanoma; myeloma; neuroblastoma; oral cavity cancer (e.g., lip, tongue, mouth, and pharynx); retinoblastoma; rhabdomyosarcoma; rectal cancer; cancer of the respiratory system; sarcoma; skin cancer; stomach cancer; testicular cancer; uterine cancer; cancer of the urinary system, as well as other carcinomas and sarcomas Examples of disorders such as a cancer associated with STAT protein activity dysfunction, e.g. a STAT3 activity dysfunction, include: Acute Lymphoblastic Leukemia, Adult Hairy Cell Leukemia, Acute Lymphoblastic Leukemia, Head and Neck Cancer, Childhood Hepatocellular (Liver) Cancer, Adult, Acute Myeloid Leukemia, Adult (Primary), Acute Myeloid Leukemia, Childhood Hepatocellular (Liver) Cancer, Childhood, Adrenocortical Carcinoma (Primary), Adrenocortical Carcinoma, Childhood Hodgkin's Lymphoma, Adult AIDS-Related Cancers Hodgkin's Lymphoma, Childhood AIDS-Related Lymphoma Hodgkin's Lymphoma During Pregnancy Anal Cancer Hypopharyngeal Cancer Astrocytoma, Childhood Cerebellar Hypothalamic and Visual Pathway Glioma, Astrocytoma, Childhood Cerebral Childhood Basal Cell Carcinoma Intraocular Melanoma Bile Duct Cancer, Extrahepatic Islet Cell Carcinoma (Endocrine Pancreas) Bladder Cancer Kaposi's Sarcoma Bladder Cancer, Childhood Kidney (Renal Cell) Cancer Bone Cancer, Osteosarcoma/Malignant Kidney Cancer, Childhood Fibrous Histiocytoma Laryngeal Cancer Brain Stem Glioma, Childhood Laryngeal Cancer, Childhood Brain Tumor, Adult Leukemia, Acute Lymphoblastic, Adult Brain Tumor, Brain Stem Glioma, Leukemia, Acute Lymphoblastic, Childhood Childhood Leukemia, Acute Myeloid, Adult Brain Tumor, Cerebellar Astrocytoma, Leukemia, Acute Myeloid, Childhood Childhood Leukemia, Chronic Lymphocytic Brain Tumor, Cerebral Leukemia, Chronic Myelogenous Astrocytoma/Malignant Glioma, Leukemia, Hairy Cell Childhood Lip and Oral Cavity Cancer Brain Tumor, Ependymoma, Childhood Liver Cancer, Adult (Primary) Brain Tumor, Medulloblastoma, Liver Cancer, Childhood (Primary)Childhood Lung Cancer, Non-Small Cell Brain Tumor, Supratentorial Primitive Lung Cancer, Small Cell Neuroectodermal Tumors, Childhood Lymphoma, AIDS-Related Brain Tumor, Visual Pathway and Lymphoma, Burkitts Hypothalamic Glioma, Childhood Lymphoma, Cutaneous T-Cell, see Mycosis Brain Tumor, Childhood Fungoides and Sézary Syndrome Breast Cancer Lymphoma, Hodgkin's, Adult Breast Cancer, Childhood Lymphoma, Hodgkin's, Childhood Breast Cancer, Male Lymphoma, Hodgkin's During Pregnancy Bronchial Adenomas/Carcinoids, Lymphoma, Non-Hodgkin's, Adult Childhood Lymphoma, Non-Hodgkin's, Childhood Burkitt's Lymphoma Lymphoma, Non-Hodgkin's During Carcinoid Tumor, Childhood Pregnancy Carcinoid Tumor, Gastrointestinal Lymphoma, Primary Central Nervous System Carcinoma of Unknown Primary Macroglobulinemia, Waldenström's Central Nervous System Lymphoma, Malignant Fibrous Histiocytoma of Primary Bone/Osteosarcoma Cerebellar Astrocytoma, Childhood Medulloblastoma, Childhood Cerebral Astrocytoma/Malignant Melanoma Glioma, Childhood Melanoma, Intraocular (Eye)Cervical Cancer Merkel Cell Carcinoma Childhood Cancers Mesothelioma, Adult Malignant Chronic Lymphocytic Leukemia Mesothelioma, Childhood Chronic Myelogenous Leukemia Metastatic Squamous Neck Cancer with Chronic Myeloproliferative Disorders Occult Primary Colon Cancer Multiple Endocrine Neoplasia Syndrome, Colorectal Cancer, Childhood Childhood Cutaneous T-Cell Lymphoma, see Multiple Myeloma/Plasma Cell Neoplasm Mycosis Fungoides and Sézary Mycosis Fungoides Syndrome Myelodysplastic Syndromes Endometrial Cancer Myelodysplastic/Myeloproliferative Diseases Ependymoma, Childhood Myelogenous Leukemia, Chronic Esophageal Cancer Myeloid Leukemia, Adult Acute Esophageal Cancer, Childhood Myeloid Leukemia, Childhood Acute Ewing's Family of Tumors Myeloma, Multiple Extracranial Germ Cell Tumor, Myeloproliferative Disorders, Chronic Childhood Nasal Cavity and Paranasal Sinus Cancer Extragonadal Germ Cell Tumor Nasopharyngeal Cancer Extrahepatic Bile Duct Cancer Nasopharyngeal Cancer, Childhood Eye Cancer, Intraocular Melanoma Neuroblastoma Eye Cancer, Retinoblastoma Non-Hodgkin's Lymphoma, Adult Gallbladder Cancer Non-Hodgkin's Lymphoma, Childhood Gastric (Stomach) Cancer Non-Hodgkin's Lymphoma During Pregnancy Gastric (Stomach) Cancer, Childhood Non-Small Cell Lung Cancer Gastrointestinal Carcinoid Tumor Oral Cancer, Childhood Germ Cell Tumor, Extracranial, Oral Cavity Cancer, Lip and Childhood Oropharyngeal Cancer Germ Cell Tumor, Extragonadal Osteosarcoma/Malignant Fibrous Germ Cell Tumor, Ovarian Histiocytoma of Bone Gestational Trophoblastic Tumor Ovarian Cancer, Childhood Glioma, Adult Ovarian Epithelial Cancer Glioma, Childhood Brain Stem Ovarian Germ Cell Tumor Glioma, Childhood Cerebral Ovarian Low Malignant Potential Tumor Astrocytoma Pancreatic Cancer Glioma, Childhood Visual Pathway and Pancreatic Cancer, Childhood Hypothalamic Pancreatic Cancer, Islet Cell Skin Cancer (Melanoma) Paranasal Sinus and Nasal Cavity Cancer Skin Carcinoma, Merkel Cell Parathyroid Cancer Small Cell Lung Cancer Penile Cancer Small Intestine Cancer Pheochromocytoma Soft Tissue Sarcoma, Adult Pineoblastoma and Supratentorial Primitive Soft Tissue Sarcoma, Childhood Neuroectodermal Tumors, Childhood Squamous Cell Carcinoma, see Skin Pituitary Tumor Cancer (non-Melanoma) Plasma Cell Neoplasm/Multiple Myeloma Squamous Neck Cancer with Occult Pleuropulmonary Blastoma Primary, Metastatic Pregnancy and Breast Cancer Stomach (Gastric) Cancer Pregnancy and Hodgkin's Lymphoma Stomach (Gastric) Cancer, Childhood Pregnancy and Non-Hodgkin's Lymphoma Supratentorial Primitive Primary Central Nervous System Lymphoma Neuroectodermal Tumors, Childhood Prostate Cancer T-Cell Lymphoma, Cutaneous, see Rectal Cancer Mycosis Fungoides and Sézary Renal Cell (Kidney) Cancer Syndrome Renal Cell (Kidney) Cancer, Childhood Testicular Cancer Renal Pelvis and Ureter, Transitional Cell Thymoma, Childhood Cancer Thymoma and Thymic Carcinoma Retinoblastoma Thyroid Cancer Rhabdomyosarcoma, Childhood Thyroid Cancer, Childhood Salivary Gland Cancer Transitional Cell Cancer of the Renal Salivary Gland Cancer, Childhood Pelvis and Ureter Sarcoma, Ewing's Family of Tumors Trophoblastic Tumor, Gestational Sarcoma, Kaposi's Unknown Primary Site, Carcinoma of, Sarcoma, Soft Tissue, Adult Adult Sarcoma, Soft Tissue, Childhood Unknown Primary Site, Cancer of, Sarcoma, Uterine Childhood Sezary Syndrome Unusual Cancers of Childhood Skin Cancer (non-Melanoma) Ureter and Renal Pelvis, Transitional Skin Cancer, Childhood Cell Cancer Urethral Cancer Uterine Cancer, Endometrial Uterine Sarcoma Vaginal Cancer Visual Pathway and Hypothalamic Glioma, Childhood Vulvar Cancer Waldenström's Macroglobulinemia Wilms' Tumor.

The disorders of uncontrolled cellular proliferation, e.g. a cancer, that can be treated or prevented by the compositions disclosed herein include.

Thus, provided is a method for treating or preventing a disorder of uncontrolled cellular proliferation, comprising: administering to a subject at least one disclosed compound; at least one disclosed pharmaceutical composition; and/or at least one disclosed product in a dosage and amount effective to treat the disorder in the subject.

a. Treatment of a Disorder Associated with STAT3 Activity Dysfunction

In one aspect, the invention relates to a method for the treatment of a disorder associated with STAT3 activity in a mammal comprising the step of administering to the mammal at least one disclosed compound or at least one disclosed product in a dosage and amount effective to treat the disorder in the mammal.

In one aspect, the invention relates methods for the treatment of a disorder associated with STAT3 activity in a mammal comprising the step of administering to the mammal a therapeutically effective amount of at least one compound having a structure represented by a formula:

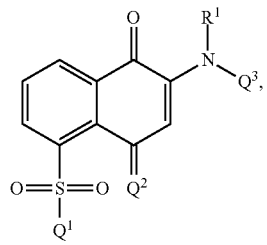

wherein $R^1$ is selected from hydrogen and C1-C3 alkyl; wherein $Q^1$ is —$NR^{2a}R^{2b}$ and wherein $Q^2$ is O; or wherein $Q^1$ and $Q^2$ are together N; wherein each of $R^{2a}$ and $R^{2b}$, when present, is independently selected from hydrogen and C1-C3 alkyl; wherein $Q^3$ is selected from —(C1-C6)-$Ar^1$, $Ar^1$, —(C1-C6)-$Cy^1$, and $Cy^1$; wherein $Ar^1$, when present, is selected from phenyl, naphthyl, monocyclic heteroaryl, and bicyclic heteroaryl; and wherein $Ar^1$ is substituted with 0, 1, 2, or 3 groups independently selected from halogen, —CN, —OH, —$NH_2$, —$NO_2$, C1-C6 alkyl, C1-C6 monohaloalkyl, C1-C6 polyhaloalkyl, C1-C6 hydroxyalkyl, C1-C6 monoalkylamino, C1-C6 dialkylamino, —(C1-C6)$NR^{4a}R^{4b}$, —(C1-C6)-(C=O)$R^3$, —(C1-C6)-(C=O)$OR^3$, —(C1-C6)(C=O)$NR^{4a}R^{4b}$, —(C1-C6)-$Ar^2$, $Ar^2$, —(C1-C6)-$Cy^2$, $Cy^2$, and —$S(O)_n NR^{5a}R^{5b}$; wherein n is 0, 1, or 2; wherein each $R^3$, when present, is independently selected from hydrogen, C1-C6 alkyl, C1-C6 monohaloalkyl, C1-C6 polyhaloalkyl, C1-C6 hydroxyalkyl, and C1-C6 aminoalkyl; wherein each of $R^{4a}$ and $R^{4b}$, when present, is independently selected from hydrogen, C1-C6 alkyl, C1-C6 monohaloalkyl, C1-C6 polyhaloalkyl, C1-C6 hydroxyalkyl, and C1-C6 aminoalkyl; wherein each of $R^{5a}$ and $R^{5b}$ when present, is independently selected from hydrogen, C1-C6 alkyl, C1-C6 monohaloalkyl, C1-C6 polyhaloalkyl, C1-C6 hydroxyalkyl, C1-C6 aminoalkyl, and —(C=O)$NR^{6a}R^{6b}$; wherein each of $R^{6a}$ and $R^{6b}$, when present, is independently selected from hydrogen and C1-C6 alkyl; wherein each $Ar^2$, when present, is independently selected from is phenyl and monocyclic heteroaryl; and wherein $Ar^2$ is substituted with 0, 1, 2, or 3 groups independently selected from halogen, —CN, —OH, —$NH_2$, —$NO_2$, C1-C6 alkyl, C1-C6 monohaloalkyl, C1-C6 polyhaloalkyl, C1-C6 hydroxyalkyl, C1-C6 aminoalkyl, C1-C6 monoalkylamino, and C1-C6 dialkylamino; wherein each $Cy^2$, when present, is independently selected from C3-C8 cycloalkyl and C2-C7 heterocycloalkyl; and wherein $Cy^2$ is substituted with 0, 1, 2, or 3 groups independently selected from halogen, —CN, —OH, —$NH_2$, —$NO_2$, C1-C6 alkyl, C1-C6 monohaloalkyl, C1-C6 polyhaloalkyl, C1-C6 hydroxyalkyl, C1-C6 aminoalkyl, C1-C6 monoalkylamino, C1-C6 dialkylamino, —(C=O)$R^7$, —(C=O)$OR^7$, —(C=O)$NR^{8a}R^{8b}$, —(C=O)—(C1-C6 alkyl)$Ar^3$, —(C=O)—O—(C1-C6 alkyl)$Ar^3$, and —(C=O)—$NR^{8a}$—(C1-C6 alkyl)$Ar^3$; wherein each $R^7$, when present, is independently selected from hydrogen, C1-C6 alkyl, C1-C6 monohaloalkyl, and C1-C6 polyhaloalkyl; wherein each of $R^{8a}$ and $R^{8b}$, when present, is independently selected from hydrogen, C1-C6 alkyl, C1-C6 monohaloalkyl, and C1-C6 polyhaloalkyl; wherein each $Ar^3$, when present, is independently selected from phenyl and monocyclic heteroaryl substituted with 0, 1, 2, or 3 groups independently selected from halogen, —CN, —OH, —$NH_2$, —$NO_2$, C1-C6 alkyl, C1-C6 monohaloalkyl, and C1-C6 polyhaloalkyl; wherein $Cy^1$, when present, is selected from C3-C8 cycloalkyl and C2-C7 heterocycloalkyl; and wherein $Cy^2$ is substituted with 0, 1, 2, or 3 groups independently selected from halogen, —CN, —OH, —NH$_2$, —NO$_2$, C1-C6 alkyl, C1-C6 monohaloalkyl, C1-C6 polyhaloalkyl, C1-C6 hydroxyalkyl, C1-C6 monoalkylamino, C1-C6 dialkylamino, —(C1-C6)NR$^{4a}$R$^{4b}$, —(C1-C6)-(C=O)R$^3$, —(C1-C6)-(C=O)OR$^3$, —(C1-C6)-(C=O)NR$^{4a}$R$^{4b}$, —(C1-C6)-Ar$^2$, Ar$^2$, —(C1-C6)-Cy$^2$, Cy$^2$, and —S(O)$_n$NR$^{5a}$R$^{5b}$; or a pharmaceutically acceptable salt, solvate, or polymorph thereof.

In a further aspect, the compound administered exhibits inhibition of STAT3 activity with an IC$_{50}$ of less than about 30 µM. In a still further aspect, the compound administered exhibits inhibition of STAT3 activity with an IC$_{50}$ of less than about 10 µM. In a yet further aspect, the compound administered exhibits inhibition of STAT3 activity with an IC$_{50}$ of less than about 5 µM. In an even further aspect, the compound administered exhibits inhibition of STAT3 activity with an IC$_{50}$ of less than about 1 µM. In an even further aspect, the compound administered exhibits inhibition of STAT3 activity with an IC$_{50}$ of less than about 100 nM. In a still further aspect, the compound administered exhibits inhibition of STAT3 activity with an IC$_{50}$ of less than about 50 nM. In a yet further aspect, the compound administered exhibits inhibition of STAT3 activity with an IC$_{50}$ of less than about 10 nM.

In a further aspect, the STAT3 activity of the compound administered is determined using a fluorescence polarization assay.

In various further aspects, the STAT3 activity of the compound administered is determined by measuring cell growth. In a still further aspect, cell growth is determined using an osteosarcoma cell-line. In a yet further aspect, the cell-line is selected from RD2, RH30, and U2OS cells.

In a further aspect, the mammal the compound is administered to is a human. In a still further aspect, the mammal has been diagnosed with a need for treatment of the disorder prior to the administering step.

In a further aspect, the method further comprises the step of identifying a mammal in need of treatment of the disorder.

In a further aspect, the disorder is associated with constitutively active STAT3. In a still further aspect, the disorder is associated with dysregulation of STAT3 activity. In a yet further aspect, the disorder is associated with upregulation of STAT3 activity.

In a further aspect, the disorder is selected from psoriasis and pulmonary arterial hypertension.

In a further aspect, the compound is administered for the treatment of a disease of uncontrolled cellular proliferation. In a still further aspect, the disease of uncontrolled cellular proliferation is a cancer.

In a further aspect, the compound is administered for the treatment of a solid tumor. In a still further aspect, the compound is administered for the treatment of a cancer selected from a cancer of the head, neck, pancreas, brain, ovary, kidney, prostate, breast, lung, colon, bladder, and liver. In a yet further aspect, the compound is administered for the treatment of a cancer selected from melanoma, glioma, medulloblastoma, renal cell carcinoma, pancreatic adenocarcinoma, ovarian carcinoma, rhabdomyosarcoma, and osteosarcoma. In an even further aspect, the compound is administered for the treatment of a cancer is selected from a cancer of the breast, ovary, prostate, head, neck, and kidney. In a still further aspect, the compound is administered for the treatment of breast cancer. In a yet further aspect, the compound is administered for the treatment of pancreatic cancer.

In various further aspects, the compound is administered for the treatment of brain cancer. In a further aspect, the brain cancer s selected from a glioma, medulloblastoma, primitive neuroectodermal tumor (PNET), acoustic neuroma, glioma, meningioma, pituitary adenoma, schwannoma, CNS lymphoma, primitive neuroectodermal tumor, craniopharyngioma, chordoma, medulloblastoma, cerebral neuroblastoma, central neurocytoma, pineocytoma, pineoblastoma, atypical teratoid rhabdoid tumor, chondrosarcoma, chondroma, choroid plexus carcinoma, choroid plexus papilloma, craniopharyngioma, dysembryoplastic neuroepithelial tumor, gangliocytoma, germinoma, hemangioblastoma, hemangiopercytoma, and metastatic brain tumor. In a still further aspect, the glioma is selected from ependymoma, astrocytoma, oligodendroglioma, and oligoastrocytoma. In a yet further aspect, the glioma is selected from juvenile pilocytic astrocytoma, subependymal giant cell astrocytoma, ganglioglioma, subependymoma, pleomorphic xanthoastrocytom, anaplastic astrocytoma, glioblastoma multiforme, brain stem glioma, oligodendroglioma, ependymoma, oligoastrocytoma, cerebellar astrocytoma, desmoplastic infantile astrocytoma, subependymal giant cell astrocytoma, diffuse astrocytoma, mixed glioma, optic glioma, gliomatosis cerebri, multifocal gliomatous tumor, multicentric glioblastoma multiforme tumor, paraganglioma, and ganglioglioma.

In a further aspect, the compound is administered for the treatment of a hematological cancer. In a still further aspect, the hematological cancer is selected from acute myeloid leukemia (AML), acute lymphoblastic leukemia (ALL), chronic myeloid leukemia (CML), chronic lymphocytic leukemia (CLL), hairy cell leukemia, chronic myelomonocytic leukemia (CMML), juvenile myelomonocytic leukemia (JMML), megakaryocytic leukemia, and large granular lymphocyte leukemia. In a yet further aspect, the hematological cancer is selected from Hodgkin lymphoma, Non-Hodgkin lymphoma, EBV-related/Burkitt's lymphoma, cutaneous T-cell lymphoma, and anaplastic large T-cell lymphoma. In an even further aspect, the hematological cancer is selected from multiple myeloma, solitary myeloma, localized myeloma, and extramedullary myeloma.

b. Inhibition of STAT3 Activity in a Mammal

In one aspect, the invention relates to a method for inhibition of STAT3 activity in a mammal comprising the step of administering to the mammal a therapeutically effective amount at least one disclosed compound or at least one disclosed product in a dosage and amount effective to treat the disorder in the mammal.

Thus, in various aspects, the invention relates to methods for inhibition of STAT activity in a mammal comprising the step of administering to the mammal a therapeutically effective amount of at least one compound having a structure represented by a formula:

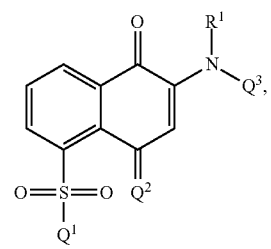

wherein R$^1$ is selected from hydrogen and C1-C3 alkyl; wherein Q$^1$ is —NR$^{2a}$R$^{2b}$ and wherein Q$^2$ is O; or wherein Q$^1$ and Q$^2$ are together N; wherein each of R$^{2a}$ and R$^{2b}$, when present, is independently selected from hydrogen and C1-C3 alkyl; wherein $Q^3$ is selected from —(C1-C6)-$Ar^1$, $Ar^1$, —(C1-C6)-$Cy^1$, and $Cy^1$; wherein $Ar^1$, when present, is selected from phenyl, naphthyl, monocyclic heteroaryl, and bicyclic heteroaryl; and wherein $Ar^1$ is substituted with 0, 1, 2, or 3 groups independently selected from halogen, —CN, —OH, —$NH_2$, —$NO_2$, C1-C6 alkyl, C1-C6 monohaloalkyl, C1-C6 polyhaloalkyl, C1-C6 hydroxyalkyl, C1-C6 monoalkylamino, C1-C6 dialkylamino, —(C1-C6)$NR^{4a}R^{4b}$, —(C1-C6)-(C=O)$R^3$, —(C1-C6)-(C=O)$OR^3$, —(C1-C6)-(C=O)$NR^{4a}R^{4b}$, —(C1-C6)-$Ar^2$, $Ar^2$, —(C1-C6)-$Cy^2$, $Cy^2$, and —$S(O)_nNR^{5a}R^{5b}$; wherein n is 0, 1, or 2; wherein each $R^3$, when present, is independently selected from hydrogen, C1-C6 alkyl, C1-C6 monohaloalkyl, C1-C6 polyhaloalkyl, C1-C6 hydroxyalkyl, and C1-C6 aminoalkyl; wherein each of $R^{4a}$ and $R^{4b}$, when present, is independently selected from hydrogen, C1-C6 alkyl, C1-C6 monohaloalkyl, C1-C6 polyhaloalkyl, C1-C6 hydroxyalkyl, and C1-C6 aminoalkyl; wherein each of $R^{5a}$ and $R^{5b}$, when present, is independently selected from hydrogen, C1-C6 alkyl, C1-C6 monohaloalkyl, C1-C6 polyhaloalkyl, C1-C6 hydroxyalkyl, C1-C6 aminoalkyl, and —(C=O)$NR^{6a}R^{6b}$; wherein each of $R^{6a}$ and $R^{6b}$, when present, is independently selected from hydrogen and C1-C6 alkyl; wherein each $Ar^2$, when present, is independently selected from is phenyl and monocyclic heteroaryl; and wherein $Ar^2$ is substituted with 0, 1, 2, or 3 groups independently selected from halogen, —CN, —OH, —$NH_2$, —$NO_2$, C1-C6 alkyl, C1-C6 monohaloalkyl, C1-C6 polyhaloalkyl, C1-C6 hydroxyalkyl, C1-C6 aminoalkyl, C1-C6 monoalkylamino, and C1-C6 dialkylamino; wherein each $Cy^2$, when present, is independently selected from C3-C8 cycloalkyl and C2-C7 heterocycloalkyl; and wherein $Cy^2$ is substituted with 0, 1, 2, or 3 groups independently selected from halogen, —CN, —OH, —$NH_2$, —$NO_2$, C1-C6 alkyl, C1-C6 monohaloalkyl, C1-C6 polyhaloalkyl, C1-C6 hydroxyalkyl, C1-C6 aminoalkyl, C1-C6 monoalkylamino, C1-C6 dialkylamino, —(C=O)$R^7$, —(C=O)$OR^7$, —(C=O)$NR^{8a}R^{8b}$, —(C=O)—(C1-C6 alkyl)$Ar^3$, —(C=O)—O—(C1-C6 alkyl)$Ar^3$, and —(C=O)—$NR^{8a}$—(C1-C6 alkyl)$Ar^3$; wherein each $R^7$, when present, is independently selected from hydrogen, C1-C6 alkyl, C1-C6 monohaloalkyl, and C1-C6 polyhaloalkyl; wherein each of $R^{8a}$ and $R^{8b}$, when present, is independently selected from hydrogen, C1-C6 alkyl, C1-C6 monohaloalkyl, and C1-C6 polyhaloalkyl; wherein each $Ar^3$, when present, is independently selected from phenyl and monocyclic heteroaryl substituted with 0, 1, 2, or 3 groups independently selected from halogen, —CN, —OH, —$NH_2$, —$NO_2$, C1-C6 alkyl, C1-C6 monohaloalkyl, and C1-C6 polyhaloalkyl; wherein $Cy^1$, when present, is selected from C3-C8 cycloalkyl and C2-C7 heterocycloalkyl; and wherein $Cy^2$ is substituted with 0, 1, 2, or 3 groups independently selected from halogen, —CN, —OH, —$NH_2$, —$NO_2$, C1-C6 alkyl, C1-C6 monohaloalkyl, C1-C6 polyhaloalkyl, C1-C6 hydroxyalkyl, C1-C6 monoalkylamino, C1-C6 dialkylamino, —(C1-C6)$NR^{4a}R^{4b}$, —(C1-C6)-(C=O)$R^3$, —(C1-C6)-(C=O)$OR^3$, —(C1-C6)-(C=O)$NR^{4a}R^{4b}$, —(C1-C6)-$Ar^2$, $Ar^2$, —(C1-C6)-$Cy^2$, $Cy^2$, and —$S(O)_nNR^{5a}R^{5b}$; or a pharmaceutically acceptable salt, solvate, or polymorph thereof.

In a further aspect, the STAT activity inhibited is STAT3 activity.

In a further aspect, the STAT activity is inhibited in a human.

In a further aspect, the compound exhibits inhibition of STAT activity with an $IC_{50}$ of less than about 30 µM. In a still further aspect, the compound exhibits inhibition of STAT activity with an $IC_{50}$ of less than about 10 µM. In a yet further aspect, the compound exhibits inhibition of STAT activity with an $IC_{50}$ of less than about 5 µM. In an even further aspect, the compound exhibits inhibition of STAT activity with an $IC_{50}$ of less than about 1 µM. In a still further aspect, the compound exhibits inhibition of STAT activity with an $IC_{50}$ of less than about 100 nM. In a yet further aspect, the compound exhibits inhibition of STAT activity with an $IC_{50}$ of less than about 50 nM. In an even further aspect, the compound exhibits inhibition of STAT activity with an $IC_{50}$ of less than about 10 nM.

In a further aspect, the STAT $IC_{50}$ is the $IC_{50}$ for STAT3 inhibition.

In a further aspect, the STAT $IC_{50}$ is determined using a fluorescence polarization assay. In a still further aspect, the STAT $IC_{50}$ is determined by measuring cell growth. In a yet further aspect, cell growth is determined using an osteosarcoma cell-line. In an even further aspect, the osteosarcoma cell-line is selected from RD2, RH30, and U2OS cells.

In a further aspect, the mammal has been diagnosed with a need for inhibition of STAT activity prior to the administering step.

In a further aspect, the STAT activity is inhibited in a mammal diagnosed with a need for inhibition of STAT3 activity. In a still further aspect, the method further comprises the step of identifying a mammal in need of inhibition of STAT. In a yet further aspect, the further step of identifying a mammal in need of inhibition of STAT comprises identifying a mammal in need of inhibition of STAT3 activity.

In a further aspect, inhibition of STAT activity treats a disorder associated with a STAT dysfunction. In a still further aspect, the STAT dysfunction is a STAT3 dysfunction. In a yet further aspect, the STAT3 dysfunction is constitutively active STAT3. In an even further aspect, the STAT3 dysfunction is upregulation of STAT3 activity.

In a further aspect, inhibition of STAT activity treats a disorder selected from psoriasis and pulmonary arterial hypertension.

In a further aspect, inhibition of STAT activity treats a disease of uncontrolled cellular proliferation. In a still further aspect, the disease of uncontrolled cellular proliferation is a cancer.

In a further aspect, inhibition of STAT activity treats a solid tumor. In a still further aspect, inhibition of STAT activity treats a cancer is selected from a cancer of the head, neck, pancreas, brain, ovary, kidney, prostate, breast, lung, colon, bladder, and liver. In a yet further aspect, inhibition of STAT activity treats a cancer is selected from a cancer of the breast, ovary, prostate, head, neck, and kidney. In an even further aspect, inhibition of STAT activity treats breast cancer. In a still further aspect, inhibition of STAT activity treats pancreatic cancer.

In a further aspect, inhibition of STAT activity treats a brain cancer. In a still further aspect, inhibition of STAT activity treats a brain cancer selected from a glioma, medulloblastoma, primitive neuroectodermal tumor (PNET), acoustic neuroma, glioma, meningioma, pituitary adenoma, schwannoma, CNS lymphoma, primitive neuroectodermal tumor, craniopharyngioma, chordoma, medulloblastoma, cerebral neuroblastoma, central neurocytoma, pineocytoma, pineoblastoma, atypical teratoid rhabdoid tumor, chondrosarcoma, chondroma, choroid plexus carcinoma, choroid plexus papilloma, craniopharyngioma, dysembryoplastic neuroepithelial tumor, gangliocytoma, germinoma, hemangioblastoma, hemangiopercytoma, and metastatic brain tumor. In a yet further aspect, the glioma is selected from ependymoma, astrocytoma, oligodendroglioma, and oligoastrocytoma. In an even further aspect, the glioma is selected from juvenile pilocytic astrocytoma, subependymal giant cell astrocytoma, ganglioglioma, subependymoma, pleomorphic xanthoastrocytom, anaplastic astrocytoma, glioblastoma multiforme, brain stem glioma, oligodendroglioma, ependymoma, oligoastrocytoma, cerebellar astrocytoma, desmoplastic infantile astrocytoma, subependymal giant cell astrocytoma, diffuse astrocytoma, mixed glioma, optic glioma, gliomatosis cerebri, multifocal gliomatous tumor, multicentric glioblastoma multiforme tumor, paraganglioma, and ganglioglioma.

In a further aspect, inhibition of STAT activity treats a hematological cancer. In a still further aspect, the hematological cancer is selected from acute myeloid leukemia (AML), acute lymphoblastic leukemia (ALL), chronic myeloid leukemia (CML), chronic lymphocytic leukemia (CLL), hairy cell leukemia, chronic myelomonocytic leukemia (CMML), juvenile myelomonocytic leukemia (JMML), Hodgkin lymphoma, Non-Hodgkin lymphoma, multiple myeloma, solitary myeloma, localized myeloma, and extramedullary myeloma.

c. Inhibition of Angiogenesis in a Mammal

In one aspect, the invention relates to a method for the inhibition of angiogenesis in a mammal comprising the step of administering to the mammal a therapeutically effective amount at least one disclosed compound or at least one disclosed product in a dosage and amount effective to inhibit angiogenesis in the mammal.

Thus, in various aspects, the invention relates to methods for the inhibition of angiogenesis in a mammal comprising the step of administering to the mammal a therapeutically effective amount at least one disclosed compound having a structure represented by a formula:

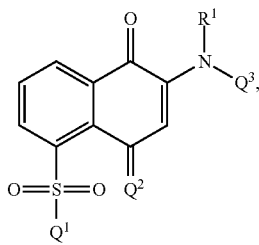

wherein $R^1$ is selected from hydrogen and C1-C3 alkyl; wherein $Q^1$ is —$NR^{2a}R^{2b}$ and wherein $Q^2$ is O; or wherein $Q^1$ and $Q^2$ are together N; wherein each of $R^{2a}$ and $R^{2b}$, when present, is independently selected from hydrogen and C1-C3 alkyl; wherein $Q^3$ is selected from —(C1-C6)-$Ar^1$, $Ar^1$, —(C1-C6)-$Cy^1$, and $Cy^1$; wherein $Ar^1$, when present, is selected from phenyl, naphthyl, monocyclic heteroaryl, and bicyclic heteroaryl; and wherein $Ar^1$ is substituted with 0, 1, 2, or 3 groups independently selected from halogen, —CN, —OH, —$NH_2$, —$NO_2$, C1-C6 alkyl, C1-C6 monohaloalkyl, C1-C6 polyhaloalkyl, C1-C6 hydroxyalkyl, C1-C6 monoalkylamino, C1-C6 dialkylamino, —(C1-C6)$NR^{4a}R^{4b}$, —(C1-C6)-(C=O)$R^3$, —(C1-C6)-(C=O)$OR^3$, —(C1-C6)(C=O)$NR^{4a}R^{4b}$, —(C1-C6)-$Ar^2$, $Ar^2$, —(C1-C6)-$Cy^2$, $Cy^2$, and —S(O)$_n$$NR^{5a}R^{5b}$; wherein n is 0, 1, or 2; wherein each $R^3$, when present, is independently selected from hydrogen, C1-C6 alkyl, C1-C6 monohaloalkyl, C1-C6 polyhaloalkyl, C1-C6 hydroxyalkyl, and C1-C6 aminoalkyl; wherein each of $R^{4a}$ and $R^{4b}$, when present, is independently selected from hydrogen, C1-C6 alkyl, C1-C6 monohaloalkyl, C1-C6 polyhaloalkyl, C1-C6 hydroxyalkyl, and C1-C6 aminoalkyl; wherein each of $R^{5a}$ and $R^{5b}$ when present, is independently selected from hydrogen, C1-C6 alkyl, C1-C6 monohaloalkyl, C1-C6 polyhaloalkyl, C1-C6 hydroxyalkyl, C1-C6 aminoalkyl, and —(C=O)$NR^{6a}R^{6b}$; wherein each of $R^{6a}$ and $R^{6b}$, when present, is independently selected from hydrogen and C1-C6 alkyl; wherein each $Ar^2$, when present, is independently selected from is phenyl and monocyclic heteroaryl; and wherein $Ar^2$ is substituted with 0, 1, 2, or 3 groups independently selected from halogen, —CN, —OH, —$NH_2$, —$NO_2$, C1-C6 alkyl, C1-C6 monohaloalkyl, C1-C6 polyhaloalkyl, C1-C6 hydroxyalkyl, C1-C6 aminoalkyl, C1-C6 monoalkylamino, and C1-C6 dialkylamino; wherein each $Cy^2$, when present, is independently selected from C3-C8 cycloalkyl and C2-C7 heterocycloalkyl; and wherein $Cy^2$ is substituted with 0, 1, 2, or 3 groups independently selected from halogen, —CN, —OH, —$NH_2$, —$NO_2$, C1-C6 alkyl, C1-C6 monohaloalkyl, C1-C6 polyhaloalkyl, C1-C6 hydroxyalkyl, C1-C6 aminoalkyl, C1-C6 monoalkylamino, C1-C6 dialkylamino, —(C=O)$R^7$, —(C=O)$OR^7$, —(C=O)$NR^{8a}R^{8b}$, —(C=O)—(C1-C6 alkyl)$Ar^3$, —(C=O)—O—(C1-C6 alkyl)$Ar^3$, and —(C=O)—$NR^{8a}$—(C1-C6 alkyl)$Ar^3$; wherein each $R^7$, when present, is independently selected from hydrogen, C1-C6 alkyl, C1-C6 monohaloalkyl, and C1-C6 polyhaloalkyl; wherein each of $R^{8a}$ and $R^{8b}$, when present, is independently selected from hydrogen, C1-C6 alkyl, C1-C6 monohaloalkyl, and C1-C6 polyhaloalkyl; wherein each $Ar^3$, when present, is independently selected from phenyl and monocyclic heteroaryl substituted with 0, 1, 2, or 3 groups independently selected from halogen, —CN, —OH, —$NH_2$, —$NO_2$, C1-C6 alkyl, C1-C6 monohaloalkyl, and C1-C6 polyhaloalkyl; wherein $Cy^1$, when present, is selected from C3-C8 cycloalkyl and C2-C7 heterocycloalkyl; and wherein $Cy^2$ is substituted with 0, 1, 2, or 3 groups independently selected from halogen, —CN, —OH, —$NH_2$, —$NO_2$, C1-C6 alkyl, C1-C6 monohaloalkyl, C1-C6 polyhaloalkyl, C1-C6 hydroxyalkyl, C1-C6 monoalkylamino, C1-C6 dialkylamino, —(C1-C6)$NR^{4a}R^{4b}$, —(C1-C6)-(C=O)$R^3$, —(C1-C6)-(C=O)$OR^3$, —(C1-C6)-(C=O)$NR^{4a}R^{4b}$, —(C1-C6)-$Ar^2$, $Ar^2$, —(C1-C6)-$Cy^2$, $Cy^2$, and —S(O)$_n$$NR^{5a}R^{5b}$; or a pharmaceutically acceptable salt, solvate, or polymorph thereof.

In a further aspect, the compound exhibits inhibition of angiogenesis with an $IC_{50}$ of less than about 30 μM. In a still further aspect, the compound exhibits inhibition of angiogenesis with an $IC_{50}$ of less than about 10 μM. In a yet further aspect, the compound exhibits inhibition of angiogenesis with an $IC_{50}$ of less than about 5 μM. In an even further aspect, the compound exhibits inhibition of angiogenesis with an $IC_{50}$ of less than about 1 μM. In a still further aspect, the compound exhibits inhibition of angiogenesis with an $IC_{50}$ of less than about 100 nM. In a yet further aspect, the compound exhibits inhibition of angiogenesis with an $IC_{50}$ of less than about 50 nM. In an even further aspect, the compound exhibits inhibition of angiogenesis with an $IC_{50}$ of less than about 10 nM.

In a further aspect, the inhibition of angiogenesis is determined in an in vitro assay. In a still further aspect, the in vitro assay for angiogenesis is an endothelial cell tube formation assay. In a yet further aspect, the cells utilized in the endothelial cell tube formation assay are HUVEC cells (human umbilical vascular endothelial cells). In an even further aspect, the in vitro assay for angiogenesis is an endothelial cell tube formation assay spheroid formation assay. In a still further aspect, the cells utilized in the endothelial cell spheroid formation assay are HUVEC cells (human umbilical vascular endothelial cells). In a still further aspect, the in vitro assay for angiogenesis is an endothelial cell tube migration assay. In a yet further aspect, the cells utilized in the endothelial cell tube migration assay are HUVEC cells (human umbilical vascular endothelial cells). In an even further aspect, the endothelial cell migration assay is as previously described in PLoS One. 2012; 7(4): e35513. doi: 10.1371/journal.pone.0035513.

In a further aspect, the mammal has been diagnosed with a need for inhibition of angiogenesis prior to the administering step.

In a further aspect, the angiogenesis activity is inhibited in a mammal diagnosed with a need for inhibition of angiogenesis activity. In a still further aspect, the method further comprises the step of identifying a mammal in need of inhibition of angiogenesis. In a yet further aspect, the further step of identifying a mammal in need of inhibition of angiogenesis comprises identifying a mammal in need of inhibition of STAT activity. In an even further aspect, the further step of identifying a mammal in need of inhibition of angiogenesis comprises identifying a mammal in need of inhibition of STAT3 activity.

In a further aspect, inhibition of angiogenesis treats a disorder associated with a STAT dysfunction. In a still further aspect, the STAT dysfunction is a STAT3 dysfunction. In a yet further aspect, the STAT3 dysfunction is constitutively active STAT3. In an even further aspect, the STAT3 dysfunction is upregulation of STAT3 activity.

In a further aspect, inhibition of angiogenesis treats a disease of uncontrolled cellular proliferation. In a still further aspect, the disease of uncontrolled cellular proliferation is a cancer.

In a further aspect, the inhibition of angiogenesis treats a solid tumor. In a still further aspect, the inhibition of angiogenesis treats a cancer is selected from a cancer of the head, neck, pancreas, brain, ovary, kidney, prostate, breast, lung, colon, bladder, and liver. In a yet further aspect, the inhibition of angiogenesis treats a cancer is selected from a cancer of the breast, ovary, prostate, head, neck, and kidney. In an even further aspect, the inhibition of angiogenesis treats breast cancer. In a still further aspect, the inhibition of angiogenesis treats pancreatic cancer.

In a further aspect, the inhibition of angiogenesis treats a brain cancer. In a still further aspect, the inhibition of angiogenesis treats a brain cancer selected from a glioma, medulloblastoma, primitive neuroectodermal tumor (PNET), acoustic neuroma, glioma, meningioma, pituitary adenoma, schwannoma, CNS lymphoma, primitive neuroectodermal tumor, craniopharyngioma, chordoma, medulloblastoma, cerebral neuroblastoma, central neurocytoma, pineocytoma, pineoblastoma, atypical teratoid rhabdoid tumor, chondrosarcoma, chondroma, choroid plexus carcinoma, choroid plexus papilloma, craniopharyngioma, dysembryoplastic neuroepithelial tumor, gangliocytoma, germinoma, hemangioblastoma, hemangiopercytoma, and metastatic brain tumor. In a yet further aspect, the glioma is selected from ependymoma, astrocytoma, oligodendroglioma, and oligoastrocytoma. In an even further aspect, the glioma is selected from juvenile pilocytic astrocytoma, subependymal giant cell astrocytoma, ganglioglioma, subependymoma, pleomorphic xanthoastrocytom, anaplastic astrocytoma, glioblastoma multiforme, brain stem glioma, oligodendroglioma, ependymoma, oligoastrocytoma, cerebellar astrocytoma, desmoplastic infantile astrocytoma, subependymal giant cell astrocytoma, diffuse astrocytoma, mixed glioma, optic glioma, gliomatosis cerebri, multifocal gliomatous tumor, multicentric glioblastoma multiforme tumor, paraganglioma, and ganglioglioma.

In a further aspect, the inhibition of angiogenesis treats a hematological cancer. In a still further aspect, the hematological cancer is selected from acute myeloid leukemia (AML), acute lymphoblastic leukemia (ALL), chronic myeloid leukemia (CML), chronic lymphocytic leukemia (CLL), hairy cell leukemia, chronic myelomonocytic leukemia (CMML), juvenile myelomonocytic leukemia (JMML), Hodgkin lymphoma, Non-Hodgkin lymphoma, multiple myeloma, solitary myeloma, localized myeloma, and extramedullary myeloma.

d. Inhibiting STAT3 Activity in Cells

In one aspect, the invention relates to a method for inhibiting STAT3 activity in at least one cell, comprising the step of contacting the at least one cell with an effective amount of at least one disclosed compound or at least one disclosed product in a dosage and amount effective to treat the disorder in the mammal.

Thus, in various aspects, the invention relates to methods for inhibiting STAT3 activity in at least one cell, comprising the step of contacting the at least one cell with an effective amount of at least one compound having a structure represented by a formula:

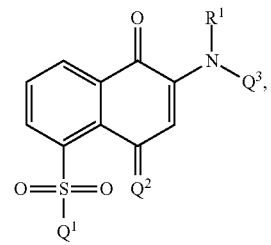

wherein $R^1$ is selected from hydrogen and C1-C3 alkyl; wherein $Q^1$ is $-NR^{2a}R^{2b}$ and wherein $Q^2$ is O; or wherein $Q^1$ and $Q^2$ are together N; wherein each of $R^{2a}$ and $R^{2b}$, when present, is independently selected from hydrogen and C1-C3 alkyl; wherein $Q^3$ is selected from $-(C1-C6)-Ar^1$, $Ar^1$, $-(C1-C6)-Cy^1$, and $Cy^1$; wherein $Ar^1$, when present, is selected from phenyl, naphthyl, monocyclic heteroaryl, and bicyclic heteroaryl; and wherein $Ar^1$ is substituted with 0, 1, 2, or 3 groups independently selected from halogen, —CN, —OH, —NH$_2$, —NO$_2$, C1-C6 alkyl, C1-C6 monohaloalkyl, C1-C6 polyhaloalkyl, C1-C6 hydroxyalkyl, C1-C6 monoalkylamino, C1-C6 dialkylamino, $-(C1-C6)NR^{4a}R^{4b}$, $-(C1-C6)-(C=O)R^3$, $-(C1-C6)-(C=O)OR^3$, $-(C1-C6)-(C=O)NR^{4a}R^{4b}$, $-(C1-C6)-Ar^2$, $Ar^2$, $-(C1-C6)-Cy^2$, $Cy^2$, and $-S(O)_nNR^{5a}R^{5b}$; wherein n is 0, 1, or 2; wherein each $R^3$, when present, is independently selected from hydrogen, C1-C6 alkyl, C1-C6 monohaloalkyl, C1-C6 polyhaloalkyl, C1-C6 hydroxyalkyl, and C1-C6 aminoalkyl; wherein each of $R^{4a}$ and $R^{4b}$, when present, is independently selected from hydrogen, C1-C6 alkyl, C1-C6 monohaloalkyl, C1-C6 polyhaloalkyl, C1-C6 hydroxyalkyl, and C1-C6 aminoalkyl; wherein each of $R^{5a}$ and $R^{5b}$, when present, is independently selected from hydrogen, C1-C6 alkyl, C1-C6 monohaloalkyl, C1-C6 polyhaloalkyl, C1-C6 hydroxyalkyl, C1-C6 aminoalkyl, and $-(C=O)NR^{6a}R^{6b}$; wherein each of $R^{6a}$ and $R^{6b}$, when present, is independently selected from hydrogen and C1-C6 alkyl; wherein each $Ar^2$, when present, is independently selected from phenyl and monocyclic heteroaryl; and wherein $Ar^2$ is substituted with 0, 1, 2, or 3 groups independently selected from halogen, —CN, —OH, —NH$_2$, —NO$_2$, C1-C6 alkyl, C1-C6 monohaloalkyl, C1-C6 polyhaloalkyl, C1-C6 hydroxyalkyl, C1-C6 aminoalkyl, C1-C6 monoalkylamino, and C1-C6 dialkylamino; wherein each $Cy^2$, when present, is independently selected from C3-C8 cycloalkyl and C2-C7 heterocycloalkyl; and wherein $Cy^2$ is substituted with 0, 1, 2, or 3 groups independently selected from halogen, —CN, —OH, —NH$_2$, —NO$_2$, C1-C6 alkyl, C1-C6 monohaloalkyl, C1-C6 polyhaloalkyl, C1-C6 hydroxyalkyl, C1-C6 aminoalkyl, C1-C6 monoalkylamino, C1-C6 dialkylamino, —(C=O)R$^7$, —(C=O)OR$^7$, —(C=O)NR$^{8a}$R$^{8b}$, —(C=O)—(C1-C6 alkyl)Ar$^3$, —(C=O)—O—(C1-C6 alkyl)Ar$^3$, and —(C=O)—NR$^{8a}$—(C1-C6 alkyl)Ar$^3$; wherein each R$^7$, when present, is independently selected from hydrogen, C1-C6 alkyl, C1-C6 monohaloalkyl, and C1-C6 polyhaloalkyl; wherein each of R$^{8a}$ and R$^{8b}$, when present, is independently selected from hydrogen, C1-C6 alkyl, C1-C6 monohaloalkyl, and C1-C6 polyhaloalkyl; wherein each Ar$^3$, when present, is independently selected from phenyl and monocyclic heteroaryl substituted with 0, 1, 2, or 3 groups independently selected from halogen, —CN, —OH, —NH$_2$, —NO$_2$, C1-C6 alkyl, C1-C6 monohaloalkyl, and C1-C6 polyhaloalkyl; wherein $Cy^1$, when present, is selected from C3-C8 cycloalkyl and C2-C7 heterocycloalkyl; and wherein $Cy^2$ is substituted with 0, 1, 2, or 3 groups independently selected from halogen, —CN, —OH, —NH$_2$, —NO$_2$, C1-C6 alkyl, C1-C6 monohaloalkyl, C1-C6 polyhaloalkyl, C1-C6 hydroxyalkyl, C1-C6 monoalkylamino, C1-C6 dialkylamino, —(C1-C6)NR$^{4a}$R$^{4b}$, —(C1-C6)-(C=O)R$^3$, —(C1-C6)-(C=O)OR$^3$, —(C1-C6)-(C=O)NR$^{4a}$R$^{4b}$, —(C1-C6)-Ar$^2$, Ar$^2$, —(C1-C6)-Cy$^2$, Cy$^2$, and —S(O)$_n$NR$^{5a}$R$^{5b}$; or a pharmaceutically acceptable salt, solvate, or polymorph thereof.

In a further aspect, the cell contacted is mammalian. In a further aspect, the mammalian cell contacted is a human cell.

In a further aspect, the compound exhibits inhibition of STAT3 activity in the contacted cell with an IC$_{50}$ of less than about 30 µM. In a still further aspect, the compound exhibits inhibition of STAT3 activity in the contacted cell with an IC$_{50}$ of less than about 10 µM. In a yet further aspect, the compound exhibits inhibition of STAT3 activity in the contacted cell with an IC$_{50}$ of less than about 5 µM. In an even further aspect, the compound exhibits inhibition of STAT3 activity in the contacted cell with an IC$_{50}$ of less than about 1 µM. In a still further aspect, the compound exhibits inhibition of STAT3 activity in the contacted cell with an IC$_{50}$ of less than about 100 nM. In a yet further aspect, the compound exhibits inhibition of STAT3 activity in the contacted cell with an IC$_{50}$ of less than about 50 nM. In an even further aspect, the compound exhibits inhibition of STAT3 activity in the contacted cell with an IC$_{50}$ of less than about 10 nM.

In a further aspect, the STAT3 IC$_{50}$ is determined using a fluorescence polarization assay. In a still further aspect, the inhibition of STAT3 IC$_{50}$ is determined by measuring cell growth. In a yet further aspect, cell growth is determined using an osteosarcoma cell-line. In an even further aspect, the osteosarcoma cell-line is selected from RD2, RH30, and U2OS cells.

In a further aspect, the at least one cell has a STAT3 dysfunction. In a still further aspect, the STAT3 dysfunction is constitutively active STAT3. In a yet further aspect, the STAT3 dysfunction is upregulation of STAT3 activity.

In a further aspect, the contacting the cell is in vitro. In a still further aspect, the contacting the cell is in vivo.

In a further aspect, the contacting the cell in vivo is by administration of the compound to a mammal. In a still further aspect, the compound is administered to a mammal, and the mammal is a human. In a yet further aspect, the compound is administered orally, intraarterially, intravenously, subcutaneously, or intraperitoneally. In an even further aspect, the compound is administered orally. In a still further aspect, the compound is administered intravenously.

In a further aspect, the contacting the cell in vivo is by administration of the compound to a mammal diagnosed with a need for inhibiting STAT3 activity in a cell prior to the administering step. In a still further aspect, the method further comprises the step of identifying a mammal in need of inhibiting STAT3 activity in a cell.

In a further aspect, inhibiting STAT3 activity in a cell treats a disorder in the mammal. In a still further aspect, inhibiting STAT3 activity in a cell treats a disorder selected from psoriasis and pulmonary arterial hypertension.

In a further aspect, inhibiting STAT3 activity in a cell treats a disorder disease of uncontrolled cellular proliferation. In a still further aspect, the disease of uncontrolled cellular proliferation is a cancer. In a yet further aspect, inhibiting STAT3 activity in a cell treats a solid tumor.

In a further aspect, inhibiting STAT3 activity in the cell treats a cancer is selected from a cancer of the head, neck, pancreas, brain, ovary, kidney, prostate, breast, lung, colon, bladder, and liver. In a still further aspect, inhibiting STAT3 activity in the cell treats a cancer is selected from melanoma, glioma, medulloblastoma, renal cell carcinoma, pancreatic adenocarcinoma, ovarian carcinoma, rhabdomyosarcoma, and osteosarcoma. In a yet further aspect, inhibiting STAT3 activity in the cell treats a cancer is selected from a cancer of the breast, ovary, prostate, head, neck, and kidney. In an even further aspect, inhibiting STAT3 activity in the cell treats breast cancer. In a further aspect, inhibiting STAT3 activity in the cell treats pancreatic cancer.

In a further aspect, inhibiting STAT3 activity in the cell treats brain cancer. In a still further aspect, the brain cancer selected from a glioma, medulloblastoma, primitive neuroectodermal tumor (PNET), acoustic neuroma, glioma, meningioma, pituitary adenoma, schwannoma, CNS lymphoma, primitive neuroectodermal tumor, craniopharyngioma, chordoma, medulloblastoma, cerebral neuroblastoma, central neurocytoma, pineocytoma, pineoblastoma, atypical teratoid rhabdoid tumor, chondrosarcoma, chondroma, choroid plexus carcinoma, choroid plexus papilloma, craniopharyngioma, dysembryoplastic neuroepithelial tumor, gangliocytoma, germinoma, hemangioblastoma, hemangiopercytoma, and metastatic brain tumor. In a yet further aspect, the glioma is selected from ependymoma, astrocytoma, oligodendroglioma, and oligoastrocytoma. In an even further aspect, the glioma is selected from juvenile pilocytic astrocytoma, subependymal giant cell astrocytoma, ganglioglioma, subependymoma, pleomorphic xanthoastrocytom, anaplastic astrocytoma, glioblastoma multiforme, brain stem glioma, oligodendroglioma, ependymoma, oligoastrocytoma, cerebellar astrocytoma, desmoplastic infantile astrocytoma, subependymal giant cell astrocytoma, diffuse astrocytoma, mixed glioma, optic glioma, gliomatosis cerebri, multifocal gliomatous tumor, multicentric glioblastoma multiforme tumor, paraganglioma, and ganglioglioma.

In a further aspect, inhibiting STAT3 activity in the cell treats a hematological cancer. In a still further aspect, the hematological cancer is selected from acute myeloid leukemia (AML), acute lymphoblastic leukemia (ALL), chronic myeloid leukemia (CML), chronic lymphocytic leukemia (CLL), hairy cell leukemia, chronic myelomonocytic leukemia (CMML), juvenile myelomonocytic leukemia (JMML), megakaryocytic leukemia, and large granular lymphocyte leukemia. In a yet further aspect, the hematological cancer is selected from Hodgkin lymphoma, Non-Hodgkin lymphoma, EBV-related/Burkitt's lymphoma, cutaneous T-cell lymphoma, and anaplastic large T-cell lymphoma. In an even further aspect, the hematological cancer is selected from multiple myeloma, solitary myeloma, localized myeloma, and extramedullary myeloma.

2. Manufacture of a Medicament

In one aspect, the invention relates to a method for the manufacture of a medicament for STAT, such as STAT3, activity in a mammal comprising combining a therapeutically effective amount of a disclosed compound or product of a disclosed method with a pharmaceutically acceptable carrier or diluent.

3. Use of Compounds

In one aspect, the invention relates to the use of a disclosed compound or a product of a disclosed method. In a further aspect, the use relates to the manufacture of a medicament for the treatment of a disorder associated with STAT, such as STAT3, dysfunction in a mammal. In a still further aspect, the disorder is associated with upregulation of STAT3 activity. In a yet further aspect, the disorder is selected from psoriasis and pulmonary arterial hypertension.

In a further aspect, the use relates to the manufacture of a medicament for the treatment of disease of uncontrolled cellular proliferation. In a yet further aspect, the disease of uncontrolled cellular proliferation is a cancer. In a still further aspect the cancer is a solid tumor. In an even further aspect, the cancer is selected from a cancer of the head, neck, pancreas, brain, ovary, kidney, prostate, breast, lung, colon, bladder, and liver. In a still further aspect, the cancer is selected from melanoma, glioma, medulloblastoma, renal cell carcinoma, pancreatic adenocarcinoma, ovarian carcinoma, rhabdomyosarcoma, and osteosarcoma. In a yet further aspect, the cancer is selected from a cancer of the breast, ovary, prostate, head, neck, and kidney. In an even further aspect, the cancer is breast cancer. In a further aspect, the cancer is pancreatic cancer.

In a further aspect, the use relates to the manufacture of a medicament for the treatment of a brain cancer. In a still further aspect, the brain cancer is selected from a glioma, medulloblastoma, primitive neuroectodermal tumor (PNET), acoustic neuroma, glioma, meningioma, pituitary adenoma, schwannoma, CNS lymphoma, primitive neuroectodermal tumor, craniopharyngioma, chordoma, medulloblastoma, cerebral neuroblastoma, central neurocytoma, pineocytoma, pineoblastoma, atypical teratoid rhabdoid tumor, chondrosarcoma, chondroma, choroid plexus carcinoma, choroid plexus papilloma, craniopharyngioma, dysembryoplastic neuroepithelial tumor, gangliocytoma, germinoma, hemangioblastoma, hemangiopercytoma, and metastatic brain tumor. In a yet further aspect, the glioma is selected from ependymoma, astrocytoma, oligodendroglioma, and oligoastrocytoma. In an even further aspect, the glioma is selected from juvenile pilocytic astrocytoma, subependymal giant cell astrocytoma, ganglioglioma, subependymoma, pleomorphic xanthoastrocytom, anaplastic astrocytoma, glioblastoma multiforme, brain stem glioma, oligodendroglioma, ependymoma, oligoastrocytoma, cerebellar astrocytoma, desmoplastic infantile astrocytoma, subependymal giant cell astrocytoma, diffuse astrocytoma, mixed glioma, optic glioma, gliomatosis cerebri, multifocal gliomatous tumor, multicentric glioblastoma multiforme tumor, paraganglioma, and ganglioglioma. In a further aspect, the cancer is a hematological cancer.

In a further aspect, the use relates to the manufacture of a medicament for the treatment of a hematological cancer is selected from acute myeloid leukemia (AML), acute lymphoblastic leukemia (ALL), chronic myeloid leukemia (CML), chronic lymphocytic leukemia (CLL), hairy cell leukemia, chronic myelomonocytic leukemia (CMML), juvenile myelomonocytic leukemia (JMML), megakaryocytic leukemia, and large granular lymphocyte leukemia. In a still further aspect the hematological cancer is selected from Hodgkin lymphoma, Non-Hodgkin lymphoma, EBV-related/Burkitt's lymphoma, cutaneous T-cell lymphoma, and anaplastic large T-cell lymphoma. In a yet further aspect, the hematological cancer is selected from multiple myeloma, solitary myeloma, localized myeloma, and extramedullary myeloma.

In a further aspect, the use is inhibition of STAT3. In a still further aspect, the compound inhibits STAT3 activity with an $IC_{50}$ of less than about 30 µM. In a yet further aspect, the compound inhibits STAT3 activity with an $IC_{50}$ of less than about 10 PM. In an even further aspect, the compound inhibits STAT3 activity with an $IC_{50}$ of less than about 5 µM. In a still further aspect, the compound inhibits STAT3 activity with an $IC_{50}$ of less than about 1 µM. In a yet further aspect, the compound inhibits STAT3 activity with an $IC_{50}$ of less than about 100 nM. In an even further aspect, the compound inhibits STAT3 activity with an $IC_{50}$ of less than about 50 nM. In a still further aspect, the compound inhibits STAT3 activity with an $IC_{50}$ of less than about 10 nM.

In a further aspect, the STAT3 $IC_{50}$ is determined using a fluorescence polarization assay. In a still further aspect, the STAT3 $IC_{50}$ is determined by measuring cell growth. In a yet further aspect, cell growth is determined using an osteosarcoma cell-line. In an even further aspect, the osteosarcoma cell-line is selected from RD2, RH30, and U2OS cells.

4. Kits

In one aspect, the invention relates to a kit comprising at least one of the disclosed compounds, or a pharmaceutically acceptable salt, hydrate, solvate, or polymorph thereof; and one or more of: (a) at least one agent known to decrease STAT3 activity; (b) at least one agent known to increase STAT3 activity; (c) at least one agent know to treat a disease of uncontrolled cellular proliferation; (d) at least one agent known to treat psoriasis; (e) at least one agent known to treat pulmonary arterial hypertension; or (f) instructions for treating a disorder associated with a STAT3 dysfunction. In a further aspect, the at least one compound or the at least one product and the at least one agent are co-formulated. In a further aspect, the at least one compound or the at least one product and the at least one agent are co-packaged.

In a further aspect, the compound exhibits inhibition of STAT3 activity with an $IC_{50}$ of less than about 10 µM. In a further aspect, the compound exhibits inhibition of STAT3 activity with an $IC_{50}$ of less than about 5 µM. In a further aspect, the compound exhibits inhibition of STAT3 activity with an $IC_{50}$ of less than about 1 µM. In a further aspect, the compound exhibits inhibition of STAT3 activity with an $IC_{50}$ of less than about 100 nM. In a further aspect, the compound exhibits inhibition of STAT3 activity with an $IC_{50}$ of less than about 50 nM. In a further aspect, the compound exhibits inhibition of STAT3 activity with an $IC_{50}$ of less than about 10 nM.

In various further aspects, the STAT3 activity is determined using a fluorescence polarization assay. In a further aspect, the STAT3 activity is determined by measuring cell growth. In a further aspect, cell growth is determined using an osteosarcoma cell-line. In a still further aspect, the osteosarcoma cell-line is selected from RD2, RH30, and U2OS cells.

In a further aspect, the at least one agent of the kit is a hormone therapy agent. In a still further aspect, the hormone therapy agent is selected from one or more of the group consisting of leuprolide, tamoxifen, raloxifene, megestrol, fulvestrant, triptorelin, medroxyprogesterone, letrozole, anastrozole, exemestane, bicalutamide, goserelin, histrelin, fluoxymesterone, estramustine, flutamide, toremifene, degarelix, nilutamide, abarelix, and testolactone, or a pharmaceutically acceptable salt, hydrate, solvate, or polymorph thereof.

In a further aspect, the at least one agent of the kit is a chemotherapeutic agent. In a still further aspect, the chemotherapeutic agent is selected from one or more of the group consisting of an alkylating agent, an antimetabolite agent, an antineoplastic antibiotic agent, a mitotic inhibitor agent, a mTor inhibitor agent, MEK inhibitor agent, or other chemotherapeutic agent. In a still further aspect, the at least one agent of the kit is a chemotherapeutic agent. In a still further aspect, the chemotherapeutic agent is selected from one or more of the group consisting of an alkylating agent, an antimetabolite agent, an antineoplastic antibiotic agent, a mitotic inhibitor agent, a mTor inhibitor agent, or other chemotherapeutic agent.

In a further aspect, the antineoplastic antibiotic agent is selected from one or more of the group consisting of doxorubicin, mitoxantrone, bleomycin, daunorubicin, dactinomycin, epirubicin, idarubicin, plicamycin, mitomycin, pentostatin, and valrubicin, or a pharmaceutically acceptable salt, hydrate, solvate, or polymorph thereof.

In a further aspect, the antimetabolite agent is selected from one or more of the group consisting of gemcitabine, 5-fluorouracil, capecitabine, hydroxyurea, mercaptopurine, pemetrexed, fludarabine, nelarabine, cladribine, clofarabine, cytarabine, decitabine, pralatrexate, floxuridine, methotrexate, and thioguanine, or a pharmaceutically acceptable salt, hydrate, solvate, or polymorph thereof.

In a further aspect, the alkylating agent is selected from one or more of the group consisting of carboplatin, cisplatin, cyclophosphamide, chlorambucil, melphalan, carmustine, busulfan, lomustine, dacarbazine, oxaliplatin, ifosfamide, mechlorethamine, temozolomide, thiotepa, bendamustine, and streptozocin, or a pharmaceutically acceptable salt, hydrate, solvate, or polymorph thereof.

In a further aspect, the mitotic inhibitor agent is selected from one or more of the group consisting of irinotecan, topotecan, rubitecan, cabazitaxel, docetaxel, paclitaxel, etopside, vincristine, ixabepilone, vinorelbine, vinblastine, and teniposide, or a pharmaceutically acceptable salt, hydrate, solvate, or polymorph thereof.

In a further aspect, the mTor inhibitor agent is selected from one or more of the group consisting of everolimus, siroliumus, and temsirolimus, or a pharmaceutically acceptable salt, hydrate, solvate, or polymorph thereof.

In a further aspect, the MEK inhibitor agent is selected from dabrafenib, trametinib, cobimetinib (GDC-093), pimasertib, selumetinib, refametinib, ARRY-162, ARRY-300, RO4987655, RO5126766, WX-554, MEK162, MEK300, AZD8330, and AZD6244. In an even further aspect, the MEK inhibitor agent is selected from dabrafenib, trametinib, cobimetinib (GDC-093), pimasertib, selumetinib, and refametinib. In a still further aspect, the MEK inhibitor agent is selected from dabrafenib and trametinib.

In a further aspect, the instructions of the kit further comprise providing the compound in connection surgery. In a still further aspect, the instructions provide that surgery is performed prior to the administering of at least one compound. In a yet further aspect, the instructions provide that surgery is performed after the administering of at least one compound. In an even further aspect, the instructions provide that the administering of at least one compound is to effect presurgical debulking of a tumor. In a still further aspect, the instructions provide that surgery is performed at about the same time as the administering of at least one compound.

In a further aspect, the instructions of the kit further comprise providing the compound in connection with radiotherapy. In a still further aspect, the instructions provide that radiotherapy is performed prior to the administering of at least one compound. In a yet further aspect, the instructions provide that radiotherapy is performed after the step of the administering of at least one compound. In an even further aspect, the instructions provide that radiotherapy is performed at about the same time as the step of the administering of at least one compound.

In a further aspect, the instructions further comprise providing the compound in connection with at least one agent that is a chemotherapeutic agent.

In a further aspect, the instructions of the kit further comprise providing the compound in connection with co-treatment with a MEK inhibitor. In a still further aspect, the instructions of the kit further comprise providing the compound in connection with co-treatment with a MEK inhibitor selected from dabrafenib, trametinib, cobimetinib (GDC-093), pimasertib, selumetinib, refametinib, ARRY-162, ARRY-300, RO4987655, RO5126766, WX-554, MEK162, MEK300, AZD8330, and AZD6244. In an even further aspect, the instructions of the kit further comprise providing the compound in connection with co-treatment with a MEK inhibitor selected from dabrafenib, trametinib, cobimetinib (GDC-093), pimasertib, selumetinib, and refametinib. In a still further aspect, the instructions of the kit further comprise providing the compound in connection with co-treatment with a MEK inhibitor selected from dabrafenib and trametinib.

In a further aspect, the at least one compound and the at least one agent are co-formulated. In a still further aspect, the at least one compound and the at least one agent are co-packaged.

The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is contemplated that the disclosed kits can be used in connection with the disclosed methods of making, the disclosed methods of using, and/or the disclosed compositions.

5. Non-Medical Uses

Also provided are the uses of the disclosed compounds and products as pharmacological tools in the development and standardization of in vitro and in vivo test systems for the evaluation of the effects of the disclosed compounds, compositions, and methods of STAT, such as STAT3, related activity in laboratory animals such as cats, dogs, rabbits, monkeys, rats and mice, as part of the search for new therapeutic agents of therapeutics, such as cancer therapeutics.

G. References

Mandal, P. K.; Gao, F.; Lu, Z.; Ren, Z.; Ramesh, R.; Birtwistle, J. S.; Kaluarachchi, K. K.; Chen, X.; Bast, R. C., Jr.; Liao, W. S.; McMurray, J. S. Potent and Selective Phosphopeptide Mimetic Prodrugs Targeted to the Src Homology 2 (SH2) Domain of Signal Transducer and Activator of Transcription 3. J. Med. Chem. 54, 3549-3563.

Mandal, P. K.; Ren, Z. Y.; Chen, X. M.; Xiong, C. Y.; McMurray, J. S. Structure-Affinity Relationships of Glutamine Mimics Incorporated into Phosphopeptides Targeted to the SH2 Domain of Signal Transducer and Activator of Transcription 3. *J. Med. Chem.* 2009, 52, 6126-6141.

Liu, A.; Liu, Y.; Xu, Z.; Yu, W.; Wang, H.; Li, C.; Lin, J. Novel small molecule, XZH-5, inhibits constitutive and interleukin-6-induced STAT3 phosphorylation in human rhabdomyosarcoma cells. *Cancer Sci.* 102, 1381-1387.

Liu, Y.; Liu, A.; Xu, Z.; Yu, W.; Wang, H.; Li, C.; Lin, J. XZH-5 inhibits STAT3 phosphorylation and causes apoptosis in human hepatocellular carcinoma cells. *Apoptosis* 16, 502-510.

Song, H.; Wang, R.; Wang, S.; Lin, J.; Stark, G. R. A Low-Molecular-Weight Compound Discovered through Virtual Database Screening Inhibits Stat3 Function in Breast Cancer Cells. *Proc. Natl. Acad. Sci. U.S.A.* 2005, 102, 4700-4705.

Schust, J.; Sperl, B.; Hollis, A.; Mayer, T. U.; Berg, T. Stattic: A small-molecule inhibitor of STAT3 activation and dimerization. *Chem. Biol.* 2006, 13, 1235-1242.

Lin, L.; Benson, D. M., Jr.; DeAngelis, S.; Bakan, C. E.; Li, P. K.; Li, C.; Lin, J. A small molecule, LLL12 inhibits constitutive STAT3 and IL-6-induced STAT3 signaling and exhibits potent growth suppressive activity in human multiple myeloma cells. *Int. J. cancer.* 2012, 130, 1459-69.

Hajduk, P. J.; Greer, J. A decade of fragment-based drug design: strategic advances and lessons learned. *Nat. Rev. Drug Discov.* 2007, 6, 211-219.

Lima, L. M.; Barreiro, E. J. Bioisosterism: a useful strategy for molecular modification and drug design. *Curr. Med. Chem.* 2005, 12, 23-49.

Bhasin, D.; Cisek, K.; Pandharkar, T.; Regan, N.; Li, C. L.; Pandit, B.; Lin, J.; Li, P. K. Design, synthesis, and studies of small molecule STAT3 inhibitors. *Bioorg. Med. Chem. Lett.* 2008, 18, 391-395.

Matsuno, K.; Masuda, Y.; Uehara, Y.; Sato, H.; Muroya, A.; Takahashi, O.; Yokotagawa, T.; Furuya, T.; Okawara, T.; Otsuka, M.; Ogo, N.; Ashizawa, T.; Oshita, C.; Tai, S.; Ishii, H.; Akiyama, Y.; Asai, A. Identification of a New Series of STAT3. Inhibitors by Virtual Screening. *ACS Med. Chem. Lett.* 1, 371-375.

Turkson, J.; Kim, J. S.; Zhang, S. M.; Yuan, J.; Huang, M.; Glenn, M.; Haura, E.; Sebti, S.; Hamilton, A. D.; Jove, R. Novel peptidomimetic inhibitors of signal transducer and activator of transcription 3 dimerization and biological activity. *Mol. Cancer Ther.* 2004, 3, 261-269.

Ren, X. M.; Duan, L.; He, Q. A.; Zhang, Z.; Zhou, Y.; Wu, D. H.; Pan, J. X.; Pei, D. Q.; Ding, K. Identification of Niclosamide as a New Small-Molecule Inhibitor of the STAT3 Signaling Pathway. *ACS Med. Chem. Lett.* 1, 454-459.

Siddiquee, K. A. Z.; Gunning, P. T.; Glenn, M.; Katt, W. P.; Zhang, S.; Schroeck, C.; Sebti, S. M.; Jove, R.; Hamilton, A. D.; Turkson, J. An oxazole-based small-molecule Stat3 inhibitor modulates Stat3 stability and processing and induces antitumor cell effects. *ACS Chem. Biol.* 2007, 2, 787-798.

Faruqi, T. R.; Gomez, D.; Bustelo, X. R.; Bar-Sagi, D.; Reich, N. C. Rac1 mediates STAT3 activation by autocrine IL-6. *Proc. Natl. Acad. Sci. U.S.A.* 2001, 98, 9014-9019.

Yu, H.; Pardoll, D.; Jove, R. STATs in cancer inflammation and immunity: a leading role for STAT3. *Nat. Rev. Cancer* 2009, 9, 798-809.

Levy, J. B.; Schindler, C.; Raz, R.; Levy, D. E.; Baron, R.; Horowitz, M. C. Activation of the JAK-STAT signal transduction pathway by oncostatin-M cultured human and mouse osteoblastic cells. *Endocrinol.* 1996, 137, 1159-65.

Hermanns, H. M.; Radtke, S.; Schaper, F.; Heinrich, P. C.; Behrmann, I. Non-redundant signal transduction of interleukin-6-type cytokines. The adapter protein She is specifically recruited to rhe oncostatin M receptor. *J. Biol. Chem.* 2000, 275, 40742-8.

Hintzen, C.; Evers, C.; Lippok, B. E.; Volkmer, R.; Heinrich, P. C.; Radtke, S.; Hermanns, H. M. Box 2 region of the oncostatin M receptor determines specificity for recruitment of Janus kinases and STAT5 activation. *J. Biol. Chem.* 2008, 283, 19465-77.

Gomez-Lechon, M. J. Oncostatin M: signal transduction and biological activity. *Life Sci.* 1999, 65, 2019-30.

Huey, R.; Morris, G. M.; Olson, A. J.; Goodsell, D. S. A semiempirical free energy force field with charge-based desolvation. *J. Comput. Chem.* 2007, 28, 1145-1152.

Suite. *Ligprep*, Schrodinger, LLC, New York, N.Y., 2012: 2012.

Suite. *Protein Preparation*, Schrodinger, LLC, New York, N.Y., 2012: 2012

H. Experimental

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Several methods for preparing the compounds of this invention are illustrated in the following Examples. Starting materials and the requisite intermediates are in some cases commercially available, or can be prepared according to literature procedures or as illustrated herein.

The following exemplary compounds of the invention were synthesized. The Examples are provided herein to illustrate the invention, and should not be construed as limiting the invention in any way. The Examples are typically depicted in free base form, according to the IUPAC naming convention. However, some of the Examples were obtained or isolated in salt form.

As indicated, some of the Examples were obtained as racemic mixtures of one or more enantiomers or diastereomers. The compounds may be separated by one skilled in the art to isolate individual enantiomers. Separation can be carried out by the coupling of a racemic mixture of compounds to an enantiomerically pure compound to form a diastereomeric mixture, followed by separation of the individual diastereomers by standard methods, such as fractional crystallization or chromatography. A racemic or diastereomeric mixture of the compounds can also be separated directly by chromatographic methods using chiral stationary phases.

1. Fragment-Based Drug Design (FBDD)

Described herein and shown in the Examples the concept of in silico site-directed FBDD as a computational FBDD approach can be used to identify inhibitors of STAT3. The overall strategy is shown in FIG. 10.

In the in silico approach, fragment libraries are built from known inhibitors and are divided into binding site specific sub-libraries according to docking poses. Linkers from the known inhibitors are the first choices to join fragments, however new linkers based on the concept of bioisosterism[9] can also be applied to join fragments. New linkers designed in this fashion can often maintain the original binding interactions or even enhance binding. Merging, the joining of fragments and linkers is different in our computational approach compared to conventional FBDD. Conventional approaches randomly merge fragments together while our pre-sorted, site-specific fragment sub-libraries are recombined to maximize the possibility of obtaining high affinity lead molecules. Merged potential candidates can be quickly screened via computational docking methods to further narrow the number of molecules that are synthesized and tested. The comparisons between conventional and in silico site-directed FBDD methods are summarized in Table 1.

TABLE 1

THE COMPARISON OF CONVENTIONAL FBDD AND IN SILICO SITE-DIRECTED FBDD

| | Conventional FBDD | In silico site-directed FBDD |
|---|---|---|
| Fragments library | Screened by X-ray, NMR and other methods | Built from known inhibitors and divided into binding site specific sub-libraries according to docking poses |
| Linkers | Selected from linker libraries or from chemical intuition | Original linkers or bioisosteres derived from original linkers |
| Merge methods | Fragments are randomly merged together | Fragments selected from sub-libraries are merged together |
| Pre-selected candidates | According to structural variety, purchase/synthesis availability or chemical intuition | According to computational docking results |

This approach was applied to identify STAT3 inhibitor designs. The STAT3 fragment library was generated from nine known inhibitors with proven affinity and established pharmacological activities for STAT3. New leads were designed to target site 705 and the side pocket (FIG. 9). The STAT3 fragment library was divided into two specific sub-libraries (site 705 and side pocket) based on the docking poses of the inhibitors to the crystal structure of STAT3 SH2 domain (PDB: 1BG1).

To efficiently evolve the fragments into leads, several considerations were made when choosing the linker and performing the merging. A desirable linker should allow sufficient flexibility for the fragments to maintain their poses in the binding sites and enhance binding affinity and/or biophysical features such as water solubility. Also, the chosen linker should not complicate synthesis. In this case, a secondary amine was chosen as the linker.

The merged candidates were then screened via computational docking, and the compounds with the most favorable docking energies and well-clustered binding poses were selected for synthesis and experimental testing. This led to a new class of STAT3 inhibitors.

2. Results and Design a. Step 1: Fragment Libraries were Categorized from the Known STAT3 Dimerization Inhibitors Based on their Binding Modes To build fragment libraries from the known STAT3 inhibitors (for description of known STAT3 inhibitors, see: Liu, A., et al., *Cancer Sci.* 2011 102, 1381-1387; Song, H., et al., *Proc. Natl. Acad. Sci. U.S.A.* 2005, 102, 4700-4705; Schust, J., et al., *Chem. Biol.* 2006, 13, 1235-1242; Lin, L., et al., *Int. J. cancer.* 2012, 130, 1459-69; Bhasin, D., et al, *Bioorg. Med. Chem. Lett.* 2008, 18, 391-395; Matsuno, K., et al., *ACS Med. Chem. Lett.* 1, 371-375; Ren, X. M., et al., *ACS Med. Chem. Lett.* 1, 454-459; Siddiquee, K. A. Z., et al., *ACS Chem. Biol.* 2007, 2, 787-798; and Debnath, B., et al., *J. Med. Chem.*, 2012, 55, 6645-6668), the compounds were docked to the STAT3 SH2 domain (PDB: 1BG1). The initial docking results are shown in FIG. 11. Based on the binding modes, the fragments were divided into libraries specific for each of the two binding sites: site pY705 and side pocket (FIGS. 12 and 13).

b. Step 2: Fragment Libraries were Built by Linking Selected Fragments from Different Fragment Sub-Libraries Based on the docking modes for known STAT3 inhibitors, 5H-Naphth[1,8-cd]isothiazol-5-one, 1,1-dioxide (compound 1) exhibited the most interactions with site pY705 by forming two hydrogen bonds with Arg609 and an additional hydrogen bond with Ser613. Additionally, as part of 13 (LLL12), one of the most potent small nonpeptidomimetic inhibitors of STAT3 dimerization, 1 is an attractive starting point for the synthesis of new STAT3 inhibitors. Therefore, 1 was selected as the component targeting site pY705 and was randomly linked to fragments from the side pocket sub-library to form new potential inhibitors.

The linker was designed based on the rationales described previously, that the new linker could maintain or even enhance the binding affinity of the two fragments and that the synthetic strategy would be feasible. Based on the docking mode of 13 in FIG. 11, the phenol ring of 13 is the original linker of 1. Given the difficulty of synthesis, the original linker was simplified into an isopropyl group which was subsequently derived into an isopropyl amine group based on bioisosterism. To further reduce the synthetic difficulty, the isopropyl amine was modified to a dimethyl amine linker as shown in FIG. 14. Finally, the dimethyl amine group was selected as a suitable linker after docking results indicated that candidates with this linker could form hydrogen bonds with the backbone of Ser636 in a similar fashion as the hydroxyl group of 13 (FIG. 15).

c. Step 3: Final Leads for Further Synthesis and Tests were Selected by Repositioning the Compounds from Lead Library to STAT3 SH2 Domain Docking the new lead library to the STAT3 SH2 domain, compounds were ranked based on the docking scores and clustering, and compounds that could not reposition to the binding pockets were removed from consideration. The compounds that were ultimately selected for synthesis and testing are shown in Table 2.

TABLE 2

CHEMICAL STRUCTURES, DOCKING SCORES, AND IC$_{50}$ OF THE DESIGNED STAT3 INHIBITORS

| Compound | R | Docking score[a] (kcal/mol) | IC50[b] (µM) | Compound | R | Docking score (kcal/mol) | IC50 (µM) |
|---|---|---|---|---|---|---|---|
| LY-5 | 3-pyridyl | −7.3 | 0.5 | LY-2 | phenyl | −7.1 | 5.0 |
| LY-9 | 2-methylphenyl | −7.2 | >5.0 | LY-3 | 3-chloro-4-methyl-nitrobenzene | −8.4 | 1.4 |
| LY-7 | methylnaphthyl | −8.0 | 2.5 | | | | |

3. General Procedure of Fragment-Based Drug Design (FBDD)

Computational docking program AutoDock4 was used to dock all the existing inhibitors and our designed small molecules to predict their binding modes and approximate binding free energies to the STAT3 SH2 dimerization site (see Huey et al. J. Comput. Chem. 2007 28:1145-1152). Compounds were docked using the Lamarckian Genetic Algorithm. The docking procedure involved the preparation of the ligand and macromolecule using the Schrodinger software (see Suite Ligprep, Schrodinger, LLC, New York, N.Y., 2012:2012 and Suite Protein Preparation, Schrodinger, LLC, New York, N.Y., 2012:2012). AutoDockTools was used to assign Gasteiger charges to the ligands. AutoGrid maps were then precomputed for all atom types in the ligand set. After 10 million energy evaluations were completed, all the resulting conformations of the ligands in the binding pocket of the macromolecule were clustered into groups according to their conformations with a root mean square deviation threshold of 1.5 Å. The most significant low energy clusters were identified and binding energies were evaluated.

4. General Chemistry Methods

All solvents and reagents used were obtained from commercial suppliers and used without further purification. Thin layer chromatography (TLC) was performed with fluorescent silica coated aluminum sheets. Silica gel was purchased from Sigma-Aldrich Chemical Co. (Milwaukee, Wis.). The purities of all tested compounds are higher than 95% by HPLC, which were performed by analytical HPLC. Analytical HPLC was carried out with a Gemini 5µ C18 110A Column (250×4.6 mm) supplied by Phenomenex Inc. CA, USA. Two different gradients [water (0.1% TFA)/acetonitrile (0.1% TFA) and water (0.1% TFA/methanol (0.1% TFA)] were used at 1 mL/min flow rate (method: 100:0 to 0:100 over 20 min followed by 0:100 to 100:0 over 10 min). Melting points (mp) were determined on a Thomas Hoover capillary melting point apparatus. $^1$H NMR were obtained with a Bruker Avance 300 (300 µMHz) spectrophotometer (Billerica, Mass.).

a. Preparation of Naphthalenesulfonamide

The structure of naphthalenesulfonamide is shown below:

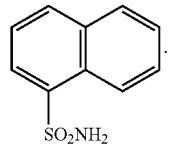

Naphthalenesulfonylchloride (16.8 g, 74.3 mmol) was dissolved in acetone (100 mL) and was stirred at 0° C. for 5 minutes. Ammonium hydroxide (100 mL) was dropped into the above mixture and stirred at room temperature for 3 hours. Precipitated white crystals were filtered then acetone was removed at reduced pressure. The residue was washed in ethylacetate (3×10 mL), producing a white solid powder which was used without further purification, yielding naphthalenesulfonamide (15.9 g, 90.2%); mp (147-149° C.).

b. Preparation of 5,8-dioxo-5,6,7,8-tetrahydronaphthalene-1-sulfonamide (Compound 1)

The structure of 5,8-dioxo-5,6,7,8-tetrahydronaphthalene-1-sulfonamide (Compound 1) is shown below:

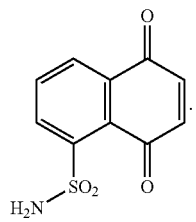

The numbering scheme for Compound 1 is shown below:

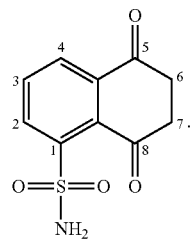 [SMILES: NS(=O)(=O)c1cccc2c1C(=O)CCC2=O]

5,8-dioxo-5,6,7,8-tetrahydronaphthalene-1-sulfonamide was synthesized as previously described (Lin, L., et al. Int. J. cancer. 2012, 130, 1459-69) with some modifications; procedures are shown in Scheme 1. Naphthalenesulfonylchloride reacted with ammonium hydroxide at room temperature, precipitated white crystal naphthalenesulfonamide with high purity ready for next step synthesis and 90.2% yield. Naphthalenesulfonamide was oxidized by chromium trioxide in an acidic environment. This reaction is highly time sensitive, since the longer reaction times result in more byproducts. To achieve the optimal reaction time, the solvent can be preheated to reflux, and then add chromium trioxide into the reaction system. 5H-naphth[1,8-cd]isothiazol-5-one, 1,1-dioxide was not very stable during the column separation, so flash column was used for purification.

SCHEME 1

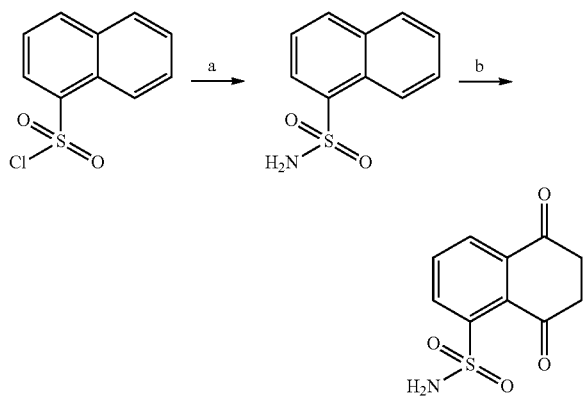

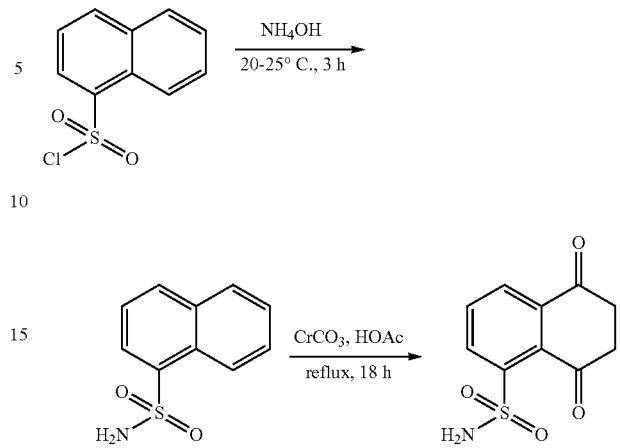

Naphthalenesulfonamide (500 mg, 2.41 mmol) was dissolved in slowly warming glacial acetic acid (5.0 mL). The mixture was heated to 90 OC and chromium trioxide (1.08 g, 10.85 mmol), which was dissolved in a mixture of water and glacial acetic acid (1:1 v/v, 3 mL), was added to the mixture solution. The above solution was stirred under reflux for 18 minutes. The solution was cooled to 0° C. and water (50 mL) was added and stirred overnight at room temperature. The precipitated yellow powder was filtered and the remaining solution was extracted with ether (3×100 mL). The organic layer was collected, dried, and removed at reduced pressure. The yellow powder was combined and purified with silica column chromatography ethyl acetate-hexane (2:3 v/v) to yield the desired sulfonamide (110 mg, 19.3%); mp (186-188° C.).

In other experiments, Compound 1 was prepared at larger scale. Briefly, naphthalenesulfonylchloride (16.8 g, 74.3 mmol) was dissolved in acetone (100 mL) and was stirred at 0° C. for 5 minutes. Ammonium hydroxide (100 mL) was dropped into the above mixture and stirred at room temperature for 3 hours. Precipitated white crystals were filtered then acetone was removed at reduced pressure. The residue was washed in ethylacetate (3×10 mL), producing a white solid powder which was used without further purification, yielding naphthalenesulfonamide (15.9 g, 90.2%); mp (147-149° C.). Naphthalenesulfonamide (500 mg, 2.41 mmol) was dissolved in slowly warming glacial acetic acid (5.0 mL). The mixture was heated to 90° C. and chromium trioxide (1.08 g, 10.85 mmol), which was dissolved in a mixture of water and glacial acetic acid (1:1 v/v, 3 mL), was added to the mixture solution. The above solution was stirred under reflux for 18 minutes. The solution was cooled to 0° C. and water (50 mL) was added and stirred overnight at room temperature. The precipitated yellow powder was filtered and the remaining solution was extracted with ether (3×100 mL). The organic layer was collected, dried, and removed at reduced pressure. The yellow powder was combined and purified with silica column chromatography ethyl acetate-hexane (2:3 v/v) to yield 5,8-dioxo-5,6,7,8-tetrahydronaphthalene-1-sulfonamide (Compound 1) (110 mg, 19.3%); mp (186-188° C.).

5. General Analog Route

Compound 1 and aromatic amines were catalyzed by Cu(OAc)$_2$·H$_2$O in an acidic environment (Scheme 2 below). The reaction system was heated to reflux and terminated when 1 was consumed completely. This reaction is a novel regioselective method which can selectively react to position 6 of compound 1. No regioisomers at position 7 were detected in the byproducts. The purification of STAT3 inhibitors is also very interesting. As the bands of novel STAT3 inhibitors were red or brown, the elution of products was quickly monitored based on the visible bands. As reported in other naphthoquinone coupling reactions, solvent has a large effect on the yield. Glacial acetic acid was the best choice for the reaction. If water is added to the reaction, the yield typically decreases. However, if glacial acetic acid is the only solvent, the major product will be cyclized compounds since the sulfonamide group can attack the nearby 1-ketone and deplete a water molecule to form the cyclized products, such as LY-2, LY-3, and LY-6. In order to keep the free sulfonamide group to maintain the best docking pose, a mixed solvent system was used by adding water to glacial acetic acid in a volume ratio 1:10. This decreased the yield by approximate 20%. Following these procedures, the examples described in greater detail below (LY-2, LY-3, LY-5, LY-6a, and LY-7) were prepared.

cated in the description of each product. The solvent was removed under reduced pressure to give the desired products.

a. Preparation of 4-(Phenylamino)-5H-naphtho[1,8-cd]isothiazol-5-one 1,1-dioxide (LY-2)

The structure of 4-(phenylamino)-5H-naphtho[1,8-cd]isothiazol-5-one 1,1-dioxide is shown below:

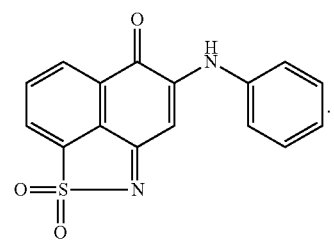 [SMILES: O=C1C(Nc2ccccc2)=CC2=NS(=O)(=O)c3cccc1c32]

SCHEME 2

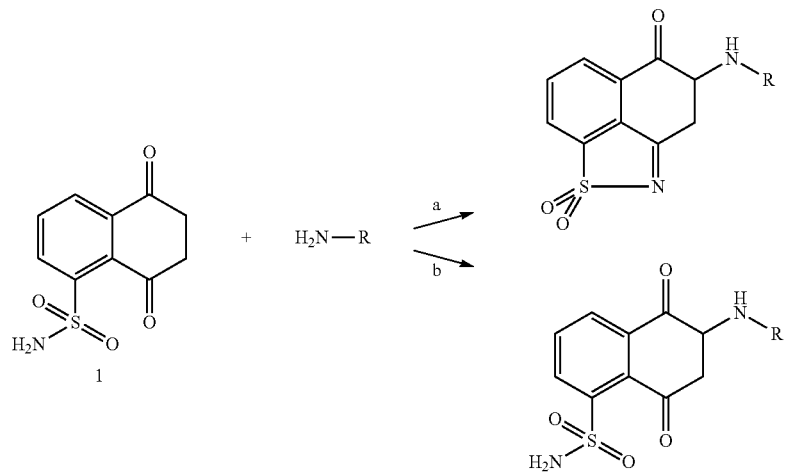

a: Cu(OAc)$_2$*H$_2$O, AcOH
b: Cu(OAc)$_2$*H$_2$O, AcOH and H$_2$O (1:10 v/v)

6. General Analog Route I

As shown above in Scheme 2 (a), 5,8-Dioxo-5,8-dihydronaphthalene-1-sulfonamide (237 mg, 1.0 mmol), amine (1.2 mmol) and Cu(OAc)$_2$·H$_2$O (20 mg, 0.1 mmol) were solubilized by gently warming in AcOH (5 mL), reflux for about 3 hours. As detected by TLC, after 1 had completely reacted, all the volatiles were removed under reduced pressure. The resulting crude product was dissolved in a minimal volume of CH$_2$Cl$_2$ and applied to a column of silica gel. The column was eluted with CH$_2$Cl$_2$ or other solvents as indicated in the description of each product.

The reactant amine is aniline (0.11 mL, 1.2 mmol). The product was purified by silica gel column chromatography eluting with CH$_2$Cl$_2$. Red crystals (143 mg, yield: 46%); mp (>260° C.). $^1$H NMR (300 μMHz, DMSO) δ 9.78 (s, 1H), 8.39 (d, J=7.1 Hz, 1H), 8.04 (q, J=7.3 Hz, 2H), 7.55-7.33 (m, 4H), 7.25 (t, J=6.9 Hz, 1H), 6.14 (s, 1H). HRMS (ESI) of C$_{16}$H$_{10}$N$_2$O$_3$SNa [M+Na]$^+$ calcd, 333.0304. found, 333.0329.

B. Preparation of 4-((2-chloro-4-nitrophenyl)amino)-5H-naphtho[1,8-cd]isothiazol-5-one 1,1-dioxide (LY-3)

The structure of 4-((2-chloro-4-nitrophenyl)amino)-5H-naphtho[1,8-cd]isothiazol-5-one 1,1-dioxide is shown below:

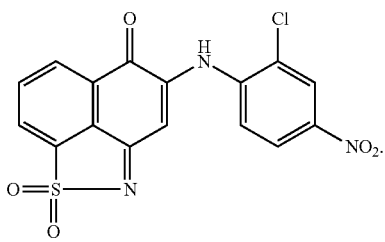 [SMILES: O=C1C(Nc2ccc([N+](=O)[O-])cc2Cl)=CC2=NS(=O)(=O)c3cccc1c32]

The reactant amine is 2-chloro-4-nitroaniline (206 mg, 1.2 mmol). The product was purified by silica gel column chromatography eluting with $CH_2Cl_2$, followed by a $CH_2Cl_2$/EtOAc (8:1 v/v). Orange crystals (189 mg, yield: 48.6%); mp (>260° C.). $^1H$ NMR (300 μMHz, DMSO) δ 10.19 (s, 1H), 8.51 (d, J=2.0 Hz, 1H), 8.45-7.93 (m, 4H), 7.83 (d, J=8.8 Hz, 1H), 6.15 (s, 1H). HRMS (ESI) of $C_{16}H_8ClN_3O_5SNa$ $[M+Na]^+$ calcd, 411.9765. found, 411.9764.

c. Preparation of 4-(naphthalen-2-ylamino)-5H-naphtho[1,8-cd]isothiazol-5-one 1,1-dioxide (LY-6)

The structure of 4-(naphthalen-2-ylamino)-5H-naphtho[1,8-cd]isothiazol-5-one 1,1-dioxide is shown below:

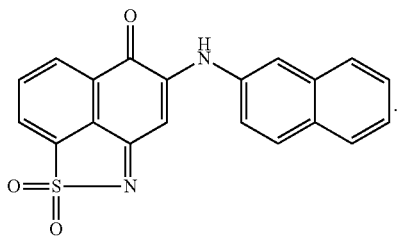 [SMILES: O=C1C(Nc2ccc3ccccc3c2)=CC2=NS(=O)(=O)c3cccc1c32]

The reactant amine is 2-naphthylamine (172 mg, 1.2 mmol). The product was purified by silica gel column chromatography eluting with Hexane/$CH_2Cl_2$ (1:4 v/v), followed by $CH_2Cl_2$. Red crystals (170 mg, yield: 47.3%); mp (>260° C.). $^1H$ NMR (300 μMHz, DMSO) δ 10.00 (s, 1H), 8.44 (dd, J=7.2, 1.3 Hz, 1H), 8.31-7.86 (m, 7H), 7.78-7.30 (m, 4H), 6.33 (s, 1H). HRMS (ESI) of C20H14N2O4SNa [M+Na]+ calcd, 383.0466. found, 383.0453.

7. General Analog Route II

As shown above in Scheme 2 (b), 5,8-Dioxo-5,8-dihydronaphthalene-1-sulfonamide (237 mg, 1.0 mmol), amine (1.2 mmol) and $Cu(OAc)_2 \cdot H_2O$ (20 mg, 0.1 mmol) were solubilized by gently warming in AcOH and $H_2O$ (1:10 v/v, 5.5 mL), reflux for about 3 hours. As detected by TLC, after 1 had completely reacted, all the volatiles were removed under reduced pressure. The resulting crude product was dissolved in a minimal volume of $CH_2Cl_2$ and applied to a column of silica gel. The column was eluted with $CH_2Cl_2$ or other solvents as indicated in the description of each product. The solvent was removed under reduced pressure to give the desired products.

a. Preparation of 5,8-dioxo-6-(pyridin-3-ylamino)-5,8-dihydronaphthalene-1-sulfonamide (LY-5)

The structure of 5,8-dioxo-6-(pyridin-3-ylamino)-5,8-dihydronaphthalene-1-sulfonamide is shown below:

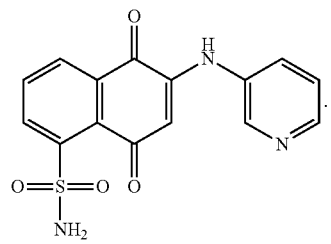 [SMILES: NS(=O)(=O)c1cccc2c1C(=O)C=C(Nc1cccnc1)C2=O]

The reactant amine is 3-amine-pyridine (113 mg, 1.2 mmol). The product was purified by silica gel column chromatography eluting with $CH_2Cl_2$/EtOAc (8:1 v/v), followed by $CH_2Cl_2$/EtOAc (2:1 v/v). Bright red crystals (89 mg, yield: 27%); mp (>260° C.). $^1H$ NMR (300 μMHz, DMSO) δ 9.52 (s, 1H), 8.63 (s, 1H), 8.44 (d, J=7.9 Hz, 2H), 8.35 (d, J=7.5 Hz, 1H), 7.96 (t, J=7.7 Hz, 1H), 7.84 (d, J=7.7 Hz, 1H), 7.48 (s, 1H), 7.35 (s, 2H), 6.13 (s, 1H). HRMS (ESI) of $C_{15}H_{11}N_3O_4SNa$ $[M+Na]^+$ calcd, 352.0362. found, 352.0358.

b. Preparation of 5,8-dioxo-6-(phenylamino)-5,8-dihydronaphthalene-1-sulfonamide (LY-7)

The structure of 5,8-dioxo-6-(phenylamino)-5,8-dihydronaphthalene-1-sulfonamide is shown below:

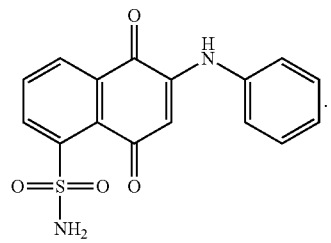 [SMILES: NS(=O)(=O)c1cccc2c1C(=O)C=C(Nc1ccccc1)C2=O]

The reactant amine is aniline (0.11 mL, 1.2 mmol). Then the product was purified by silica gel column chromatography eluting with $CH_2Cl_2$, followed by $CH_2Cl_2$/EtOAc (8:1 v/v). Red crystals (85 mg, yield: 26%); mp (>260° C.). $^1H$ NMR (300 MHz, DMSO) δ 10.00 (s, 1H), 8.58-8.49 (m, 2H), 8.47-8.35 (m, 3H), 8.38 (dd, J=30.5, 19.8 Hz, 4H), 7.40 (s, 2H), 6.33 (d, J=8.5 Hz, 1H), 5.75 (s, 1H). HRMS (ESI) of $C_{16}H_{12}N_2O_4SNa$ $[M+Na]^+$ calcd, 351.0415. found, 351.0423.

8. Representative Compounds

Table 3 below lists specific compounds prepared by the general methods and in the experimental examples described herein above. The compounds in Table 3 were synthesized with methods identical or analogous to those shown herein. In the table below, "n.d." indicates the $[M+Na]^+$ or $[M+H]$ were data not determined. The requisite starting materials were commercially available, described in the literature, or readily synthesized by one skilled in the art of organic synthesis.

TABLE 3*

| No. | Ref. No. | Structure | [M + Na]⁺ |
|---|---|---|---|
| 1 | LY-2 | 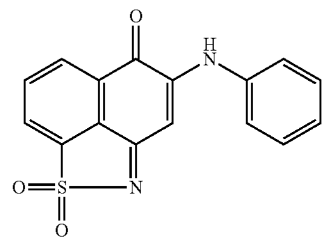 [SMILES: O=C1C(Nc2ccccc2)=CC2=NS(=O)(=O)c3cccc1c32] | 333.03 |
| 2 | LY-3 | 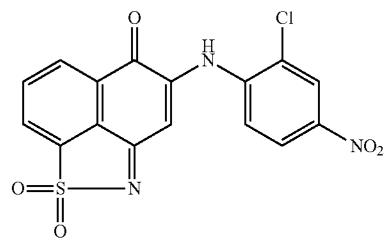 [SMILES: O=C1C(Nc2ccc([N+](=O)[O-])cc2Cl)=CC2=NS(=O)(=O)c3cccc1c32] | 411.98 |
| 3 | LY-4 | 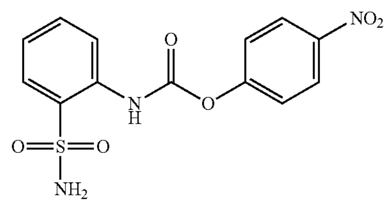 [SMILES: NS(=O)(=O)c1ccccc1NC(=O)Oc1ccc([N+](=O)[O-])cc1] | 373.31 ([M + H]) |
| 4 | LY-5 | 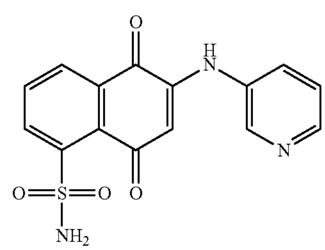 [SMILES: NS(=O)(=O)c1cccc2c1C(=O)C=C(Nc1cccnc1)C2=O] | 352.04 |
| 5 | LY-6 | 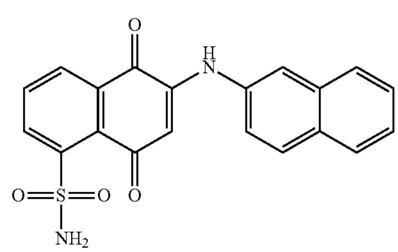 [SMILES: NS(=O)(=O)c1cccc2c1C(=O)C=C(Nc1ccc3ccccc3c1)C2=O] | 401.66 |
| 6 | LY-7 | 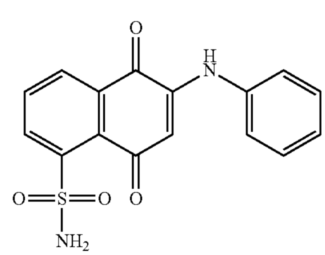 [SMILES: NS(=O)(=O)c1cccc2c1C(=O)C=C(Nc1ccccc1)C2=O] | 351.04 |

TABLE 3*-continued

| No. | Ref. No. | Structure | [M + Na]+ |
|---|---|---|---|
| 7 | LY-8 | 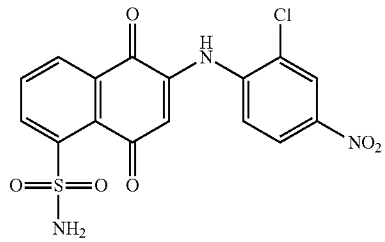 [SMILES: NS(=O)(=O)c1cccc2c1C(=O)C=C(Nc1ccc([N+](=O)[O-])cc1Cl)C2=O] | 429.99 |
| 8 | LY-9 | 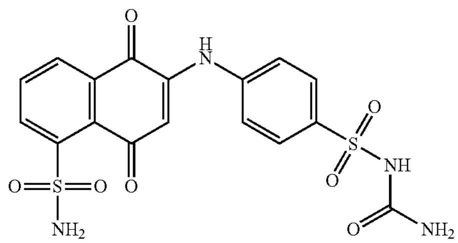 [SMILES: NC(=O)NS(=O)(=O)c1ccc(NC2=CC(=O)c3c(cccc3S(N)(=O)=O)C2=O)cc1] | 472.67 |
| 9 | LY-10 | 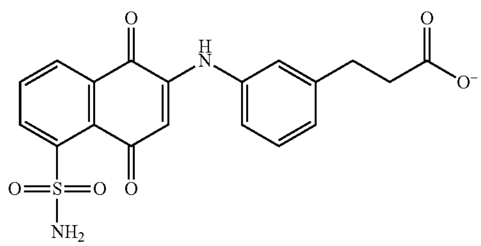 [SMILES: NS(=O)(=O)c1cccc2c1C(=O)C=C(Nc1cccc(CCC(=O)[O-])c1)C2=O] | 423.06 |
| 10 | LY-11 | 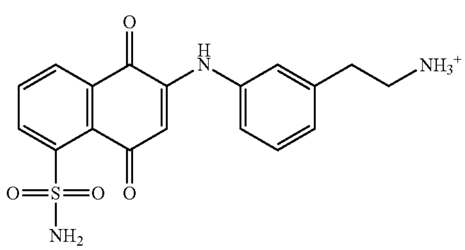 [SMILES: NS(=O)(=O)c1cccc2c1C(=O)C=C(Nc1cccc(CC[NH3+])c1)C2=O] | n.d. |
| 11 | LY-12 | 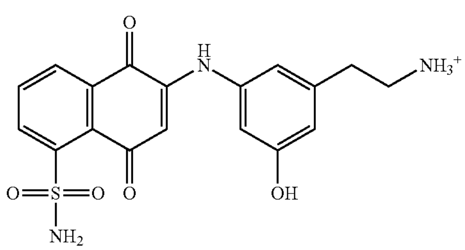 [SMILES: NS(=O)(=O)c1cccc2c1C(=O)C=C(Nc1cc(O)cc(CC[NH3+])c1)C2=O] | n.d. |
| 12 | LY-13 | 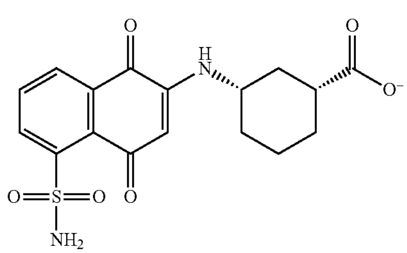 [SMILES: NS(=O)(=O)c1cccc2c1C(=O)C=C(N[C@H]1CCC[C@@H](C(=O)[O-])C1)C2=O] | 401.08 |

TABLE 3*-continued
| No. | Ref. No. | Structure | [M + Na]+ |
|---|---|---|---|
| 13 | LY-14 | 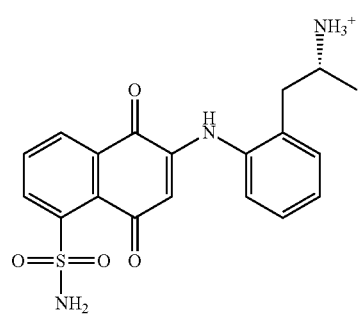 [SMILES: C[C@@H]([NH3+])Cc1ccccc1NC1=CC(=O)c2c(cccc2S(N)(=O)=O)C1=O] | n.d. |
| 14 | LY-15 | 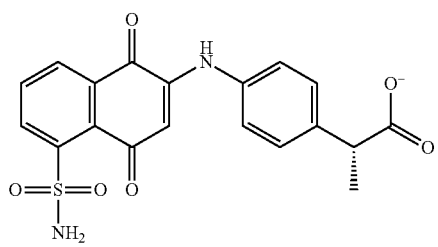 [SMILES: C[C@@H](C(=O)[O-])c1ccc(NC2=CC(=O)c3c(cccc3S(N)(=O)=O)C2=O)cc1] | n.d. |
| 15 | LY-16 | 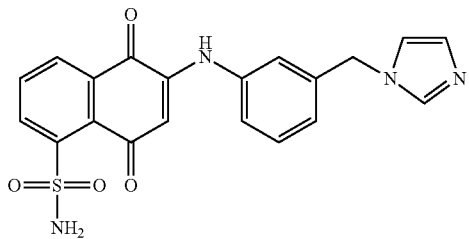 [SMILES: NS(=O)(=O)c1cccc2c1C(=O)C=C(Nc1cccc(Cn3ccnc3)c1)C2=O] | n.d. |
| 16 | LY-17 | 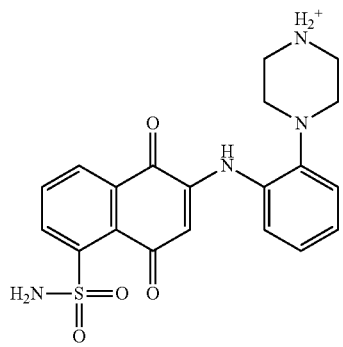 | 413.24 ([M + H]) |

TABLE 3*-continued

| No. | Ref. No. | Structure | [M + Na]+ |
|-----|----------|-----------|-----------|
| 17 | LY-18 | 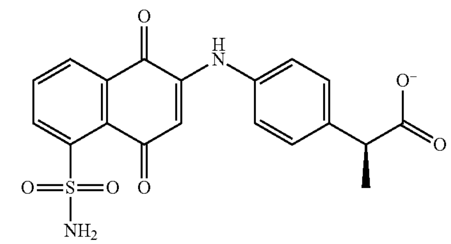 [SMILES: C[C@H](C(=O)[O-])c1ccc(NC2=CC(=O)c3c(cccc3S(N)(=O)=O)C2=O)cc1] | n.d. |
| 18 | LY17-R2 | 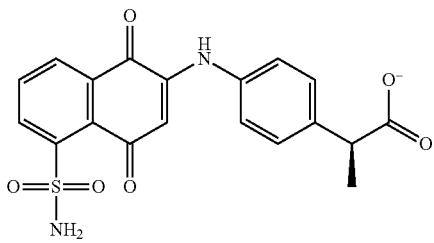 | 551.13 |
| 19 | LY17-R3 | 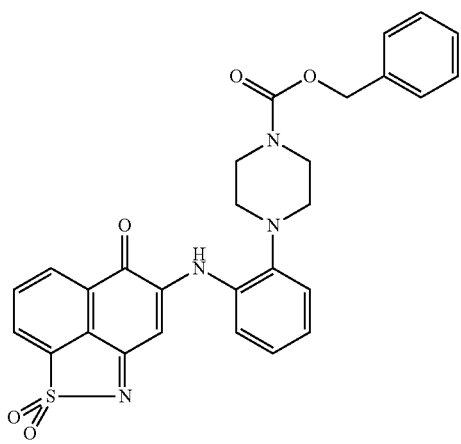 [SMILES: O=C1C(Nc2ccccc2N2CCN(C(=O)OCc3ccccc3)CC2)=CC2=NS(=O)(=O)c3cccc1c32] | 569.15 |
| | | 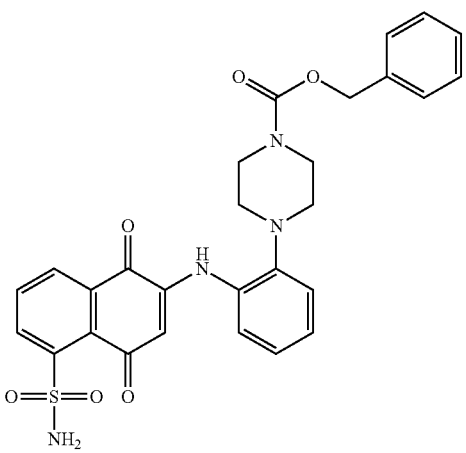 [SMILES: NS(=O)(=O)c1cccc2c1C(=O)C=C(Nc1ccccc1N1CCN(C(=O)OCc3ccccc3)CC1)C2=O] | |

*Data are shown for [M + Na]+, unless otherwise indicated.

9. Prophetic Compounds

Table 4 below lists prophetic compounds that can be prepared by the general methods and experimental examples described herein above. The compounds in Table 4 can be synthesized with methods identical or analogous to those shown herein. The requisite starting materials were commercially available, described in the literature, or readily synthesized by one skilled in the art of organic synthesis.

TABLE 4

| No. | Structure |
|---|---|
| 20 | (structure) |
| 21 | (structure) |
| 22 | (structure) |
| 23 | (structure) |

TABLE 4-continued

| No. | Structure |
|---|---|
| 24 | (structure) |
| 25 | (structure) |
| 26 | (structure) |
| 27 | (structure) |

TABLE 4-continued
| No. | Structure |
|---|---|
| 28 | 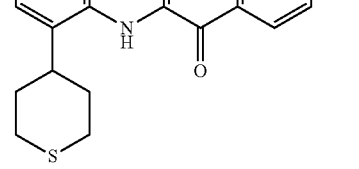 |
| 29 | 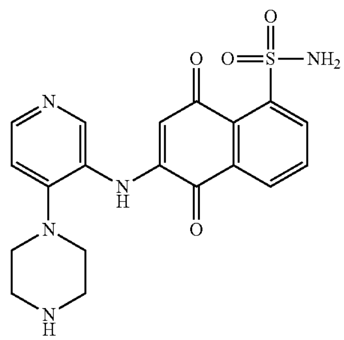 [SMILES: NS(=O)(=O)c1cccc2c1C(=O)C=C(Nc1cnccc1N1CCNCC1)C2=O] |
| 30 | 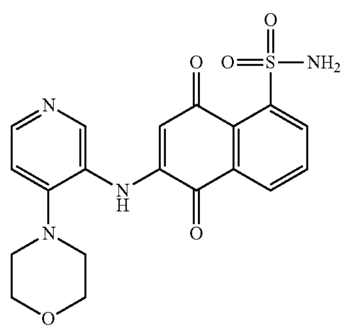 [SMILES: NS(=O)(=O)c1cccc2c1C(=O)C=C(Nc1cnccc1N1CCOCC1)C2=O] |
| 31 | 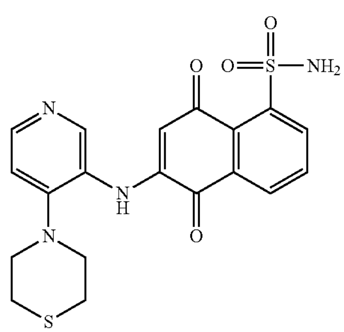 [SMILES: NS(=O)(=O)c1cccc2c1C(=O)C=C(Nc1cnccc1N1CCSCC1)C2=O] |
| 32 | 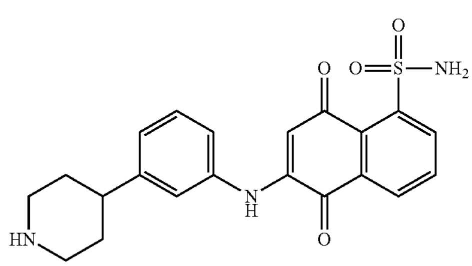 [SMILES: NS(=O)(=O)c1cccc2c1C(=O)C=C(Nc1cccc(C3CCNCC3)c1)C2=O] |
TABLE 4-continued
| No. | Structure |
|---|---|
| 33 | 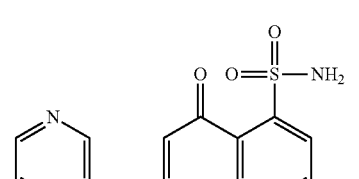 |
| 34 | 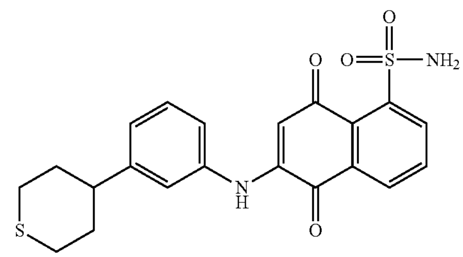 [SMILES: NS(=O)(=O)c1cccc2c1C(=O)C=C(Nc1cccc(C3CCSCC3)c1)C2=O] |
| 35 | 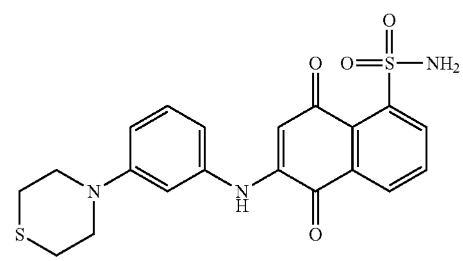 [SMILES: NS(=O)(=O)c1cccc2c1C(=O)C=C(Nc1cccc(N3CCSCC3)c1)C2=O] |
| 36 | 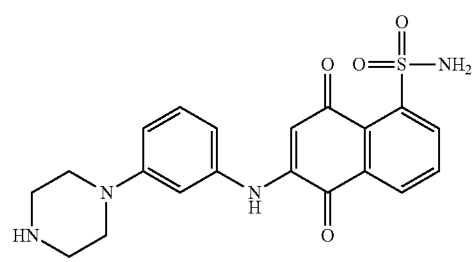 [SMILES: NS(=O)(=O)c1cccc2c1C(=O)C=C(Nc1cccc(N3CCNCC3)c1)C2=O] |
| 37 | 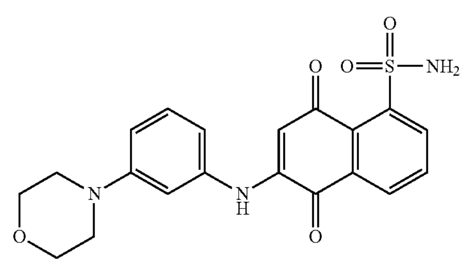 [SMILES: NS(=O)(=O)c1cccc2c1C(=O)C=C(Nc1cccc(N3CCOCC3)c1)C2=O] |
| 38 | 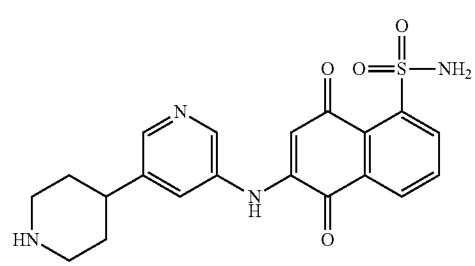 [SMILES: NS(=O)(=O)c1cccc2c1C(=O)C=C(Nc1cncc(C3CCNCC3)c1)C2=O] |

TABLE 4-continued

| No. | Structure |
|---|---|
| 39 | [Structure: naphthoquinone with sulfonamide, linked via NH to pyridine bearing tetrahydropyran] |
| 40 | [Structure: naphthoquinone with sulfonamide, linked via NH to pyridine bearing tetrahydrothiopyran] |
| 41 | [Structure: naphthoquinone with sulfonamide, linked via NH to pyridine bearing thiomorpholine] |
| 42 | [Structure: naphthoquinone with sulfonamide, linked via NH to pyridine bearing piperazine] |
| 43 | [Structure: naphthoquinone with sulfonamide, linked via NH to pyridine bearing morpholine] |

10. Dissociation Constant for Binding to STAT3 Determined by Microscale Thermophoresis The binding affinity of a representative compound (LY-17) to the target, STAT3, was determined in a biochemical assay, microscale thermophoresis. Briefly, thermophoresis is based on the directed movement of molecules along a temperature gradient, an effect termed "thermophoresis". The local temperature difference, $\Delta T$, leads to a local change in molecule concentration (depletion or enrichment), quantified by the Soret coefficient ST: chot/ccold=exp($-ST\Delta T$). The method provides the dissociation constant, $K_D$. The microscale thermophoresis experiments were carried out at NanoTemper Technologies, Inc. (Munich, Germany). In these experiments, the concentration of the NanoTemper-labeled STAT3 was kept constant (30 nM), while the concentration of the non-labeled binding partner (LY17) was varied between 1.52 nM-50,000 nM. After a short incubation the samples were loaded into MST standard glass capillaries and the MST-analysis was performed using the Monolith.NT115. All concentrations are in nM. A $K_D$ of 2,420 nM+/−256 nM was determined for this interaction. The concentration binding profile is shown in FIG. 59.

11. Kinase Screening

The potential off-target activity of a representative compound was assessed in a screen against 96 protein and lipid kinases (see FIGS. 56 and 60). The test compound, LY-5, was assessed at 1000 and 5000 nM concentration using in vitro kinase assays. The assays were carried out using standard techniques known to one skilled in the art (KINO-MESCAN™, San Diego, Calif.). The data in FIG. 60 show the % inhibition for the tested concentrations of LY-5 in the panel of kinases assessed. An interaction map is shown in FIG. 59. The interaction map provides a visualization of the relationship of these inhibition data from FIG. 60 to various kinase families. The test compound, LY-5, did not significantly inhibit any of the kinases test, except for minor activity (72% inhibition at 5000 nM and no inhibition at 1000 nM) against PLK3 (see FIG. 56B and FIG. 60).

12. Generation of Stable Cell Lines

Human breast cancer cell line (MCF-7), human sarcoma cell lines (RD2, RH30 and U2OS) and human medulloblastoma cell line (DAOY) were maintained in Dulbecco's modified Eagle medium (DMEM) supplemented with 10% penicillin/streptomycin FBS and stored in a humidified 37° C. incubator with 5% $CO_2$. Additional cell-lines used in the studies described herein, including the figures, were as shown below in Table 5. Cells were cultured using media and growth conditions as provided by ATCC, vendor, or as generally known to one skilled in the art.

TABLE 5

| Cell Line | ATCC No. | Brief Description |
|---|---|---|
| SJSA | CRL-2098 | Human osteosarcoma cells; originally from bone tissue. |
| DAOY | HTB-186 | Human desmoplastic cerebellar medulloblastoma cells; originally from the brain/cerebellum. |
| HCSMC | PCS-100-021 | Human primary coronary artery smooth muscle cells. |
| HH | CRL-2105 | Human cutaneous lymphoma T-cells; originally from peripheral blood. |
| HCT-116 | CCL-247 | Human colorectal carcinoma cells; originally from the colon. |
| UW288-1 | — | Human medullablastoma cells; available from Dr. Corey Raffel (The Research Institute at Nationwide Children's Hospital). |
| SW480 | CCL-248 | Human Dukes' type B, colorectal adenocarcinoma cells; originally from the colon. |
| DLD1 | CCL-221 | Human Dukes' type C, colorectal adenocarcinoma cells; originally from the colon. |
| UW426 | — | Human medulloblastoma cells; available from Dr. Corey Raffel (The Research Institute at Nationwide Children's Hospital) |
| HSMM | — | Human skeletal muscle myoblast cells; primary cells available from a number of sources, including commercial vendors; cells can be differentiated to form myotubes in culture. |
| HUVEC | PCS-100-010 | Human umbilical vein endothelial cells. |

13. Cell Viability Assay

Human sarcoma cell lines (RD2, RH30, U2OS) were seeded in 96-well plates at a density of 3,000 cells per well. The cells were incubated at 37° C. for a period of 24 hours. Different concentrations of LY-5 (0.1-10 µM), LY-3 (0.1-20 µM), and LLL12 (0.1-10 µM) prepared as a 20 mM stock solution in sterile DMSO were added in triplicate to the plates in the presence of 10% FBS. 3-(4,5-Dimethylthiazolyl)-2, 5-diphenyltetrazoliumbromide (MTT) was added to evaluate cell viability. The absorbance was read at 595 nm. $IC_{50}$ values were determined using SigmaPlot 9.0 Software (Systat Software, Inc., San Jose, Calif.).

Alternatively, cells were seeded in 96-well plates in triplicate at a density of 3,000 cells per well and given 24 hours to adhere. Cells were then treated with varying concentrations of the inhibitors in the presence of 10% FBS. The cells were incubated for 72 hours at 37° C. 25 µl of MTT dye (Sigma, #M5655) was added to each sample and incubated for 3.5 hours. After this, 100 µl of N,N-dimethylformamide (Sigma, #D4551) solubilization solution was added to each well. The absorbance at 450 nm was read the following day. Half-Maximal inhibitory concentrations ($IC_{50}$) were determined using Sigma Plot 9.0 software (Systat Software Inc.).

14. Activity of Compounds in Cell-Based Assay

Table 6 below lists specific compounds as well as experimentally determined STAT3 activity in a cell-based assay. The STAT3 activity was determined using the cell viability assays with human sarcoma cell line U2OS as described above. The compounds in Table 6 were synthesized with methods identical or analogous to those described herein. The compound reference numbers ("Ref. No.") in Table 6 correspond to the compound numbers used in Table 3.

TABLE 6

| No. | Ref. No. | $IC_{50}$ (µM) |
|---|---|---|
| 1 | LY-2 | 5.0 |
| 2 | LY-3 | 1.4 |
| 4 | LY-5 | 0.5 |
| 5 | LY-6 | 2.5 |
| 6 | LY-7 | >5.0 |

Table 7 below lists specific compounds as well as experimentally determined STAT3 activity in a cell-based assay. The STAT3 activity was determined using the cell viability assays with human sarcoma cell lines (RD2, RH30, U2OS) as described above. The compound reference numbers ("Ref. No.") in Table 7 correspond to the compound numbers used in Table 3.

TABLE 7

| | | $IC_{50}$ (µM) | | |
|---|---|---|---|---|
| No. | Ref. No. | U2OS | RH30 | RD2 |
| 2 | LY-3 | 1.39 | 1.14 | 2.56 |
| 4 | LY-5 | 0.52 | 0.55 | 1.39 |

Initially, $IC_{50}$ values for all of the compounds were tested with U2OS cell line. Then two most potent compounds, LY-5 and LY-3 were further tested together with LLL12 in two other RD2 and RH30 cell lines (see data in Table 8). As LLL12 had the lowest $IC_{50}$ among the known small inhibitors, it was selected as a control compound. The results showed that LY-5 had lower $IC_{50}$ than LLL12 in cell lines RD2 and U2OS and similar $IC_{50}$ to LLL12 in cell line RH30. LY-3 had a comparable $IC_{50}$ as LLL12 in cell lines RD2 and U2OS (Table 8).

TABLE 8

| | $IC_{50}$ values (µM) vs. Cell lines | | |
|---|---|---|---|
| Compound | U2OS | RH30 | RD2 |
| LLL12 (13) | 1.00 | 0.47 | 2.85 |
| LY-5 | 0.52 | 0.55 | 1.39 |
| LY-3 | 1.39 | 1.14 | 2.56 |

15. STAT3 Activity: Western Blot Analysis

RH30 cells were treated with DMSO, LY-5 (0.25-1 µM) and LY-3 (0.5-2.5 µM) prepared as a 20 mM stock solution in sterile DMSO at 60% to 80% confluence in the presence of 10% FBS for 24 hours. The sarcoma cell line EW8 was treated with DMSO and LY-5 (0.5-2.5 µM) prepared as a 20 mM stock solution in sterile DMSO at 60% to 80% confluence in the presence of 10% FBS for 24 hours. MCF-7 cells and DAOY cells were treated with DMSO, 25-50 ng/ml of IL-6, LY-5 (0.25-1 µM) or LY-3 (0.5-2.5 µM) prepared as a 20 mM stock solution in sterile DMSO, protein expressions of P-STAT3 (Tyr705) and STAT3 were tested. DAOY cells were treated with DMSO, 50 ng/ml of IFN-γ, LY-5 (1-5 µM) prepared as a 20 mM stock solution in sterile DMSO, protein expressions of P-STAT3 (Tyr705) and STAT3 were tested. MCF-7 cells were treated with DMSO, 50 ng/ml of OSM, LY-5 (1-2.5 µM) or LLL12 (1-2.5 µM) prepared as a 20 mM stock solution in sterile DMSO, protein expressions of P-STAT3 (Tyr705), P-STAT1, P-STAT5, P-ERK (T202/Y204), P-AKT, STAT3 and STAT1 were tested. Similar conditions were used for other cell-lines and/or compounds as indicated in the figures.

The cells were harvested and lysed in cold radioimmunoprecipitation assay (RIPA) lysis buffer containing proteasome inhibitor cocktail and phosphatase inhibitor cocktail, and were subjected to SDS-PAGE. Then they were transferred to PVDF membrane. Membranes were probed with primary antibodies (1:1,000) and horseradish peroxidase (HRP)-conjugated secondary antibody (1:10,000) (Cell Signaling Technology, Beverly, Mass.). Membranes were analyzed using Enhanced Chemiluminescence Plus reagents and scanned with the Storm Scanner (Amersham Pharmacia Biotech, Inc., Piscataway, N.J.).

16. Immunofluorescence Assay

Cells seeded on glass slides in 6-well plate were cultured in serum-free medium for 24 hours. After the cell density reached about 80%, cells were pretreated with LY5 (1 or 2.5 µM) for 4 hours followed by IL-6 or IFN-γ (50 ng/ml), for 30 min, and were fixed with cold methanol for 15 min. After washing in phosphate-buffered saline (PBS), the slides were blocked with 5% normal goat serum and 0.3% Triton X-100 in PBS (PBST) for 1 hour. The slides were incubated with primary antibodies (1:100) against STAT3 or P-STAT1 proteins (Cell Signaling Technology) overnight at 4° C. Then, the slides were washed with PBST and incubated with goat anti-rabbit FIFC-conjugated secondary antibody (Invitrogen, 1:200). The cells were mounted with Vectashield Hardset mounting medium with DAPI (Vector Laboratories, Burlingame, Calif., USA). Photomicrographs were captured by Leica Microsystems (Bannockburn, Ill., USA).

Figure 1:
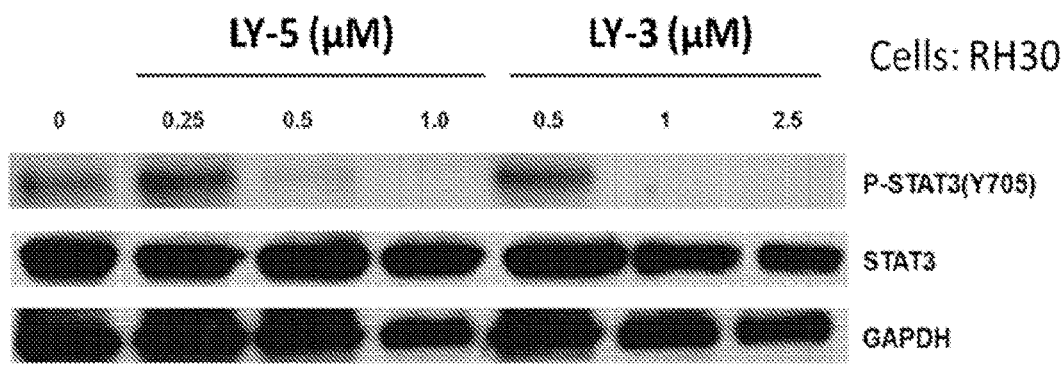
FIG. 1 shows that compounds LY-3 and LY-5 inhibit constitutive STAT3 phosphorylation. Human rhabdomyosarcoma cell line RH30 was treated with LY-3 (0.5-2.5 µM) and LY-5 (0.25-1 µM) for 16 h, then whole-cell extracts were prepared and phosphorylated STAT3 was detected by Western blot assay, revealing a decrease in STAT3 phosphorylation.
Figure 2:
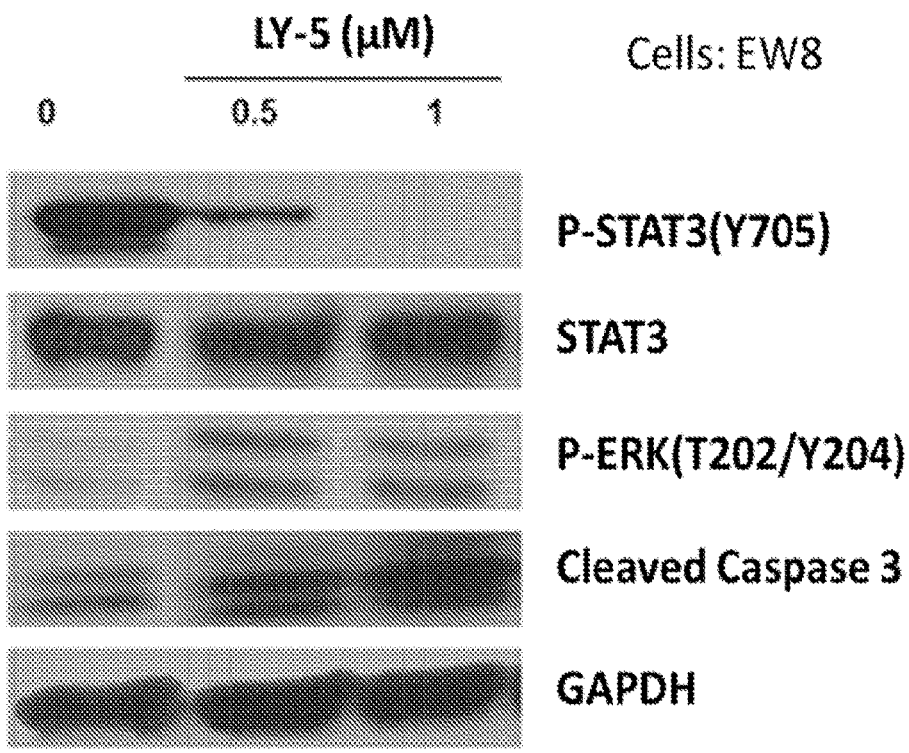
FIG. 2 shows that compound LY-5 inhibits constitutive STAT3 phosphorylation. Ewing's sarcoma cell line EW8 was treated with LY-5 (0.5-1 µM) for 8 h, then whole-cell extracts were prepared and phosphorylated STAT3 ("phospho-STAT3") was detected by Western blot assay, revealing a decrease in STAT3 phosphorylation.

17. LY-5 Inhibits Stat3 Phosphorylation and Induces Apoptosis in Human Sarcoma Cancer Cells To examine the inhibition of STAT3 phosphorylation, Western blot assays were performed to detect the abundance of phosphorylated STAT3 (P-STAT3) after RH30 cells were treated with LY-3 (0.5-2.5 µM) or LY-5 (0.25-1 µM) for 16 h. STAT3 phosphorylation was reduced in a dose-dependent manner, with LY-5 and LY-3 almost completely inhibiting Tyr705 phosphorylation at 0.5 µM and 1 µM, respectively (FIG. 1). Since LY-5 was shown to be a more potent inhibitor of STAT3 phosphorylation than LY-3 in the RH30 cell line, it was further tested in EW8 sarcoma cells. Western blots of EW8 cells treated with LY-5 (0.5-1.0 µM) for 8 h again reveals a dose-dependent decrease in formation of P-STAT3 (FIG. 2). The expression of total STAT3 was not changed in both RH30 and EW8 cell lines, indicating that the decrease of P-STAT3 was not due to a constitutional decrease of total STAT3 expression. LY-5 was not found to inhibit phosphorylation of the kinase ERK1/2. The inhibition of STAT3 phosphorylation by LY-5 seems to be consistent with the induction of apoptosis as evidenced by the presence of cleaved caspase 3 (FIG. 2).

18. STAT3 Activity: Phosphorylation Induced by IL-6

MCF-7 breast cancer cells were seeded in 10 cm plates and allowed to adhere overnight. The following day, the cells were serum-starved. The cells were then left untreated or were treated with LY-5 (0.25-1 µM) and LY-3 (0.5-2.5 µM) prepared as a 20 mM stock solution in sterile DMSO or DMSO. After 5 hours, the untreated and LY-5 and LY-3 treated cells were stimulated by IL-6 (25 ng/mL). The cells were harvested after 30 minutes and analyzed by Western blot. DAOY medulloblastoma cancer cells were seeded in 10 cm plates and allowed to adhere overnight. The following day, the cells were serum-starved. The cells were then left untreated or were treated with LY-5 (1-5 µM) prepared as a 20 mM stock solution in sterile DMSO or DMSO. After 2 hours, the untreated and LY-5 treated cells were stimulated by IL-6 (25 ng/mL). The cells were harvested after 30 minutes and analyzed by Western blot.

IL-6 can induce the activation of STAT3. The MCF-7 breast cancer cell line was used to determine the ability of LY-5 to inhibit IL-6 induced STAT3 phosphorylation, since MCF-7 cells do not express persistently phosphorylated STAT3. In control experiments, IL-6 elevated STAT3 phosphorylation in MCF-7 cells, while LY-5 and LY-3 blocked the stimulation, with phosphorylated STAT3 abrogated at low concentrations (FIG. 3). The DAOY medulloblastoma cancer cell line was used to further determine the ability of LY-5 to inhibit IL-6 induced STAT3 phosphorylation. In control experiments, IL-6 elevated STAT3 phosphorylation in DAOY cells, while LY-5 blocked the stimulation, with phosphorylated STAT3 abrogated at low concentrations (FIG. 4). Control experiments (0−/+) illustrate the ability of IL-6 to induce phosphorylation. Inhibition of phosphorylation is compared to a positive control enzyme, GADPH.

19. STAT1 Activity: Phosphorylation Induced by IFN-γ

Figure 5:
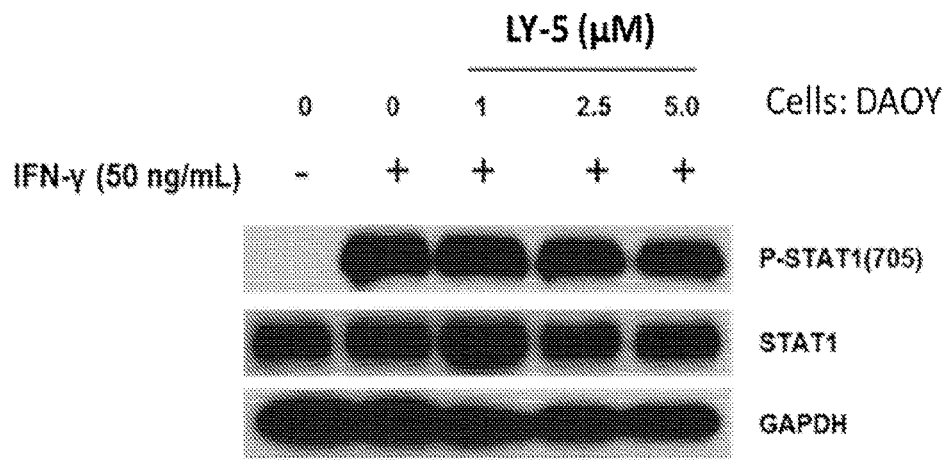
FIG. 5 shows that IFN-γ induced STAT1 phosphorylation in DAOY cancer cells. The DAOY cells were serum-starved overnight, then left untreated or treated with LY-5 (1-5 µM) for 2 h, followed by stimulation by IFN-γ (50 ng/mL). The cells were harvested at 30 minutes and analyzed by Western blot assays.

DAOY medulloblastoma cancer cells were seeded in 10 cm plates and allowed to adhere overnight. The following day, the cells were serum-starved. The cells were then left untreated or were treated with LY-5 (1-5 µM) prepared as a 20 mM stock solution in sterile DMSO or DMSO. After 2 hours, the untreated and LY-5 treated cells were stimulated by IFN-γ (50 ng/mL). The cells were harvested after 30 minutes and analyzed by Western blot. Control experiments (0−/+) illustrate the ability of IFN-γ to induce phosphorylation. Inhibition of phosphorylation is compared to a positive control enzyme, GADPH. The results are shown in FIG. 5.

20. STAT3 Activity: Phosphorylation Induced by OSM

MCF-7 breast cancer cells were seeded in 10 cm plates and allowed to adhere overnight. The following day, the cells were serum-starved. The cells were then left untreated or were treated with LY-5 and LLL12 (1 µM and 2.5 µM) prepared as a 20 mM stock solution in sterile DMSO or DMSO. After 3 hours, the untreated and LY-5 and LLL12 treated cells were stimulated by OSM (50 ng/mL). The cells were harvested after 30 minutes and analyzed by Western blot.

Figure 6:
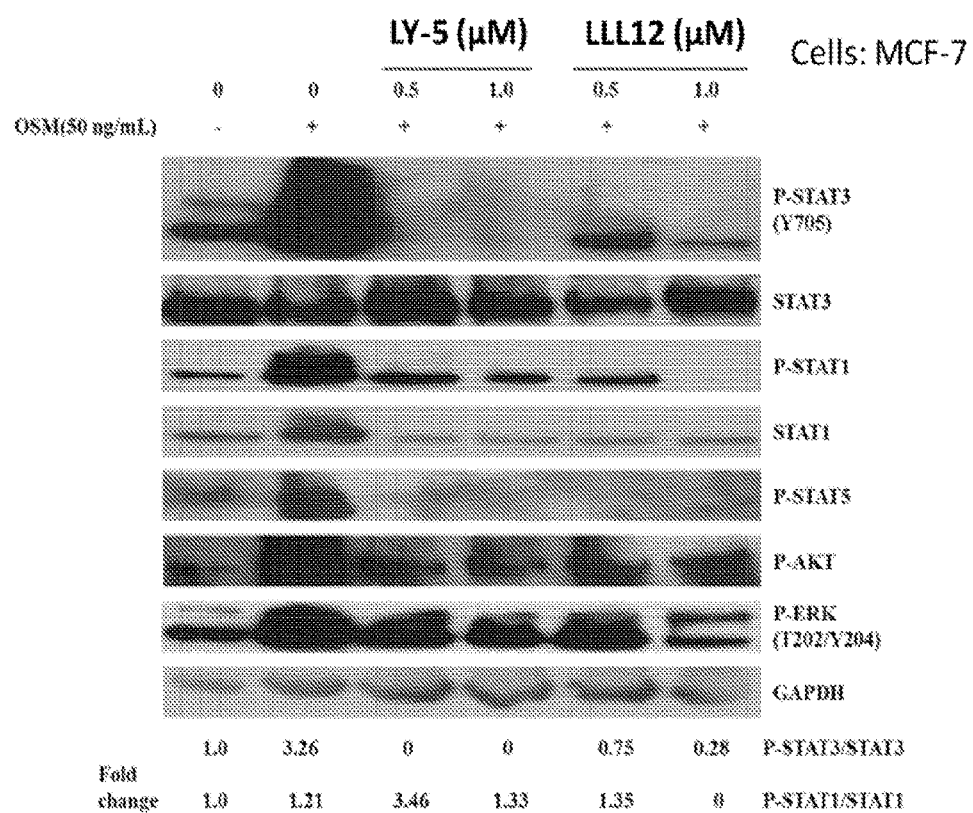
FIG. 6 shows that compounds LY-5 and LLL12 inhibit OSM induced STAT3 phosphorylation in MCF-7 cancer cells. The MCF-7 cells were serum-starved overnight, then left untreated or treated with LY-5 and LLL12 (1-2.5 µM) for 2 h, followed by stimulation by OSM (50 ng/mL). The cells were harvested at 30 minutes and analyzed by Western blot assays.

Inhibitory activity of LY-5 against OSM induced STAT3 phosphorylation as described above is shown in FIG. 6, and was carried out as described above. Control experiments (0−/+) illustrate the ability of OSM to induce phosphorylation. LY-5 was found to effect the fold change of STAT1, indicating that inhibition of phosphorylation of STAT1 by LY-5 could be attributed to a decrease in the overall expression of STAT1. Both LY-5 and LLL12 exhibit inhibition of STAT5. Additionally, the ability of LY-5 and LLL12 to selectivity inhibit phosphorylation of STAT3 over AKT and ERK 1/2 is illustrated. Inhibition of phosphorylation is compared to a positive control enzyme, GADPH.

21. Mouse Model of Xenograft Tumor Development

MDA-MB-231 human breast cancer cells ($5 \times 10^6$) were injected subcutaneously into the flank area of 6-week-old female athymic nude mice which were purchased from Harlan (Indianapolis, Ind., USA). There were two injection sites per animal, thus each animal provided two tumors for analysis. After tumor development, mice were divided into two treatment groups consisting of eight tumors per group (4 animals/group). The vehicle was as follows: 10% DMSO, 18% Cremophor EL, and 72% sterile 5% Dextrose solution. The same vehicle was used for oral administration (via oral gavage) or intraperitoneal ("IP") injection. The test compound was LY-5 was at 2.5 mg/ml in the vehicle, and 100 µL was administered daily to each animal (total dose: 5 mg/kg). For both oral and IP administration, LY-5 was administered for 21 days. Tumor growth was determined by measuring length (L) and width (W) of the tumor every other day with a caliper. The tumor volume was calculated according to the formula: Tumor volume=$0.5236 \times L \times W^2$.

Figure 7:
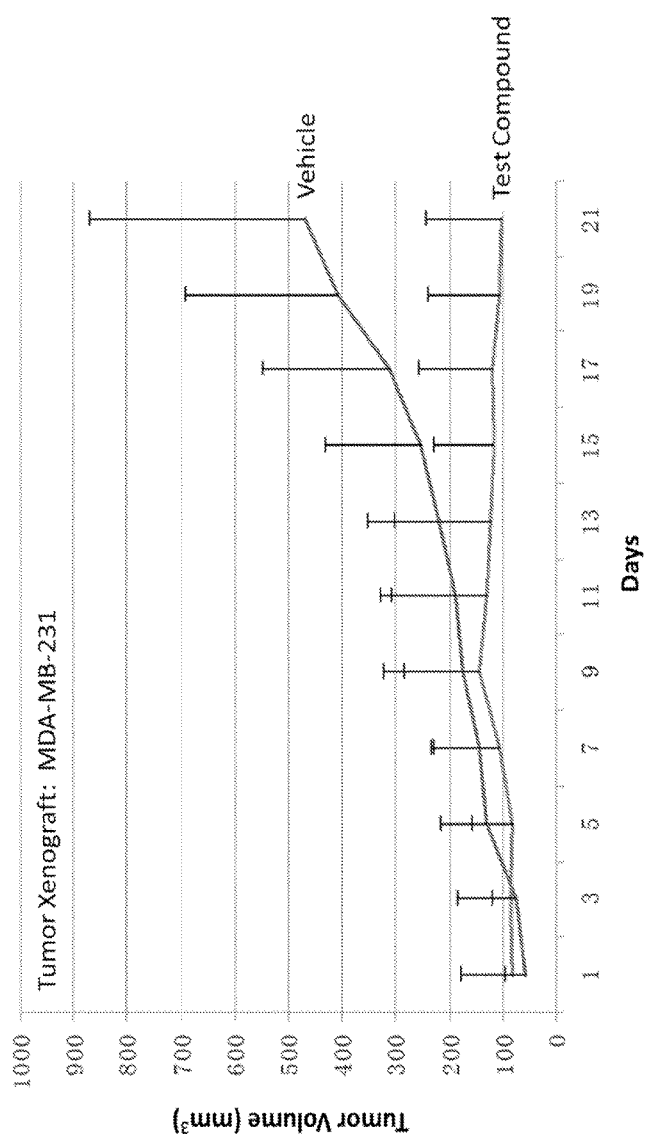
FIG. 7 shows that compound LY-5 suppresses tumor growth of MDA-MB-231 breast cancer-initiating cells in mouse tumor model in vivo. Tumor growth was determined by measuring length (L) and width (W) of the tumor every other day with a caliper. The tumor volume was calculated according to the formula: Tumor volume=$0.5236 \times L \times W^2$.

The effectiveness of a representative disclosed compound, LY-5, to suppress xenograft tumor growth when administered by IP injection was assessed, and the data are shown in FIG. 7. The study was conducted as described herein above. Activity of the compound is compared to vehicle control. The results demonstrate that LY-5 significantly suppresses (p<0.001) the tumor growth.

The study was repeated using LY-5, but administered by oral gavage per the study conditions described herein above. Surprisingly, the compound strongly suppressed tumor growth in a manner and to an extent similar to the results see when the compound was administered by IP injection (see FIG. 16; LY-5 is indicated as "test compound" in the figure and the control is vehicle, as indicated, without any compound).

Additional data for the effectiveness of LY-5 in mouse xenograft model is shown in FIG. 55. Each line in FIG. 55, panel A, represents the tumor growth results obtained in an individual mouse, either treated with vehicle or LY-5 as indicated. The test compound, LY-5, was delivered by oral gavage once per day for 21 days. The vehicle for these studies was 10% (v/v) DMSO, 18% (v/v) Cremaphor FL, and 72% (v/v) of a sterile, aqueous solution containing 5% (w/v) dextrose. The phosphorylation status of STAT3 was determined (see Panel B) using GAPDH as loading control. The data show that extracts obtained from isolated tumors no apparent phosphorylated STAT3.

22. Evaluation of STAT3 Binding: Fluorescence Polarization (FP) Assay

FP assay was used to further prove the binding of LY-5 to the STAT3 SH2 domain. Screening was performed at physiologically relevant temperature 37° C. Before each experiment, Compound LY-5 was prepared freshly from the stock solution. Compound LY-5 increased its background fluorescence reading at 595 nm at high concentrations, so the control solutions for each concentration were prepared by mixing buffer, LY-5, and fluorescence-labeled peptides together. Inhibition curves were fitted in Sigmaplot 11.0 (FIG. 8) and $K_i$ value was determined using a mathematical model developed for FP assay at 2.5 μM. So the experimental ΔG value of LY-5 is −7.9 kcal/mol, which is comparable to the AutoDock4 computed ΔG value, −7.3 kcal/mol.

Screening was performed at approximately 37° C. STAT3 protein was used at 300 nM. The final concentration of buffer components used for all FP assays was 10 mM HEPES (pH 7.5), 1 mM EDTA, 0.1% Nonidet P-40, 50 mM NaCl, and 20% DMSO. Dithiothreitol was not added. LP-5 was diluted to a series of concentrations (1-200 μM) from a 20 mM stock in DMSO. Proteins were incubated with LP-5 in Eppendorf tubes at room temperature for 60 min prior addition of the 5-carboxyfluorescein labeled peptides. The final concentration of labeled peptide is 10 nM. The mixtures were transferred to a 384 Well Costar Black plate with each concentration repeated in three wells. The mixtures were equilibrated in the incubator at 37° C. for at least 30 min. The FP readings were measured and the experiments were repeated three times. Inhibition curves with standard deviation were fitted and Ki value was determined accordingly.

The ability of LY-5 to bind to the STAT3 SH2 domain as described above is shown in FIG. 8, and was carried out as described above. LY-5 is indicated as "8" in the figure. The assay was carried out at 37° C. at the concentrations indicated. Error bars represent standard deviation.

23. Toxicity Assessment of LY-5

In order to provide preliminary data regarding potential toxicities from dosing of LY5, C57BL/6 tumor-free mice were treated with daily intraperitoneal (IP) injections of LY5 at 5 or 10 mg/kg for 7 days. Although the number of mice in each treatment group for this pilot study was low (n=2) histologic evaluation revealed no abnormalities in the kidney, liver, hematopoietic and lymphoid tissues, heart, lung, brain, or in the reproductive tract. Organ weights as a percentage of body weight did not vary significantly between vehicle and LY5 treated groups. There were also no differences in the erythrocyte, leukocyte and platelet parameters observed. Additionally, LY5 at a dose of 5 mg/kg via IP for 5 days inhibited growth of OS-1 tumor xenografts (90% tumor volume compared to baseline), while tumor in vehicle treated mice continued to grow (143% tumor volume compared to baseline). These data support the lack of acute systemic toxicities in mice treated with LY5 at doses likely to have anti-tumor activity.

24. Cell Migration Assay (In Vitro Wound-Healing Assay)

Endothelial cell (HUVEC) migration was monitored using the wound-healing assay described by Thaloor et al. (Cell Growth Differ. (1998) 9(4):305-12). Briefly, $3 \times 10^4$ cells/well were seeded in 24-well plates using M200 medium with LSGS. After cells had attached and formed a monolayer on plate completely, we scraped the cells with same width using yellow tip. After scraped, the cells were washed with PBS and incubated with the medium containing VEGF (10 ng/ml)) with or without LY5 (300 nM). Width was photographed at different time intervals (0 and 24 hours) with a magnification of 40× with a microscopic camera system (Leitz Diavert microscope, Leica, Bensheim; Axio-Cam, Carl Zeiss, Gottingen, Germany).

25. Quantitative Migration Assay

HUVECs were grown in M200 containing LSGS until 40-50% confluent. Cells were washed with PBS, trypsinized for 5-10 min, collected with 0.2% FBS and centrifuged at 300 g for 5 min. Cells were then resuspended with 0.2% FBS and counted using a Beckman Coulter Z2. A volume of 400 μl of this mix containing $5 \times 10^5$ cells was placed on to Boyden Chambers (8 μm pore) inserts with or without LY5 (300 nM) in 24 well plates with 500 μl of M200. VEGF (R and D Systems) in 1% BSA was added to a final concentration of 10 ng/ml in the lower chambers as a chemo-attractant. Cells were pretreated with antibody for 30 min in suspension, then placed in the chambers and incubated at 37° C. 5% C02 for 18-24 hrs. The Boyden chamber porous membranes were then blotted and fixed with 3.7% formaldehyde containing 0.05% crystal violet for 30 min. After repeated washes with distilled water the membranes were air-dried. The migrated cells on the bottom side of the membranes were collected by scraping the bottom of the chamber with a Q-tip, which was subsequently placed into a 1.5 ml eppendorf tube and incubated in 80% methanol to extract the dye. The remainder of the cells on top of the membrane and within the Boyden chamber, were separately incubated in 80% methanol, shaken at 500 rpm for 30 min, and the extracted dye measured at 570 nm. Migration was quantified using the ratio of the migrated cells over the total cells (migrated plus remaining cells) to determine the fraction of migrating cells in each individual experiment. Experiment was performed in duplicate on multiple occasions as described in the figure legends.

26. Invasion Assay

The Matrigel invasion assays were carried out using Matrigel precoated inserts (BD Bioscience) following the manufacturer's instructions. Six hundred μl of M200 medium with or without VEGF (20 ng/ml, R&D Systems) was placed in the lower wells. Proliferating HUVECs ($4 \times 10^5$ cells/ml) were pretreated with LY5 (300 nM) and 100 μl of cell suspension was loaded into each of the upper wells. The chambers were incubated for 18-20 hr at 37° C. After incubation, the inserts were removed, and the non-invading cells on the upper surface were removed with a cotton swab. The cells on the lower surface of the membrane were fixed in 100% methanol for 15 minutes, air-dried, and stained with Diff-Quik stain for 2 min. The cells were counted in six individual high-power fields for each membrane condition under a light microscope. Assays were performed in triplicate for each treatment group and the results were expressed as migrated cells per field for each condition.

27. Vascularization of MATRIGEL™ Plugs In Vivo

To further characterize anti-angiogenetic properties of LY5 in vivo, we performed murine MATRIGEL™ plug experiments. PBS was used as a negative control, and VEGF (100 ng/mL) as a positive control. MATRIGEL™ was injected subcutaneously into CB17SC scid−/− female mice, forming semi-solid plugs. Animals received treatment of LY5 (5 mg/kg) I.P. intraperitoneal (i.p.) injection immediately after the MATRIGEL™ injection and daily for 7 days. On day 7, plugs were excised under anesthesia, fixed in PBS-buffered 10% formalin containing 0.25% glutaraldehyde, and were processed for H&E and Masson's Trichrome staining. Vascular identity of the infiltrating cells was established with CD34 immunostaining. The regions containing the most intense area of neovascularization ("hotspots") were chosen for analysis. Eight hotspots were identified for each Matrigel MATRIGEL™ or tumor section. The ImagePro Plus analysis system (Media Cybernetics Inc, Bethesda, Md.) was used to quantify the percentage of area occupied by the vessel-like structures in each field. The mean±SE from each group were compared. The negative control was obtained by tissue staining with secondary antibody only.

28. Immunohistochemistry (IHC)

For IHC, fixed tumors were sectioned at 5-μm then dewaxed and soaked in alcohol. After microwave treatment in antigen unmasking solution (Vector Laboratory, Burlingame, Calif., USA) for 10 min, endogenous peroxidase activity was inactivated by incubating in 3% hydrogen peroxide ($H_2O_2$) for 15 min and sections were incubated with primary antibody in phosphate-buffered saline at 4° C. overnight. After washing with phosphate-buffered saline (PBS), immuno-staining was performed using the Vectastain Universal Quick Kit and DAB Peroxidase Substrate Kit (Vector Laboratories, Burlingame, Calif., USA) according to the manufacturer's instruction. Antiserum was omitted in the negative control. The number of cells staining positive was counted by a blinded observer in 5 random 40× fields and treated versus controls compared (Student t test). Images were obtained with an Olympus AX70 fluorescence microscope and Spot v2.2.2 (Diagnostic Instruments, Sterling Heights, Mich.) digital imaging system.

29. Human Angiogenesis Array

Proteome profiler antibody array (R & D systems; Cat no ARY007, Minneapolis, Minn.) was used according to manufacturer's instruction to detect the relative levels of expression of 55 angiogenesis related protein in control and treated tumors. After blocking the membranes 300 μg of protein from the tumor tissue lysate from control and LY5 treated groups were added and incubated for overnight at 4 OC. Next day the membranes were washed and streptavidin-HRP was added for 30 minutes. Immunoreactive signals were visualized by using Super Signal Chemiluminiscence substrate (Pierce) and Biomax MR and XAR film (Eastman Kodak Co.). Array data on developed X-ray film was quantified by scanning the film using Biorad Molecular Image Gel Doc™ XR+ and analyze the data using Image Lab™ software.

30. HUVEC Tube Formation and In Vitro 3D-Angiogenesis Assays

The Endothelial Tube Formation Assay (CBA200, Cell Biolabs Inc., San Diego, Calif., USA) was used in addition to the HUVEC proliferation assay. The ECM gel was thawed at 4° C. and mixed to homogeneity using cooled pipette tips. Cell culture plates (96-well) were bottom-coated with a thin layer of ECM gel (50 μl/well), which was left to polymerize at 37° C. for 60 min. HUVEC (2-3×10$^4$ cells) were stimulated with VEGF in 150 μl medium and added to each well on the solidified ECM gel. Culture medium was added to each well in the presence or absence of LY5. The plates were incubated at 37° C. for 12-18 hours and the endothelial tubes were quantified using a fluorescent microscope after staining with Calcein AM. Three microscope fields were selected at random and photographed. Tube forming ability was quantified by counting the total number of cell clusters and branches under a 4× objective and four different fields per well. The results are expressed as mean fold change of branching compared with the control groups. Each experiment was performed at least three times. The 3D in vitro angiogenesis assay was performed essentially as described by manufactures instructions (promo cell). Briefly, spheroids containing 400 cells each was prepared by the hanging drop method and implanted in collagen gels in the presence or absence of angiogenic factors. The spheroids were photographed after 24 hours and sprout formation assessed as described.

31. Confocal Microscopy

HUVEC cells were grown in Lab-Tek 4-well chamber slides (Nunc/Thermo Scientific) to approximately 60% confluence, and treated with PBS, VEGF (10 ng/mL) DMSO with VEGF, or 300 nM LY5 for 18 hrs with VEGF. The cultures were fixed in cold 4% paraformaldehyde for 20 mins at 4° C., and then cells were permeabilized in 0.1% Triton X-100 (Sigma-Aldrich). The cells were probed using 10 μg/mL mouse anti-human β-Tubulin I primary antibody (Sigma-Aldrich, clone TUB 2.1) overnight at 4° C., and then stained using 10 μg/mL goat anti-mouse Alexa Fluor® 488 conjugated F(ab')2 (Invitrogen) for 1 hr. at RT. F-actin in the cells was stained at RT for 1 hr. using 4 U/mL Alexa Fluor® 633 conjugated phalloidin (Invitrogen). The cells nuclei were then stained by incubating with 300 nM 4',6-diamidino-2-phenylindole (DAPI) dilactate (Invitrogen) for 5 mins at RT. Samples were washed 4 times in PBS after each step during processing. After mounting a coverslip, 1024× 1024 pixel images were taken using a Zeiss Axiovert 710 confocal microscope with a slice depth of 1 μm. Image processing was performed using the Zeiss Image Browser software package.

32. Statistical Analysis

Significance of correlations was done using GraphPad Prism software. Unpaired t tests were used for analyses assuming Gaussian populations with a 95% confidence interval. Data are presented as mean±SE. Differences were analyzed with the Student t test, and significance was set at P less than <0.05.

Statistical analysis for mouse xenograft tumor data was performed by fitting a mixed model to conduct the repeated measures analysis. The repeated measures in the model were the log transformed growing rates (log 10(tumor size/day one tumor size)) measured in different days (1,3, etc. as indicated). The purpose of the model was to test whether the interaction effect between measurement time and treatment group was significant. The interaction item can be interpreted as "the difference of growing rate among the groups." Probability (p) values less than 0.05 were considered statistically significant.

33. Inhibition of STAT3 by LY5 Treatment Represses Angiogenesis In Vitro

Increasing evidence suggests that STAT3 is also an important facilitator of angiogenesis under both physiological and pathological situations. Without wishing to be bound by a particular theory, the activation of STAT3 is not only understood to regulate VEGF production and function in a variety of human cancers, but also correlates with the expression of other critical angiogenic factors including angiopoietin, MMP-9, CXCL16, as well as IGFBP. To study the anti-angiogenic activity of LY5, human umbilical vascular endothelial cells (HUVECs) were stimulated with VEGF in the absence or presence of LY5 and cell migration, cell invasion, tube formation, spheroid formation as well as angiogenesis array were examined. LY5 not only significantly blocked HUVECs migration induced by VEGF (FIG. 53 and FIG. 54), but also prevented HUVECs invasion through Matrigel coated membranes (FIG. 52). LY5 had the similar effect on HUVECs tube formation as shown in FIG. 50. In further analysis using 3D-angiogenesis assay, LY5 treatment impaired angiogenic sprouting of blood vessels induced by VEGF from preformed spheroids of HUVECs (FIG. 51). This data indicates that LY5 exhibited anti-angiogenesis effect in vitro by targeting STAT3.

34. LY5 Suppresses Growth of Human Breast Tumor Xenograft and Inhibits STAT3 Activation, Tumor Angiogenesis In Vivo In order to investigate whether LY5 can inhibit tumor growth in vivo, human MDA-MB-231 breast cancer cells were subcutaneously implanted into athymic nude mice to build mouse xenograft tumor model, and then given LY5 (5 mg/kg) or DMSO daily by oral administration after tumor development. No obvious change in body weight or visible signs of toxicity, such as decreased activity, loss of appetite, or lethargy, was observed during the study. As shown in FIG. 55(A), growth rates of xenograft tumor in LY5 treatment group was significantly decreased in comparison with DMSO vehicle group (p<0.001), demonstrating LY5 inhibited tumor growth in vivo. To confirm the inhibitory effect of LY5 on aberrant STAT3 activation in vivo, the expression of phosphorylated STAT3 in tumor tissue was detected by Western blot. The level of STAT3 phosphorylation in LY5 treated tumor tissue was observed to be noticeably lower than vehicle group (FIG. 55B), suggesting that LY5 suppressed tumor growth in the mice through inhibition of phosphorylated STAT3.

Furthermore, we analyzed the inhibitory function of LY5 on angiogenesis in vivo. To directly test the anti-angiogenic activity of LY5 in vivo, Matrigel plug assay was performed in mice as described herein. VEGF was observed to increase the number of vessels detected in Matrigel plugs by >10-fold over that in PBS infused (control) plugs, however, vessel formation was remarkably decreased (by ~85%) when treated by LY5 at 5 mg/kg dose level (FIG. 52). Similar results were found in human breast cancer tumor xenograft in mice. LY5 treatment also reduced the vessel number in tumor tissue as shown by anti-CD34 antibody staining (FIG. 52). Taken together, data from the above experiments indicates that LY5 targeting STAT3 inhibited tumor growth and tumor angiogenesis in vivo.

35. Summary

As described herein, the concept of in silico sited-directed FBDD that utilizes methods of fragment-based drug design, in silico docking, and bioisosterism to recombine fragments of known inhibitors to form new lead molecules. The successful application of this method is detailed in the design of a novel STAT3 inhibitor scaffold, leading to compounds with low $IC_{50}$ values and strong binding affinity to STAT3 SH2 domain. This study has several significant findings: 1) The use of fragment sub-libraries based on the docking modes of known inhibitors was an efficient method to design potential new inhibitors. This method is potentially more reliable than virtual screening of fragment libraries and less costly than conventional methods like high-throughput screening. In addition, the final docking step of the merged fragments acts as an extra filter to assure that key interactions are maintained or even optimized prior to synthesis. 2) The secondary amine linker used in the design is a bioisostere of the hydroxyl group in 13 that can maintain both the binding poses of the fragments and the binding affinity. 3) The $IC_{50}$ of LY-5 is superior to that of 13 in two different cancer cell lines, U2OS and RD2, while 13 has the lowest $IC_{50}$ among all the reported nonpeptidomimetic small molecule inhibitors targeting SH2 domain. 4) The synthesis of novel STAT3 inhibitors presents a new highly regioselective coupling method. The major product is connected at position 6 of the napthoquinone. Compared to 13, the novel series of STAT3 inhibitors are superior with lower synthetic cost and larger space for further modification. 13 has some disadvantages such as the need for the expensive synthetic material 3-hydroxy-2-pyrone, time-consuming purification to separate the regioisomers, and difficulty in modifying the three ring system. The novel STAT3 inhibitors can overcome these shortcomings. The synthetic materials for novel STAT3 inhibitors are about 10 times less costly, the reaction has much higher selectivity to react to 3-naphthoquinone than to 2-naphthoquinone, and it is very easy to modify the novel STAT3 inhibitors to fit the side pocket by alternating the amine reagents.

This method has the potential to be more efficient than conventional methods like virtual screening and high-throughput screening, but there is a drawback in the need for known inhibitors from which the fragment libraries are generated. For targets with many known inhibitors, such as kinases, in silico site-directed FBDD would likely produce many new leads. This drug design method could also be used for targets without known inhibitors, if sufficient homology exists with another protein with known inhibitors. An additional shortcoming is that ligand efficiency (LE) is unlikely to increase significantly during the fragment recombination, unless the binding modes of fragments can be greatly improved without increasing their size. One might not expect deconstruction of a potent lead to always derive high quality fragments if the synergy between two nonadjacent binding interactions is lost during the fragmentation. How reliably fragments can be recombined to maintain synergy will need to be further examined.

Recombination of two fragments from existing STAT3 dimerization inhibitors through in silico site-directed FBDD is an efficient and feasible method to design more potent STAT3 inhibitors. Linker selection was well studied so that the synthetic strategy was feasible; the linker maintained the initial binding modes of the fragments and enhanced the binding affinity of the fragments. The discovery of novel STAT3 inhibitors is a successful trial. Four out of five compounds have $IC_{50}$ lower than 5 µM for cancer cell line U2OS, among which, LY-5 has an $IC_{50}$ ranging between 0.5-1.4 µM in different cell lines. LY-5 and LY-3 have been demonstrated to significantly decrease STAT3 phosphorylation. The fluorescence polarization (FP) assay also proved that LY-5 binds to STAT3 SH2 domain with a $K_i$ value of 2.5 µM. Thus, the experimental ΔG value of LY-5 is −7.9 kcal/mol, which is comparable to the AutoDock4 computed ΔG value, −7.3 kcal/mol.

Moreover, the data provided herein above and in the figures suggest that the disclosed compounds of the present invention have the following properties: a) allosteric small molecule inhibitors of STAT3 that possesses many favorable features including ease of synthesis, ease of formulation, low molecular weight, potent and specific targeting to STAT3, good solubility, cell permeable, and orally bioavailable; b) inhibit phosphorylation of STAT3, STAT3 nuclear translocation, STAT3 downstream targeted genes, and induced apoptosis in many human cancer cell-lines; c) inhibit angiogenesis-like activities in angiogenesis assays; d) selectively inhibit STAT3 phosphorylation induced by IL-6 family cytokines and IGF-1/2 but not phosphorylation of other STAT family member proteins suggesting minimal side effects in normal human cells; e) selectivity for STAT3 in that there was no apparent inhibition of 96 human protein or lipid kinase activities, including AKT1, AKT2, BRAF, EGFR, JAK2, JAK3, KIT, MEK1/2, PDGFR, PI3KC2B, PI3KCA, PI3KCG, SRC, TYK2, and VEGFR2; f) apparently synergistic with cisplatin, tamoxifen, and MEK inhibitors; and g) exhibit potent anti-tumor activity mouse models.

36. Prophetic Pharmaceutical Composition Examples

"Active ingredient" as used throughout these prophetic examples below relates to one or more compounds disclosed herein. For example, the compound can have a structure represented by a formula:

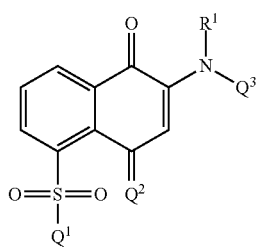

wherein $R^1$ is selected from hydrogen and C1-C3 alkyl; wherein $Q^1$ is —$NR^{2a}R^{2b}$ and wherein $Q^2$ is O; or wherein $Q^1$ and $Q^2$ are together N; wherein $Q^3$ is selected from $Ar^1$, —(C1-C6)-$Ar^1$, $Cy^1$, and —(C1-C6)-$Cy^1$; wherein $Ar^1$ is selected from phenyl, naphthyl, monocyclic heteroaryl, and bicyclic heteroaryl; and wherein $Ar^1$ is substituted with 0, 1, 2, or 3 groups independently selected from halogen, —CN, —OH, —$NH_2$, —$NO_2$, C1-C6 alkyl, C1-C6 monohaloalkyl, C1-C6 polyhaloalkyl, C1-C6 hydroxyalkyl, C1-C6 monoalkylamino, C1-C6 dialkylamino, —(C1-C6)$NR^{4a}R^{4b}$, —(C1-C6)-(C=O)$R^3$, —(C1-C6)(C=O)$OR^3$, —(C1-C6)-(C=O)$NR^{4a}R^{4b}$, —(C1-C6)-$Ar^2$, $Ar^2$, —(C1-C6)-$Cy^2$, $Cy^2$, and —$S(O)_nNR^{5a}R^{5b}$; wherein n is 0, 1, or 2; wherein each $R^3$ is independently selected from hydrogen, C1-C6 alkyl, C1-C6 monohaloalkyl, C1-C6 polyhaloalkyl, C1-C6 hydroxyalkyl, and C1-C6 aminoalkyl; wherein each of $R^{4a}$ and $R^{4b}$ is independently selected from hydrogen, C1-C6 alkyl, C1-C6 monohaloalkyl, C1-C6 polyhaloalkyl, C1-C6 hydroxyalkyl, and C1-C6 aminoalkyl; wherein each of $R^{5a}$ and $R^{5b}$ is independently selected from hydrogen, C1-C6 alkyl, C1-C6 monohaloalkyl, C1-C6 polyhaloalkyl, C1-C6 hydroxyalkyl, C1-C6 aminoalkyl, and —(C=O)$NR^{6a}R^{6b}$; wherein each of $R^{6a}$ and $R^{6b}$ is independently selected from hydrogen and C1-C6 alkyl; wherein each $Ar^2$ is independently selected from is phenyl and monocyclic heteroaryl; and wherein $Ar^1$ is substituted with 0, 1, 2, or 3 groups independently selected from halogen, —CN, —OH, —$NH_2$, —$NO_2$, C1-C6 alkyl, C1-C6 monohaloalkyl, C1-C6 polyhaloalkyl, C1-C6 hydroxyalkyl, C1-C6 aminoalkyl, C1-C6 monoalkylamino, and C1-C6 dialkylamino; wherein each $Cy^2$ is independently selected from C3-C8 cycloalkyl and C2-C7 heterocycloalkyl; and wherein $Cy^2$ is substituted with 0, 1, 2, or 3 groups independently selected from halogen, —CN, —OH, —$NH_2$, —$NO_2$, C1-C6 alkyl, C1-C6 monohaloalkyl, C1-C6 polyhaloalkyl, C1-C6 hydroxyalkyl, C1-C6 aminoalkyl, C1-C6 monoalkylamino, C1-C6 dialkylamino, —(C=O)$R^6$, —(C=O)$OR^6$, —(C=O)$NR^{7a}R^{7b}$, —(C=O)—(C1-C6 alkyl)$Ar^3$, —(C=O)—O—(C1-C6 alkyl)$Ar^3$, and —(C=O)—$NR^{7a}$—(C1-C6 alkyl)$Ar^3$; wherein each $R^6$ is independently selected from hydrogen, C1-C6 alkyl, C1-C6 monohaloalkyl, and C1-C6 polyhaloalkyl; wherein each of $R^{7a}$ and $R^{7b}$ is independently selected from hydrogen, C1-C6 alkyl, C1-C6 monohaloalkyl, and C1-C6 polyhaloalkyl; wherein each $Ar^3$ is independently selected from phenyl and monocyclic heteroaryl substituted with 0, 1, 2, or 3 groups independently selected from halogen, —CN, —OH, —$NH_2$, —$NO_2$, C1-C6 alkyl, C1-C6 monohaloalkyl, and C1-C6 polyhaloalkyl; wherein $Cy^1$ is selected from C3-C8 cycloalkyl and C2-C7 heterocycloalkyl; and wherein $Cy^2$ is substituted with 0, 1, 2, or 3 groups independently selected from halogen, —CN, —OH, —$NH_2$, —$NO_2$, C1-C6 alkyl, C1-C6 monohaloalkyl, C1-C6 polyhaloalkyl, C1-C6 hydroxyalkyl, C1-C6 monoalkylamino, C1-C6 dialkylamino, —(C1-C6)$NR^{4a}R^{4b}$, —(C1-C6)-(C=O)$R^3$, —(C1-C6)-(C=O)$OR^3$, —(C1-C6)-(C=O)$NR^{4a}R^{4b}$, —(C1-C6)-$Ar^2$, $Ar^2$, —(C1-C6)-$Cy^2$, $Cy^2$, and —$S(O)_nNR^{5a}R^{5b}$; or a pharmaceutically acceptable salt, solvate, or polymorph thereof.

a. Tablet

A tablet can be prepared as follows:

| Component | Amount |
|---|---|
| Active ingredient | 5 to 50 mg |
| Di-calcium phosphate | 20 mg |
| Lactose | 30 mg |
| Talcum | 10 mg |
| Magnesium stearate | 5 |
| Potato starch | add to make total weight 200 mg |

In this Example, active ingredient can be replaced with the same amount of any of the compounds according to the present invention, in particular by the same amount of any of the exemplified compounds.

b. Suspension

An aqueous suspension is prepared for oral administration so that each 1 milliliter contains 1 to 5 mg of one of the active compounds, 50 mg of sodium carboxymethyl cellulose, 1 mg of sodium benzoate, 500 mg of sorbitol and water ad 1 ml.

c. Injectable

A parenteral composition is prepared by stirring 1.5% by weight of active ingredient of the invention in 10% by volume propylene glycol in water.

d. Ointment

An ointment can be prepared as follows:

| Component | Amount |
|---|---|
| Active ingredient | 5 to 1000 mg |
| Stearyl alcohol | 3 g |
| Lanoline | 5 g |
| White petroleum | 15 g |
| Water | add to make total weight 100 g |

In this Example, active ingredient can be replaced with the same amount of any of the compounds according to the present invention, in particular by the same amount of any of the exemplified compounds.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound having a structure represented by a formula:

[Chemical structure diagram showing a naphthoquinone with R¹-N group, Q³, Q², and O=S=O-Q¹ substituents]

wherein R¹ is selected from hydrogen and C1-C3 alkyl;
wherein Q¹ is —NR²ᵃR²ᵇ and wherein Q² is O; or wherein Q¹ and Q² are together N;
wherein each of R²ᵃ and R²ᵇ, when present, is independently selected from hydrogen and C1-C3 alkyl;
wherein Q³ is selected from —(C1-C6)-Ar¹, Ar¹, —(C1-C6)-Cy¹, and Cy¹;
wherein Ar¹, when present, is selected from phenyl, naphthyl, monocyclic heteroaryl, and bicyclic heteroaryl; and wherein Ar¹ is substituted with 0, 1, 2, or 3 groups independently selected from halogen, —CN, —OH, —NH₂, —NO₂, C1-C6 alkyl, C1-C6 monohaloalkyl, C1-C6 polyhaloalkyl, C1-C6 hydroxyalkyl, C1-C6 monoalkylamino, C1-C6 dialkylamino, —(C1-C6)NR⁴ᵃR⁴ᵇ, —(C1-C6)-(C=O)R³, —(C1-C6)-(C=O)OR³, —(C1-C6)-(C=O)NR⁴ᵃR⁴ᵇ, —(C1-C6)-Ar², Ar², —(C1-C6)-Cy², Cy², and —S(O)ₙNR⁵ᵃR⁵ᵇ;
wherein n is 0, 1, or 2;
wherein each R³, when present, is independently selected from hydrogen, C1-C6 alkyl, C1-C6 monohaloalkyl, C1-C6 polyhaloalkyl, C1-C6 hydroxyalkyl, and C1-C6 aminoalkyl;
wherein each of R⁴ᵃ and R⁴ᵇ, when present, is independently selected from hydrogen, C1-C6 alkyl, C1-C6 monohaloalkyl, C1-C6 polyhaloalkyl, C1-C6 hydroxyalkyl, and C1-C6 aminoalkyl;
wherein each of R⁵ᵃ and R⁵ᵇ, when present, is independently selected from hydrogen, C1-C6 alkyl, C1-C6 monohaloalkyl, C1-C6 polyhaloalkyl, C1-C6 hydroxyalkyl, C1-C6 aminoalkyl, and —(C=O)NR⁶ᵃR⁶ᵇ;
wherein each of R⁶ᵃ and R⁶ᵇ, when present, is independently selected from hydrogen and C1-C6 alkyl;
wherein each Ar², when present, is independently selected from is phenyl and monocyclic heteroaryl; and wherein Ar2 is substituted with 0, 1, 2, or 3 groups independently selected from halogen, —CN, —OH, —NH₂, —NO₂, C1-C6 alkyl, C1-C6 monohaloalkyl, C1-C6 polyhaloalkyl, C1-C6 hydroxyalkyl, C1-C6 aminoalkyl, C1-C6 monoalkylamino, and C1-C6 dialkylamino;
wherein each Cy², when present, is independently selected from C3-C8 cycloalkyl and C2-C7 heterocycloalkyl; and wherein Cy² is substituted with 0, 1, 2, or 3 groups independently selected from halogen, —CN, —OH, —NH₂, —NO₂, C1-C6 alkyl, C1-C6 monohaloalkyl, C1-C6 polyhaloalkyl, C1-C6 hydroxyalkyl, C1-C6 aminoalkyl, C1-C6 monoalkylamino, C1-C6 dialkylamino, —(C=O)R7, —(C=O)OR7, —(C=O)NR⁸ᵃR⁸ᵇ, —(C=O)-(C1-C6 alkyl)Ar3, —(C=O)—O—(C1-C6 alkyl)Ar³, and —(C=O)—NR⁸ᵃ—(C1-C6 alkyl)Ar³;

wherein each R⁷, when present, is independently selected from hydrogen, C1-C6 alkyl, C1-C6 monohaloalkyl, and C1-C6 polyhaloalkyl;
wherein each of R⁸ᵃ and R⁸ᵇ, when present, is independently selected from hydrogen, C1-C6 alkyl, C1-C6 monohaloalkyl, and C1-C6 polyhaloalkyl;
wherein each Ar³, when present, is independently selected from phenyl and monocyclic heteroaryl substituted with 0, 1, 2, or 3 groups independently selected from halogen, —CN, —OH, —NH₂, —NO₂, C1-C6 alkyl, C1-C6 monohaloalkyl, and C1-C6 polyhaloalkyl;
wherein Cy¹, when present, is selected from C3-C8 cycloalkyl and C2-C7 heterocycloalkyl; and wherein Cy¹ is substituted with 0, 1, 2, or 3 groups independently selected from halogen, —CN, —OH, —NH₂, —NO₂, C1-C6 alkyl, C1-C6 monohaloalkyl, C1-C6 polyhaloalkyl, C1-C6 hydroxyalkyl, C1-C6 monoalkylamino, C1-C6 dialkylamino, —(C1-C6)NR⁴ᵃR⁴ᵇ, —(C1-C6)-(C=O)R³, —(C1-C6)-(C=O)OR³, —(C1-C6)-(C=O)NR⁴ᵃR⁴ᵇ, —(C1-C6)-Ar², Ar², —(C1-C6)-Cy², Cy², and —S(O)ₙNR⁵ᵃR⁵ᵇ;
or a pharmaceutically acceptable salt thereof.

2. The compound of claim 1, wherein Q¹ is —NH₂.

3. The compound of claim 1, wherein Q¹ is —NHCH₃.

4. The compound of claim 1, wherein Q³ is Ar¹.

5. The compound of claim 1, wherein Q³ is —(C1-C6)-Ar¹.

6. The compound of claim 1, wherein Ar¹, when present, is phenyl and is substituted with 0, 1, 2, or 3 groups independently selected from halogen, —CN, —OH, —NH₂, —NO₂, C1-C6 alkyl, C1-C6 monohaloalkyl, C1-C6 polyhaloalkyl, C1-C6 hydroxyalkyl, C1-C6 aminoalkyl, C1-C6 monoalkylamino, C1-C6 dialkylamino, —(C1-C6)NR⁴ᵃR⁴ᵇ, —(C1-C6)-(C=O)R³, —(C1-C6)-(C=O)OR³, —(C1-C6)-(C=O)NR⁴ᵃR⁴ᵇ, —(C1-C6)-Ar², Ar², —(C1-C6)-Cy², Cy², and —S(O)ₙNR⁵ᵃR⁵ᵇ.

7. The compound of claim 1, wherein Ar¹, when present, is phenyl and is substituted with 0, 1, 2, or 3 groups independently selected from halogen, —CN, —OH, —NH₂, —NO₂, C1-C6 alkyl, C1-C6 monohaloalkyl, C1-C6 polyhaloalkyl, C1-C6 hydroxyalkyl, C1-C6 aminoalkyl, C1-C6 monoalkylamino, C1-C6 dialkylamino, —(C1-C6)-Cy², Cy², and —S(O)ₙNR⁵ᵃR⁵ᵇ.

8. The compound of claim 1, wherein Ar¹, when present, is pyridinyl and is substituted with 0, 1, 2, or 3 groups independently selected from halogen, —CN, —OH, —NH₂, —NO₂, C1-C6 alkyl, C1-C6 monohaloalkyl, C1-C6 polyhaloalkyl, C1-C6 hydroxyalkyl, C1-C6 aminoalkyl, C1-C6 monoalkylamino, C1-C6 dialkylamino, —(C1-C6)NR⁴ᵃR⁴ᵇ, —(C1-C6)-(C=O)R³, —(C1-C6)-(C=O)OR³, —(C1-C6)-(C=O)NR⁴ᵃR⁴ᵇ, —(C1-C6)-Ar², Ar², —(C1-C6)-Cy², Cy², and —S(O)ₙNR⁵ᵃR⁵ᵇ.

9. The compound of claim 1, wherein Cy², when present, is a C2-C7 heterocycloalkyl and is substituted with 0, 1, 2, or 3 groups independently selected from halogen, —CN, —OH, —NH₂, —NO₂, C1-C6 alkyl, C1-C6 monohaloalkyl, C1-C6 polyhaloalkyl, C1-C6 hydroxyalkyl, C1-C6 aminoalkyl, C1-C6 monoalkylamino, C1-C6 dialkylamino, —(C=O)R⁷, —(C=O)OR⁷, —(C=O)NR⁸ᵃR⁸ᵇ, —(C=O)—(C1-C6 alkyl)-Ar³, —(C=O)—O—(C1-C6 alkyl)-Ar³, and —(C=O)—NR⁸ᵃ—(C1-C6 alkyl)-Ar³.

10. The compound of claim 1, wherein Cy², when present, is piperidinyl and is substituted with 0, 1, 2, or 3 groups independently selected from halogen, —CN, —OH, —NH₂, —NO₂, C1-C6 alkyl, C1-C6 monohaloalkyl, C1-C6 polyhaloalkyl, C1-C6 hydroxyalkyl, C1-C6 aminoalkyl, C1-C6 monoalkylamino, C1-C6 dialkylamino, —(C=O)R⁷, —(C=O)OR⁷, —(C=O)NR⁸ᵃR⁸ᵇ, —(C=O)—(C1-C6 alkyl)-Ar³, —(C=O)—O—(C1-C6 alkyl)-Ar³, and —(C=O)—NR⁸ᵃ—(C1-C6 alkyl)-Ar³.

11. The compound of claim 1, wherein Cy², when present, is morpholinyl and is substituted with 0, 1, 2, or 3 groups independently selected from halogen, —CN, —OH, —NH₂, —NO₂, C1-C6 alkyl, C1-C6 monohaloalkyl, C1-C6 polyhaloalkyl, C1-C6 hydroxyalkyl, C1-C6 aminoalkyl, C1-C6 monoalkylamino, C1-C6 dialkylamino, —(C=O)R⁷, —(C=O)OR⁷, —(C=O)NR⁸ᵃR⁸ᵇ, —(C=O)—(C1-C6 alkyl)-Ar³, —(C=O)—O—(C1-C6 alkyl)-Ar³, and —(C=O)—NR⁸ᵃ—(C1-C6 alkyl)-Ar³.

12. The compound of claim 1, wherein Cy² is unsubstituted.

13. The compound of claim 1, wherein R¹ is hydrogen.

14. The compound of claim 1, wherein R¹ is selected from hydrogen and methyl.

15. The compound of claim 1, having a structure represented by a formula:

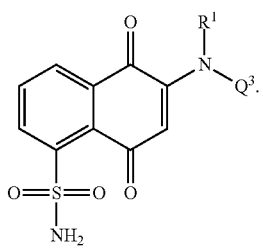

16. The compound of claim 1, having a structure represented by a formula:

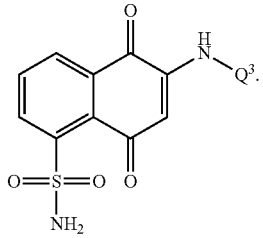

17. The compound of claim 1, having a structure represented by a formula:

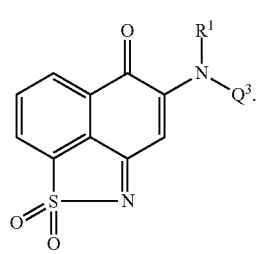

18. The compound of claim 1, having a structure represented by a formula:

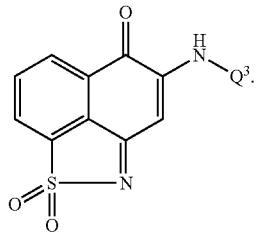

19. The compound of claim 1, having a structure represented by a formula:

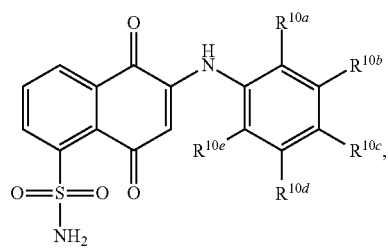

wherein each of R¹⁰ᵃ, R¹⁰ᵇ, R¹⁰ᶜ, R¹⁰ᵈ, and R¹⁰ᵉ is independently selected from hydrogen, halogen, —CN, —OH, —NH₂, —NO₂, C1-C6 alkyl, C1-C6 monohaloalkyl, C1-C6 polyhaloalkyl, C1-C6 hydroxyalkyl, C1-C6 monoalkylamino, C1-C6 dialkylamino, —(C1-C6)NR⁴ᵃR⁴ᵇ, —(C1-C6)-(C=O)R³, —(C1-C6)-(C=O)OR³, —(C1-C6)-(C=O)NR⁴ᵃR⁴ᵇ, —(C1-C6)-Ar², Ar², —(C1-C6)-Cy², Cy², and —S(O)ₙNR⁵ᵃR⁵ᵇ, provided that at least two of R¹⁰ᵃ, R¹⁰ᵇ, R¹⁰ᶜ, R¹⁰ᵈ, and R¹⁰ᵉ are hydrogen.

20. The compound of claim 1, having a structure represented by a formula:

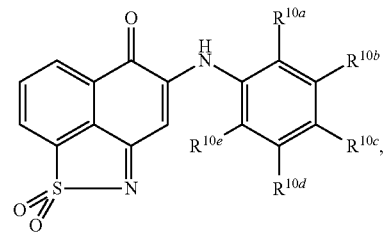

wherein each of R¹⁰ᵃ, R¹⁰ᵇ, R¹⁰ᶜ, R¹⁰ᵈ, and R¹⁰ᵉ independently selected from hydrogen, halogen, —CN, —OH, —NH₂, —NO₂, C1-C6 alkyl, C1-C6 monohaloalkyl, C1-C6 polyhaloalkyl, C1-C6 hydroxyalkyl, C1-C6 monoalkylamino, C1-C6 dialkylamino, —(C1-C6)NR⁴ᵃR⁴ᵇ, (C1-C6)-(C=O)R³, —(C1-C6)-(C=O)OR³, —(C1-C6)-(C=O)NR⁴ᵃR⁴ᵇ, —(C1-C6)-Ar², Ar², —(C1-C6)-Cy², Cy², and —S(O)ₙNR⁵ᵃR⁵ᵇ, provided that at least two of R¹⁰ᵃ, R¹⁰ᵇ, R¹⁰ᶜ, R¹⁰ᵈ, and R¹⁰ᵉ are hydrogen.

21. A pharmaceutical composition comprising a therapeutically effective amount of a compound of claim 1, or a pharmaceutically acceptable salt thereof, and a pharmaceutically acceptable carrier.

22. A method for the amelioration of breast cancer in a mammal comprising the step of administering to the mammal a therapeutically effective amount of at least one compound of claim 1, or a pharmaceutically acceptable salt thereof.

23. The method of claim 22, wherein the compound exhibits inhibition of STAT3 activity with an $IC_{50}$ of less than 5 μM.

24. The method of claim 22, wherein the compound exhibits inhibition of STAT3 activity with an $IC_{50}$ of less than 1 μM.

* * * * *